(12) United States Patent
Sacktor et al.

(10) Patent No.: US 7,790,854 B2
(45) Date of Patent: Sep. 7, 2010

(54) ATYPICAL PROTEIN KINASE C ISOFORMS IN DISORDERS OF THE NERVOUS SYSTEM AND CANCER

(75) Inventors: Todd Charlton Sacktor, Yonkers, NY (US); John Fonda Crary, New York, NY (US); Alejandro Ivan Hernandez, Queens, NY (US); Suzanne Mirra, Brooklyn, NY (US); Charles Shao, Forest Hills, NY (US)

(73) Assignee: Research Foundation of State of University of New York, Albany, NY (US)

( * ) Notice: Subject to any disclaimer, the term of this patent is extended or adjusted under 35 U.S.C. 154(b) by 0 days.

(21) Appl. No.: 10/533,595

(22) PCT Filed: Nov. 3, 2003

(86) PCT No.: PCT/US03/35231

§ 371 (c)(1),
(2), (4) Date: Apr. 27, 2006

(87) PCT Pub. No.: WO2004/041212

PCT Pub. Date: May 21, 2004

(65) Prior Publication Data

US 2006/0185026 A1    Aug. 17, 2006

(51) Int. Cl.
*C07K 16/00* (2006.01)
(52) U.S. Cl. .................................. 530/387.1
(58) Field of Classification Search .............. None
See application file for complete search history.

(56) References Cited

U.S. PATENT DOCUMENTS

2003/0068310 A1    4/2003   Yin et al.

FOREIGN PATENT DOCUMENTS

| WO | WO 93/20101 |  | 10/1993 |
| WO | WO 01/80875 | A1 | 11/2001 |
| WO | WO 02/22867 | A2 | 3/2002 |
| WO | WO 02/087417 | A2 | 11/2002 |

OTHER PUBLICATIONS

Naik et al. Journal of Comparative Neurology, 426: 243-258, 2000.*
Hrabetova et al., Journal of Neuroscience, 16(17):5324-5333, Sep. 1, 1996.*
Taniguchi T. et al., "Phosphorylation of Tau is Regulated by Pkn", *The Journal of Biological Chemistry* 276 (13):10025-10031 (2001), XP-002433229.
Hashiguchi M. et al., "14-3-3ζ is an Effector of Tau Protein Phosphorylation", *The Journal of Biological Chemistry* 275 (33):25247-25254 (2000), XP-002433230.
Christiansen V.J. et al., "Protein Kinase Cζ is Increased in Cerebral Alzheimer's Disease", *FASEB Journal* 10(6):A1015 (1996), XP-008078749.
Moore P. et al., "Protein Kinase C-ζ Activity But Not Level is Decreased in Alzheimer's Disease Microvessels", *Neuroscience Letters* 254(1):29-32 (1998), XP-002406082.
Xie J. et al., "Protein Kinase C Iota Protects Neural Cells Against Apoptosis Induced by Amyloid β—Peptide", *Molecular Brain Research* 82(1-2):107-113 (2000), XP-002406083.
Roβner S. et al., "Increased Neuronal and Glial Expression of Protein Kinase C Isoforms in Neocortex of Transgenic Tg2576 Mice With Amyloid Pathology", *European Journal of Neuroscience* 13(2):269-278 (2001), XP-002327322.
Barad M. et al., "Mice Overexpressing a Constitutively Active PKMζ Derived Transgene in Brain Under CAMKII Promoter Control, Show Defects in Memory and Increased Incidence of Neurofibromas", *Abstracts of the Society for Neuroscience, Society for Neuroscience* 24(1-2):328 (1998), XP-002967921 (Abstract).
Moscat J. et al., "The Atypical Protein Kinase Cs", *EMBO Reports*, 1(5):399-403 (2000).
Shao C.Y. et al., "Atypical Protein Kinase C (PKC) Colocalizes with Tau-and α-Synuclein-Related Inclusions in Neurodegenerative Disorders", *Society for Neuroscience Abstracts 02-07* (2002), Abstract 592.9.
Shao C.Y. et al., "Association of PKC, P62 and Ubiquitin with Inclusions of Neurodegenerative Disease", *Society for Neuroscience Abstracts 08-12* (2003), Abstract 203.22.
Hopf F.W. et al., "Atypical Protein Kinase C is a Novel Mediator of Dopamine-Enhanced Firing in Nucleus Accumbens Neurons", *The Journal of Neuroscience*, 25 (4):985-989 (2005).

* cited by examiner

*Primary Examiner*—John D. Ulm
*Assistant Examiner*—Stacey MacFarlane
(74) *Attorney, Agent, or Firm*—Scully, Scott, Murphy & Presser, P.C.

(57) ABSTRACT

The present invention establishes a link between altered aPKC function and nervous system disorders and cancers, such as Alzheimer's disease (AD) and neuroblastoma. Methods of using aPKC in diagnosis, drug screening and gene therapy in nervous system disorders and cancers are provided.

1 Claim, 14 Drawing Sheets

11A RT-PCR

11B RNase protection

11C Northern blot

SEQUENCE LISTING

<160> NUMBER OF SEQ ID NOS: 16

<210> SEQ ID NO 1
<211> LENGTH: 16

-continued

```
<212> TYPE: PRT
<213> ORGANISM: Homo sapiens

<400> SEQUENCE: 1

Thr Asp Pro Lys Met Asp Arg Ser Gly Gly Arg Val Arg Leu Lys Cys
1               5                   10                  15

<210> SEQ ID NO 2
<211> LENGTH: 16
<212> TYPE: PRT
<213> ORGANISM: Homo sapiens

<400> SEQUENCE: 2

Thr Leu Pro Pro Phe Gln Pro Gln Ile Thr Asp Asp Tyr Gly Leu Cys
1               5                   10                  15

<210> SEQ ID NO 3
<211> LENGTH: 14
<212> TYPE: PRT
<213> ORGANISM: Homo sapiens

<400> SEQUENCE: 3

Glu Tyr Ile Asn Pro Leu Leu Leu Ser Ala Glu Glu Ser Val
1               5                   10

<210> SEQ ID NO 4
<211> LENGTH: 2349
<212> TYPE: DNA
<213> ORGANISM: Homo sapiens

<400> SEQUENCE: 4
ggcacgaggg ccccgcgcgc cgccggagtt ccgcggagtt gaccgggtcg gcgccgtcgg      60
tcctgagcgc tgccttccgc gttccgccgc ggccccacct ggagcccccg ccccgcgcca     120
tggccggagc tcccggggcg cagcgctgac ggcggcgggg ggagcgcgcc atgcccagca     180
ggaccggccc caagatggaa gggagcggcg gccgcgtccg cctcaaggcg cattacgggg     240
gggacatctt catcaccagc gtggacgccg ccacgacctt cgaggagctc tgtgaggaag     300
tgagagacat gtgtcgtctg caccagcagc acccgctcac cctcaagtgg gtggacagcg     360
aaggtgaccc ttgcacggtg tcctcccaga tggagctgga agaggctttc cgcctggccc     420
gtcagtgcag ggatgaaggc ctcatcattc atgttttccc gagcacccct gagcagcctg     480
gcctgccatg tccgggagaa gacaaatcta tctaccgccg gggagccaga agatggagga     540
agctgtaccg tgccaacggc cacctcttcc aagccaagcg ctttaacagg agagcgtact     600
gcggtcagtg cagcgagagg atatgggggcc tcgcgaggca aggctacagg tgcatcaact     660
gcaaactgct ggtccataag cgctgccacg gcctcgtccc gctgacctgc aggaagcata     720
tggattctgt catgccttcc caagagcctc cagtagacga caagaacgag gacgccgacc     780
ttccttccga ggagacagat ggaattgctt acatttcctc atcccggaag catgacagca     840
ttaaagacga ctcggaggac cttaagccag ttatcgatgg gatggatgga atcaaaatct     900
ctcaggggct tgggctgcag gactttgacc taatcagagt catcgggcgc gggagctacg     960
ccaaggttct cctggtgcgg ttgaagaaga tgaccaaat ttacgccatg aaagtggtga    1020
agaaagagct ggtgcatgat gacgaggata ttgactgggt acagacagag aagcacgtgt    1080
ttgagcaggc atccagcaac cccttcctgg tcggattaca ctcctgcttc cagacgacaa    1140
gtcggttgtt cctggtcatt gagtacgtca acgcggggga cctgatgttc cacatgcaga    1200
ggcagaggaa gctccctgag gagcacgcca ggttctacgc ggccgagatc tgcatcgccc    1260
```

-continued

```
tcaacttcct gcacgagagg gggatcatct acagggacct gaagctggac aacgtcctcc    1320
tggatgcgga cgggcacatc aagctcacag actacggcat gtgcaaggaa ggcctgggcc    1380
ctggtgacac aacgagcact ttctgcggaa ccccgaatta catcgccccc gaaatcctgc    1440
ggggagagga gtacgggttc agcgtggact ggtgggcgct gggagtcctc atgtttgaga    1500
tgatggccgg cgctccccg ttcgacatca tcaccgacaa cccggacatg aacacagagg     1560 actaccttt ccaagtgatc ctggagaagc ccatccggat ccccggttc ctgtccgtca      1620 aagcctccca tgttttaaaa ggatttttaa ataaggaccc caagagagg ctcggctgcc     1680 ggccacagac tggattttct gacatcaagt cccacgcgtt cttccgcagc atagactggg    1740
acttgctgga agaagcag cgctcccctc cattccagcc acagatcaca gacgactacg      1800
gtctggacaa ctttgacaca cagttcacca gcgagcccgt gcagctgacc ccagacgatg    1860
aggatgccat aaagaggatc gaccagtcag agttcgaagg ctttgagtat atcaacccat    1920
tattgctgtc caccgaggag tcggtgtgag gccgcgtgcg tctctgtcgt ggacacgcgt    1980
gattgaccct ttaactgtat ccttaaccac cgcatatgca tgccaggctg ggcacggctc    2040
cgagggcggc cagggacaga cgcttgcgcc gagaccgcag agggaagcgt cagcgggcgc    2100
tgctgggagc agaacagtcc ctcacacctg ggcccgggca ggccagcttc gtgctggagg    2160
aacttgctgc tgttcctgcg tcgcggcgga tccgcgggga ccctgccgag ggggctgtca    2220
tgcggtttcc aaggtgcaca ttttccacgg aaacagaact cgatgcactg acctgctccg    2280
ccaggaaagt gagcgtgtag cgtcctgagg aataaaatgt tccgatgaaa aaaaaaaaa     2340 aaaaaaaaa                                                            2349
```

<210> SEQ ID NO 5
<211> LENGTH: 2252
<212> TYPE: RNA
<213> ORGANISM: Homo sapiens
<220> FEATURE:
<221> NAME/KEY: CDS
<222> LOCATION: (638)..(1864)

<400> SEQUENCE: 5

```
cgaugucgca uuucaaggu ccgcugaguc cgagcccugc cugggucugg cugcugcccg      60
cccgcucucu ggacugugcu gaugcagaga ugcuuguuuu ccugugacgu cagcgucagc    120
uccugcacau ccaugccgug uuuuaguuug ugccucagcu gcuggcuaca gcuuccgggg    180
ggagccgggu accaccgggg ccuggagaca ugaggaggca gggaugugag gggcgggga     240 caggacagcc ggccuuccgu uaaauaucug cuccucgcgc ucgagccucc cugccuauug    300
ucggggccgg aggcgagccg acgcagcauc agcucgucaa cgggaaggaa gaugccuccc    360
ugcacgcccg ccgcgcacag agcauaaaga aucugcgcug aggaggcagg agaagaaagc    420
cgaaucuauc uaccgccggg gagccagaag auggaggaag cuguaccgug ccaacggcca    480
ccucuuccaa gccaagcgcu uuaacaggag agcguacugc ggucagugca gcgagaggau    540
auggggccuc gcgaggcaag gcuacaggug caucaacugc aaacugcugg uccauaagcg    600
cugccacggc cucgucccgc ugaccugcag gaagcau aug gau ucu guc aug ccu     655
                                       Met Asp Ser Val Met Pro
                                       1               5 ucc caa gag ccu cca gua gac gac aag aac gag gac gcc gac cuu ccu      703
Ser Gln Glu Pro Pro Val Asp Asp Lys Asn Glu Asp Ala Asp Leu Pro
         10                  15                  20 ucc gag gag aca gau gga auu gcu uac auu ucc uca ucc cgg aag cau      751
```

```
                Ser Glu Glu Thr Asp Gly Ile Ala Tyr Ile Ser Ser Arg Lys His
                             25                  30                  35 gac agc auu aaa gac gac ucg gag gac cuu aag cca guu auc gau ggg       799
Asp Ser Ile Lys Asp Asp Ser Glu Asp Leu Lys Pro Val Ile Asp Gly
        40                  45                  50 aug gau gga auc aaa auc ucu cag ggg cuu ggg cug cag gac uuu gac       847
Met Asp Gly Ile Lys Ile Ser Gln Gly Leu Gly Leu Gln Asp Phe Asp
55                  60                  65                  70 cua auc aga guc auc ggg cgc ggg agc uac gcc aag guu cuc cug gug       895
Leu Ile Arg Val Ile Gly Arg Gly Ser Tyr Ala Lys Val Leu Leu Val
                75                  80                  85 cgg uug aag aag aau gac caa auu uac gcc aug aaa gug gug aag aaa       943
Arg Leu Lys Lys Asn Asp Gln Ile Tyr Ala Met Lys Val Val Lys Lys
            90                  95                  100 gag cug gug cau gau gac gag gau auu gac ugg gua cag aca gag aag       991
Glu Leu Val His Asp Asp Glu Asp Ile Asp Trp Val Gln Thr Glu Lys
            105                 110                 115 cac gug uuu gag cag gca ucc agc aac ccc uuc cug guc gga uua cac      1039
His Val Phe Glu Gln Ala Ser Ser Asn Pro Phe Leu Val Gly Leu His
120                 125                 130 ucc ugc uuc cag acg aca agu cgg uug uuc cug guc auu gag uac guc      1087
Ser Cys Phe Gln Thr Thr Ser Arg Leu Phe Leu Val Ile Glu Tyr Val
135                 140                 145                 150 aac ggc ggg gac cug aug uuc cac aug cag agg cag agg aag cuc ccu      1135
Asn Gly Gly Asp Leu Met Phe His Met Gln Arg Gln Arg Lys Leu Pro
                            155                 160                 165 gag gag cac gcc agg uuc uac gcg gcc gag auc ugc auc gcc cuc aac      1183
Glu Glu His Ala Arg Phe Tyr Ala Ala Glu Ile Cys Ile Ala Leu Asn
                170                 175                 180 uuc cug cac gag agg ggg auc auc uac agg gac cug aag cug gac aac      1231
Phe Leu His Glu Arg Gly Ile Ile Tyr Arg Asp Leu Lys Leu Asp Asn
            185                 190                 195 guc cuc cug gau gcg gac ggg cac auc aag cuc aca gac uac ggc aug      1279
Val Leu Leu Asp Ala Asp Gly His Ile Lys Leu Thr Asp Tyr Gly Met
200                 205                 210 ugc aag gaa ggc cug ggc ccu ggu gac aca acg agc acu uuc ugc gga      1327
Cys Lys Glu Gly Leu Gly Pro Gly Asp Thr Thr Ser Thr Phe Cys Gly
215                 220                 225                 230 acc ccg aau uac auc gcc ccc gaa auc cug cgg gga gag gag uac ggg      1375
Thr Pro Asn Tyr Ile Ala Pro Glu Ile Leu Arg Gly Glu Glu Tyr Gly
                235                 240                 245 uuc agc gug gac ugg ugg gcg cug gga guc cuc aug uuu gag aug aug      1423
Phe Ser Val Asp Trp Trp Ala Leu Gly Val Leu Met Phe Glu Met Met
                250                 255                 260 gcc ggg cgc ucc ccg uuc gac auc auc acc gac aac ccg gac aug aac      1471
Ala Gly Arg Ser Pro Phe Asp Ile Ile Thr Asp Asn Pro Asp Met Asn
            265                 270                 275 aca gag gac uac cuu uuc caa gug auc cug gag aag ccc auc cgg auc      1519
Thr Glu Asp Tyr Leu Phe Gln Val Ile Leu Glu Lys Pro Ile Arg Ile
280                 285                 290 ccc cgg uuc cug ucc guc aaa gcc ucc cau guu uua aaa gga uuu uua      1567
Pro Arg Phe Leu Ser Val Lys Ala Ser His Val Leu Lys Gly Phe Leu
295                 300                 305                 310 aau aag gac ccc aaa gag agg cuc ggc ugc cgg cca cag acu gga uuu      1615
Asn Lys Asp Pro Lys Glu Arg Leu Gly Cys Arg Pro Gln Thr Gly Phe
                315                 320                 325 ucu gac auc aag ucc cac gcg uuc uuc cgc agc aua gac ugg gac uug      1663
Ser Asp Ile Lys Ser His Ala Phe Phe Arg Ser Ile Asp Trp Asp Leu
            330                 335                 340
```

```
cug gag aag aag cag gcg cuc ccu cca uuc cag cca cag auc aca gac    1711
Leu Glu Lys Lys Gln Ala Leu Pro Pro Phe Gln Pro Gln Ile Thr Asp
        345                 350                 355 gac uac ggu cug gac aac uuu gac aca cag uuc acc agc gag ccc gug    1759
Asp Tyr Gly Leu Asp Asn Phe Asp Thr Gln Phe Thr Ser Glu Pro Val
360                 365                 370 cag cug acc cca gac gau gag gau gcc aua aag agg auc gac cag uca    1807
Gln Leu Thr Pro Asp Asp Glu Asp Ala Ile Lys Arg Ile Asp Gln Ser
375                 380                 385                 390 gag uuc gaa ggc uuu gag uau auc aac cca uua uug cug ucc acc gag    1855
Glu Phe Glu Gly Phe Glu Tyr Ile Asn Pro Leu Leu Leu Ser Thr Glu
                395                 400                 405 gag ucg gug ugaggccgcg ugcgucucug ucguggacac gcugauuga             1904
Glu Ser Val cccuuuaacu guauccuuaa ccaccgcaua ugcaugccag gcugggcacg gcuccgaggg  1964
cggccaggga cagacgcuug cgccgagacc gcagagggaa gcucagcgg gcgcugcugg   2024 gagcagaaca gucccucaca ccuggcccgg caggcagcuu cgucuggag gaacuugcug   2084 cugugccugc gucgcggcgg auccgcgggg acccugccga gggggcuguc augcgguuuc  2144
caaggugcac auuuuccacg gaaacagaac ucgaugcacu gaccugcucc gccaggaaag  2204
ugagcgugua gcguccugag gaauaaaaug uuccgaugaa aaaaaaaa              2252

<210> SEQ ID NO 6
<211> LENGTH: 80928
<212> TYPE: DNA
<213> ORGANISM: Homo sapiens

<400> SEQUENCE: 6
gcgcggttcc ggctgctccg gcgaggcgac ccttgggtcg gcgctgcggg cgaggtgggc    60
aggtaggtgg gcggacggcc gcggttctcc ggcaagcgca ggcggcggag tccccacgg   120 cgcccgaagc gccccccgc accccgggcc tccagcgttg aggcggggga gtgaggagat   180
gccgacccag agggacagca gcaccatgtc ccacacggtc gcaggcggcg cagcgggga   240 ccattcccac caggtccggg tgaaagccta ctaccgcggg tgagtgtcct gggacagggc   300
ggtgggcggg aggggacagg ccggctccac tcggcctgga ggagggagg gtgaggggct   360 ggaggtgttg tgggcggatt gggctgggcg gcgggcggc tccggtgact cagggtgagt   420
gacgaagtga tagggtggg ggcgaagcaa ggggatgcag tactgggggc gcccccaggt   480
atggcggtgc ggggagccga ggggccagag tagggtccga aaggaagct agggttagag   540 taggtgcacc tggtgtggac gagagactcg cctcctgaga gctttgtagg ggccttgcat   600
ccttaagtct gggtgtattt ggggttgcga gttgaggatt ccaagtgatg ccttagttaa   660
ctcagtttgc tgtggggata gaaaacggga cttcttcagt tagctgtccg ttttgattac   720
cagcaggcct aacgctctg gttctctgag atatacctcc atccccgttg tgttcacgta    780
gtgtatctgc actgccagta tattagacat aggggttgta tttaagaatc aagtcgatgc    840
gttttcaggg acgtgcagtg ggtacttacg tgtcgtcaag attaagttgc atgtgtgtaa    900
atcaaaattt tgtgagcctt tcttctcag tgttgttca acgactaccc gatagggtga    960
gatactgcaa ggtgaggaga ctagcctagt tacagttta aattctctga tcttcactcc   1020
cttactatgg ttacaagaaa aaacccagtt ctaagttcat tgtgttaaat cattttctat   1080
cagtgacgca aagtgccccc cttcctttaa attcagttgt ggtttgaatt ttttttgag   1140 ataattatgt ttaggagcat tagaaacgtg aaatgttagt gtgaccataa aggttggaga   1200
```

```
ctgagaagtc acagaaaacc cagctacttt ggcttgcctt actgcttgtc caggtagaag    1260
taaattgctt taaaaaactc aagcagtgct aggttgaaat tttaatgcat acttttacat    1320
tcctgagagg atcagtgaag atagcaaact ctcaaactac ctctcttgtt ttgatttcaa    1380
agaaaatctg agcccctaaa tgttgtattg atttgatgta aggactttt ttttattat     1440 tatactttaa gttttagggt acatgtgcac aatgtgcagg ttagttacat gtgtatacat    1500
gtgccatact ggtgtgctgc acccattaac tcgtcattta cattaggtat atctcctaat    1560
ggtatccctc cccctcccc caccccaca acagtcccca gggtgtgatg ttccccttcc      1620
tgtgtccatg tgttctcatt gttcaattcc catctgtgag tgagaacatg cggtgtttgg    1680 tttttgtcc ttgatgtaag gactttaaa tttgctgcca tgaagcctct ggcctctgtt      1740
tattattagc ttgactgtat gcaggagtag tttattggag ttatattgga cagtatgata    1800
actttgtgtt taagcaggta aaactgatta aggaggtttt tatttaaat cagtaccaag     1860 aaacgtgtgg atattttta agtttgtag ttgtcacaag agctgttttg acttgaggat      1920
ggtcagccat gaactttgca aggtgagaaa aaagcttcct ttgcttttt tttttaaac      1980 ccttacctga aatttgatga atgagatgtt tcactttatt cttttatttt attttgttt     2040 gtttgttttt gagacagggt cttactctgt tacccatgct ggagtgcagt ggcacaatct    2100
cggctcactg cattctccgc ctcccgggtt caagcaattc gcctgcctca gcttctgag     2160 tagctgggat tacaggcatg tgccaccaca cccggctaat ttttgtattt ttagtagaga    2220
cggggtttca ccatattggc caggcatgtc ttgaactcct ggcctcaaat gatgcgctcg    2280
tcttggcttc ccaaattgct gggattacag gcatgagcca ctgcgcctgg ccctaaggct    2340
ttcaataaat tcttattaat tgagatcatc ttctccaatg agtctatgaa aggtaagaaa    2400
ttagtgcttc tattttccca tttgtattag tttgacacat gtaaataggc ccagttagta    2460
aatgaaaatc attgtaaact cctttgagaa gaaatcaaag tcttgctgta cttcatgaat    2520
ttagatagca aattatcttg gcttattgct ccagttatta aaagaagag aataaggaca     2580 tacagcttct ttagtgtttg actgcaattt ttccaagaca ttcaaggtaa cattgtcttt    2640
taaaatctgt gaaattttgc tgcggcgcaa ataacctctt gcccattgta tactggtctt    2700
tgctcaatga aagctttcta atggtaccct catttcaagc ctcatttaaa gacaatatca    2760
gcactctaaa ttgtaccaaa ttcctgtcct ctgaaattag atgttaagat tatgtgtttg    2820
tatagtctaa actgatgatt gtggtattac atagtcagct gctcattaat atagatgaag    2880
ctaaaatgag tcacggacaa ggatagttaa taaacaggtt ggctaactag aacacctacc    2940
tgattttaaa atagaaaatc cttcctttat accaagaaat gtgagaacat tctgcatttg    3000
aaaagttttt cttttctctc caatcttctg aagggccatt attacatagc atttcctcta    3060
tccctctaca cttttctttt cttttttttt ttttaaata gagacaaggt ctcaccgtgt     3120
tgcccaggct aatcccaaac tcctgggctc aagtgatcct cctgcctcag cctctcaaag    3180
tgctgggatt acaggtgtga gccactgtac ctggctccac tacccttttc taacaatatt    3240
tctttccagt gaatgttgac tcatttaata gccagcattt ttttagtga aaaaattgcc     3300 ctctcttttc aaagatgtgt atagtgttat tattctgtta agcttgatct cagtgaaaac    3360
gtgtaatctc tctagatcta ataacattta attttttct aattttatt ttattttatt     3420 ttatttattt attttttgg agatggagtc tcgctctgtc acctgggctg gagtgcagtg     3480
gcgtgatctc ggctcattgc aacctccgcc tcccaggttc aagggattct cctgcggctg    3540
cctcccgagt aggtgggact acaggcgccc accaccacgc ccagctaatt tttgtatttt    3600
```

```
agtagagacg ggttttcacc atgttggcca ggttggtctc ccaacttctg acctcaagtg   3660
atccacccac ctcggtctcc caaagtgttg ggattacagg aatgagccat cttgcccagc   3720
caatttacat ctagttttta agcaagagat taatagcact gaaaattcaa ttttattgga   3780
caccacatct tacttagatg cctttctcat ggcctgcacc cgtctttcc tagcaaggaa    3840 gcttttcagt gaggggcctt cagttattac ctagtgctag tagtttggag gaagagaaac   3900
aggtttcatt aattagtgat aaactgtcaa tgtatgtgct tatccttata taaaattact   3960
tgctattatg ggatagactt taacaaggca acatctggac tgctcatttc tttacattat   4020
atatgtatgg aaattttgc agaaagcttg tgaaagttct ttttaaaccg ctgctgtcaa    4080
gtagtaataa caatacagag gattccttct gtgcacatct agaaataaaa gattaactct   4140
ttgcatattt ggaatagctg cttcagtgaa gaagtatgta ggattttct tactgtgaac    4200 aagtcttggc aagacttgtt tttgaaagaa atgcaagatt attttagcaa tatacttag    4260 taatggttct gaggaaatac aagtggtatc ttgagggttg gggggatgtt agctaattgg   4320
tcttagagct tcagccatgg cacctaatcc tagggcagct gatccatagc ttggccaaag   4380
agagaaaaaa atagagcatg ctagcctggt gccaaaaaac ccaaaccaaa cacaaaaaac   4440
cctcagaaat ttgaatgaga aaatatgag ataaaattgg tcagcactgg gaactgaagc    4500
tggagttgga gggagagtct ggcgaggcca gaactgacaa tgtgcaaatg aaagatgtga   4560
agaagcagaa actgaggaag caaggagaa aggagcaact ctgcacagaa aaattctccc    4620
cacaggtcct tagttcatga tggctttcta atgcaactgc agccctcctt ttacaacttt   4680
agtgtctgtt tttttatga ttgaaatgag cctaatttaa acatagattt taaaaattcc    4740
agtcttgctt aagatttcaa atataaccag agatcattca aactgagttt agtaaatatt   4800
gttgaacgtc cgtaatccag gcacatgatg ctgtcgtagg cacagagaat gtagaggtag   4860
gtaaggctct gcctttaagg aattaagaga cttgtggagg gaaggacata taagagttac   4920
aatagaaaca atttaatttg aagtacctat gtaaggtatt tgcaggaata gacgttgggg   4980
aggagtttgg ggtgatggaa gccttcctag aggaaatgtc tgaggctttt aaaggataac   5040
taggagtttg cctggtgaat aatgatgtta ggtgggtgtt ataggcatta acaaccaca    5100 tggtaagttt gcagaattaa gatcactttg gctgttagtc tcatattcat tccttattag   5160
gatataaagt atgaagtggg cactgatgag aaatgaggct aagaaagttc acaggggcta   5220
gattgtaaag acccttgaat gtcatactgc agagtttaga cttttctca ttgatgaaaa    5280 ttctaagtaa gagaaataca tgatcagatt tgcatttag aaagataaca cttgaaatta    5340
gtatgggaga tggattggtg atggatgaaa ctaatttgga ggcttttgaa gtagtccaga   5400
tgagatattt taaggagaga gaaagagtg tatggattcg gtggaaattt taaggggtag    5460
tatcagtaga attaaagata gtcttgtagg ggtgacggga gttggacaac tcataggttt   5520
ctcgtttaag agagactggg gaatgtggaa gagatttgtg ggagaagtta attaattggc   5580
tggaacaatt cactgaattt tgagttctag gtgtttatga ggcattcagg aggaaatgtc   5640
agaaagaatg gagcaattat ttattgtctg tctactctgt gttgcaagca ctgtgcttga   5700
cagctaacct atgtaggaat gtggctgaga acgataatag aaacaaaaat gacaccagtg   5760
gccaaataca gatcacaaag gcaaggcact aaaactaaat tttaaaaata tagaaataca   5820
gaaagaggct gggtatggtg gttcatgcct gtaatcccag cactttggga ggtcaggca   5880 ggtgaatcac ttgagcccag gaattggaga ccagcctggg ctgaatgtgg tgaaaccta    5940
```

```
tctctacaaa aaaattagcc tgtagtccta gctactagga gggcgaggtg ggagaatcac    6000
ctgaggccag gaagtcaagg ctgcagtgag ctgtgattgc accactgcac tccagcctgg    6060
gcaacagagt gagaccctgt ctcacacaca cacagacata cacacacaca aatatatata    6120
tatatacaca cacacacaca cacacacaca tatacataca cacacatata aagttcccct    6180
gtagtctctc actcccacct tattttattt tattagttta ttttatata tttaagggt     6240
acaagtgcag atttctttct ttcttacatg tttgtatcat gtagccatga agtctggtca    6300
cttagtgtac ccatcaccgg aacagtaaac agtaaaaccc agaaaattac ctgtacccga    6360
taggtatttt tcaaccctca ccccctccc accttttgta gtctccaatg tctactattc     6420
cctctttatg tccatgtgta ccctttgttt agctctcact tataagtgag aatatgtggt    6480
atctggcttt ttgtttctga ttttttttgac tagggataat ggccttcagt tccatccatg   6540
ctggtgtaga agacgtgatt tcattatttt ttatggctgt ctcactccca ctttctagag    6600
atagccattg ttaacagtta gggatattct atatcatatc ggtatattta taagtataga    6660
tatgtatgtg catacacaca cacagacata cccttttatt tttccaataa atgagttcat    6720
atttccacac atgcatctgc aacttgattt taaaaatcgt ggtcatcttt tcattccagg    6780
gtagacagac ctctttatag ttggtaatac agtgttctac agttgttgtt gttgttttaa    6840
gagacagagt ctgattctgt tgcctacgct ggagtgcagt ggcatgatct aggccctctg    6900
cagcctcaac cactctgggt tcaagcagtc ctcccacctc agcctcctga gtagctagga    6960
ttagctcacg ccactaggct cagctaattt tttttaatat gttttgtagg dacggggctg    7020
gtctcaagct cctgtgctca agtgattctc ctgcctcggc ctctcaaagt gtagaaatta    7080
caggcatgag ccattgcgcc cagccaccat aatatgttta atctttttc ggattgatga     7140
acatttaaag ttgtcttcat caactcacta tttcaaataa tgttgaagga acctccttat    7200
atttaataca tattcttgta aatatggtca aagatatgcc tatcttgaaa tatgatattg    7260
tttcccaaaa gagcttaatt tacattctta acaacaggac tagtgaagct tctgccttat    7320
attcccattg catgttatct gtcttttaaa ttttgactg tcagattggc aaaaaatggt     7380
aatttatttt tacaagtatc ttttatatat taatgatcat ttgtatttct tctggattgt    7440
tcctatttta cccatttct attgtattat ttttcttatt aatttgttga caggacattg    7500
acatttgtt aaagttgcca gcattccccc aatctgttgc tagtctggag ttttcgttt    7560
ttatgtcatc aaacctgtcc ttttaaaaa tttccttgat agtttctgga tttactgtct    7620
taggtaaaag tgttttcat ctaaaaatat tctatttttc ttctattatg caacttttt    7680
ttttttttt ttgagacaga gtcttgcttt gttgcccagg gtagaaccca gtggcgtgat    7740
ctcgtcttac tgcaacctt gcctcctggg ttctaacaat cctcctgcct cagcctccta   7800
agtagctggg attataggcg cacgccacaa cacccggcta attttgttt gtttttgag    7860
acaaggtctt gctcagtcgc ccaggctgga gtgcagtgg acgatcctgg ctcactgcag    7920
cctctgcctc ctgggttgaa gtgattctcc tgcctcagcc tcccaagtag ctgggattac    7980
aggcatgcgc caccatgtcc ggctaatttt tattttttag tagagacagg ttttgccat    8040
gttggccagg ctggtcccaa actcgtgacc tcaagtgatt cacccgctgt ggcctcccga    8100
agtgctggga tttaggcgt gagccactgc gcctggctta ttatgaaact tttaaagtga    8160
ttatcttttc agtgaatctg gtattttggg gtttagtcat ttataggtta ctgacacaac    8220
tttttttttc tccaaaattt attctaatac cattattggg cagattgtcc tttcaccact    8280
gatttgaaat ggtaactctg ttatgtacta aatttcccac aatgtgcgta ggtactttct    8340
```

```
attgtttcat tgattttagg ggagagatct attttttgcac ataccactat tggtttaatt      8400
attgtaatat tatagttaac tttgatatat gttatggaat ggcttgattc attatttaat      8460
tttttttttt tgtttttttt tttttttgaga tggagccttg cactgtcacc caggctggag     8520
cgcagtggcg tgatcttggc tcactgcaac ctccgcctcc caggttcaag cgattctcca     8580
gtctcagtct ctcaagtagc tgggattaca ggcaaggcgc taccatgcct ggctaatttt     8640 tgtatttta  gtgaaaatgg ggtttcacca tgttggccag gctggtctgg aactccttac     8700
ctcaggtgat ccatctgcct cggcctcccg gagtgttgag attacaggct tgagccaccg     8760
tgcccggcct attcctatat attttataat catgtgcttt tgtgaatggg gtcttcttgt     8820
agacctatta catactgttt ctttttgta  tgtttaaatt aaactttcca ccttactaat     8880
aatttaactg tcttagaatt tttaagctag ataatgtcat ctgcaagtag caattttgcc     8940
tcttcttttc tatatcttat ttatttatt  attatttatt ttatgttttt tgagacagag     9000
tctcactctg tcgcccaggc tggagtgtag tggcgtgatc tcggctcact gcaacctccg     9060
cgtcccaagt tcaagtgatt ctcctgcctc agcctcctga gtagctagga ttacaggcgt     9120
gcaccaccac acctggctaa ttttttgtagt tttagtagag atggggattc gccatgttgg     9180
ccagactggt ctcgaacgcc tgacctcagg taatccaccc accttggcct cccaaagtgc     9240
taggattaca ggtgtgagcc actgcgccca gccttattta tttttagcca taggctagaa     9300
ttttctagac agtattgaat tatagtaata atctcttatc ttagtgaaat ataatagaaa     9360
aatttctgtc aattaaagaa aaaagctttt aagaattaa  agttagtgtt attcagaaat     9420
gttactgagg ccgagtgtgg tggctcacgc ctgtaattgt gccactgcac ttcaacctgg     9480
gtgacagagc gagactctgt ctcaaaaaaa actcaactga aaaagtgga  acaaaagaaa     9540 aagaaccatg ataagtattt tgcacttttt tttttttga  ggcacatttc tactctgtca     9600
cccaggctga gtacagtggt gtaatcacag ctcactgcag ccttaactgc ccaggctcac     9660
gcagtcctcc tacctcagcc tcccaagtag ttgggactgt aggcacacac cactatgtct     9720
ggctaatttt taattttttt gtagagacaa ggtctccctg tgttgcccag gcaggcctcg     9780
aactcctgta ccgaagcgat cctcccacat tggcctttca aagtgctggg attatggcat     9840
gagccacctt gcctggctgc actcatttat tttcatttat ttttcatttt ttgagtcagt     9900
gtcttcctcc atcacccagg ctagagtgca atgacatagt cacagctcac tgcagcctca     9960
acttcctggg ctcaagctgc acttatttag tcttcatgat aatactcaga ggcagatatg    10020
attatctcca ttttttcagat aacattgaga cttactaacc cacaatacaa agctgggtgt    10080
gttttttttt ttagagacag agtccttgctc tgtcgcccaa gctgaagtcc aatggctcga    10140
tcatggctca ctgcagcctt gaactcctgg gctcaaatga ttctcgtgag tagctgggac    10200
tacgctatgc ttggctaatt acaaaaaaat tttttttaga dacagggtct tgttctgtca    10260
ctgaggctgg ccttgaactc ctgaggtgat cctcccgcct cagcatcctg agtaggtggg    10320
attacaggca cgagccacct tgcccagcca aaactggacc ttgaacttca aagagatttc    10380
tcttttcccc ttactacatt gacagggctt tataacattg cttttttact ttattgttac    10440
attcatattt cacaattgtt attttttgaat tcactatctt cttcattatt aaaggtgga    10500 aattgcttta tgaccttttt tataattaat aatttggggg gtgatacttt gagattatat    10560
gaatactcta gtccccccaaa acattttgcc caatggtctt accattcatg gataatcctg    10620
cctaaaccaa ttattataat ggttattgca aataaaagta ttttttcgaa tagcctaatt    10680
```

```
tagaagaaaa gcttacactg aggtagcaga aggactgaat gtgattcttt tgggggttta   10740
tttttaaaag caattagtcc taaggaaaaa ctttataata gattctatat tttagaatat   10800
aggcacattg aaagcagttt gtcttctgaa gctcaatagc aaaataaaaa atgcttaaaa   10860
aaattcagct aaaaccatat ctaaatttgc cattttggga atctttgtga taaagcagat   10920
tatattctgt tgaggatcag tggtaaaata atttatgcta gtgctgaagt taaactggaa   10980
aaaacatcat acgtgcataa tttgttttat acctttagaa tgtaatatct ttattttgca   11040
gttcattttt agctttggta ctgtaacaag gatctggtga ttgtggaatg ttatgaacat   11100
agtggtttcg caattactga gagctaagtg tttatataaa actcccttga atgttttagt   11160
tcctggaact taaggagtgg tagttgataa agcataactc cttcattgag tctctgatgg   11220
gtatctatac ttaaactttt ttttttttaa acagaatctc actttatcat ccaggctgga   11280
gtgcagtgac gcaatcacgg ctcactgcag cctccgcctc ctgggttcaa gcggttatcc   11340
tgcctcagcc tcccaggtag ctgggattat aggcacccac caccatgcct ggctaatttt   11400 tgtatttta gtagagacgg agtttcactg tgtttgccgg gctgatttcg aactcctgac   11460
ctctagtgat ccgcccacct cagcctccca aagtactggg attacaggtg tgagccacca   11520
cacccagcct atacttacac tttttttttt tttttttttg agatggagtt tcgctcttgt   11580
tgcccaggct ggagtgcaat ggtgtgattg gttcactgca atctccgcct cccgggttca   11640
agcgattctt ctgccccagc ctcctgagta gctgggatta caggcatgtg ccaccacacc   11700
cagcaaattt tttattttta gtagagtcag ggtttctcca tattggtcag ctggtctcg   11760 aactcccaac ctcaggtgat ccatctgcct caggctccca aagtgctggg ttacaggtg   11820 tgagccacca cgcccagcct tatacttata cttttttaagt attacacaga tgtcttaaaa   11880
gtatttgtat gttctgataa gtgtttttta gcttttgaaa agtaaaattt atgaaaaagc   11940
cttgttgttt acaaatatgt ttacctttct gttaatttta aatgtggact ttgataagga   12000
agttatattt cgatgatatc cagtgtaact aatttttcc ctcttattca agaaagataa    12060
ttttacactt attctttgac agagaaattt catagaattt tcttcttcta atttaattcc   12120
agaatacatt ctctcaaccc tatgccctca tactagtaac cttgagggtt ctttgaaaga   12180
aaaattgctt taaatcaagc aattctcttt tgtcattaaa ataagctatt ttctattttt   12240 attttaaaa actatttaaa acaatataat tatgcaagtg tgtatatatg tatttgattt   12300
ttttgttttc ttttgttttt atttattttt ttgacacagt ctcctctgtt gcccaggctg   12360
gagtgcagtg atgtgatctc agctcactgt aacctacacc tcccatgttc ccccctgag   12420 aaggatcctc ccacctcagc ctctggctaa ttttttttt gtattttag tagagacggg   12480 gtttcaccat gttgcccagg ctggtcttga gctcctgggc taaagtgatc tgcccagctc   12540
agcctcccaa agtgcatgag ccaccgtgcc cagcttgata ttttaatttt tacttgaatg   12600
aaatcattta ctgaaagcaa tacatgttga tgcacacaca aaattactga agttcatcaa   12660
attgtcaagc attcagtaat atatacagca ttattatttt taatcatttt caaactgaaa   12720 actcctttc ttttcaggg atatcatgat aacacatttt gaaccttcca tctcctttga    12780
gggcctttgc aatgaggttc gagacatgtg ttcttttgac aacgaacagc tcttcaccat   12840
gaaatggata gatgaggaag gtgagtggta aagacagggc tgcctgtgta agcattttaa   12900
gatcttattc tatcatttgt tgtaaaaata taatgagtcc taaaagttt aagaggaaag    12960 actattagaa atttgatgcc attcttgttt tttcttaag tatttaaaag aatactgaag    13020
agcacaatct ttttttgcc ccttttacgc caaaatgatg tgaaattaac ttgacttttt    13080
```

```
tttttttttt ttgagacgga gtctcgctct atcgcccagg ctagagtgca gtggcctaat   13140
cttggctcac caaaacctcc acctcccggg ttcaagcgat tctcctgcct cagcctccca   13200
agtagctggg actacaagtg tgcaccacca tgcccggcta attttttgtat ttttagtaga   13260
gacgggggtt tcgctatgtt ggccaagctg gtctcaaact cctgacctta tgatctgccc   13320
acctcggcct cccaaagtgc tggcattgca ggcgtgagcc actgtgccca gcctaacttg   13380
acttttttaa gcataaggta agcatctcat caaatagtgt gatgttttac tttaattttg   13440
tttttctttt gaattaaatt tttttttttt atttttttaaa gacagggtct tgctaagttg   13500
tccaggctgg tctccaactc ctggcctcaa gtgatcttcc catcatgacc tcccaaagta   13560
ctgggattgc aagcaggagc cactgcattc agcttcactt tatttttttaa tttaaatttt   13620
ttttttttga gacagagtct ggctctgtcg cccaggctgg agtgtagtgg catgatatca   13680
gctcactgta acctccgcct ccaaggttca agcaattctt gtgcctcagc ctcccaagta   13740
gctgggatac aggggtgcac caccacaccc agataatttt tgtatttgta gtagagacgg   13800
ggttttgccg tgttgcccag gctggtcttg aactcctggc ctcaagtgat ctgcccacct   13860
aggcctccca aagtgctggg attacaggta tgggccacca cacctggccc ccagcttcac   13920
tttaattttg aatatgtgtt gtcttatatt ttaatttaag agattaccta ttttttaagct   13980
gaatattacc ttaaagaaaa tattgtggaa tgaaagtgat tttgacaatc attatttcaa   14040
agtagtggca gaaacctgat acctcagtga cttgtactca gaaaacattt atcatatatg   14100
taggcttacg cctgtaatcc cagcacttta gagtctgagg tgggaggatt gcttgaggcc   14160
aggagtttga aacagcctg ggcaacattg tgagaccctg tctctacaaa aagttttttaa   14220
aacttatctg gtggtagcgt gcacctgtgg tcccagctac ttgggaggct gaggtgggaa   14280
gattgctcga gcctggaagg tcaaggctga agatgggccc tgattgtgcc actgcactcc   14340
agcaacaaag caagcaaagc aagacccctgt ctcaaaaaaa aaaaaaaaag aaagaaaaag   14400
ggaaaaagaa gcaaatatct gtgtgctgag gacagacatt tcctatcctc aaacccatag   14460
tctgataggg agatggacac atgtgtaaca aatgtgataa attctggaac ataaacgcat   14520
agggggccttg aggaatacaa aggaagacac atctataata catctgcaat gtttgacata   14580
aacctgtaac agagtagaag ttttttgaggt agaggaggtg aggagaaaac catataggct   14640
gaagaagaat atgtagaaag gcacagaaat gtgaagaaca tgatgagtga aaagcagtaa   14700
ttcactgtat ctgaagtatg aagtggtgaa gtatgaattg gcctacagtt taacaggctc   14760
cacgggtgag ttgtatgaat acagaaattt gtttgagaag catgagacta gatccccaag   14820
agctttgcag atcacattaa attttatttt acatgactat tatggaagtc tagttaaaag   14880
gtaccctaaa gaaagggtgg gttgggggtg agggataaag gcctacatat tgggtacagt   14940
gtacactgct caggtgatag gtgcagcaaa atctcagaag tcaccactaa agaacttac   15000
tcatgtaacc aaacaccacc tgctccttga aaacctgtgg aaataaaaaaa agagagaaga   15060
taccctaaat atactacttt ttttacaata gttttctgtt aattgttata caaatagaat   15120
ttcatttta ggaatgtcat aatatttagc tcaatatttg ggatcatttc tatcttccct   15180
gatataaaga actctggaaa gtcattattg aagctccaag ctataggtaa acataaacac   15240
attctcattt tttaaaacag tgttcctgaa gtaattcatg ttcactgttc aggaaaaaaa   15300
gtagtgcaaa aatttatgaa atgtaaaaag aagcctcctg ttttttccttt tttctctctc   15360
ctccctcacc aattccaatt gtaagagaat agcttagtat gtatccttct atatattttc   15420
```

```
tatgcatttg caaacgtgta tgtatgtttc tataaattct ttattaacag ttttattaac    15480
atgacaaatg acatacagct gatattttgc agacctggtg ggcatgggga gcttggagcc    15540
cagtgccacc caccctggcc ctccatggcc ttaaaaaaaa attatatggg gccgggcatg    15600
gtttctcatg cctataatcc cagcattttg ggaggccgag gcgggtggat ggcctgaggt    15660
caggagttcg agaccagcct gaccagcata gtgaaacccc atctctactg aaaatagaaa    15720
aattacctga gcgtggtggc gggtgcctgt aatcccagct actagagagg gtgaggcagg    15780
agaatcactt gaacctggga gacggaggtt acagtgagct gagattgtgt cgttgtactc    15840
ctgcctgggc aacagagcga gactccattt caaaaaaaaa aaaattatat acaaatcgtt    15900
atgcagtgtt ttcctttata gtatgcgctg gacattttt catttcagtg tacttcaatt    15960
tgcatcatta ctctttttt tttttagta ctgcatagta ttacatatta tagatgtttc    16020
atgattaatc ccttatcgat ggacatttgg actatttcta gttttcact accataaaca    16080 atatataatg aacatttctt ttctttttt tttttttt gagacagtct cactctgttg    16140
cccaggctgg agtgcagtgt ctcgatctcc gcccactgca acctcctcct ccttggttca    16200
agcaattctt gtgccccagc ctcctgagta gctgggatta caagcgtgca acaccatgcc    16260
tgcctaattt ttgtattttt agtagagacg gggtttcacc atgttggcca ggctggtctt    16320
gaactctggc ctcaagtgat ccacccgcct tggcctccca agtgctggg attacaggca    16380 tgagccacca ctcccagcct tatttattta tttctctttt aatacagagg ctgggttctc    16440
actatgttgc ccaggctagt cttgaactct ggccttaagt gatcctcctg acctagcctc    16500
ccaaagtgct gggattacag gtgtgagcca ctatgtcaaa acatatgtat atcaaaacat    16560
catgttatat accataaata taattttgt ccattaaaaa attaaactag tttttcacac    16620
aactacatga aatgagagga ttttcatt cttgcccta ccaaccttag atatgaatca    16680
taaacatttt taaagatcag taagtgaaat gctaacctgg tatttcaaat tttgcattaa    16740
gaggaaagtt gagtatcttt atctttga cctaccctat cacaaagata gtttaaatat    16800
ggttacttat aaatgtcatg actatctcac aatatgtctt cagccagaaa atgagactat    16860
atataattta gcacagtgtg caacttatgc ttagcattca ataaaatgct tcttatcata    16920
aatgaatatt cttatttaa tcctgatcat ttcataccat ttatttgctg attagagttg    16980
tttttcagtc aatgattttc aaattgcagc acacataggc atcactggat aatgcttttt    17040
attagacgta cttagtttag cgatagtcca ttaaacgttt ttataatacc tttgtattat    17100
ccttgcctgg agagttctgt tcccagattg tcacctggct gtctctcatc attcaggttt    17160
taactcaaat gtcatgtcct ccaagaagcc ttcctatctc cattcatttt gtatcttctt    17220
gccctgtttt ttctcttgta tggtagagtg ttttttttt tttgtatggt agagtgtaag    17280
ctccatgaga gcagaggtct tgtctgtttt gttcatgttg gagctgcagt gcctagagca    17340
atactaaata atactatgct caaaaatat ttgtggctga gtgcggtggc tcatgcttgt    17400
aatcccagca ttttgggagg ccaaggcaga aggatccctt gagcccagaa gtttgagacc    17460
agtctgggca acatagtgag atagtgagac cctgtcccta caaaaaaat ttttttta    17520 gttagctggg catggtggta cacacctata gtctcagcta ctcaaaaagc taaggtggaa    17580
ggattgcttg agcatgggag atggaggctg cagtgagcca tgattgtgcc actgcactcc    17640
aacctaggca acaaagcaat accctgtttc caaaaaaag atatatgtgt atatatatat    17700
ttgtgagttg tacaagaggc tagcaacaag ccttcccctg gttaattttt gcttcagtta    17760
ttggagactt aagcattgac agttactgtt tattctgttt ttttttcctt aaagtagcat    17820
```

```
attttaatta acagatgcac atagtaaatt aactttctga tgcaacagtc ttattataat    17880
gcatttcata cttctttctc cctaagtagc tattaagttt ccaagttttc tggggaaagc    17940
tatgaagctc taggctttgt cttgttcaag taaaaggtta aatttttcat taaggtctgt    18000
tgattcccat gcgatccttc tcaccttgct taattctgat accaatcttt tcttaatttt    18060
aggcatacag agccaacagt aattattttt aagttacttt caattagttt tcagttgtaa    18120
ttttgtcacc tttgttttta atcatgtagg cattggggca tgtcggtctg atctggagaa    18180
aaaaaattct ctaggatcaa agacaggaca gtcacttgat ttctctggca tatgagaagt    18240
gctgttcctc aagccaaaca tttaattgtt ggaattttat gttggagcaa gtaaagatct    18300
taagcttact tcatctgttt aaagagattt aagacaactg cccttttttcc ttgtactcaa    18360
aaccagtctt agtgatttgt tttactgtgg aaaaactggt ttgcttaatc taactaaaca    18420
ttttagaatg agtagtaatt ttgtaaccat catgccacac tcctcttcct cataaattct    18480
tgtgtaacaa aagtgtggga cagggaatga caaatgtgac tttattttt taacaaatgt    18540
aagttttcag ttctttttt taaattttta attaacagat aataattgta tatgttcgtg    18600
ggatacagtg tgatgtttca atacatgtat atgttgtgga atgaaaaaat cagggtaatt    18660
aacacatcta ttacctcaaa tacttatttc tttgtggtga ggacatttaa aatccactct    18720
ttttgttatt ttgaaataca caatacatta ttatgaattg tagtcaccat gctatgcaat    18780
agatcaccag aacttactac tcctgtctaa ccacaacctt gtacccttta actggcacct    18840
cctttctcta tctaacccac tccctccagc ctctggtact ctctacgtgt atgagttcaa    18900
cttttttaga ttccatatat catgtggtgt ttgcctttgt atgcctggct tatgcttatt    18960
tcacttagca taatgtcctc taggttcatc catgttgttg aatatgacat aattttctgc    19020
ttgaggctga gtagtattcc attgtgtgta tatgccatat ttatttcatc tgtttatcca    19080
ttgatgggca tttcaattgt ttccatatct tagctattgt gaatgatgca gatgctacag    19140
cgtagttcac ctttgttttg agagagggag agagagagac agagacagag agagagagag    19200
aaaaggcctc actctgttac tcaggctgga gtgtactgat gcaattatag ctcactgcag    19260
cctcaaacct atgggctttt gagatcctcc catcgcagcc tcttagctac aggtgtgtac    19320
caccatgcct agctacttta aaaaaaattc ttttggctgg gtgcagtggc tcacacctgt    19380
aatctcagca cttggggagg ctgaggcagg aggatcacct gaggtcgggc aacatggag    19440
aaaccctgtc tctactaaaa gtacaaaatt agctgggcgt ggtagtgcat gcctgtaatc    19500
ccagctactt gggaggctaa ggtaggagaa ttgcttgaac ccgagagatg gaggttgcgg    19560
tgagccgaga tcgtgccatt gcactctagc ctgggcaaca atagcaaaac tccgtctcaa    19620
aaaaattttt tttgtagaga cagggtcttg ttacattgtt gcccaggctg gtcttgaact    19680
cctggcctta gccaggagtt gaattcaacc aactctttgg ctgaatgtgt agccaatgct    19740
acttcaccta tttagatagc tgtattatgg ctccaaagct gaaaactgaa aaattaatat    19800
taacagccag gcatagggct catgcctgta attccagcac tttgggaggc tgaggcaaga    19860
ggattgctta gcccaggagg ttgaggctgc agtgagccaa gattgcacca ctgcactcta    19920
gcctggacca cagagtgaga ccccatctca aagaaaaaa gaaaagaaa agacaagaaa    19980
agaaaaaatt aacagcactt agaaaggaa agctaagtac ctccaagcat atctagtttt    20040
gtaacttata tagttttcct tttataatgtt aaaacattat aatgttataa tgtaaagaac    20100
ttatacatta tgaattatta tacattatta cattatttat aatgtaatgt aaagaacttc    20160
```

```
ctttaacatt tcttttgttt ttgttttgtt ttgttttgag atggatcctt gctctgtcgc   20220
ccaggctggg gtgcagtggt gtgatctcgg ctcactgcaa cctcgacctc ctgggttcaa   20280
gcgattgtcc tgcctcaacc tcccgagtag ctgggattac agacacctgc caccatgccc   20340
ggctaatttt tgtatttta gtagagatgg ggttttgcag tgttggccag gctggtctcg   20400
aactccagac gtcaggtgat ccgcctgcct cagcctccca agtgctggg attacaggag    20460
tgagccactg cgcccggcct cttgaacatt tcttatagaa aagttctgct ggtgagaaat   20520
tattcatgtt tttaatttca cttaaaaata gatttattga ggtataattg acatatatat   20580
gtatacataa tatatataat aagttataca tattaaaact ttacagttgg atgagttttg   20640
atacctagga acccatcagc acaagcaagg tagagaacgt atctgttatc cccaaatgtt   20700
tccttgtgct aagcagtgcc tcactcctgc tcttttgtcc tcaggctact actaatctgc   20760
tttctgttac tacagattag tttgcatttt ttagaatttt atatggatag aatcatcata   20820
tagcatgtac ttttggtgg gatgtgtgta tcagtagttc attccttctt attgctgagt    20880
agtattctat cctgtggatg tactacaatt cattaatctg ttgaagatca ttgggattgt   20940
ttttggtttt ggctgtttta aataaaggtg ctatgaacag tcatgtacaa gtccttcctt   21000
gtatggaaat atatttccat ttttcttgag tcaaacctag aaatagaata gctggatcat   21060
gtggtaggta tatgctgc ttttataaaa tggaaaaga agattttgaa aaggagatga      21120
gatgggcac ttcatcccag gcacatcctt gggcagatgg tttttagtaa ggaattcaca    21180
aggaagttga ggatcaggaa attgattcct tttaaaaact gtctatgcct gttagtccct   21240
gaaaagtttt cctgcactcc aggggtactg tattccaatt agaagatagc tgacttagag   21300
atgtccccag ctacttctct tagttctggc ctctgcccca gctctgttct tcagacggac   21360
cttatgccca ggaaattctg gctgccatct tttacacacc aggctgtctg gaggcctggg   21420
agaaaaagga attagactgg ggttcacctg ggagaaaccc ttggcagtgg tggagtgggg   21480
atggattcag aagtgaggta tgatactata atataatgaa aaaatgtatc tgctattcat   21540
cgctggttcc tgacagtgcc taaaacccct tgttcaagtaa aaggttaaat ttttcattaa   21600
ggtctgttga ttcccatgag atcctgagta atagaagtga aagagcatc ttttgttatt    21660
tatgataagc ccctgccaac caaacctgat tttatgctaa tgaggtggct cttggaggat   21720
ggcttctggt tgccagagga atcaaccatg tggttatctc taaggtggga cttttcagcc   21780
tacctccccc ttatttctga ggagggcaga ggggcctgga gatggagtta atcaccagca   21840
gccagtggtt taatcagtct tgcttaggta atgggacccc cttaagaact caaaatgtag   21900
gggttcagag agcttcctgc tcggtgaaca aatcaaggtc ctgggagggt ggtacatctg   21960
gacccggctt ggaagctctg tgtcccccg taccttgtcc cattacctct tcatctggct    22020
gttcatttgt atcctttata atatccttta taataaagtg ttttgtagc aaattgttta    22080
acatgaggag ggggttgtgg gtgtaggggc agggaaaag cttccccatt gatctccaaa    22140
ggtttgctga aaatcaact cacaagaggc agattaattg gagaaaagtc atacagattt    22200
tattacatgt acacggggga accacagaga ttactcaccc cccatgggg ttcggaagca    22260
tgtataatat cctggcaaaa caggttatat ggctggtcca ggtgcagtgg tgtttacagc   22320
taattgatca cagccagtta cagatttctt tgttccttcc actcccactg cttcacttga   22380
ctagcctaaa aaattaatta attaaataaa acaggttata ggagaaggga gaagaggaat   22440
tctgttgtga ggattactag gaagaatgaa tggatcaggg aagggagatt aacttgtaca   22500
ttatcttgtg gaaggatctg ttcaggtgtg attacattct tggtcttact gggaggggaa   22560
```

```
tgcaaaacag ttgttctcgg tgggtctgga ttttaggcga taaaggaact tcagagaacg   22620
tcattctgac tttgggagaa gtcagttgta ggggtgggtg gttgggggaa gtcagagaga   22680
ccctgaggta ttggttactg agtcccaaca tgggaatgcc cagtttgtag ccaagtcaga   22740
ctaatttgac tgatttgtgg ctaatttgag gatccactac ttgcaattag catctgaagt   22800
tgggggtagt ctgtgggact gagccctaaa cctacggggg tctgtgctaa ctccaggtgg   22860
tgtcagaatt taattaaatt gtaggacgct cgattggtct ccacagagaa tagatttgct   22920
tctggaaaac tcacacatct ggtgtcgaaa gcattgtgag tggagaaaca gttttttatt   22980
tatgaggcaa gagaggctat gggggtcttg aggcggtatt ggggacctta gatgctatca   23040
tctgctccag tatctgggaa ggtctgtcct cctcattggc atcccgtctc cagttgccct   23100
gtcttcttcc tctccctcat agaccactgt tcacacggga tacacttatg atccccacac   23160
tgttttctcc ttactctcac ttctccatcc taggcaatc actgatctgc tttctgtcac    23220
tattccatac atataaatga caaaatatag tgggtttttt tgttttgaa agacaggatc    23280 tcactgtgtt gctcaggttg gcctccaact cctgggctca agcagtcctc ctagctgaaa   23340
ctacagatgc acaccatgac tcctggctca agcacagtgt ttttgtactt tttaataaat   23400
gacattatat atcccatatt ctgaaatgtc tcttttttcc ctggatgtta tgtctttgtt   23460
tttttttttt tttttttttc tgacacaaat cctttctttg tcacccaggc tggaatgcag   23520
tggtgtgatc atggctcact gcagcctacc tctcaggcta aagcagtccc cctgcctcag   23580
cctcccgagt agctggaact acaggagtgc tccaccacgc ccagctaatt ttttttcttt   23640
tttttctttt tgagacagag tctcgctctt gtcacccagg ctgtagtgct cgctcttgcc   23700
gcccaggctg gagtgcagtg gcatgatctt agcccactgc aacctccgcc tcccgtgttc   23760
aagtgattct cttgcctcag cctcctgagt agctgggatt acaggcgcct gccaccatgc   23820
ccagctaatt tttgtacttt tagtggaaac agggttttgc catgttggcc aggctggtct   23880
tgaactcctg acctcaagtg atccgcccgc ctcggcctcc taaagtgctg ggattagagg   23940
gctgagccac tgggcccagc ctaaattttt tattttattt tttgtagaga cagagtcttg   24000
ctatgttgcc caggctggtc tcaaaactcc taagcccaag tgatcctccc gctttgctct   24060
cccaaagtgt taggattaca ggcatgagcc accatgccca gcagatgtct tgagatctgt   24120
taatgtagtt agagaactag tgtaccctt aaaaattttt ttattgtaat taaatataaa    24180
taagaaaatt taccagttcg accactctta agtgtacagt tcagtggtat aagcacattc   24240
acagtgttgt acaactatta acagtatcct tctgtttcca gaacttttca ccatcccaat   24300
cagaaactgt acccattaaa caataactcc ctatccctcc ttttgcagtc cctagtaacc   24360
tgtattaaac tttctgtcta tgaatttacc tatgcttggt cacctttgtt tttgtgtttt   24420
tgaaagatga ttgtgattgg taaataactc caggttggaa gttttttgttt ttttttctcg   24480 ttcagtaccc tgtcttatag cttgcattgt ttctgatgca aaatctgcta tcaacttcct   24540
ttctgtatgt gaagcatctc tttggctgct tttaagactt ttttgttttg ttttgttttg   24600
gagacagagt ctttgcctgg agtgcagtgg tacagtcatg gctcactgca gccttgacct   24660
cccaggctca agcagtcctc ccacctcagc ctcccaagta ggtgtgcgcc accatgccca   24720 gctactttt tagtttttttt tttaaataga gatgggatct tgctatgttg cccaggctgg   24780
tcttgaactc ttggactcaa gcaatcctcc caccttggcc tcccaaagtg ctgggattac   24840
aggcgtgagc cactgcagct agcccttaaac cactgtttaa tccagtgttt taaaattgtt   24900
```

```
ttagagggag ggttatgtct attcctatta cttcatctct cctgatgtga atgttgaggc  24960
tggatgcggt ggctcacacc tgtaatccca gcactttggg aggcagaggc gggcggatca  25020
cctgaggtcg ggagttcgag accagcctga ccaacatgga gaaatgccgt ctctactaaa  25080
aatacaaaat tagctgggtg tggtggtgca tgcctgcaat cccaactatt gggaggctg   25140
aggcagaaga atcacttgaa cctgggaggt ggaggttgca gtgagccaag atcgtgccat  25200
tgcactccag cctgggcaac aagagcaaaa ctctgtctca aaaaaaaaa aaaaaaaaa    25260
aaaaaaaaag ttgaggatga gcggcttcat gggatggcat gtatttctgt aaccactgac  25320
ttccacctcc cagaaaaagg aagcaacaag ccaaaaattc actactgttg ttattgggcc  25380
tgatagtgaa aggatgacca cctaaaaatt atggcatcct tggaaaattt ttgcaaatct  25440
gtattttaag cagtgtaacc ctttacagta agggagtaca gtgacttttg caagtggttt  25500
agtgttctga ctgcatatcc agaggcagga tggcagtacg aaggtcctag tgggaacaga  25560
gagtgagagt ctgtgagtct gtggctaact cagacatcag ggagaagaat gtgtgatact  25620
gtctcagagg ttgccaactt tggtattagg ctgtgttctt tgaaatgtgg ggcactgaat  25680
ttaggcatat actgaaataa ctaaataaaa caagagttac atatatgttt catgttctac  25740
atcctgtcag gttatctcat ataaataatt ggattgtgaa tatttaccta acttttgag   25800
gtctaatgcc ctaatttgct gctttctttt tgtaggtaaa gaacaacagc agcaacaaaa  25860
acaaaaacag tagatatatt gggggggga aaaaacctgc tggttaatat acagatttca   25920
ttaccttgaa gttcactgca ctgaacaatt ctcactctgg atgtattcct gctctaggat  25980
gtgaatttag acttttgtaa tagagtgggc tttgagaaat agcttttctg ctcattttag  26040
tttcatgatg actgcatgga atgttttgct tcacgcttat gcattgagtt ttatcaagca  26100
ttaagcagtt ggccgaaaca ggtaatactt gaacattcag tccaagaaaa acaaaatgga  26160
tttgaacata cgtagaatca gtaactctta ttttcatact tccttatggt tattcagaag  26220
tgttggtctc taggtacatt ttgaaagcaa gtacttgatc tggcttaggt tttaactaac  26280
agcaagcaga tactgccctg ataaaaagat gatgtacagc aaaagtgaga tggtcagaat  26340
tggcttttt ctttttcttt tctttttttt ttttgagagg gagtcttgct ttgtcaccca   26400
ggctgtagtg cagtggcatg atctcagttc actgcaagct ccacctccca ggttcatgcc  26460
attctcctgc ctcagcctcc tttgtagctg ggactacagg tgcccgccgc cacgcttggc  26520
taattttttt gtattttcag tagagacggg gtttcaccat gttatccagg atggtctcga  26580
tctcctgacc tcgtgatctg cccacctcgg tctcccaaag cgctgggatt acaggcatga  26640
gctaccgcgc ccggccagaa ttggcttttt tcattataga ctactacagt aaaatcatcc  26700
taactgcaga agtcacttga aatgtggaaa tcacagtttg ctatgtattt gatttggttc  26760
aatctttttt tttgctttct gggacatcaa aatcagccag cgagtctagg gaaatttgga  26820
cttaaggttt taatgtttag attttgaaaa gccaggatgc ttataaaaca ctcattgta   26880
tcatttacga cagagagaga gagagaaagg agagagagag agagtgcgtg tgtgcgttta  26940
tgtgtgtatg tatatcttgt ttaaaaaaca gtctggactc agttttctca cctggaacat  27000
tagaaatgaa gtgttagctg ggcgtggtgg ctcacgcctg taatcccagc acttttggag  27060
accaaggtga gacgattgct tgagcctagg agtttaagac cagcctggtc aacatagga   27120
gacgctgttt ctacaaaaaa agaaaggaaa aaaagccagg catggtggca tgagcctgtg  27180
ggattcagct cccaccttgg aaggctgaag taggaggatg gcttgagcct gggaggtcaa  27240
ggctgcagtg aaccaagatc atgccactgc attccagctt agacaacaga gtgagactct  27300
```

```
gtctcagaaa aaaaaaaaaa aatgatacca actttcatat ttgtggcaaa atgagataaa   27360
tttacgtaac tgaaaagggg agtcttttttt taatgaatta ctttatttct ttgaggaaaa   27420
ataaaacaga tttgtaaact ttgctcctgg actagaatgc tactttgcag gcaaacttac   27480
ttttgtaaaa atgctagact ctggccagac atggtggctc acacccataa tcccagcact   27540 tgggaggcc taggccggtg gatcacctga ggtcagcagt ttgagaccag cctggcctct   27600
gtcgctatta aaaaaataca aaaacaaaaa aattagctgg acgtggtggc acacacctgt   27660
aatcccagct actagggagg ttgaggcagg agaatcactt gaacctggga gctggaggtt   27720
gcagtgagcc gaggtgtcac caccacactc cagcctgggt gacagagtga gacttggtct   27780
gaaaaaaaaa aaaagctaga ctccacattc tttaaaaaaa aaaaacaact ttgctaagat   27840
ataattcacc aatgtaaagt gtacaattca ttggttttta gtataatcac agagttgtgc   27900
agctgttatc accatcaatt atagaacatt ttcattacca accccccccc cccaaaaaaa   27960
aatctcgtgt ctattagcag ttgctacttg tttccccccct accccttttct ctgcaggccc   28020 cagacctaga caaccactaa tccacgatat gtttctacag atagactgat tctagacatt   28080
tcctatacag tgtcattact aattcctttt atgggtggat aatattccat tgtatggata   28140
tacatatttt atttatccat ttatcaattg atggacaatt ggctattgtg agtaatgttg   28200
ctacgaacat ttggttacaa cttttttgtgt gaatatgttt tcattcata tggtaactgt   28260 ttaaccttgt gaggaactgc cagttttcca gagtggctac accatttacc ttcctaccag   28320
cagtgtatga gaattccaat ttctctatat acacttagac ttgttattta tcagtgtact   28380
gagttttgat caaaaatagt gtacctgtgt agtgtggtta aatcatgttg acctcactct   28440
ctttcatcta gcctcttaaa atatcaatac taagacttat aaaatgagca tatgaaaacc   28500
agtaactttc cttcctacag attgaaaata ctcaatcaga agtatattc aaagaaaata   28560 tttaatccac agtagcgaca taaaaatagg ttttaaaaaa aatctagtaa taaaccttag   28620
agaaatttga agaaactata taagaaaaca agaaactcaa ttgagtgtca taaaacgaaa   28680
cttgaatgaa tggtttggga aaaagcaaca ttatacaaag tgaattccct gcatatcaat   28740
ctgtgaagaa acatttctc ccaaatttcc aacaggattt taaatctgac aaaaatttca   28800
tcaggaaaaa taaatgctca acaataaaca ggaaaatttt gaaaagaaa gtttggaaag   28860 agaagacttt tcctaatgtt gtatacagga atagtaacaa ctgagagaaa atatttgcaa   28920
catttacaac aaaggattac tatctctatt gtacaataaa tgccaagaag aaatagatga   28980
aaaatctaca taatgaggta taaatagtca attcataaat aacaggctca aaaatcacta   29040
ataattaaag aagtttttgaa atattaaagt gagacattac ttttcaccta ttggactgga   29100
aaatacagaa tttagtaatt atctctaaga aattagggcc aggtgtggtg gctcacacct   29160
gtaatcccag cactttggga gaccaaaaca ggtggatcac ttgaggtcag gagttcaaga   29220
ccagccaggc caacatggtg aaaccctgtc tctactaaaa atacaaaaac tagctgggca   29280
tggtggtggg cgcctgtagt cctagcact caggaggctg aggcagaaga attgcttgaa   29340
cccaggaagt ggaggttgca gtgagccgag atcacgccac tgcactccag cctgggcaac   29400
aacaagactg tctcaaaaaa aaaaaagaaa ttaggaaaga ttggccgggt gcggtggctc   29460
acgcctgtaa tcccagcact tgggaggcc gaggtgggtg gatcctgagg tcaggagatc   29520
gataccatcc tggctaacac agagaaaccc tgtctctact aaaaatacaa aaattagcca   29580
ggcgtggcgg cgtgtgcctg tagtcccagc tgctggggag gctgaggcag gaaaatggca   29640
```

```
tgaacttggg aggcggagct tgcagtgagc cgagattgcg ccactgccct ccagcctggg    29700
tgacagagcg agactccgtc tcaaaaaaaa aaaaaagaaa ttaggaaaga taccctgttg    29760
gttgaatgaa tgtatgtgtc ataactcttt tggaggacag ttggaaatac ttggccaaat    29820
tttaaatggg cagactttt tttgttaatt ttttacttta attttaatgg atacatagta     29880
ggtgtatgtg tttatggggt acatgagcta ttttgatgca ggcatacagt gcataatcat    29940
gttgcgtaaa tgggatattc atcacctcaa gcatttatca tttatttgtg ttacaaatat    30000
tccaattata ctcttttagt tatttttaaa tatacaataa attttgttga ctgtaattac    30060
cctgttgtgc tatcaagtac tagatctttt ttttcttttt tacttttttct aacctttttt   30120 tttttctgag acagtgtctc actcttgctc aggctggagt atagtagcat gatcacagct    30180
cactgcagcc ttgacctccc atgctcaagc agtcctcctg cctcagccta ctgagactac    30240
aggcttgagc caccattcct ggctgttttt taaaattttt tgtagagatg gaggtctcac    30300
tgtgttgccc ggggtggtct tgaaccaaat actagatctt actcattctg tgtgagtata    30360
gttttgtacc cactctccac cactatcgtt cccagcttct ggtagctatc attctactct    30420
ctatctccat gagttcaact gttttaattt ttagcttcca caaatgagtg agaacataag    30480
gtttgtcttt ctgtatctgg cttatttcac ttgacacaat gtcttccagt ttcatccatg    30540
ttgttgcaag tgacaggatc tcattctttt tgtggctga atagtactcc cattgtattg     30600
ctagacactt aagttgcttc caaatcatgg ctattgtgaa tagtgctgca ataaatatgg    30660
gagtgtacat atctcttcaa tatactgatt ccctttcttt tgggtgtata tctagtggtg    30720
ggatttctgg atcatatggt aggtgtgtgt ttagttttct gagaaatctc tatactgttc    30780
tccatagtga ctgtactaaa gtacattccc accaacagca tgtgagggtt ccctttctg     30840 catatccttt ccagcatttg ttattgcctc tcttttggat aaaaaccatt ttaactggaa    30900
tgagatgata tcttgatgta gttttgattt gcagttccct gatgatcaat gatgttgaac    30960
accctttcat atacctgttt gccgtttgta tgtctccttt taaaaatgtc tgttcaggag    31020
ccgggcacag tggctcacgc ctgtaatccc agcactttgg gaggttgagg tgggcagatc    31080
ttgaggtcag gaaatcgaga ccatcctggc taacatggtg aaaccccgtc tctactaaaa    31140
atccaaaaaa ttagccgggc gtggtggcag gtgcctatag tcccagctac tcaggaggct    31200
gaggcaagag aatggcatga acctgggagg cagagcttgc agtgagccga gatcgtgcca    31260
ctgcactcca gcctgggcga cagagcaaga ctccatctaa aataaaaaaa aatgtctatt    31320
cagggctagg gatggtgtct cacgcttgta atccccaccac tttgggaggc cgaggcgggc   31380
ggatcacttg aggtcaggag ttccagacca gccaggccaa catggtgaaa ccctgtctct    31440
actaaaacta caaaaattag ctgggcatgg tggcacgtgc ctgcaatccc agctacttgg    31500
gaggccgagg cagtagaact acttgaaccc aggaggcaga ggttgcagtg agccaagatt    31560
acgccactgc actccagcct gggtgacaga gcaagatccg tttccaaaaa aaaaaagga    31620 aaaatgtcta ttcatatctt ttgcccatta tttaatcaga ttattaggtt tttttttcc     31680 tattgagttg tttgaactcc ttgtctattc tggttattaa tcctttgtca gatgcatagt    31740
gtgcaaatat tttctcccat tctgtgggtt gtctcttcat ttttttgatt gctttgtttt    31800
gcagaaacct aagttgatgt gatcccactt acctatttt gctttgatta cctgtgattg    31860
cggggtgcta ctcaagaatt acttgcctgg accagtgtca tggagagttt ccacagtttt    31920 ttctttagt agttgcatag tttgaggttt tggatttaag tctttaattc attttgattt    31980 gattttgta tatggcgaga aataggggtc tagtttcatt cattcttctg catgtggata     32040
```

```
tcttgttttc ccagcactat ttattgacag tcttatttat tgaaggctgt cttttcccca    32100
gtgttatgtt cttggcacct ttgtaaaaaa tgagttcact ctagatgtat ggatttattt    32160
ctgggttctc tcttctgttc catcggttta tgtgtctgtt tttatgccag caccatcctg    32220
ctttggttac tacagtttgt agtataattt aaaggcatag aatgtgatcc ctccagtttt    32280 gttcttttg ttcaggctag ctttggccat tctgggtctt ttgtggttcc atataaattt     32340
acaatgattt ttttctattt ctgtgaagaa tgttattggt attttgatag ggattacact    32400
gaatctgtag attgctttca gtagtatgga cattttaaca gtattgattc ttccaatcca    32460
tgaacatgga atatctttcc tttttttttt ttaatgtgta tgtcttcttc agtttcttgt    32520
atcagtattt tatgattttc attgtaaaga aagagatctt tcacttttt tttttttttt     32580 ttttttgaga cagagtttca cttttgttgc ccaggctgga gtgcaatggc acgatctcag    32640
ctcactgcaa cctccacctc ccgggttcaa gtggttctcc tgcctcagtc tcccgagtag    32700
ctgggattac agggatgcac caccatgcct ggctaatttt gtattttag tggagacgag     32760 gtttctccat gttagtcagg ctggtctcga actcctgacc tcaggtgatc ctcccacctc    32820
ggcctcccaa agtgcaggga ttacaggtgt gagccaccgc gcctggctga gatctttcac    32880
ttcttttgtg atacttattc ataggtattt ttttatttgc agttactgta aatggaatta    32940
cttttttgat tactttttca gattatttgc tgtggcatat agaaatgcta ctgattttg     33000 tgtggtgatt tcatatcctt cgactttact gaattagttt atctgttcta atagttttt     33060 tgtggagtct ttaggttttt ccaaatatat aagatgatat catctgcaaa caaggataat    33120
ttgacttctt cttttctaat ttggatgccc tttatttctt tctcttgtct cattgctcta    33180
gcttggactt ccattactat gttgaataat agtggtgaaa gtgggcatcc ttgtcttgtt    33240
ccaaatctta gagaaagact ttcaattttc tcccattcag tatgatacta ggtgtgggtc    33300
tgtcttatat ggcttttatc gtgttgaggt atgttccttc tatccccagt ttttttgga    33360 tttttgtcat gaagggatgt tgaattttac caaatgcttt tttagcatc aattgaaatg     33420 atagtatgat ttttgtcctt tattctgttg tatcatgttt tattctgttc tatcatgtga    33480
tatatcacgt tgattgattt gcatgtgttg aaccatcctt gcatccctgg aacaaattcc    33540
agttggtcat gatgaatgat ctttttaatg tgttgttgaa ttcagtttgc tagtgttttg    33600
ttgaggattt ttgcatcaat gttcatcaga gatattgacc tgtagttttc tctcttttg     33660 acatatttgt ctggttttag taatactgat gagtattact gggtcttaga atgagtttga    33720
aactattccc tcctcctcca tattttggaa tattttgagt aggattggta ttagttttc     33780 tttaaatggc actgaagcca ttggatcctg ggcttttctt tgctgagaga cttttatta     33840 tggcttcgat ctcattactt gttagtactc tagtcaggct ttggatttct tcatggttca    33900
atcttggtag gttgtatgtg tctaggaatt tatccatttc ttctaggctt tctgatttgt    33960
tggcatatag ttgctcatcg tagcctctaa tgatcctttg agtttctgca gtattagttg    34020
tattgtctcc ttttcatct gtgatttgat ttctttgggt cttgtatctt ttatttag      34080 tccggttaaa ggtttgttga tactatttgt cttttcaaaa aaatcaagtt tacatttgt     34140 tgatcttttg tgtgttttgt ttcaatttca ttcatttctg ccccgatctt tattacttct    34200
tttcttctac taattttgtg tttggtttgc tctcgctttt cttgttcttt aagatgcatc    34260 attagttttgt tcatttagcg cctttctcct tttttgatg tgggcactta ttgcttgcta    34320
taaactcacc tcttagtact gctttcactg tatcccattg gttttggtag tagttgtgtt    34380
```

```
tctattttca ttttttttcaa gaaattttc aattttttc ttaattttgt attgaccccc    34440
tgcttaataa ggggcatatt gttaactttc atgtgttttt gtagttccca aagtccatct    34500
tgttactgat ttctagtttt gttccattgt ggtcagagaa gatacttgtt agttttttgta   34560 ggttagtaac aatatttgga ttatactaag gagttttat ctagagttat agagattttc     34620
ttagaatgct gccatggtag agaataagtg ggtgggtata taggggaaaa caacatttg      34680 aaatatgttt caaattttcc agattaaaca gttaaaaaga acaggtggtg aacctagaga    34740
atagtgtttt agaaaccgag acacaggatt tcttaatagt gggcaacttt gtcagggact    34800
gcaagagaga tcacctagaa taaggactga aaagatgtca taggtttcag cagctggttt    34860
catgaccttt gcaaccgcag ttttggtgga gtgtttgggc taaaacctgg cagcagcatt    34920
ttgagaaatg tgtggaaggt aagaacatgg agaaaggata tgatcactat gtgaaaaaaa    34980
gttgtttcat tataaaagat tacaaactta tgattttaa aatattaaag agaagtatga     35040
agtgaaaaaa aaccctgccc cttttccttt ctcatcttct cacctgtttc ctccagtttt    35100
agtctctagt tttactcttg agatttgtgg ctactgaatg aatggagtgt caatctgaat    35160
gggaaagaga attttttttt ttttttttt gagacaaagt ctcgctcttg ttgcccaggc     35220
tggagtgcaa tggtgtgatc tcggttcgct gcaacctccg cctcccaggt tcaagcgatt    35280
cgcctgcctt agcctcctga gtagctggga caacaggcac gtgccaccac gcccagctaa    35340
tttttgtgtt ttcgtagaga cggggtttca ccatgttggc caggctggtc tcaaactcct    35400
gacctcaggc gatccaccca ccttggcctc ccaaagtgcc gggattccag gtgtgagcca    35460
ctgcacctgg cctgaaagag gttttgtgaga gggagactca gaaacgcctt tgcctgagaa    35520
gagctaggaa atagaaggaa agaaaaaaat ggaacagagg agctcagaga agataaaagg    35580
aagtagggat gcagtggtca agtgggagaa aaaaaaggag aggcactctt ttctttgagt    35640
agccaggaaa aaatgacttt gttttctttt ctcaattagc agaccaagct gtatgctggt    35700
gattgaggtt tggatagggt tggtggcatc tagtgtgtag taactatggg aattagcaaa    35760
tcaatggcag agtgaaggac tcactttcac tcgctcaggt ccaaactagg ctttaaatga    35820
cttctttttt ttttgagaca gtcttgcttt gttgcccagg gtggagttca gtagcacaat    35880
cttgactcac tacaccctct gcttcctagg ttcaagcgat tcttctgcct tagcctcccg    35940
agtagctggg actgcaggca cacaccactg tgcctggcta atttttgtat ttttagtgga    36000
gatgggcttt catcatgttg gccaggctgg tctcgaactc ctgacctcaa cccgcctgcc    36060
tcggcctcgc aaactgttgg gattacaggc accacacct ggcctgaatg acttttttcac     36120 tgaggaatgc catagtccag gcagatgtgc cacctcattg atcgccaggg atgactcagt    36180
tgtctggcta gttgggtaag ggaggtgttt ttttccatcac ttctgtgtgt ctgttactaa    36240
aactgttcat ttatatttca cagcagctca agtgcaactg ttcttcagta cttttgtagc    36300
ttttcatttc tgtgactcct ttgaggaggc tctgtcatgt gaaaggaaaa atttgataaa    36360
atgattacat ggagacttct aactaatcgt attgtggcaa tggaactact ttcacttcct    36420
cttttaaaga aacaggtaac agaaagcctc tctctttagac tttcccatta gacacatagc    36480
agtgacaatt taaactgtgg tcagtagcca ggcatggtgg tgcacttctg tagtcccagc    36540
tatttggaag gctgaggcag gagaatcgct tgaacccagg aggcggaggt tgcagtgggc    36600
caagataaca ccattgcact ccagcctggg caacaagagc caaactccat ctcaaaaaaa    36660
aagaaaaaaa atgtggtcag gaatagattc tgtttgctgt atttgggata tatacaatgt    36720
taagaacaaa atggccaggt gtggtggctc atgcccataa ttccagcact tgggaggcc     36780
```

```
caggcgggag gattgcttga gcccaggagg tcgaggctgt agtgagccgt gatcatgtca   36840
ctgcattcag ccttgagtga cagagtgaga ccctgtctca ccaaaaaaga aaccaaaga    36900 acaaaatttt atatctatat acattggtgt ctgtgaacct catgtggtat ttttatgcaa   36960
atagaaatgg aagttatatg ttacctactt cagaaaattg aattgtctaa ataaatatct   37020
aaatatttgt ccttaggcca ggcacggtgc ttcacgccta taatcccagc actttgggag   37080
gccgaggcag gcggatcacc tgaggtcagg agttcaagac cagcctggac aacatggtga   37140
aaccctgtct ctactaatac aaaaattagc tgggtgtggt ggcacacacc tgtaatccca   37200
gctactcggg aagctgaggc aggagaatcg cttgaacctg ggaggcagag gttgcagtga   37260
gccaggatca tgccactgca ctccagcctg ggtggcaaga gcaaaactct gtctccaaat   37320
aataataata ataagtaaat aaatatttgt ccttgtcata tatttgttta taaatatgag   37380 attattttt ctaaaaattt acattatgaa atttgtttag taatcatcac atttaggggt    37440
tttaaagtga cctttacttt acttttgtgt ttttaggag acccgtgtac agtatcatct    37500
cagttggagt tagaagaagc ctttagactt tatgagctaa acaaggattc tgaactcttg   37560
attcatggta agagagtagt catttcatac tcgtccagac tgataatttc tttgaaatca   37620
ctctttattc ttcaccattt tgaaacataa tcttaatgtc attttctcaa tctctgtgac   37680
tcatgcctaa gtaattgtcg ttatttagta gtttctcacg tgctacagaa ggtaaaatta   37740
atctgctgct tatagtctgg ggaattttgt ggtctctgta tgtcttgttg gatattaaaa   37800
tgtgatatct cagtgtatca cagcaaattt atgatagaac ttaaaaattg agagcctggg   37860
gaatctaagt catctacttg aaattttgtt atgtatacaa ataatgacct ccaaaggtaa   37920
ggtatcttaa atatcctttc ttttgcttaa aggttaatag tgaaactatt tacatgattc   37980
ctttattttt gagacagtct cactctgtca cccaggttgg agtacagtgg tatgatctcg   38040
gcccactgca acctctgcct cctgggttca agcatctcag cctcccaagt agctgggatt   38100
acaggtgtgc accaccatgg ctggctaatt tttatatttg tagtagagac agggtttcac   38160
catgttggcc aggctggtct cgaactcctg gcctcaagag atccgcctgc cttggtctcc   38220
caaagcactg agattacagg catgagccac tgcaccaggc ccatttacat gatgctttag   38280
agacattaat atgtttatac ctcagcaacc ttgagatgta ggaagtggca tagaagaagt   38340
aacctaaact cagttatcat tgtaactggc acgttgtaga cctggattgt gaatctagga   38400
attctgattc caaatttgtg tttcattcaa ctatgctaac catcaaaagt catgtaaaac   38460 ttttttttg tttgtttttt tgaggcagtt tctctcgctc tgttgcccag gctggagtgc   38520
attggtgcag tcatagctca ctgcagcctt gacttcccag gttcaagcga tcctcccacc   38580
tcagcctcct gagtaactga gaccacaggc actgccgcac cactatgact ggctaatttt   38640
tttttttttt ttttgtatag atcggatatc actatgatgc ccaggctggt ctcaaactcc   38700
tgtgctcaaa gagtcctacc acctgggcct cccaaagtgc tgggattaga ggtgtgaacc   38760
accatgccca gccaagaacc tcttaatata ctgcatttaa ttgcaatata ttgacagtat   38820
ttcgttgaac atttttgaga gctatgagac cagacttagg aatcttctaa aaaagtgaaa   38880
cgaatgtaaa tctttcctta agtataatga atcatttcag tgccttatta ttatttcttt   38940
gtattttcct ttacagtgtt ttttttttaa aaaaaaaaa aaaacagtgg tttgatttta   39000
tatttatttt gagacacagt ttcactctgt tgcccaggct agagggcagt ggcacagtct   39060
caactcactg caaccttggc ctcctgtgtt caagtgattc tcatgcctca gcctccaaag   39120
```

```
tacttgggat tacaggcgcc taccaccatg cccagctaat ttttgtattt ttagtagaga    39180
tggggtttca ccatgttggc caggctggtc tcgaactcct gacctcaggt gatctgcctg    39240
ccttggcctc ccaaagttct gggattacag gcgtcagcca ctacgcctga cctgattttt    39300
ttctacctcc agaatttgac atagtgactc acaagggatc cataatgtac tttgttgaga    39360
ttctaaaaga gctttaagag tctattttt tgtcatctc tttccagaat aaaattacaa     39420
tgaatgcata aagaagtgat tgatgaatgg tattaaacag tcagttttaa gtcttattgc    39480
cttttaatac tacatcacag atgttttcag aagctagctt acgtttcagc ttttaaaaat    39540
atgcattagg aactgtgctt cctatagtct gtgctcttta ttaaactgtg tcctttagta    39600
catcacagac taagaatagc tgactagata ttcataaata cattgttgct ttatattcta    39660
ccttgttata aaaatggttt taattagtat atacatttaa agtttctaat gtaaatttac    39720
atttttgatt ttggtactgt ttctggtgtt aatttattcc taagtttagt atacatcttt    39780
taaaaaccaa tattttatgt tccatatttg tatacatttt tgtaatttaa ttttcatcct    39840
tcattgtgac aaacttgtcc tactatacca aggatttaag gcgatattag ttaatgattt    39900
ctttaaggat aagaaaataa ttcatgatgt aacaggagct ggaattagtc atttgagctt    39960
ctgatgcatt ggttttttg ttttgttttg ttttgtttt tgtttctgag atggtgtctc      40020
attctgtcac ctgggctgga gtgcagtggc atgatctcag cttactgcaa ccttcgcctc    40080
ccaggttcaa gtgattcccg ggcctcagcc tcctagggag ctgggattac aggcacatca    40140
ccatgccagg ctaatttttt tgtattttt tggtagagac agagttttac catgttggcc    40200
aggctggcat cccctgacct caagtcatcc acccaccttg gcctcccaga gtgctgagat    40260
tagaggcgta agccaacgtg cccagcctaa tgcattgttt atagacatgt ttgttttcat    40320
aagaactttt ttctttcttt cttttttttt ttttttttta acatcaacaa agcaaggcaa    40380
ataaaaccttt cttttgtggc cgggcgcggt gactcacgcc tgtaatccca gcactttggg    40440
aggccgagac aggcggatca tgaggtcagg agatcgagac catcctggct aacacggtga    40500
aaccccgtct ctactaaaaa tacaaaaatt agccgggcat ggtggcgcgt gcctgtagtc    40560
ccagctacac gggaggctga ggcaggagaa tggcgtgaac ccgggaggcg gagcttgcag    40620
tgagtcgaga tcgcgccact gcactccagc ctgggcgaca gagcgaaact ctgtctcaaa    40680
aaaaaaaaaa aaccttcttt tatatggcct tggtaaaatg aatccctttg gcaaataata    40740
ttgatcacat gctaagtatc ttgtctcaag tgaagagagg gtcaggttga aatctgggtc    40800
agtttctttt acatttgaat tttaaattct gtgtaatttg tatgttttaa atatgctgtt    40860
aactcatgtt cgtttatttt ctttcagtgt tcccttgtgt accagaacgt cctgggatgc    40920
cttgtccagg agaagatagt gagtgtttat atacttcata cctttttacaa gagttactat   40980
gctatggtac aagtgaaaaa gaaatcagag atagaatttt tagctaggtg cagtggacag    41040
tggctaatgc ctgtaatccc agcactgtgg gaagctgagg tgggaggatc gcttaagccc    41100
aggagttcaa gaccagcctg ggcaacaaag tgagaccttg tctttccaaa aacacacaaa    41160
aaaattagca tggtgtgtgc ctataatctc agctacttgg gaggttgagg tgggaggatc    41220
ccttgagccc aggagtttga ggctacagtg agccaaggtc gcactacttg cactctagtg    41280
tgggtgacag agacaggcct tgtctcaagg ggaaaaaaaa aaaggaaata gaagttctaa    41340
ttcatttgat ttcttttcca ttttcagtc aatttagaat atattagtga ctgcccaaat     41400
gctactttgc cagatcaaat tcagatagtt cttagttaca acttacatga ttgcctgttg    41460
cacatatgaa aggaatatta agttaaattt aagttttaaa attcaatttt ggaaatgttc    41520
```

```
aaacctatac agaagttgaa acaacatgga aaacaaggat acctatatat cctttgccca   41580
gatttaccaa ttttttaacgt tttccctgtt tgctttatct ctgtatctgt ctatatctca   41640
tatatgcatg cacagttata cataacaaac acattttttt tttttttggtt ataccacttg   41700
agactgacat gacactcagc acatgtaatt aggaattggc tttttttttt tctgcagtgt   41760
tttttactta aacaggtatt aagtcacttt tgttgttgtt gttttttgaga cagaatctcg   41820
ctttctcacc caggctggag tgcagtgacg caatcttggc tcattgcaac cttcacctct   41880
ggggttcaag caattctcct gcctcagcct cctgagtacc tgggattaca ggcgccaaca   41940
ccatgctcag cttatttttg tacttttagt agagttgagg tttcaccatg ttggccaggc   42000
cggtgtcgaa ctactgacct caggtgatcc acctgcctca gcctcccaga gtgctgtgat   42060
tacaggtgtg agccactgca cctggcccca agtcacttat taaatgtctt taaatattgc   42120
agacttccta cagttgaccc agagaaatgt gtatatttat tagatctcca attcctagta   42180
acttcaggta accaaccaga gtccacagtg gaacggtgat tcttacccctt ggacacatta   42240
aaattgtggg atggagggaa tgatcaatgc caaatttcca tccccaagct taatgaatta   42300
gtgtggaggt gaaatctgga tatctttgta ttttaaaatg gactctcaaa atgtagccat   42360
tgggtcccac agcatcagct tcacctgaga actgaataga aactgcactc caggctgggt   42420
gcagtggctc atgcctgtaa ccctagcact ttgggaggct gaggcaggca gatcacctga   42480
ggtcaggagt tcaagaccag cctggccaac atggtgaaag cccatctcta ctaaaaatac   42540
taaaaaagtt agctgggtgt ggtggtgcat acctgtaatc ctagctacct gggaggctga   42600
ggcaggagaa ttgcttgaac ctgggaagcg gaggttgcag tgagctgagg tcgcgccagt   42660
acattccaat ctggacaaca gagcgagact ctgtctcaaa aaaaaaaaa agaaaaaaac   42720
tgcactccaa tctacgtgat tcataaactc ttggactggg gctgagctac cagatttaac   42780
aagctcttca ggtgattctg atgcacacta agtttgaga accaccattt aaaagcttcc   42840
ccaggtcagg aattgttaac ggaatttctt tggaatatct aagccaatgg ttactattaa   42900
tgagatgaac taagagtgtc caactactct ttgttctaat gtaatttaat atgcaaactt   42960
atgtttgatt gtaagttatt gcttttggta ttttggcata atttactaat tgtggatatt   43020
aggcaactca ttttcatttg tggtttctgc acatgcccat cactttagaa ggaatagtgg   43080
taaatgcttt gctttgaatt aatcgaaata gctctaaact ttctttttct tttttttttt   43140
tttgagatgg tcttgctctg tcgcccaggc tggagtgcag tggcgagaac tcggctgact   43200
gcaagctctg cctcctgggt tcatgccatt cagcctcctg agtagctggg attttaggtg   43260
cccactacca cgcccgtcta atttttttttt ttgtattttt agtagagatg gggttttgta   43320
tttttagtag agtgctagcc aggatggtct caatctcctg atcttgtgat ctgcccacct   43380
cggcctccca aagtgctggg attacgggcg tgagccaccg cgcccggcct aaactttcaa   43440
ttctgtatta agctatcctg agatttctaa ttgagagcat tgcaactggt ctttagtatc   43500
ttaattttaa atagtaaacc cattgctata tttgctttaa aatatgactt tgggaacctg   43560
ttgtaatctt tctatggtat taactattac tgttattacc attactgtgg gatgttatta   43620
ttaatgacta atagacaata tataaaataa tgatggactt aaaaatatga aggtggacta   43680
gatttgatcg tttggaacct cttctctaa ctatatttga gaaacatatt aatataaaga   43740
ccactggatg aaaagttgtt ggggaaaaag atatgcttct ggtacaaaat atcactttac   43800
agattagtta caaagactga aatgtacctt tacaatgaag agatctagca gtcactacct   43860
```

```
ttaatggtta ttgaacatca gtagtgggag ttgataatcc gacatttgtg tacctcatga   43920
aaagtaatga gataagaaat acacaacact acctatgtgt tattttttgcc aaaggtattt   43980 aatactgcct ctaatcgtaa gtaaacagac aaatccagaa tgtgggatat aatatgaaac   44040
aactaaccag actctttaaa aaaaaaaaaa agtcaacata atgaaaagga agtaacaaca   44100
aataaggcag agtgaatgtt ttaaaatgtt aaggagacca aaaaaagcat gatcaaatgc   44160
agtccctgaa tcttgattgc atcctggata gaaaaagtga gctttgaaag tcactttggg   44220
gcctggcatg gtggcccatg cctgtaatcc cagcgctttg ggaggctgag gcagacagat   44280
cacctgaggt cagtagtttg agaccagcct ggccaacgtg gcaaaacccc atctttacta   44340
aaaatacaaa aattagccgg gtgtggtggt gtgtacctgc aatcccagct actcgggtgg   44400
ccgaggcagg agaattgctt aaacccagga ggcggaggtt gcagtgggct gagattgcac   44460
cactggactc cagcctgggt gatggagtga gactgtgtct caaaaagaa agtcactttg    44520 agaccagtta gggaagtttg tatatgaatt gtatactggt tgatattgaa ttaatgttga   44580 tttctaaga catggtaaat ggtattgtgg ttaggtagaa ttgggtggcg gggggtgcg     44640 gaatatcctt aatctcagac aatggatact tgggtattaa agggtattta agtgccatga   44700
tgtctgcatt ttacttccaa gtaattcaga aaaaaaaag tattttttt gtagtgatga     44760 aagtaaatat gacaaaacat gaataattgg taaatctcgg tgaaagatgc aggtgtctat   44820
tcttttacct tttctgtggg attaaaagat gttcaaaata aaagttgga ggaaattt     44880 taaaagaaa agcagtagta ggccgggcgc gttggctcac gcctgtaatc ccagcactat    44940
gggaggccga ggcgggcgga tcatctgagg tcgggagttc aaggccagcc tgaccaacat   45000
ggagaaaccc tgtctctact aagaatacaa aattagctga gcatggtggt gcatctctgt   45060
aatctcagct acttgggagg ctgaggcagg agaatcactt gaacccggga ggtggaggtt   45120
gcagtgagct gagactgtgc caccgcactc cagcctgggt gacagagcaa gactccatct   45180
caccaaaaaa aaaaaaaaaa aaaggacaa gcagtaggca gtagtagtca aatatttata    45240
ctctgtggtc tttattttc tttggtccct tgatgaatct attttatttt ttgacgttca    45300 ggttttatc agtatttttt tttcttgcag tgagtatcat gaaaaaatta cagacttaat    45360
tataaaatga tttttactca aacttgctct tttttctttt tttaactatt actctgtctt   45420
cagaatccat ctaccgtaga ggtgcacgcc gctggagaaa gctttattgt gccaatggcc   45480
acactttcca agccaagcgt ttcaacaggg taaacatagt ttgttgaatg tcgataatgt   45540
gaaacagcta ttttttccct ttctactatg aaagaaaggt agtttgttat taagtcttgt   45600
tatacacttt taaatacata agtagcatga ccttacattt ccagtttgcc tgaggcagta   45660
tgcctataat ttttaatagc atctctttca ctcttaaaaa tgctccaggc caggtgtggt   45720
ggctcaggcc tataatccca gcacattggg aggccaaggc tgccggatca gttgaggcca   45780
ggagttcata ccagcctggc caacatgca aaaccttatc tctattaaaa atacaaaaat    45840
tagccaggtg cagtcacatg cacctgtagt cccagctact cgggaggctg aggcaggaga   45900
atcacttgag tctgggaggc agaggttgca gtgagccgag attgtgccac tgcactccag   45960
cctgggcaat ggagcaagac tcagtttcaa aaaaaaaaaa aaaagctcc agattggatg    46020 attaattatt ccacataata taccctagct gtaagaaaat tgaattttaa aatataattt   46080
aaggcaacca gaaaacaagc aaggtttatt tatttaatat taatctttat ttttccagtt   46140
agtgttgtaa tttgattttc actgtttaga aaataataat agcaaacact tatctgggtt   46200
gtactacgta ccaggcactt ttccaaatgc cttatataca ttgattcatt tcatccttac   46260
```

```
aacaaccctg taagataggt actatatgtt tccactttat agatggcaaa actcaagtgc    46320
agggcagtaa cttgcccaag ataatacagc tagtaagtga tagaaccaaa gtttgaaagc    46380
agcagtctgt cttcagaagt cagttattca tttattattt atttattttt tttttatttt    46440
aaagacagag tcccgctcta tcgcccaggc tggagtgcaa tggcacagtc tcagctcact    46500
gcaacctgca tctcttgggt tcaagcgatt cttgtgcctc agcctcctga gtacctggga    46560
ccacaggcat cagccaacag gcctggctat ttttgtatt tttagtagag atggagttat     46620
accttgttgg ccaagctggt ctcaaactcc tgacctcgcg tgatccgtcc gcctcggcct    46680
cccaaagtgc tgggattaca ggcttgagcc accatgcctg gccagaaacg aatttttaa     46740 atactcttga taaccgcaaa ttttggatg ccatttccat tctaaaacta atgccatgta     46800
attaattaat gtaaatagaa accaccaccc gaaatccctc tccaaactct cttacttcca    46860
gtagcactga catttaagaa ggctttgagg ctgggtgcaa tggcacatgc ctgtaatccc    46920
agcagtttgg gaggctgcga agggggaaca ctgaagccca ggagtttgag accagccagg    46980
gtaacgtagt gtgagatccc atctctacaa aaatacaat cattagcagg gcatggtggc      47040
acacacctgt agtcctagct actcaggaag cttgagccca ggacgttgag gctgcagtga    47100
atcaaagtga ctccactgga ctccagcctg gctgacagag caagaccctg tctcttaaaa    47160
ataaataaat aaataaaaag agagaccaag tgcggtggct cacacgtgta atcccagcac    47220
tttgggaggc tgaggtgggt ggatcacctg aggtccagga gtttgagacc agcctgacca    47280
acatggtgaa accccatctc tactaaaaat acaaaactta gccaggtatg gtggcgcata    47340
cctgtaatcc cagctactct ggaggctgag gcaggagaat cacttgaacc cgggaggcgg    47400
aggttgcggt aagctgagat tgtgccattg cattccagcc tgggcaacaa gagtgaaact    47460
ctgtctcaaa aaaaaaaag aaagaaaaga agaagaaggc ggctttgaaa tgagaagtca     47520
ctttaggtta ttgctctta agaaaacaga gctttgtttt gacctctgaa cagcctgcaa      47580
ggtttatgtt tgcttaggag tccttcaatg gctttttctg ccatatatat ttctagttta    47640
attctgtttt cattattttg aacttgatta tgtaaagact gaaaattctt agacttagaa    47700
agaaatgtgg ttgcagattt cactgtctct ttaaaataag ctctgttttt cgctgacctt    47760
catagctttt aaaaaattat gtatgaggaa gctttgtttt gcttttgttt ttgttttgt      47820 tgtgggctga cagttgacac cgtgacaaag ggaattgagt cagcaaacta tttgggaaat    47880
ggttatgacc ttcttggtta ataaatatt gttgaattac tcttttcagc gtgctcactg      47940
tgccatctgc acagaccgaa tatggggact tggacgccaa ggatataagt gcatcaactg    48000
caaactcttg gttcataaga agtgccataa actcgtcaca attgaatgtg ggcggcattc    48060
tttgccacag gtaagatgtc tgtccttttt ttttttttt tttttaagag cgtgcttgat      48120
aacactgcta taacagagtg ctaaaatagg gaggtgttca ggaattacag cacaacagag    48180
tagctacaga gtatggggag gaataacctta cgttactgtt aacacaccgt gaactttgga     48240
acttcgaaat atctgtggta atacttgtct gtgggacaca gttaacttct ttacctgctg    48300
taaaatcctc tggtctaaat taggaagcta tagagagaac catttaagag ttttttcccc    48360
ctctccttta atctgaacgt attagtttat agctcacatt attctagctt ctatcctaag    48420
cagatatcag gtaagaagag tcaaaggtat catgtttgtt atttaaactg tgagattact    48480
ggcgaggaaa gcatttaaaa tttttattta ttaatttcta tttaaatat ataaaacatg     48540 tttgttatcg aaaaaaatac agaatacaga tgaataaaga aaactaagta aaagtccaca    48600
```

```
tatattctac catgtaaagg taattgtcat ttggtggata tccttccaga acttttcctg   48660
tgcaaattta tatgcataaa catttttaat tttccatatg gaaaaaatgt aaacatgtat   48720
aagagtaggt ggaacactat aatgaactcc catttactag acatccagct ccaacagtta   48780
tcaactcatg tctaatcttg gtttcatctg taccccatt cacttaactt cccttgccc   48840 tgtattattt tcaaacaaat ctcagacata tttcagtatg tacctctaaa agagaaggac   48900 tttttttaaaa acctaactaa aaaacaaatt ctttatgtca aatatccagt aagtgttctc   48960
ataaatatta taattttgtt tttatagttt tcattatgaa tcaggatcca aatgaaatgc   49020
acttgtacaa ttgattgatc tctttagatat tctttaattt actggttctt tcttcatttc   49080
tctctcttct tttttccctt acaatttaat tgtaaaagaa acagttattt gtcatttaca   49140
ctgttgtaaa attttgctca ttacttctcc atggttatgt tcagtatgtt attgtcttct   49200
ttattctttt atcttgtaca gtagttggat gtcgaggttt gattagattc tggggttggt   49260
ttgtttgttt tggtggattg ttttttgagtc gactttacag agggttgttt atccaccaga   49320
aggcacatgt gcttgcctgt gtctttttg ttattgtttt gagacagagc ctcgctctgt   49380
cttccaggct ggaatgtagt ggcacaatct ggctcactg caacctccac ctcccaggtt   49440
caagtgattc tcctgcctca gcctcccaag tagctgggat tacaggtgtg tgccaccatg   49500
cccagctaat ttttgtattt tcagtagaga tggggttttt gccacgttgg ccaggctggt   49560
cttgaattcc tgacctcagg tgatccacct gcctcggtct cccaaagtgc tggaattaca   49620
ggcgtgagcc actgcacttg gccaatctta gtgaactttc tggcaaatct tacttcctta   49680
aggatccaga attagaatta ctgggttaaa agatacgcat ttaaaaaaat acctggatgc   49740
agctatctaa gcacactgcc tatcgattag ccctgctcca caggaacag tcaaaaaaag   49800 aaagaaaaat acctggatgc atctttctaa attgtccttt agaattgtta ttccatgttt   49860
attcatggga cttgctttgg acattgtgaa agcaggttat taccggtagc tctttggtat   49920
tagaatcttt aattagttca tataagctta ggaatgggtt tgtagtaaag gggaaaatcc   49980
aatcttaagg aaaacagaa ggctgactat ttccaacata tttatgtagg ttactattaa   50040 tattttttgag tattctttgg tgacatatgg aaggaaaggg ggcagggtta gtgattatat   50100 tgaagttttta aaaatcctta agcttactta tgagcctttc tttaacgcag ccttgaaatg   50160
ctaactgtat cattaatgtt ctttctcaag tttactttt cctgctggta ttcattaaat   50220
gtgagtctaa gaataaatca gtaataactt gggtttgaat ttacctttt cctgagatta   50280 ttcgccatta tttgggtaag ttggattcta gaaagtattt cttttctctt ttttgggcc   50340 actgacaccc ttgagaatct tcaggaaaat gggaaaccca caaattttta catgtaattt   50400
taagaggtta tagacatcct gaagtctacc ccggacccca gctaaagaat gcatattcca   50460
gaaacttatt tttgccaaag atctgaagtg gagcttgaag gaagaatagg tagtgttgaa   50520
gagaagcaaa gcagaatata tggcagttta atatgatttc taattggtgg tctgaaatta   50580
gttttgtatt ttcttttctg taaaatgtga ctaacattac ctcattcaca gcagtattgt   50640
atagtttcat aaaacaaaat taaagtaaa ttctcactta agttatattc tttcaaaatt   50700 aaatttaat atgctgtgtg ttgttgaaat agtgttattt ctggtgtaat agaggtactc   50760
cactgagtta ctgtgtcttt ggaaatgttt gtaggaacca gtgatgccca tggatcagtc   50820
atccatgcat tctgaccatg cacagacagg taagagtggt gctggcacaa cccattgttc   50880
attcacagag tagcatgtaa agacttactt aggtgactct cttacccaag tttaaaaaca   50940
tttacttctt cccaattaaa agtaaataca tatattttgt agtggtgaaa tcagtcacac   51000
```

```
tatttaacat acacatttgg cattttaaa agacaactgt gggctgggtg cggtggttca   51060
cacctgtaat cccagcactt tgggaggctg aggcaggtgg atcacctgag gtcaggagtt   51120
cgagaccagc ctggccaacg tggtaaaacc ccgtctctac taaaaataca aaaattagca   51180
gggtgtggtg gcacactcct gtagtcccag cttctcagga ggctgaggcg ggaaaatcgc   51240
ttgaacccag aagttggagg ttgcagtgag ccaagatcat gccactgcac tctagcctgg   51300
gtgacagaac aagactccat ctcaaaaaag agagagagaa aaaaaaaga caactgtggg   51360 ctgggtgtgg tggctcacgg ctgtaatctc atcactttgg gaggtcgagg cagaaggatc   51420
ccttgagctc aggagttcaa gaccagcctg gccaacacag ggagactctg tctctattta   51480 aaaaaaaaa aagtatgtaa actacaacaa atgactattt tttctagttc acataaattt   51540
cttttgagac gcctttaaat tcagcaaact cagttttttt ccataatgaa aaacatgagg   51600
ctgattttgt ggcccatgtt gactgtgttc aggtgactcg cttttttctt tttctttcga   51660
gacagagtct tgctctgttg cccaagctgg aatgcagtgg cgtgatctcg gctcactgca   51720
tcctccacct cccaggttca agtgattctc ctgcctcagc ctcctgagca tctgggatta   51780
caggttcatg ccaccatgcc cagctaattt ttttgtattt ttagtagaga tggggtttca   51840
ccatgttggc caagctggtc tcgaattcct gacctcaagt aatccacccg ccttggcctc   51900
ccaaagtgct gggattacag gcatgagcca tgcacccag ctgaagtgac ttgttttat   51960 taaaagcttt attatcagaa gtagaaatta tgtgaaacat agagagatgc aatataggaa   52020
attccaggaa gatggtgtaa ctgaaaacgt tagatagata caaaacctta aacacgtatc   52080
tgggaaattt ggagagcagt gcaaggaggt agaacagcat gatcttctct ggactaaatc   52140
aagaaaggga aaacaaggga gtttttctgg aaagacaaaa tgcaatctcg tagtcataga   52200
atgatcaact ctatgaaatg caggctcttt tttttttgcc ccaagtagct ttaagaagta   52260
gaagttccat ccttgtctgt tctttacttg accattgtgg tagttaggaa aattctgagt   52320
acaatggagt gagaagtgaa aaccagaggt cctgtatctc tatgtcttag tcatactaaa   52380
aaatttaaac atatcttata gagtcatttg tttagaagga agtgtttgat taatttgtaa   52440
agaagagaaa tgttttaaaa ataacgaaag tacttgttaa aagcagtact tggctaccag   52500
gttgtgatgc ttgctctctt taccctcact aaagattagg atttaactat tgtatttaca   52560
tacaatttgt tattagtagg acagatagtc agttttaaat aatgaaaatt tattcagaag   52620
taaaaactaa aataaaaatc aggagacaat ttttatttca aactcattaa tggttgctgt   52680 tttttctcc tgcaccttt tttttttttt ttttaatgtt tggtattggg tttttagtaa   52740
ttccatataa tccttcaagt catgagagtt tggatcaagt tggtgaagaa aaagaggtaa   52800
gataatttgt cttattgtac attatatcat tagcttttta ataaggctca ggagtttaaa   52860
agtatgacat attgacctgc ttagactta gatcataatg gtgaaatgca aaatgatttt   52920
gtaatgattc cagagttta ttctgattta atttagtaat taaattacta atttaaacta   52980
ggaaataatt tagtgggata acttattttc attttaaat agcttaatct gaaaaattaca   53040 atgtatttaa ggatactgtt taaaatactt ggtagtattg tttaaaatat atagtagacc   53100
cttccgtttt gtgcctgaat tgcttattta gacaataaat gattaaacat attaactgtc   53160 attgttttt tgactattaa gtattttatc agttttaaa acaaaacaaa taattaaaat   53220
gatttgatta aaataataat cagttttttg aaaaaagctt atagtgaaaa agataatcat   53280
gtctcccacc ttccactccc agtttggctt cttggcaacc ttttaaacca tttctagtta   53340
```

```
tgtccataat atttatattt ctgttttca atttttatt tttgtgtatt tctggacatg    53400
aaagatttag ttcacactgc ctcctctctt tcccgtatca ttcttttttt tttttttttt  53460
gagttgggt cttgctgtgt tgcccaggct ggagtgcagt ggtgtgatta tggctcactg   53520
caaccttaaa ctcctgggct caagttatct tcccaccta gcctcccgag tagctaggac   53580
tatagccctg tgccaccaca cccagctaat ttttcattt tctattttgt agagacagag   53640
tctcactatg ttgcccaagc tagtcccgaa ctcctggcct caagcagttc tcccaaatca  53700
gcctctctaa gtgttaggat tacaggcatg agccaccatg cccagccaaa actttgaaac  53760
ataaataaaa gtaaacaata atataacaaa gcccttgtat ctattgttag ttaaaacagc  53820
tatcaattca tgtctagcct tattttgtct actcacttcc ctcactcctg tattattttg  53880
aagaaacctg ttagtcacct atttgatgtt atgttttagt ttcttgttct gtttgtctga  53940
aaaagtcttt ttttctttt aacttttttt tttcttttta ttttttttgt gagacaggat  54000
tattgcacag gcaccgtgc agtggtgcaa tgatggctca ctacagcctc aacttcttga  54060
gttcaagcca cctcagcctc tcaggtagct gggactacag gcatgtgtca ccactggacc  54120
ctcatcacaa tatacaaaaa tttactcaag gtggaataaa gatttaaatg taatacctca  54180
aactataaaa atcctagaag aaaacctagg aaatatcctc tcgacattgg ccccggcaaa  54240
gaattttgg ctaagtctcc gaaaacaatt gcaacaaagc caaaaattga caagtgggac  54300
ctaattaaac tacagagctt ccacgcagca aaagaatcca ccaataaaca gacaacctaa  54360
agaatgggag aaaatagtca caaactatac atccaacaaa gatctcatat ccagaattta  54420
taaggaactt aacagcaaaa aacaacccca ttaaaaaatg agcaaagggc tgggcatggt  54480
ggcttacacc agtaatccca gcactttggg aggcagagtc aggcagatca cttgaggcca  54540
ggagtttgag atcagcctgg ctgacatagt gaaacccat gtctactaaa aatacaaaaa  54600
aaaaaaaaaa attagggcgt ggtggcacac acctataata ctagctactt aagaggttga  54660
ggcacgaaaa tcattggaac tggggaggcg gagattacaa tgagccaaga tcatgccact  54720
gcactccagc ctgggcgaca gagcaagaca ctgttaaaa aaagaaaaaa aaagggcaa   54780
aggacatgaa cagacatatc tcaaaataag acctataagc agccaacaca catgaaaaac  54840
cactcatcgt cactaattat cagagaaata gaaatcaaaa ccacagtgag ataccatctc  54900
acaccagtca gaatagctgt tactaaaaaa tcaacttggg cgtgatggct cacacatgta  54960
atcccagcac tttgagaggc taaggcggaa ggattgagcc tgagagttca agagcagcct  55020
aggcaacata gtctctacta aaaatacaaa aaattagcca ggctcggtgg caggcgcctg  55080
tagtcccagc tgctcgggag gctgaggcag gagaatggtg tgaacccagg aggcggagct  55140
tgcagtgagc agagactgta ccagtgcact ccagcctggg cgaaagagcg agactccgtc  55200
tcaaaaaaa aaaaaaaaga aaattacaaa taacactttt actgtttctc tagaagatgc  55260
agtgaccttg gcacaccta aattcattcc ttttccattc ctgcctttgg gtgttattat  55320
tatcagagtt taaaattctg tgtgtgtgta tatttgtttt tttaaacagt tactccttat  55380
gtagatttac ccacattta ccctttttgt ttttctttcc ttcctacgtc tgttcctcca  55440
tctgagatca tgcatttct ccttcaagaa ctcaatttag ttttccttt agtgagcacc   55500
tagtagtgat ggatccactc agtttttctt tgtctgaaaa tgttttcttt tcactttcac  55560
tttgtgagct acttttgcag gatagagaat tctaggtcag ctgtttttctt ctttttagg  55620
ccctttgaag atgacatttc actgttaagt ggcgtctatc atttcattca gccttattat  55680
tgtgtcggtg aagttaactc tatctttttt gctccacttg attctctctt atagtttcca  55740
```

```
gttagccata tttcaagtct atgtgttgac ttactttctt acacttctct tctttcttaa    55800
ccttctcaaa cctggtttct tttcactctg ctgtatttac ccttgtgtgt tagtctgttt    55860
tgtgttgtta caaggaata cctgaaggtt gggtgtggca gctcacacct ataatcctag     55920
gactttagac cgggaggatc atttgaggcc agtagttcag gaccagcctt ggcaacatag    55980
caagaccctc catgtctaca aaaataaat aaaaattagc cgggtttgga ggcacatgcc     56040
tgtagcccca gctacttggg agactgaggc aggaggatca cttgagccca ggagttcatg    56100
gctgcagtga gctatgttcg tgccactgca ctgcagcctg ggtgacagaa caagaccttt    56160
tcttaaataa ataaataaat gaaggaagga ataaggaat acctaaggct gggtaattta     56220
tacaagattt atttggtgca cggttctgca ggctgatcag taagtattgc actagcatct    56280
gcttctcagg aagctttcag tcttggcaga aggcaaaggg gaagcaggtg tgccacatgg    56340
caagagaggg agcaagggag tcaggggagg tgccacactc tgaactcact cattacacag    56400
gaacacacca agccattcat gaggaatctg tccctgtgac ccaaacacct cccactaggg    56460
atcacatttc agcatgagat ttgagattg gaggggtcag atatacaaac tatcaccttg     56520
ttaccaaatc aaattattat tattattact attattgaca gggtctcact tgtgatgca    56580
ggctggagcg cactggcaca atcacagctc actgcaacct tgacctgcct ggctcaggtg    56640
atcctcccac ctcagcctcc caggtagctg ggactacagt gcacaccacc aacatccggc    56700
taattttgt atattttggt agagatgagg tttcttggca cattgcccag gctggtcttg     56760
aactcctggg ctcaatcagt ccacctgctt cagcctccct aagtgctgaa atacaggca    56820
tgagccactg tgcgcagcct aaattattat ttctaagttt ttaagttgtc attctcactc    56880
agttttcta atacccttct ttcagttttg tgcttgcggg tttctttatc tttctcaaaa     56940
tttactattt gcttttcttg gtattcttca cttcagagat ttcatacttt attctcatgg    57000
gtccattgtg tgctgatgat tttgcaggca tctaataaaa gactgtcttc aggcttctct    57060
gtaaattgct agaagcttac atttgtagtt gtgaatgaat tttaaggctt actttgtcgt    57120
cccaaagggg tcttggtatt ctgtggaaaa gaatgtcttc cattcgctga actacttcat    57180
gcttgttttc tgtctatagc atccaaaaac gcctctgaat gtgtgctctc actagcttac    57240
attctatgta tcaagcttcc agcagactct ttcatcttga tgtctcatta aacttctga    57300
atttatcatg aaaaacccaa tcgttctctc cagtaacttt gtcaatctta tcctagccac    57360
acacttgacg ttccctgtca gtggtacccc caatctcttg gtcaccaagg ttaatgtgtt    57420
ttttaattc ctgcatctct attgcctctg tacccaaaag ttatcgtatc cttttaaga     57480
catccttcga tgttttgtg atttcaactc cctcccatt cttattacca tccctcttat      57540
ctcaaaattc atccatataa tctggatagt tagattattt ggtttggaat gacatttgaa    57600
aaatattaag aacttaaaat atttttatgt taggaaaata tctttaaatc gttataggta    57660
caactaggtg ttagaaatat aatgtactac gcaaagcatt tcccattata actctgatac    57720
aaatgttctc aacaggcaat gaacaccagg gaaagtggca aagcttcatc cagtctaggt    57780
cttcaggatt ttgatttgct ccgggtaata ggaagaggaa gttatgccaa agtactgttg    57840
gttcgattaa aaaaaacaga tcgtattat gcaatgaaag ttgtgaaaaa agagcttgtt     57900
aatgatgatg aggtaagcac tgcatatttt attgcttcta aactgcttga gaatactatt    57960
cttttttttt tttgaaacgg agtttcgctc ttgtcaccca gctggagtg ctagtggtgc     58020
aatcttggct cactgcaacc tctgcctccc aggttcaagt gattctcctg cctcagcctc    58080
```

```
ccaagtagct gggattacag gcatgcacca ctatgcccag ctaatttttg tattttagt   58140
agagatgggg tttcaccatg ttggccaggc tgctcttgaa ctcctgacct caagtgatcc   58200
acccgcctca gcctcccaaa gttgctagga atataggcgt gagccaccgc acccagccaa   58260
gagtactatt ttaaagaaaa cctctatgtt tgtgctttat tatctcattc tgcttttcta   58320
aatatgtgct aagtaaatga atatatattat ttcggtttac ttttcttata gatggtataa   58380
gatatttaaa gtaatttgat tattagattt ttttaaaaaa acaaaaatca aaccacatta   58440
ttatcaggag aaatacttga gctttgtaaa agttttctag acagttttat aatactgaaa   58500
gattgactag tgttattttt ctctttgtat gtaaattttc gtttcatgat tatcaatggt   58560
tttgatattt agcctagtta accattgcat ttgtgaccat tgaattgctc agagcaaatt   58620
tatcattaat tgtgatatca gtttgacata gatttcttac atgtttcaaa ataggatatt   58680
gattgggtac agacagagaa gcatgtgttt gagcaggcat ccaatcatcc tttccttgtt   58740
gggctgcatt cttgctttca gacagaaagc aggtaagatt gaaagatagt agaatgatta   58800
ctgggcttca tattttttggt catattacac agttagaacc tttctgccct aattcatgaa   58860
gttgatatca tggaggatgc aacagtgtta ggcttataac ttcctgctaa taatactgcc   58920
atcagtgata tcagtttgat attagatcag cattaggaaa tgacctactt taggcagaac   58980
aggaaatagc catgtcgtaa ttatggcagt agaaatccaa cctttaaat atccccagta   59040
ttctagttt atgacttaaa attttctagc atttaacaag gaggaaaaat accttgacag   59100
tcgaaaatga cttatttagc aaatgctaaa attaggatgg taatgagtgg ctctggattg   59160
caagtggtac tactttagaa cagaagtagt aggttacaaa attattatca tgctggttta   59220
ctttctcgta tgttccgtac cctagatacc ctttgttttcc accaaaattt tggcatcttt   59280
ttaaaggcta aatagtagag aatgctctct gttgtgatgg tttctgaaaa tgcaaagtta   59340
cactacctta ttttggatct tgatttcatg ggttctctcc tgtgttttag attgttcttt   59400
gttatagagt atgtaaatgg aggagaccta atgtttcata tgcagcgaca aagaaaactt   59460
cctgaagaac atgccaggtg agttttgtt tactgtttgt gttgttttct ttttggggcc   59520
atgtggcttt ttatgtgcag tggttggaaa cagtagataa ataatttatt ttgatactag   59580
ttaattattt gtaagtcatg cagaggctga gctaaaagtt aatttacatt atatatatgt   59640
aaaacaatta tatattcttt tacatttata cacatacatg tacatacaca tgcacacagt   59700
gcttcctaag caattgaaaa gtgtgaacag tattaaaagg caaacccttta gtctgctaaa   59760
accaatcctt ttcaaatatt atgtctatgt agcatcagcc atttaaataa ttgagactaa   59820
taaacactta ttagtctttt caggtttgta gtggtctctc agagagttct tcacgataag   59880
agtgctattc atacatactt gagagtaatt aaacgatccc tctggctggg cacagtggct   59940
cacacctcta atcccagcac tttgggaggc tgaggcgggc ggatcacctg aggtcaggag   60000
tttgagacca gcctggccaa catggtgaaa ccctgtctct actaaaaata caaaatttg   60060
ctggtcgtgg tggcgggtgc ctgtaatccc agctactcag gaggctgagg caggagaatt   60120
gtctgaaccc ggaaggcgga ggttgcagtg agcccagatc gcaccactgc actccagcct   60180
ggccaacaga gcaagactct gtctcaaaaa aaaaaaaaa agatccctct taaactagta   60240
tatacttctg actgttcttc ctgtgattta ttgttctttg gcttttttt cctctaatcc   60300
cataattatt gatgaataaa ataatatcga ataggccagg cgcagtggct catgcctgta   60360
atcccagcac tttgggaggc cgaggcgggt ggatcatgag gtcaagaaat cgagaccatc   60420
ctggccaaca tggtgaaacc ccatctctac taaaaatata aaaattagcc gggcgtggtg   60480
```

```
gcgggcacct gtggtcccaa ctacttggga ggctgaatta ggagaatcgc ttgagcccgg   60540
gaggcggagg ttgcagtgag ctgagattgc gccactgcac tccagcctgg gtgaaagagc   60600
gagactccgt ctcaaaaaaa aaaaaaaaag tattgaatat taattttgtg cccttaattt   60660
gatattaata tacaagactg taaattgttt atgtgttgga tggaggagat aggtgggaag   60720
ggatcatggc cttgagtaaa aagtttaatc catcagtacc atgttttgtt tcttatccgt   60780
aatcagcagt aattctcacc ctttcctact tcacaagagt aatgccaaaa tgaagcatgt   60840
gagtttgtat atgtatgtta ttatcatgca gggaataaat attagaaatt tcatttaaat   60900
taaaaacttg tagaaaattt gctacttcat tattgcttgt caaaaatttc ataagaagat   60960
ataaattgta cttgtctaat cttgaggcca acctgggttt tttgtttatt tgggtttttt   61020
tgttgttgtt ttggtgttca tttatgttca ttgtgtattt atgccttatc aaatggtcac   61080
ccttcataga gccacagatg atattttgaa ttgtgaacat agccaatatt tgttccttgt   61140
ttgttcagtt gaatgtggga aagctagtct ggttttact atattaatgt gccagttttg   61200
gttttatacc atctttgctt ttgtaagaac taaagcccag acaagggct taagttccca   61260 aatcacggaa ttaagtagct aggaggtgta tgttacgtac ctccacacat gatcatgata   61320
atgtgccacc aaagcagcca tacatcagct caggcattcc attttcatta ttcaggccaa   61380
aagttctggg ttgtcaccag tgagttggta gcagttttt taagttcttc atttaatatt   61440
aaattttaca gttgtttata gttgtagaat attttcattt aattccttt ctaaaacctt   61500 catgaggatt ttatagtatt gagtagtcag cttgtagtat tctttctatt ctcgacccca   61560
ttagtggttc ttagccttct cggaggatca cgggtccctt agagaagtga tgaaagcttt   61620
gaggactctg tagatactgt gcatgtacat acgggcatac acctttgccc ccagttgtag   61680
aagtatggac tgcctgaagt tcacccaagg acccagattg agaacccctg tttgagacta   61740
tcaaattaat agctttatga aaatgtgag tttaagttag acaggaactt ttacaattgt   61800
gtcttgggct cagatgtttt aaagtggtac ttcagttcat ttttcaaatt gttcctaaa   61860 atcactggga gaaaaaata tgttttaata tgaatttttg tgtttccagt tgtaaatgta   61920
gaacttaaat atggttgaat caaatgactt attttttatt taatttaga ttttactctg   61980 cagaaatcag tctagcatta aattatcttc atgagcgagg gataatttat agagatttga   62040
aactggacaa tgtattactg gactctgaag gccacattaa actcactgac tacggcatgt   62100
gtaaggtgag gaaaattttc tagttatttt aaaaggtctt cagcagctag tagtctttgt   62160
aaaataactt catgtttaaa gatgaggaaa tgattactaa ttttgctaat ttacttaagc   62220
tttgtggaat tctagcacaa agacaaatgt acttttttc taaccatttg caaaatttgt   62280
atcttctgtg ttatgtgtac tacaataaga gctaatttct tttattata cataacttt   62340 tatcttgaaa gttgaaatac aattgaagac aatttggaaa taaaaattgt ctgcaattcc   62400
actacttaac acaaccattt gcatatgacc ttccaatttt tgccatttag tagtgaatct   62460
tatataatgc attcaggatt ttcctcagaa gtcaaacatt ttttatattt aaattttaaa   62520
catctgacat aaagcataat aggataaaac aagaatttca gttactcccg gaatatgtct   62580
tcatttcttt ttttttttt tttttgaga cagggtcttg ctctgtcccc caggctggag   62640
tgcagtggcg caatctcggc tcagtgccag ctccgcctcc cggggttgacg ccattctcct   62700 gcctcagcct cccgagtagc tgggactaca ggcgcctgcc accacgccca gctaagtttt   62760
tgtattttta gaagagacgg ggtttcacca tgttagccag gatgatctca atctcctgat   62820
```

```
ctcatgatcc gcctgcctca gcctcccaaa gtgctgggat tacaggcgtg agccatcgcg   62880
cctggcctat ttcttgatgt tttattcttt tataacagtg ttccatttta aatgtctgat   62940
attttcccac taaatgtgta aggaactatt ccttgttaag gtaactggta caaaattatc   63000
ctcacatagc aatacaacaa ccagtatgta aatgtgtgaa ttgcattccc tgttcacctg   63060
tgggaagtgc ctccagagcc tggagattat ctaaatgcta acaacatggc atatgacaac   63120
ctagttgtat cgaagattta actttattat ctgttcagca tgcattaaag aataaaatct   63180
tcacttaaac tatgtttgct tttatgtaca gaattcaacc gtacttttca catgatactt   63240
attaattaat tattgttgtt tttttttttt ggagacagag tctcgctctg tcgtccaggc   63300
tggagtgcaa tggcacaatc ttggctcact gcaacctccg cctcctggat tcaagccgtt   63360
ctccagcctc agccttccaa gtagctgaga ttaaggtgcg ccccaccatc cctggctaat   63420
tttaattttt ttttttttt tttaattttt gagacagagt tttgctctta ttgcccaggc   63480
tggagtacaa tggcacaatc tcggctcact gcaacctcca cctcccaggt tcaagcaatt   63540
ctcctgcctc agcctcctga gtagctggga ttacaggcac ctgccaccat gcccggctaa   63600 ttttttttgta tttttagtag agacggggtt tcaccatgtt ggccaggctg gtcgcgaact   63660
cctgacctca ggtgatccac ccgcctcagc ctcccaaagt gctgggatta cagatgtgag   63720
ccaccatgcc cggcccttac gtatttatat tatacaagtt ttcaatcata acaattaga   63780 aagcttagcg agtggaaccc ctatgtacct atcacttata tttgtggtac cttttttgatc  63840 tctgtgtcat tttttttcct aagggatttt tttctcattt cagaaaaaag tgacagtgat   63900
agaggagtct tatccccaag aataaatgaa actgaacaaa aaacatggag agtattaccc   63960
ttcatacgaa gtgcacaaat taaaacaatg aggcttttt tttttttttt tttttgcct    64020 gtgagatacg ggttttaaag ttagaatagc ctgtatgtac aagagtttaa agaaatgggc   64080
atatgtcact ggtgtgtata taaattgtta caaaccttt gagaagcagt ttgatggggg    64140
aattatcagg aatcctaaag atggccatgt tctttgatcc ggtaattctg cccttggata   64200
ttctgagtaa atattttggt ttatgaggag agatttctga ccaaaacttt tattgtagtt   64260
tatgatcaat attataaagt catttaagaa gatctttatt tttattttat ttttactttc   64320
tttttttttt ttttaaatag agacgaggtc tcgctgtgtt gcccaggctc gtctcaaacc   64380
caagagttca taatgttagc atttagataa tctccaggct ctggaggcac tttcctcagg   64440
tgaatgggga atgcagttca tacatttaca tatttgtcat gttactatgt gaggataatt   64500
ttgttccagt taacaaggaa agcaagccac cacgcccgac tgaagatatt tgtaaaaaat   64560
acataacaca tgatggctca gacctgtaat cccagcaatt tgggaggccg aggcaggcag   64620
attgctggag ctcagaagtt cgacaccagc ctgggcaaca tggcaaaact ccatctctac   64680
aaaaaatagg aaaattacac tgggttggtt gtgcttgtag tcccagctac ttgggaggct   64740
gagatggggg gatcacttga gcctgggggct gtagtgagct gtaatcgcgc cactgcactc   64800
cagtctgggt gacagagtga gatcctatct aaaatatata tatatataga gagagagaga   64860
gtaataaata tatatgta tatacataat gcttataaca gatgaagtct taacatatag    64920
aattgtctga ttcttttatg tatcattctg ttatgtagca tcacacgttg attctgttta   64980
cttttcagca tttttcaagt tgttatttta aaatgttatg ttaaatgtgg ttaccaattg   65040
cattacagta cactaatgca ttttaataac attttaaaat gttattttta aataacacct   65100
ttaatggaat cactgcattg tttaaacaat caaaatgggc agggtgtgat ggctcacacc   65160
tgtaatctca gcactttggg aggcccggca ggcagatcac ttgaggtcag gagtttgaga   65220
```

```
ccagcctggc caacatggta aaatcttgtc tctactaaaa acaccaaaag attagctggg   65280
catggtggca cacctgtggt cccagctact caggagacta aggcaggaga attgcttgaa   65340
cctggaggca gaggttgcag tgagtggaga ttgtgccact gcactccagt ctgggtgaca   65400
aagtgagact ctgtctcaaa aaaaaaaaaa aaaaaaaaag aaaatcacaa aaatgaatta   65460
agacttttct cttggccggg tgcggtggct tgcacctgta atcccagcat tttgggaggc   65520
cgaggcaggc ggatcacagg tcaggagatt gagaccatcc tggctaacat ggtgaaaccc   65580
cgtctctact aaaaatacaa aaaaattagc caggcgtggt ggcggacgcc tgtagtccca   65640
gctactcggg aggctgaggc aggagaatgg cgagaacccg ggaggcggag cttgcagtga   65700
cccgagatcg cgccactgca ttccagcctg gcaacagag tgagactacg tctcaaaaaa   65760 aaaaaagga cttttctctt tttgtctttc ttagtctttt gttactctta ctggaaaata   65820
atattggctt cttatacatt ttcatttctt acagggatcc tcaatcaagt tagtcaaggt   65880
gtttcataaa tctgagatct ttatcgagta ggtctttaaa tcaaatgtcc tcctacctcc   65940
ctttctgcct ttcctccttc tccaagagct gcctagggcg ggtgcagtgg ctcacgccta   66000
taattccagc actttgggag gccaaggcag gcggattact tgaggtcagg agtttgagac   66060
cagcctggcc aacatggtga aaacccatct ctgctaaaac cacaaaaact agccaggtgt   66120
ggtggcgagt gcctgtaatc ccagctactt gggaggctga ggcagaagaa tctcttgaac   66180
ctggggtggg gtggagattg cagtgagcta agatcacacc actgcactgc actccagact   66240
gggcaacaga gtgagactcc gcctcaaaat atatacatat aaaataaaat aaaaaataaa   66300
gcttatgaga aattaaccct ccaaaagttt gaatgctctt ttatgactta gtgtcaatat   66360
ttaacttacc tgaagcttga cttcatgcaa gtgttggatg aatttcttta taagattgc    66420 agaggatagt gatgaaaact tgaattagta tctttagagt tatgtttgaa atattttatg   66480
aacgttgatt ttattaagtg gcagcctttc gtggttttat gaactgatgt gcctttaagt   66540 gttttttttca tcaacagagg aattctaata atatctgtta tgctgcagaa aacttagcaa   66600
atggacctac attctgacat tcagtcaaca agtgaatgat taagcatagc tgttacaagt   66660
taacagacta catctcttac ctctgactat tgtactgaaa gtacatgtca tttttcatga   66720
gaatgtattg ccgttgccaa taatagaaaa caataaaaac catattcata tttctaaaaa   66780
tagcatataa tatcccttt agaaatcatt ttaaaattct tggagtcaca acatattact    66840
aaatatttct tctagatgtt tatagcagtg ttatatataa cagggtgaaa tttgaagaaa   66900
aatatgttca ccatgcccag aatgtctctg gagggccaca taatagtggt tgcctctagg   66960
gagctggaac tgggtgagtc agggacaaga atggaaggaa gggccgggca cagtgctcac   67020
gcctgtaatc gcagcacttt gggaggctaa ggtgagtgaa tcacctgagg tcaggagttt   67080
gagaccaacc tggccaacat ggcaaaaccc catctctact aaaaatacaa aaagccagag   67140
gctcggcaca gtggctcact cctgtaatcc cagcactttg ggaggccgag gcgggtggat   67200
cacttgaggt caggagttcg agaccaacct gaccaacatg gtgaaacccc gtcactacta   67260
aaaatagaaa attaggtggg cgtggtggtg catatctgta atcccagcta cttgggaggc   67320
tgaggcagga gaatcgcttg aacctgggag gcagaggttg cagtgagccg agatcgcacc   67380
attgcactcc agcctgggta acgagcgaaa ctccatctta aagaagaaa aaaaagccag    67440 gcgtggttgc atgcacctgt aatcccagct acttgggagg ctgaggcgtg agaatcactt   67500
gaacctggga gacagaggtt gcaatgagcc aagatcacgc cactgaactc cagcctggat   67560
```

```
gacagagcga aactcggtct caaaaaaaaa aaaaaggaag gcttgagttt tgtgctgccc   67620 ctctttttg gtttagaatt ttgtaccgta taatctatag gaaagtggtt aagttctagg    67680
tacatatgtt ctgttgaatt tcatatagtt gttaatatta gaaagtcttc ggttgtgtag   67740
gaaatgctta caaagtttta aaacatgctt aattatgtat gattcagttg tctttagact   67800
tttttattgt tgatttttt tttatttgcc ttttggccag agaatggttt gaatattagt    67860
tcattggaat acattgagat ttcctttatg acctaatata tggccagtag cccatgtgta   67920
cttaaaagga tatataatct ttacatgcag ggagtctctc tctctaatgt ctctcttcct   67980
tctccctcac tccacacaca catatagacg tacatatatt ctacatgtat atgtattttg   68040
tatatatata tatatatttt aactctagct ttttccaaa tctttctctg cctactgatt    68100
tttagtatgt gtgatctatc attttctaat atagattatt ctcatattaa cttctcctat   68160
tatgattgga gattgtgaaa ttctcctaat aattttgtcc tttttactc tttgtattt     68220 gaggccatgt tgttgagtgt atgcaagtgt atatttgtta caatttcttg gtgattgtcc   68280
cattaattat tgggtagttc ctttactctg cctgttagtg tgttttgcct tattttttt    68340 ccatcctaca gctattaaaa tacaggcccg gcatggtggc ttatgcctgt aatcccagca   68400
ctttgggagg ccgaggtggg cagatcatct ggtcaggagt ttgagaccag cctgagcaac   68460
atggagaaac cccatttcct actaaaaata caaaattagt tgggtgtggt ggcacacgcc   68520
tataatctca gctactctgg aggctgaggc aggagaattg cttgaatccg ggaggcggag   68580
gttgcagtga gctgacattg tgccattgca ctccagcctg gcaacaaag tgaaactctg    68640 tctccaaaaa aaaaaagtg ttcttaggaa aaataaacag aaggaaaata ttgtagtctt    68700
atcaatggtt gtattaggag gtgagattta aagtgcttct tttcttcatg aaatatgcct   68760
tattctacta atattaaaat tttgttatta aattttaact tgtatgtaaa ttattttaaa   68820
ttcaagtcgt accttaattg aatcaactct agcaacatct aatgaggaca ggttttcttc   68880
aagctattta gtggtgatct gtgattttaa taataaaggc agttgccagg catgatggct   68940
catgcctgta atcccagcac tttgggaggc cgaggcaggt ggatcacttg aggccaggag   69000
atcgagacca gcctggccaa catggtgaaa ccctgtctct actaaaaata caaaaattag   69060
ctgggtgtgt tggtgcatgc ctgtaattcc agctactcag gaggctgaga cacaagaatt   69120
gcttgaaccc aggaggtgga ggttgtagtg agctgagatc gtgccactgc atgccagcct   69180
gggcgacaga gcaagaccct gtcaaaaata ataataataa taaaggcaat tgttctagtg   69240
atgttaagtg agcttaatgt atcactgcag atgctgaact tatatgatag gtgaaataga   69300
aagggtgaat ttaaaacaga acttttatc tcattctttc tttctgttct ttttaataaa    69360
aggaaggatt acggccagga gatacaacca gcactttctg tggtactcct aattacattg   69420
ctcctgaaat tttaagagga gaagattatg gtaataaata aattggtggt attattttag   69480
ctattgctag atgggtggta aaatgtggta ccaattgcat tacagtacac taatgcattt   69540
tgacgtgatc ttattaatat aaggattctt gatcctgtta aaaactacat ggagagtccc   69600
agactttgaa atcgagacag tgggaccttg gcagtatttg ggggtaccaa gctgaataat   69660
attttattag tggcaaacac taaacagtag caggcactat tctaagcagt ttacatatat   69720
taactaagtt aatcctctta acaaccctgt gaggtaagta ctattaattc tccttttaca   69780
gttgaagaaa ctgacatacg gaaagtttaa ataactcgcc taaggtcaag gattcagaac   69840
agcacccatg tgactccaga gtcatgaacc cctggaaaat ttttcagatt tcctgggata   69900
tttgccccag gaatctgaaa gatggtggaa agattaactg tatctcaggc acccgaagat   69960
```

```
acacttatct tgagaaaaca tttgacttttt tgggttttgg ccctctgcct tcagcagata    70020
taaaggacaa tgtggtactt gtgagagctg ctcaaagtct gaatccactg tccttcactg    70080
gtctttatca gctagcaaaa gatcaagttt aagaccaagg aggcaggaga atggcgtgaa    70140
cccgggaggc ggagcttgca gtgaaccgag attgtgccac tgcactccag cctgggcgac    70200
agagtgaaac tctgtctcaa aaaaaaaaaa aaagccccctg tccacacctc cagcagttgc    70260
caacatatag ccgggcgcgg tggctcacac ctgtaatccc agcactttgg gaggccgagg    70320
caggcggatc acgaggtcag gaatcgaga ccattctggc taacatggtg aaaccctgtc    70380
tctactgaaa acacaaaaaa ttagccgggc gtgttcacag gtgcctgtag tctcagctac    70440 tcggaggcc gaggcaggag aatggcgtga acccgggagg tggagcttgc agtgagccga    70500
gattgcacca ctgcactcca gcctgggcga cagagtgaga ccccatctca aaaaaaaaaa    70560 aaaaagacc aaggagatta ctctgaaata caatttaatt atatcctcaa cacacaatat    70620
tagatattgg gcatgagtct gaaagtagaa atacatggag aaagaaagtt ttttttctc    70680 ataattttat ttttaaaatt atcttttagg tacctaccct tgttgataaa tgaagcattt    70740
ctataatctt cagtgcctac catgatagtt ggaatgcatt tagagtttac tttttcattg    70800 tttcttttc ctttatgtga taaaatttcc agttactaac tttcaagaat gcaaagtgta    70860
taatttattg ctttaaaatt tctttctgaa ggtttcagtg ttgactggtg ggctcttgga    70920
gtgctcatgt ttgagatgat ggcaggaagg tctccatttg atattgttgg gagctccgat    70980
aaccctgacc agaacacaga ggattatctc ttccaaggta atttggagta ttttacagag    71040
attctctgag aaaaacctat tctagagtac aaatgagagt gattcaggtt actactttga    71100
gtaagaaaaa tgagcataat ctggaaaata taatcctgac tggtggtatt aggttttgtt    71160 gttgttttg tttgtttttg agacaaggtc tcactctttt gcccaggctg gagtgcaggg    71220
gcgcaatctc ggctccatgc aacctccacc tccctggttc aagcaattct tctgcctcag    71280
cctcccgagt aactgggatt acaggcacac tcccgagtaa ctgggattac aggcacacac    71340
cactatgccc ggctaaattt tgtatttta gtagagacag gtctcaccca tgttggccag    71400
gctggtcttg aactcctgac ttcaagtgat ctgcccacct cagcctcccc agcatgctga    71460
gattacaggc atgagccact gcacctggcc tctgtgtatt aggttttgat gttttttaat    71520
acattctttc ttttctatag tcttcactcc tgttcacagt taccttctca tactcaaaat    71580
cataacaggg gttatttaga attatccatc acaaacagat tggagaaagg aatcctgtgg    71640
ctagagagat aatctttaca cagggaccct gaggctgagt gcataagttc aagaacagta    71700 tgagggggaaa atagagcacc aagatgatga gtgatcaaaa gatggggaaa aaaggcccca    71760
catcagggaa tatacagaat tgacagaaac aagcagacaa gtgcagggac ctctagcaca    71820
gaatccaaag aagtatgaaa actactataa aattctacat ttaataatta aagccatcac    71880
aggatataaa taggcatttc atgcccaaat ggccatggaa tatgtgaaaa gacattcagt    71940
ctcactagca attaagggaa tgcacattaa atgttaatga gttaccattt catatcggta    72000
catttgatca aaatattaaa gttgggtaat accagtgctg gtgaggatgt ggagcaactg    72060
gaactcttct agactgctgg taggaatgaa aactgacaca acagctttaa agaataattt    72120
ggcagtgtcc aaaaaaattg catattatat atgctaagca ttttacaaat gttaactcat    72180
ttaaacctca taacaatcct atgaagtatt ttttattcc tattttacag atgaggaaac    72240
tgaggcataa ttaggtagtc aaagaataag acattcatgt aaatgataaa tagtattcag    72300
```

```
attagaggct tctctgaga agatgggaaa agaaggggtt taggaaagta caggaggcac    72360
ttcagttata tatgtaatat cttatttttt ttcctggaat gccttaaata tcttataata    72420
aaaatttaaa gattgcaccc aggcatagtg gctcacatct gtaatcccag cactttggga    72480
ggccgagatg ggcggatcac ttgaggttag gagtttgaga ccagcctggc caacatggca    72540
aaaccccgtc tctactaaaa ataaaaaaaa attagctggg cgtcgtggcg ggcacctgta    72600
atcctaacta ctcaggaggc tcaggcagga gaatcacttc agcctggagg cggaggttgc    72660
agtgagctga gatcgtgcca ctgcactcca gtctgggcaa gacagtgaca ctctgtctca    72720
aaaaaaaaag aaaaaagaaa tttaaagatt gccaggtgca gtggttcaca cctgtaatcc    72780
cagcactttg ggagtccaag gcaggaggat tgcttgaacc caggagttca agaccagctt    72840
gagcaatatg gtgagaccct tatctctaca aaaaaattta aaattagcca gccattgctg    72900
ggcgcagtgg ctcacacctg taatcccagc actttgggag gctgaggtgg gcggatcact    72960
taccttcatg aggtcaggag tttgagacca gcccggccag catggtgaaa ccccatctct    73020
accaaaaaca caaaactcac tgggcatagt ggcacacgcc tgtaatccca gctactcagg    73080
aggctgaagt ggtagaagca cttgaacccg ggaggcagag gttgcagtga gctgagatcg    73140
tgccactgtg ctccagcctg gatgacaaaa caagactcca tctcaaaaaa aaaaaaaaaa    73200
aaaatttagc cgagcgtgat ggtggcgcct gtggtcccag ctacttggga ggttgaggtg    73260
gaaggattgc ttaagcccgg gaggtcaaag ctgcagtgag ctgtgattgc atcactgcac    73320
tccaacctgg gcaacagaac aagccccttt caaaaaagaa gaaaaaagat taaagccatg    73380
taaaagttaa atataatact ataatttta tctttctagt tattttggaa aaacaaattc    73440
gcataccacg ttctctgtct gtaaaagctg caagtgttct gaagagtttt cttaataagg    73500
tataaattgt gtataagaat attttgtgat ttgtctcttt ctatatatat caaactggtc    73560
agtagcggtt tgggaaatgt aaaattccaa aacagtagag aatgtaactt tttcagtttg    73620
acccagaatt tgtctcttac ccaaagagta attgacagca ttagatcctg agataagtta    73680
gttgtccttt ccatttggc aataaaattt actccccagc tatatattac ataattttg    73740 tgtatgtgta aataatatat accatattct cacatagggg aagagttaat ctttgggttt    73800
agccataatt gtactttgaa ctctgttcc attttctctg tatcattatc catagaatct    73860
atttattacc atgtactttt tgagcacgtg ggccgcagtg ctccctacaa attctcatgt    73920
caaaaatgct ataattaggt aagattcgga agaaatgaaa tgctatcttt ggctcttaaa    73980
aatgtgaaca tcattcaatt gtttgttgct gttggtaggc tagaggagtt ttaggatcta    74040
ggagtgtggt cttggcaatt ataaattcta ctttaaataa atggtatgat agaaaagttg    74100
atgtacattt accttctaag gtaaatagat aagataatga gttttaataa aataagaaat    74160
tgaagccttt taaaaaatga acaatttatg tgaggaaaga tttaaacttg aaacctaatt    74220
tttcacatag tgaaaaatga aggcaagagg tgttgatatg caaaataaaa tacctttat    74280 cagaaagaaa aatgggaaca tattctcatt catagtgatg aataagccaa gacttttat    74340 aagttgcagg ctcctcagtc cagtgattca gataatggtt gtatcattgt cttacacagg    74400
tggtggtttg ttgctataat tgggcatggg gatttaaat taagctaaaa acaaacttct    74460
catgaagttt ggaggtttgc atgttttgac tctcacacta ggtcatgcaa agaaatggct    74520
gggtgctgtc aaatgattct gctgttctct ttttcctcct gttttctttt agcaaggaat    74580
tggtgatgat tctctgtttt aattacatga tgggtggaga aagtgccttg aggaatcaca    74640
agtttcaaat aactcaattt gttctggagt tgtactttct agaaataaaa ggtagaccat    74700
```

```
tccaacttca gaaataagag tatcatgtga gggcacacaa cacagatcac aaagatgatt    74760
tattttaaag catgacattc acccaattct tgaaacattt ctttcaccat aggaccctaa    74820
ggaacgattg ggttgtcatc ctcaaacagg atttgctgat attcagggac acccgttctt    74880
ccgaaatgtt gattgggata tggtatgtaa attttgatta ctcaactatt aggtttcatt    74940
attatcttgg gccaattttt tgttgttgtt ctgtttgttt ttagacagag tcttgctctg    75000
tcaccgaggc tggagtacaa tggcacgatc tcagctcact gcaacctccg cctcgcgagt    75060
tcaagcagtt ctgtctctgc ctccctagta gctggaatta cagtcactca ccaccatgcc    75120
cagctaattt ttgtattttt agtagagatg ggggggtttt cacaatgtcg gccaggctgg    75180
tctcgaactc ctgaccctcag gtgatacacc cacctcggcc tcccaaagtg ctgggattac    75240
agatgtgagc caccacaccc ggcctatctc gggccaaatt ttattgtctt agctaacata    75300
tcacagcttt aaaaacttaa aaccactttc taaactgctt tttagaaaac ttttaaaaca    75360 aaaaaaaat tcaattttt tttaatttat tatttttttt ctgagacgga gtctcattct    75420
gtcacccagg ctggagtgca gtagtgtgat ctctgctcac tgcaacctcc acctcctggg    75480
ttcaagcaat tctgcctcag cttcctgagt agctgggatt acaggcacac gccaccacgc    75540
ccagctaatt tttgtatttt tagtagagac ggggtttcat catgttggcc aggctggtct    75600
tgaactcttg acctcaagtg atccacccgc ctcagcctcc caaagtgctg ggattccagg    75660
ggtgagccac catgcccagc caaaaaattg aatattaatg taataaagca ggttgtaatg    75720
ttattaaggc ccatatcaat gtttatactt gttttttattt ttttaggaga aacagtctca    75780
gtccgttgcc caggctgtag tgtagctcac gacagccttg attgaactcc tgagcttaag    75840
agatcctcct gtgtaacctc ccaagtagct gggactacag gcataagcca tggtacccag    75900
ctaattttca atttttttt ttttttttt tgagatggtg tcttgctctg tctcccaggc    75960
tggagtgtag tggcacaatc tcagctcact gcaaccttcg ccacctgggt tcaagcgatt    76020
tctcctgtct cagcctccag agtagctggg attacaggtg tgtgccacca cacctggcta    76080
atttcggtat ttttagtaga dacggggttt agctatgttg gccaggctgg tcttgaatcc    76140
ctgacctcag gtgatctgcg cacctttggcc tcccaaagtg atgggattac aggcgtgagc    76200
cactgcaccc agccaattttt taatttttttt atagagatgg gatcttgcta tgttgtctgg    76260
gctggtcttg aactcctggc ctcaagtgat cctcccatct caacctacca agcggttggg    76320
attacaggcg tgagccgcca tgcccagctc atatttgtaa attatgttca tcattgctaa    76380
tatcattgaa ccatgcttca ggactcactt taataaggta aacaatgagt gcagaggaga    76440
actgtagagg tggagttttt ctaagaatac agacttgagc tgtcatccag tatgtctttt    76500
cagatggagc aaaaacaggt ggtacctccc tttaaaccaa atatttctgg ggaatttggt    76560
ttggacaact tgattctca gtttactaat gaacctgtcc agctcactcc agatgacgag    76620
taagtaattc tgtacactga aatttttttt taagttcttt ggaaatccca ttttagtga    76680 ctatgcaatg tttcattatc agattatact ataattttt tatttctat tttatttcat    76740 tttattttat tttgagatgg agtctcgctc tgttgcccag gctggagtgc agtggtgcaa    76800
tctcggctca ctgcaacctc tgcctccag gttcaaatga ttctcctgcc tcagataccc    76860
tgagtagctg gtactacagg cgcgtgccgc cacgcccagc taatttttgt atttttagta    76920
aggacagagt ttgccatgtt ggccaggctg atcttgaact ccagacctca ggtgatccac    76980
ccaccttggc ctcttaaagt gctgggatta caggcgtgag ccactgtgcc cggcctatac    77040
```

```
tataatttat acaaccattc agttactggt atttgtatct actgtaccat tataagtttt   77100
aatagtaact gtcattttct cctttgcttt atagtgcatt atcttatttt cacaacaact   77160
ttgtaatcta gttactgtca tcttcgtttt acagatgagg aaaccaaggc tcagagaggt   77220
taagcaaagt tacacagcta tcaggtggca gagtcaggat tcaaacccaa atctgactga   77280
ctaaggcctg tgctctttct accacgctgc actgtttccc atttgacaag gactgtcttt   77340
gagttcctga gtattgcctt aagatagatt cctagaaaga gaattaggtc agagggtatt   77400
aacattttaa agctcttgta ttgccaaatt gctttttta agaaattaca ttgagttatt   77460
aaatccagcc atcagtgatc tggtatattt tttgtgctta tacttcatct tttaaacatg   77520
tagtttggaa taattgggag atattttgat tatttacctg ttgttacaga ttcattctct   77580
ctaatctcag ggaggcccott attgtttggc agtcatttca cttctatctc atttcttacc   77640
acatttctcc cagcacctgc tccaaacagt ctcttcattt cagaagcctt cagttctact   77700
ccttttttcca tcactgttaa tggattaacc ttgtcttaat ttgatgcaag gactgataac   77760
ctctctgacg tgaccttgcc tcctttgcag ctgtccccag accaccttgc atctcagaat   77820
tgctttctaa ctcttttcat cattttctta ttccctactc ttggaagact ctcctttaca   77880
aggggtgtcc ctgctatttt cctagacctg tttccttagt tttctccaag atttcatttt   77940
gtcagttatc ttttttattag accttcttta tttttttcta gcttgtttcc ctctgtgtaa   78000
gcatgctcag atactctgat ttttccccct aactcatggc ccctctttga caaccacgt    78060
ttttcctcat tttcatttca tcttaaagcc tcaaaaaaaa aaagttaat agatgttcat    78120
ggtcaaagaa aaataaatac acagcacctc taatcaaact tcttcagact agtcaacatt   78180
gattgtcttg aattttttt tttttttttt ttactgtcaa cacttcaacc ccttacaatc    78240
gaacctgtcc tccagctttt gaaggttgaa tcaatttctt aatttctaaa ttgtaaagca   78300
ttttggggtc agtcctcctc tcccttgatt aatgtaaagc atttggtact catggctttg   78360
ccttgggtag cactgcctat tctggttctg tttcatctct gtgactactt tcctctcatg   78420
tgttttccct gtccccttga gaccaggatg ctccatggtt ctgttcatga cagccttctt   78480
tttgctatat gcagtttgta ccttggagat ttcagccagc cctgtagcat agataccagc   78540
taattaaatg gctctcagtt aaatggcaaa tggttattga gcaaaaggtg ttatggtaaa   78600
tactagacat tcaaagacaa tcaagacagt ctgatctccc caaaagcgtg ctgtctacta   78660
gaggagaaag atgtgtacca agtcattatt tctgacagca ttgtgtatta gaaggaacac   78720
tggatttaat caaaagatag gagtttgaat cccgatgcca cctcttacca actgggtaac   78780
cttggatagg aattgcataa cttctctgag cctgttctca aattgcctac ctcataaggt   78840
tgctgtgaag aataaatgca tgatggtttc tgaagcactt atcccctgcc gttagatctc   78900
ctgagctgca tttctgttta acacggcccc cagtttgtca gccaagcagc tcaaatatat   78960
gaagtctaaa atgaaagtaa tgacccttta tgatctcttt ctattgttct caatcagttc   79020
cttttttttt agttacctaa ttctgctcac ggtgtgtccc tgttgttcag attccagatg   79080
tcagtgattg tggactcctc cttttttctta acagattaca taatacctgc agctgccaag   79140
tctttgtctg tgttttcatt atttcatcat ttacatcaga tctttctttt ctcttcccgt   79200
tgacacaccc tagttcaggc ctcattcaag tcatacccag agtattgtat cagcctccta   79260
attgatcttt actccttcac tttgcaacct attctgtatg ccttgtgaag taccactcca   79320
attcttgaac ccctttaatt agaaaccttc agtaactcct tcattgccta tcaggtaaca   79380
tctatcctct tggctagcat ttaaggcctc cccacatctg ctccagcctg actttctagc   79440
```

| | | | | |
|---|---|---|---|---|
| gatacctctc | accataatac | aaacagtgtt | ctgatcagtc | ttagctactc | accattccct | 79500 |
| agtagtatta | ttgtctctgc | ttctgcctgt | tcattcctgt | gtatcccgcc | ttcatttta | 79560 |
| cctattgaaa | ttttcccatc | tttcagagcc | acctcagatg | caaccagatc | tttgatggat | 79620 |
| caaggtgaaa | ctccttagtg | taaacatcac | tggcctcttt | gatttagcca | ttatttttct | 79680 |
| tcagcatcat | ctaacacact | tctattcctg | tgctccaccc | taattacttg | catttcccaa | 79740 |
| gacctaccac | agtctttcat | cattccattc | attaagtgtt | tgcagaatga | atactgcctt | 79800 |
| ccttgatttc | tccaactaga | agtcacacct | ttctttagaa | ccatggttag | aacaggactt | 79860 |
| agcttattgt | gtataaaatt | taacaagtac | tgctttctct | tccagtagga | attacctccc | 79920 |
| ttccttgaag | gaagggactg | tatcctctgt | aactttgtgc | ttcttagtat | ggcataatac | 79980 |
| atttatgtat | taaatatttg | atagcactac | tcactgtata | ttaaagtaga | agcccagtgt | 80040 |
| aacaaaatgc | caacctctcc | cctctctgtg | acccatgatc | tccctgcggt | gttctctcct | 80100 |
| cattccaggt | ctctcagtgt | acttgttcct | attgcctttt | ccttttggct | aacttcttct | 80160 |
| gggctacact | atctaacatc | tggctgttga | ggtgactact | aaattgaatg | ctaattcaaa | 80220 |
| cctggatgtt | cacctgtaac | taggaatgtt | gttctggtca | aaagttaaga | ttaactggaa | 80280 |
| tggtgacaac | tggtgtcttt | tttattcgca | gtcctcagtt | ttgaactcct | ttttggctct | 80340 |
| aaacttgctt | gtgggattat | cggggttttt | taaattttca | gtactccatt | cttgattcgt | 80400 |
| ctagaaaatc | tgggggatta | atctaaaaat | ttatagattt | cctttcagta | caattagcct | 80460 |
| aattacttga | tttttaatct | tattttacca | tttaaaggtt | gaagaaatct | tgattatgat | 80520 |
| gaaaataaat | ttatttttct | ttcaacagtg | acattgtgag | gaagattgat | cagtctgaat | 80580 |
| ttgaaggttt | tgagtatatc | aatcctcttt | tgatgtctgc | agaagaatgt | gtctgatcct | 80640 |
| cattttcaa | ccatgtattc | tactcatgtt | gccatttaat | gcatggataa | acttgctgca | 80700 |
| agcctggata | caattaacca | ttttatattt | gccacctaca | aaaaaacacc | caatatcttc | 80760 |
| tcttgtagac | tatatgaatc | aattattaca | tctgttttac | tatgaaaaaa | aaattaatac | 80820 |
| tactagcttc | cagacaatca | tgtcaaaatt | tagttgaact | ggttttttcag | tttttaaaag | 80880 |
| gcctacagat | gagtaatgaa | gttatctttt | ttgtttaaaa | aaaaaaaa | | 80928 |

```
<210> SEQ ID NO 7
<211> LENGTH: 191010
<212> TYPE: DNA
<213> ORGANISM: Homo sapiens
<220> FEATURE:
<221> NAME/KEY: misc_feature
<222> LOCATION: (8258)..(8258)
<223> OTHER INFORMATION: n is a, c, g, or t
<220> FEATURE:
<221> NAME/KEY: misc_feature
<222> LOCATION: (94801)..(94900)
<223> OTHER INFORMATION: n is a, c, g, or t
<220> FEATURE:
<221> NAME/KEY: misc_feature
<222> LOCATION: (96509)..(96608)
<223> OTHER INFORMATION: n is a, c, g, or t

<400> SEQUENCE: 7
```

| | | | | | |
|---|---|---|---|---|---|
| atgcccagca | ggaccggccc | caagatggaa | gggagcggcg | gccgcgtccg | cctcaaggcg | 60 |
| cattacgggg | ggtgagcggc | ggagagggcg | gggagcggcg | cgggtgaggc | agggagggcg | 120 |
| gggagggctc | agccgtcggg | gctcctgcgc | gagagggaga | gagggaaggg | gcggcgaggt | 180 |
| cgctgcgggc | ccgggggctgt | cgcgggaggt | cctcggtccc | cgcccgtgag | cgtcacccgc | 240 |

```
ggacacgtcg tggacagcgc gggctccttc cccgggaccg ggtttccctg gggtcggccc    300
cgcgccgcga gctcctcggc ccggtcattg tggtagacgt tttcgctgga aagttgggcg    360
gggacgttcc ggccgcaaac ctgtaaggac tgaaagtttt catcaagttg tgaaaactcc    420
tggcgggttt cttaaaatca gcgtttccta aacgttctcc acgtttaccc ggtcgggggt    480
ctcgctttag ccaaaatccg gagacccggg gcgcgggcgc tgtggctcca atgcagcccc    540
cggcagggct cggggcggtc gggcggggac aggggtttct ggaggagacg gtggggccga    600
gactgaccct ggggtttgcg tcgcacccgc cccccggagg cccttgcctg gctgtgggag    660
ggggcgcggt caggtgctgg agcggagggg tcctggactc ttggccgccg cctcggggca    720
gcgctgctgg gggtggcggg ggctgcacca ggtggccggg ctcacaggca gcggaggg     780 gtcgctgccc cccgaagtgt gggcggtggg gagggagga cccgtgggtt tgttcttcca    840
cctgtgcgcg tctccaggag ccccgaactg ggacctccgc tcccgcgagg gtggctgctg    900
ctgcagagag ggaggggagc agaatgcggg ctccggactt gcactggctg gtccttggga    960
tctcgaaaag ctgctcctgc cccggtgcgt cctcagctac agcgtgggca acctgagccc   1020
cagaggcagg gacggccggc agggttaggc gggtgacatc ttccccgggc catgtcctct   1080
caggacagtg ccccggggt ctctatggtg ccctgcgagt ctgagcgggt tcagcttctt    1140
gcgaaccttg tcttggggtc tcgggtcagc catctggggc tgcttggccc cgggtttgtt   1200
gaggaggctc aattgtctct tctttgggaa ggttggggcc tctgcagctc ccctgtggca   1260
agcacctgga accttcgggg tgcagtggcc cgggtttggt gccagaacca gaagaaaggg   1320
atttctgggg gactgaccgt ccagccctac ctgaagaggt agggcagcca tgtcttttgg   1380
cctggaggtc agcaggttaa aacttggtat ggttgacgtt ctggctattg gacttgtcca   1440
gggacctggg cttcctgtct ccttgccatt ctggagccac cacactgggc aacaggtgat   1500
ggtgcggagc tcagggagt cctgcgagag ggaggtccac acccgagggg ctgcaggggc   1560 ccagacccte ctgcattccg gcgtccaatt cctgggacca aggctcggag gcaatgccac   1620
tggagttctg ggccgccccg tcctccctct gccttgcttt ggcccctggg agcactttgg   1680
tggtggggcg ggtgtaattc cacccggtga ctctggtttc ccaggctgga gagaccaggc   1740
tcccacccct tcctcttccc tcccttcccg gactctctcc cctctctccc cacccccttcc   1800 tcttcctccc tccttccctg ttgttttccc tcctcttccc gctctcccct ctctcccttc   1860
cctgccacac ctcttccttc accttcctcc cccttctagg gcacgtctcc cctctggctc   1920
ttccctgctc ctaccattcc ttctctcctc tctcccctcc caggtcctcc tcctctctgc   1980
tgcagagtgt gaagtaccct tctccccgtt ctggctcctc gtccctctgg gcacccggtg   2040
cctctctgag gggactggct gtggggtggg acactcaggc cttagggcaa tgacacagtt   2100
ccagaaagcg gctgccagga tgagtactgg gttattgaaa gccctagaaa ctctgtccct   2160
ggggtgagac gctgctgtcc gtgggggtag ctgagcgtgg acacgtggaa gactagtctt   2220
tagaaaaagg aagagcactt cagtcacccc catgggcat ggccaccccg tcatccttgc    2280
ctgtcctccc agggccctct gagcacactt gagatccaat cctcgccacc ccaccccgcc   2340
ccctgtgggc ctgaggggtc cccaggcacc tgtgttttca gggagtccca ggtggcctgg   2400
gccagactcc cacgctgagt ctcagatgcc cgctcttcta gggccacaaa cactggtgct   2460
ggctcttccc tctttcagct cagacttttt tttttttttg agtctcgctg tgttgcccag   2520
gctgcagtgg tgtggtctcg gcccactgta tccttcacct ccgaggttca agcaattctc   2580
ctgcttcagc ctccctagta tctaggacta cagacgcccg ccaccacgcc cggttaactt   2640
```

```
ttgtagtttt agtagagatg aggtttcact ttgttggcca ggctggtctc gaacttctga    2700
cctcgtgatc cgcccgcctt ggcctcccaa agcgctggga tgaaaggcgt gagtcaccgc    2760
gcctggccca gctcagacaa cgtttgtgtt cagggagctt ctgtgtgcaa agcccagggc    2820
ttggtgctga ggccaacaga gacgcaggag tctctcccgg gcggcccagc tggctgctgg    2880
gtgctgagtc ctggacgccc ctgctgaagg gcacagggca gctgtttgat tcaggattgg    2940
gatagggttg gaggtggtgg cctgacactt cccaagccct ggggttttac tggagccacc    3000
cacctggcct ctagattggc cggaaactgg cttccactgg aggcaggact gtaggggtag    3060
gggcgtgggg caggaagagg tcaaaggtga agtgatggcc gactcccact ctggagttcc    3120
tggtggtcag acttttggac tccaggtcag gcagcaggcg tggatgtcag cttgggcga     3180 ccccagggtg atgggtgtgt gaccccctc cattccttac tttcctaatc tgccatgatg    3240
ctgtgggctg tggcgaagac cagccaggtt ggttcctgtg gggtgcttgg cactggggg    3300 caggtgctgg gtggccagtt ccagcaggaa ggggtgggta gctggggcgt ctgtccccca    3360
ggcccaggtg gcccaggtg actgggtgag gcctgtgggg caggtgggcc ctgggctgct    3420
gtgtcagggc cgcggctgtg gaccgatcct gtgttctgtt tgcactggag ttcttgtctg    3480
ggatgagaac tttgtttctt gaaacttgtc tgatgaattc agataacctt gatggggagc    3540
cagcagtgtc agcgaagagc agagcctgta tctctggttg gacatctca cacccccttca    3600 ggcttctttt tataggccct gtgctcttgc cccgcgctct tgtgggtgtc agaaagccgt    3660 agattttttct gaaaattcag tgtgttcaca agggtgtgat tcccgctctg agtttcagga    3720
aacaccagct gggccctgtg gtggtccctc ccctccacgc agggtgagac cagctcttgc    3780
tcagtgcagg aggtgagggg ggacctcggg tccctatcag cagggaagtg ccagccttca    3840
aagggtgcct gggagtccgt gagcttcccc agcccctgga gttcaggtcc tgtctggggc    3900
tgaaaagata aaacacactg actctgtgtg actcggtttt aaaaaaaaaa aaatctgccg    3960
gggcttctgc cgtggctgca gcaacggacc cagtgcccac tccggggtct aaagagtggc    4020
ctttcattat ggaattattt aatccccgcc acttcaccgc tggcaccgtc gaggtctggg    4080
ggcaggtctg actggtttcc tttaccttag tgaagccggc ggcctgcacc gacccggctc    4140
gcgcccatcc cggggtcacc cacatttggg tgaacttgaa cgagtgcccg accaggtaac    4200
gttgccggac ctcccacaag agggcacttt cttttctccc attttgtcct cattctttcc    4260
agccaggtag gtcgcgcttt tttctctgtg caaggaagtt gatggtggtc attttttttt    4320
tttttttttt aatacggagt ctctctctgt cgcccaggct ggactgcagt ggcgcgatct    4380
cggctcgctg caagctccgc ctcccgggtt cacgccattc tcttgcctca gcctcccgag    4440
tagctgggac tacaggcgcc cgccaccgcg cctggctaat ttttgtatt tttagtagag    4500 acggggtttc accgtgttag ccaggatggt ctcgatctcc tgacctcgtg atccaccgc    4560 ctcggcctcc caaagtgctg ggatgacagg tgtcaggcac tgtgcttggc aatggtggcc    4620 atttttaaa ctatggttat ggttaatggt tctattttgt gtgtgggagg gggaggggg     4680 tggggctgtc atattgtctt tggggaaagt ttcatttatc taatcaatga tttggttagt    4740
tggtaatcat tttttaattt gattcaaata tgccccacgg taacagatgc ccatgtcccc    4800
tctgccccag ggacatcttc atcaccagcg tggacgccgc cacgaccttc gaggagctct    4860
gtgaggaagt gagagacatg tgtcgtctgc accagcagca cccgctcacc ctcaagtggg    4920
tggacagcga aggtagccct tgtcccatgt tggccagaat cctcagcctc agggacttc    4980
```

```
gccagggcag cctctgtgtg cggagtgtgc tcagccaatt ctgtggggag acttaaagct    5040
gtggaattaa acttgttggc gccaactttt ccccagtggg gatggtggga aagaggttgg    5100
ccacagatgc ttatcaagga cctgggccca gatgcccta ggaagggctc tggtcttgaa    5160
ctgcctgcag ggggtctccc tgccccaccc tgggcaggtc ctcacctctt cctctgacct    5220
cctttctcat gtcctggcct ttttcggtag gtgcttctga aaggatgggc tcttcatatt    5280
ctagggacca cggggagggc acaagcagcc agggcctgcc gtgtccacct cctgtctctt    5340
agacacatcc tgaaaaacaa ggggattggg agacgtccag agagacccct ttctcccagg    5400
gactggcggg cagctcttgg ccaaggacac ggccgtgcgg gtggagcctg atagcgcccc    5460
cgttgggttg ggtacagccc tgcagggcct gggttctgta cacctccatg tccctttcca    5520
gccatagagg gcaaggagct ctccctccgc ccaggactga cctccggaga gtgtcctcag    5580
ccccgctcac tgcttagccc tccaagtggt gcccagggct gcaggtgtac tgacttccct    5640
tccggggtgg ctctgacgct gcaccggggg ccaggtgact ccctagtgtg gacggccgtc    5700
cttggacctc ccgaccctgc caggaggtgg ccagtctgag catcgggact ttgcccccca    5760 ccagacccctt gtctggtgtg ctgagcgggc tcgtcacagc ccccttgcc tcgggccttc    5820 ggcgacgtca gcaccgtctc ctgccccacc caggtgaccc ttgcacggtg tcctcccaga    5880
tggagctgga agaggctttc cgcctggccc gtcagtgcag ggatgaaggc ctcatcattc    5940
atggttagtg gcggggtctg tggtgggcag ctctgggggg ctgttcctgg ctgtgggtgt    6000
ctgccgacta gctgggggat ttaaaatggt ttaaaatcct atgatgccag agaatttagg    6060
gatgtctaat ataatgccat ttgggttttt ttctttgact tttttttttt tttttgaga    6120 cggagtcttg ctctgttgcc caggctggag tgcagtggca caatctcagc tcactgcaag    6180
ctccgcctcc tgggttcatg ccattctcct gcctcagcct cccgagtagc tgggactaca    6240
ggcgcccgcc accacgcccg ctaattttt tgtatttttt gtagagacgg ggtttcaccg    6300
tgttagccag gatggtctca gtctcctgac ctcgtgatct gcctgcctca gcctcccaaa    6360
gtgctgggat tacagatgtg agccaccgcg cccggccttt tctttgacat tttattaacc    6420
caaatgaaaa ctgctcttaa caaagaaccc gtaaaccact cagaggctcc agtggccagc    6480
gtagggcccg cggcgcatgt ggacagaggg gacagcccca ccagccacct cacctgcccg    6540
gtgctcccta ggcccggctc caggctcaca gctgtcctca gctttaagtt caaagcccca    6600
tgatgagctg acgcatggga gatgtgattg tgatcatttc cactttgtct ttaggtgggc    6660
gtgggctcct ccccggtact gctggggtc tgcagggcgt ctggggcctg ggaatgtggt    6720
tccagcgctg tggccagccg gtcacgtctt tgtctctgtg tccacttctg gcgtagcttg    6780
ggctccttgc caggcgtctg gccatggacg attgagtcca agatgggacc aaagctcgaa    6840
accacccatg gatttctgac agatccatca ttctcctgga caccgggcta cctggttaca    6900
acacttaatt ttcttcgccc tttatatcaa tgaggctcta aatttaaaga ctaggccggg    6960
tgcggtggct cacaactgta atcccagcac tttgggaggt caaggtggga ggatcgcttc    7020
agcctaggag ttcaagacca acctgggcaa catagtgaga ccccccctc tccaaaactt    7080 gttttatttt tttgagacag agtctggctc tgtcccagg ctggagtgca gtggcactat    7140
ctctgttcac tgcaacctcc acctcccaga tataagcgat tgtcctgcct cagcctcccg    7200
agtagctggg actacaggca tgtgccacca cacttggcta atttttttt tttttagtt    7260 ggagtctcgc tctgtcgccc aggctggagt gcagtgacgc gatctcagct caatgcaacc    7320
tccgcctccc gggttcaagc aattcttctg cctcacccctc ccaagtagct gggactacag    7380
```

```
gcatgtgtca tcacgcctgg ctaatgtttt gtattttag tagagacgga gtttcaccat    7440
gttagccaag atggtctcga tctcctgacc tcgtgatcca cccgcctcag cctcccaaag    7500
tgctgggatt acaggcgtga gccacggtgc ccggcctaat ttttgtattt ttagtagaga    7560
tggggtctcg ccatgttggc caggctgttc tcaaactcct gaccttaggt gatctgcctg    7620
cctcagcttc ctgaagtgtt gggattacag gcgtgagcca cggtgcccgg ccccaatttt    7680
tttttttttt tttttttgat attcagacgt ggtggtgcac ctgtagtccc agttactcgg    7740
gaggctgagg tgggaggatt ccttgagcac aggaggtaga ggctacagtg aactgtgatt    7800
attccactgc actctagcct gagtgatggg gcgaaaccct gtgtcagata aataaattca    7860
tagatgtgcc taatctagtc ctttttattg tggttgtgat agtaagcaca ttttgcctct    7920
ctatgtggaa agatacagtg gcttaaaaat tcacattgtt ttctagataa aagaaaaata    7980
gggctgggtt cagtggcaca cacttgtaat cccagcactt tgggaggccg aggcaggtgg    8040
atcacttgag gtcaggagtt caagaccagc ctgaccaaca tggtgaaacc ccatctctac    8100
tataaataca aaaattagcc gggcgtggtg gtgtacactt gtaatcccag ctacttggga    8160
ggctgaggca ggagaactgc tggaacccga gaggtggagg ttgcagtgag ctgagattgt    8220
gccactgagc tccagcctgg gcacagagtg agactccnat ctgaaaaaaa ccaacaaaaa    8280
acaaaaaatg tttgttttt taaagtttca atactttat gtgtatacac acacacataa    8340
aaaagtagag atggggtttc gtcatgttgg ccaggctggt cttgaactcc tggcctgaag    8400
ccatcctctc atctcggcct cccaaagtgc tgggattgca ggcgtgagcc atcatgtcca    8460
gccaagtttt aatactttct aagcacctat tttaataatt tattgtggaa gcccaggata    8520
tatgttaaaa taatttgaa ctctgtcttg agtatgaaga agtggaatct aaagtgcttt    8580
taaaagtcag tgttcaaagt aattgcattt cttcccatt tttatatagt ttaaaaatac    8640
aaatcagtag cttcctctga tggctttgct gtccaggtcc ctctgattgc cttttactct    8700
aagtttttcc gtgggttta aagtcggagc ctggcctacg tagatgcacg gggttttgcg    8760
tctcccagga gcgggctctc attggcagtg ccacgtgcgc cttgcgtgaa gtccacgtgc    8820
tcagcctgac tgaggcggga cttcctccgt gagactgttg agtggcagcc gcagggtctt    8880
gacgctgtct ctttctctct cttgtccagt tttcccgagc accctgagc agcctggcct    8940
gccatgtccg ggagaagaca gtgagtactg gggtttccta cgccggtctc gcatgttacg    9000
gggttgaact gttgatccgt tgtgccacgg aggtggcagt ggtgccgttt cggaggttc     9060
accctcgtgg agcgtcaggg caggagcagc catggtgacc gcgggtgggg ttttcactgc    9120
agctgctgcc tgtgcgtgtt ctggctgaca gcaccacatg gcgggggact cgcttggctg    9180
gttggtagca tgagaagtcc aggggtgccc tgccgtctcc ctaggaggga ggggccaggt    9240
gggaggctgg acactgctcc tttgtggctg cctcagctca cgaccacccc taggccagtc    9300
gtctgctcct cctggtccct gctggcccct gagctggtgt gggggctccg ttcatcccac    9360
actggctcca ttgttgggag aggaaggaga gtgagtcccg ggggctgtgg cttcagaggg    9420
aagcttctga cctcacttcc tactgcatcc cggagactgt tgggccctga gcaggtggct    9480
acgctgctct cggccgcgc atcccatggc tgtgcttggt gggggttcca ccccactct     9540
ccagacccca cacggcctcc agcatccgtg ccatgccttg tttgttgtgt gggcaggagc    9600
tcctggaccg aggccgctgc ctgtccagcc cagggcacgt ggctcagtgc ccttcgggca    9660
gggcttcccc caccctgct gccagggcac acacctcgct ggcctcaggc tggatgctgg     9720
```

```
gtgttggcag tgccctgtgt tgggcgggaa ctgggggtgg gagcagattc aggccaagag    9780
ggtgagtggg cagttggggc gagagtcttg gcttccagtg agaagtgggg ctgaatagag    9840
gtttggcagt gcttagcata gggggcgaga gtctcggctt ccagcgagaa gtggggctga    9900
atagaggttt ggcagcgctt agcgtagggg aggcccagg agccatggga tttccatgat     9960
ctgcccgggg agagggcggc gtggcatccc ggttccaggc cctcagccaa ccggggtccc   10020
tgcaccgtgg ccggcaaggc cgaggagcca tccggaggtg ggccctggca ggaatggagc   10080
gggtggtctg gggctggacc tgccggcagg aggagatggg gtatgtccgt ggcaggcgga   10140
caccaccagg tggttttggc agcgcagggc gagtgtgagg aggcagggg cggggaggct     10200 ttggaggcag gtggccagac ggtgggcgtc agggccctga tcacctacgc agctgccctg   10260
gtggtgacct ttcccgggac cctccctctg ggtgcccacg cctcacggac cctggagcac   10320
gcaccctggg agggcacggt tcactgcgtt tttatagata cataaacaca taaataggac   10380
agatactccc tgtgggtgag acgatggttg tccectccac agcgccctgc agcctcatgc   10440
tgctgcttta taggagggga cccacggggcc gtgtttattt gccacctggg tgattttttg   10500
acttggtgac aggactgtgc tcctctgtcc catgtgtgct gagactgtgc actcccagag   10560
gtatccacat gcggccagtg tagcccctgg gcgcggggga agcccaccgt atttctccga   10620
catgtctgcc tcttgtctca accctgcctg ggggcctggg gtctgctctt tctgtctacg   10680
acctcggcat tgcctctctg cccgtgtgga caacctgccg gccttgcgta gggaagggag   10740
gcccgcattt gctcggccac tgcagtggag aagggggagg ttggggggtc acaggatgtc   10800
cagaggcctg agctctgaag gggagtgtgt catgggggtg gcagccgagt caccgtgggg   10860
aatgcggaga atgtggccaa gccccgagga aggacctcct gggacacgtg agtaggtcct   10920
tgagatgttt accaggggtg gctccacggc ttcggggacc actcagcctg gttggggaca   10980
ttccgccaga gcctctgggg cagcctttgc cgaggaggtc agaggcgggt gctggggtg    11040 gggagccctg ccctgccctg tgtgctgatg tccacccgga cgtgggttgg gtttcatggc   11100
gctagtgtca ggagtgtgtg agaacacact gcccactcgg ggtccaggc caccagggct    11160 taggggggctg gcgctctccc tgatgtcctg tgctttcttt cactctgact gtggtgctca   11220
tctcagacag gacaccctgc tctggttgcc agtggccgcc gcctgggggct ctgtggtttt    11280 agcgcctgtg ggggtgttca caggtgtttt tgacctcagg cagcactgcc caggctgagg   11340
gtcagtgaga agggtcggac tgggaggtgt gtacagtgga tggagcacgc cagaggcaga   11400
cgagggcagg actgcggctg taccgtgggc ctggttcaga cggctggacg tgcctgtctc   11460
accgtcagca gaggaccttc tggcacattc tatgtgtgtc tatatgagtg aattggtttt   11520
atagattttt aaaaaaattc taaagtatac ttacaactat catctctatg tagttacaaa   11580
cccaaaatat attcaaaaag gaacccccgt gcccgtcatc ggtcactccc tgttctgccc   11640
cagccccacc tccgctcagc ctctgtctct gtggccctgc ggattctgga cgtttggtgt   11700
ccgtggaatc ctgcatgttt gtccttttgc ctctagtggc tttcacccgc ctgacctttc   11760
caaggttcat ccatgatggg gcattcttgg cgctgcagat ctttttttcta ttctggtaaa   11820 atgcacataa catctatttt tgccatctta actttttttt tttttttttt ggcagagggg   11880
ggacggagtt ttgttctgtc acccaggctg gagtgcatgg tacaatcttg gcttactact   11940
actctgcctc tcaggctcaa gcggtcctca tgcctcagcc tcccgagtag ctgggattac   12000
aggtgtgtgt caccacactt ggccgagttt tcttttttgt agagttgggg ttttaccatg   12060
ttgcccaggc tagtctcgaa ctcctgggct caagtgacct acccatcttg gcctcccaaa   12120
```

```
gtgctgggat tatagatgtg agccaccgag cctgtcccca tcttagccat taaaatttaa   12180
aggttcaatt cactggtatt cgatattcgc attgctgtcc agtcatcatc accgcccatc   12240
tccagaactc tcttcatctt cccagactca gcctctgtct ccatgaaaca ctcactcccc   12300
attctgcctc ccccagcccc catcacccac ccgccgcttt ctgtttctgt gactttggtg   12360
actctagggg cctcctgtga gtggaatcgc acaggatctg tccttttgtg acagcttatt   12420
tcactcagca ccatgtcctc aaggcgcagc catgcgtagc ctgtgtcaca gtctccttcc   12480
ttctcaagac tgaaccgcag gctgctgtat ggatgtattt tgtttaccca tttctgtcag   12540
tggacacacg ggtgacttcc acagtttagc tgtcgtgaat gatgctgctg tgagcacggg   12600
tgcacagtga cctctggaga ccctgccttc agttctgggt gtagacccgg aagtgagatt   12660
gctggatcat tgatcattct atttttattc atttattttt gagatagcgt ctcgctctgt   12720
cgcttaggct ggagttcagt ggcacgatct cggctcactg cagcctccat ctcctgggct   12780
caagcgattc tcctgtctca gcctcccaag tagctgggac taaaggcatg tgccaccacg   12840
cccagctaat ttttgtactt tttgtagaga cagggtttca tcatgttgcc cagactggtc   12900
ttgaactcct gggctcaagc agtctgccca cctcggtctc ccaaagtgtt gggattacag   12960
gcgtgagcca ctgcacctgg ccgataattc tgtttaaaga gccgccgtgc catttcccat   13020
ggtgcctgca gcattttcca cccctgcaa tagtgcacga gcgccactgt ctccgcatcc   13080
tttccagctc ttgtcgtttt ctgtttttg acagtatctt atgggcgtga ggtggcatat   13140
cattgtggtt ttggttctca tttccctggt gataagtgat gttgagcatt ttttcatgtg   13200
cctgttggcc atttcttttt tttttttttt tttgagttgg agtcttggtc tgttgcccag   13260
gttggagtgc agtggcacga tcatggctca ctgcaatctc cgcctcccag attcaaatga   13320
ttctcctgtc tcagcctcct gagtagctgg gattacaggc acccgccacc atgtccagct   13380 agttttttgta tgtttagtag agttgggggt tcaccatct tggccaggtt agtcttgaac   13440
tcccgacctc aagtgatcca cccacctcgg cctcccaaaa tgctgggatt ataggcgtga   13500
gctgccgtgc ccggctttgt tggccatttc tgtgtcttct ttggtgaaat gtcttttcgc   13560
gtcctgtgtc catttttgaa tgggttgttt ggttttttg ttggtgagtg ttactagttc   13620
tctgtcctgg atgttaatcc cgtagcagat atatgattag caaatatctt ctcctgcttt   13680
gtgggttgtt tttttacttt gttgatagtg ccttttgatg gacaaagttt taaaattttc   13740
ctgaaatcct gcttaatgtt ttttctttt gttgcctgtg tatttggtgt cacatccaag   13800
aaatcactgc caaatcgaat gttgtgaagc ttttcccctt ctctttcatc taaggatttt   13860 ataatttag gttttatgtt taggtcatgg attatcctga gttaattttt gtatgtggtg   13920
taaggtaagc atctaacttc attcctttgc atgtggaggt ccagttttct tagcaccatt   13980
ggtgaaaaga ctccccattg gactgcattg gcacccttgt tgaaaatcgt ttcaccatat   14040
atgggagggt tcatttgtgg agtctcttct agtccattgg tctctgtgtc tctctttgag   14100
ccagtgccac actgttttga tcactgtagc tttgtaggaa gttttgaaat caggaagtgt   14160
gagccctcca gctttgttct tccttttcaa gattgttttg gggtcctctg agattccaga   14220
tgaattttag dacaggcttt tctatttctg caaaaaacat tattgtgatt tttgcaggga   14280
ttgcattggc tctgtagatc actttgggta gtgctgacat cttaacagta tgaagacttc   14340
caatccatga actgaagtgt gtttctgttt gtttatgttt tctttgattt ctttcagcag   14400
tgttttacag ttttccttgt acaagtcttt caccccttg gttaattcct aaacgttta   14460
```

```
ttcttttttga tgctgttgca agtggaattg tttccttgat ttcccttttg ggttgtttat   14520
tgtaagtgta taaaagtgca gttgatttt  gtgtgttgac ttttttgcct gctgttttgc   14580
tgaatttatc agttctaaca actttctgtg gaaactttag ggcttttctta catgtaagat   14640
catatcatct gtatacagag ataattttac ttttccttc ctaatttgga tgccttgtat    14700
ttctttttct tgcctaattg ttctggctag aattccacta ctctgttgaa taaaagtggt   14760
gtgatcggcc gggcgcggtg gctcacgcct gtaatcccag cacttggga ggcccaggcg    14820
ggtggatcac gaggtcagga gatcgagatc gtcctggtta acacggtgaa accccgttct   14880
ctactaaaaa tacaaaaaat tatccgggcg tggttgcagg cgcctgtagt cccagctact   14940
cgggaggctg agccaggaga atagcctgaa cccgggaggc agagcttgca gtgagcggag   15000
atcgtgccac tgcactcctg cctgggcaac agagccagac tctgtctcaa aaaaaaaaaa   15060
aaaaaaaaaa aagtggtgtg atcaatcatc cctgcctttg tcctgattgt caagaaaag    15120
cttcaggtt  ttcatcactg agtgtgatgt ctgctgtggg ttttcatac atggtttta     15180
ttatgtcgag atagtttcct tctattccaa gtttgtcaat tgtttttatc aggaaagggc   15240
tttgaatttt gtcacatgct tcttctgcat cagttgagac gatcatgtgt ttttttacc    15300
ttcattttgt taatgtggta tattacttta attttcattc attgaaccat ccttgcatcc   15360
catgaaaaaa tccttcttgc tcttggtgtg taattttctt gatatgctgc cgaattcatt   15420
ttactagtat tttcttgagg attttacat ccgtgtttat aaaggacaat tacatctgtg    15480
ttaataaagg ataattatgt ccatgttctt aagactcaat ggtcagaggc tttcttgtcg   15540
tgactttgtt gggctttggt gtcagagtag tgctggcctc acaggatgag tgaggaagtg   15600
ttccttcctc tttaattttt ttggaaaagt ttgagaaaaa ctggtgttag ttcttcaagt   15660
gtttggtaga atttgcctgt gaagacatca gtccctgggc tttgctttgt tgggaggttc   15720
tcttctttc tctctctctc tgtctgtctc tctgatggag agagtgcagt ggctcgatct    15780
cagctcatgt caacctctgc tcctgggtt caagtgattc tcctgcctca gcctcctgag    15840
tagctggcat tacaggcaca tgccatcaca cccagctgat ttttgtaatt ttagtagaga   15900
tgtggtttca catgttggcc aggctggtcc cgaactcctg acctcagatg atccacccac   15960
cttggcttcc caacgtgtag ggatttcggg catgagctgc tgcgcccggc cctgctctca   16020
tctttattat tcccatcctt ctgccagctt ttggtttgtt cttttttctgg ttccttgaag  16080
tgtaaaattc ggttgttaat ttgagatctt tcttgttttt ttatttcaaa tatttatcac   16140
catagccagg cgccatggct catgcttgta atctcagtgt tttgggaggc tgaagaggga   16200
ggatcacttg aggccaggag ttggagacca gccttgggcc acatggcaaa actgtgtttc   16260
acacacacaa aaagttcatc actataaatt ttctccttag cattgctttc cctgcatccc   16320
tgaaatgttg atatgttgtg tttctgtttt cattcatctc tcagcatttt tctgattttc   16380
tttgtggttt catcttctat ccattggttg agtgtgtagt gttatttcca tatatttgcg   16440
aattcttctg ttttctttct gttaactgat ttctaagttc atcttgatgt ggttggagaa   16500
tatactttgg ataatgtctg tttttttgaaa tctaccgcgg ctgagtctgt ggctcacttg  16560
tgttctgttc tggaaaacgt cccgtgtgcg ttgagggtgt gcagccgctg tgggtacagc   16620
gctctgctgt gtctgtcaga gctatgcggg ttactgtgtt gttcaagttc tctgtttctt   16680
tacgtgttct ccctagttgc tttttcattc ctttttatgg ctggatgaat tctgtgatgc   16740
gattcaccct gtctgtccgt tcctctgctg atggacactg gtggggctg ggtcgttcgg    16800
ggctgagcgt gtgatgagat caggagcgcc tggttttttg ggggaggtga gggctggtca   16860
```

```
cgccccggtc gagtggggat cccctgtgtg catctgtggc ggcctcagtg gtgttggggt   16920
ggagtaatcg ggcggtggag ctggggtctg tgggctccac ctgctgccac gtgtgccggg   16980
ctgcccaggg cccatgaggg tggtggcacg ggggtccgca tgaggggccg caggtgcctc   17040
gggcccctct cccgcttgtt tctccatctt cactgtccgt tcactgcagt gccgggtgag   17100
gccagtgtgt ggccggtaga ttcccgggta cctcttcttt gccctcctt gctgtatctg    17160 gtcacacaga aatggtatgt gtgattttg tttcaatact caaatctgtt aatattttcc    17220
cttctggctt ccctagtga tacaaatata ttttcttcca ttttggtctt tgagctgctt    17280
tgcctgtctg tgtctggggt ggcatccgct ggcacctggg ctgacctggg acggggccct   17340
tctcttggac ttgagcagat gagactcaca gcccgaaatg cagcagatcc ctcaggccac   17400
gggactctgg acgtgtggcg gccctgtcgg cctgagccac atctgctgtg agaggcagca   17460
gtacgttcct tggggcagca gcgagagcaa ggctggatcc aaagacctcc gagcagctcc   17520 tccgggcag tccccagctg caagccacag cccggccctg gtaacgggag agcatcgcta    17580 gggagggtg gggcggcccg gcttcgatgc ggccatgtgg gagggccact ctcagagacc    17640
ccccgccttc cttgccaccc ccaccccaga ggggaagctg gagctgggag gctgcagacc   17700
caggccaagg tgtggccagg gctggctttc ttgggaggct ttgagcatcc tgcttcctgg   17760
ccacccagct ctggggctgc tgtcaactct tgatttgtag acatcactcc agcctctggc   17820
ctgtcaccct gaacctcccc catgtctgtg tcttttctca ctggaacacc ggtggtcggc   17880 tttgggccc accagggcag tccaggacat tcaccttgag acctggcctt aatcacacgt    17940
gcaggaaccc ttttccaaag gagggtcacg ctcacagctt ctggagtagg acatggactt   18000 gtcttttttgg aggcccatcc tcaacgcacc acagttgact acatcaaggt ctgcctctga  18060
tctggtggga gtgctgggtg gtctgtctcc accagcactt tgtgggtggg ctctgtcccc   18120
aggaaatgct ctctgcccag gccccgccc cgtgagaggt tcgtgctgcc agtggcgctg    18180
gtcattggga ccatgtgctg ggccggcgcc tggcaggaca gacagcaggt ggctcttctg   18240
taggttcttc tggctgggac aggcccagcc ggtgctcagc ggaactgaga ctgacgcccc   18300
tttcggaccc ctctaagaag ggaggcctgg gtgggcagcc tcccctcaga gttggggaaa   18360
cgtggcccag ttcccgccag tcaccaccct gccggctgcc acggggacac gtggcctggt   18420
tcctgctggt caccacccg ccagccacat cttgaacggc gtccgttctg cagtcgcttg    18480
tccttagtgt tccagcaaca ccccaaccaa tgcgaccccc ggaacctccg tcagccccgc   18540
ccgggagagc cctcccctgc atccgtgctg tgcttgttga aactgagatc ctctagcctt   18600
tggcctctcc ggacccagcc ccagctgcag gccccagcca tggtggtccc tttgggaggc   18660
gtggtccagg aggtgatggg cagctggaga accccgtga gtggaggctg ctgtacctgg    18720
cagggagggt cctgggcaag ggggcatgga gtggaaaggg agtgggtgtc cagaaagttc   18780
ctggggctcc accaaccaga acgttgccat taccttgagc aaacgacctg tttagtggtg   18840
ccttttcttt acctgtaaaa cggggtgatt gtaaataaaa tcgtgtgtaa aagtgcttag   18900
gaccagaccc ccattggagc gagtgttgat acctgtctca aaggacagta ggtggacgtg   18960
gcagggaggg agatgtcaag acgacagcca gggcccttc tgccacttcc cctggtgggt    19020
ggtgggcggt ccctgaacc ctggcagtaa gcgagggacc tcccgacacc ctggctcctc    19080
cgtgttggct ccaggggctt cctgtttcta gatggccggg cccatcatgt gcagggaggg   19140
gtggatgcta taggcagcag ccccagtctt cctttgggtg gggttatttc tgctgctgct   19200
```

```
gcagtccaga ggctctgggg ctcctcagtg ggtagcctca ggcctgggca gcgtccatgg   19260
gacagggtgg tccccagtca ggccccattg gcctccctgt ggtgtgtggt aaagactcag   19320
ggtgcccgcc ctgtggagga ggtgccgggg gtagcctggc tttgcaccca gaccctgctg   19380
agggcagcgc tggatggtca gctggaccag gcctccgagg tccttagagt ccatggagga   19440
aatacaaagt ccgctgggct gggcagccgc agaccccact tagcagctgg tggtgtcctc   19500
ggggtcatca gagccagtgc tggctgccct gtgcatttca tgttgttggt tcctgcctgt   19560
ccacagcaca gatggcatac ccgggcagcg ggaccctgct ccagcctgca ccctggggaa   19620
aggtgtccta cattccacat tctgcccgta gcaggcagcc ccaccccact gtagcccatc   19680
ttgtcactta gggtggtccc ggtagtggct tctggagcct ggaacgcttg ggtcaggccc   19740
caggcagctg ggaccctccc gagcctcacc ccttgggtct ggtggggccc ctggggtttg   19800
gccgggagga caccgtgact actgcctttg cctctgggta tattccctgc tcagcccctg   19860
aacccagctc caaggccatt tctacttggc aagcggagg ttttcatggc cagggatgtt   19920
aatagcaggt ctctggatgc aagggtggca aagtcgcctt ggcctgtgta ggggaagtgg   19980
aggaacctgg gctctcccgg gccggtggtc tggggcaga tagcagggga aggggctgca   20040
gccatgtggg tggagccatg ggggccgtgg aggggcctt cctgaccca cagtgggggc   20100
cagggtgggg ctggcggggg acagtcctca gctgcagggg ctggggtgag gctggcgggg   20160
gacagtcctc ggctgcgggg gccggggtgg gccaggaagg ggaagggct cttgaggctc   20220
cggggccttc tggctgtagt gtctcacttg gagcaatggc gggatcccca gatccatccc   20280
ctggcccgtc tgcctcccgc cctcatagcc ctgtagccta gggcagagag gggtccttgg   20340
ccgggacacc atcccacag ggacgtggag ggtgctgggc ccggggctac catggagtcg   20400
cctgctggga gcagccagta cacctgggcg tgcgacctgg gcaatgcggg ggccgattgc   20460
tcagggggc gcctgcactg ccaggttcaa accccaccgg cagggagcct gcgctgtgac   20520
ttcaggcatg tgggtggggc tccccgtgcc ccgtgcctca gtttcctcct ctgtaaaagg   20580
gggctttgtg aggctcgaca gggtttagag gagctcctgg aacatagtaa gtgcttagca   20640
aggccgtctt gccgtctctc ccacccaggg agggtcaagt gggaagagag cggccccacc   20700
gagtgtgttc caggccccgg cggcgtctga gaggaggcgg ccaaacctag tggggctgcg   20760
cgaccgcctg tggaacagtg gggacgctgc tggtgtcctc caggcctggg tgggcgggtt   20820
accacggaag cctatcaacg gatgcctgtg attccctggt atttataggt atgtctattg   20880
ttttattaaa aatccagtt tcattcagct ttgtctcaaa ttatttgcaa caaactggaa   20940
aagctagttt tccccctaaa ataggcttct aataaaattg gcaatttgcc tgctgagcct   21000
gaatatccta gagttctgca aagctggata tttttgggatg gattagaaga gaggagttgg   21060
ctgaaggaca gtggtcgtgc tgctgagccg gccgtctgtg tgaagtttac actggaccag   21120
gataaatgcg tatttcctgt gggagctcag cgtggccatg gtattcggtg gtcttatgat   21180
tttataggcc tagccagggg tctgcgagct gcttctgtcc agggccaggt agttgaagcc   21240
tggggttctg agcaggcgtg ggcagcaccc aaggaggtgc atggccgtgt cctagtgaaa   21300
ctttatgcac gctgaaatct gaattttata gactcttccg gtgtttcaaa atattatcct   21360
tttcatttta ttcagccaat taaaagcgta gaaatcctag cttgctgatt tggagcacta   21420
ggcagtgtag gttgccagcc ctcgttcccc atagatttgg gaagtcgagt gaaacgcatg   21480
tgttaggttt atatgtttca cattttacgg aatgcccctc atgcagctgg tcagccgcct   21540
gacgagggaa gcttggccct ttggagaagt ggccgtgcct cgtggtgagc tgctgacaga   21600
```

```
gctggaattt gaacccgggg ctctggcccg gagtccactc cgtgaatgca gataaacaca    21660
ggtttatgag cttgatgatt taaatggagg ttttattact gttcaggcag gtgtgggagg    21720
ccagccatca ggagatgatg ccgttgagaa ggtcgtttat tactcagctt ctgagaggag    21780
acctcctctt gcctcgcggg gccatgcggg caagcgccgg gtgggttgga ggcaggggga    21840
tgtgtgggtg gggcctttac tgtggttcc atgggaaagg tgtggggagc aggcattggg    21900
tcggccaggt ggagtaactt cagcaggctc tggggtgcag gggctgtccc tgtgacctgg    21960
ggaggcccct ggggcgactg ggggcccgtg taggaggtgg gcccaggtga gagttctggg    22020
ttggtgggtt tgcatttgaa aggttcgctg tgggacaagt cctttgctgt ctctaggaat    22080
cggttggcct ctcggggccg tccctccagg gtcagcaggg ccataggtgc tggagcatcg    22140
agggcacagc acgtatgaat gcagggagcg tgtggtgtga ctggtcagag ccagaggtct    22200
gcaggacact cccctctgtc cctctgcacc cccagtgcga agcggcccat gtaggctcag    22260
cacgagtgcc gagtgcgttt ggggaagtgg gcagaattcc cagctgagca ccccgcgacc    22320
ccccatgttt tttatgattg gaggaaaatg ccaggtctca cttgccagtg atgaccaggt    22380
cccagggttt gtcagggtac cagggtaggg gttggagggt caggccaccc agcggcggtg    22440
gcggctctgg gtctccctag gagcccgggc tggccacagc caggcacagc acagcccgtg    22500
aggtctggtc ttgggaatgc gggtgtctcc tgccttaggc tgagggtgtg cgtttccagg    22560
ccagccggga cagttttcag cctggggaag cttggccttt cctgttcctg cccccagtg    22620
cccaccgtcc ccacacacac tggtgggtt tgtggggtgg acacaaccac atcgcaaggc    22680
ccctatgcct cctctcctcc cgctccgttc ctgggctgcg ggacagtgct cggggccctt    22740
ggccattggt gtcgagccca ttcacagcct ctggacgcag gtcagaggtc actcgccacg    22800
gccacagctg cgctgtcccc cactcccagc ctggcagacc aacctgcagg accccgggct    22860
tagctgggtt ctgttccgat gtcgcatttt caaggtccgc tgagtccgag ccctgcctgg    22920
gtctggctgc tgcccgcccg ctctctggac tgtgctgatg cagagatgct tgttttcctg    22980
tgacgtcagc gtcagctcct gcacatccat gccgtgtttt agtttgtgcc tcagctgctg    23040
gctacagctt cccggggag ccgggtacca cccgggcctg gagacatgag gaggcaggga    23100
tgtgagggc ggggacagg acagccggcc ttccgttaaa tatctgctcc tcgcgctcga    23160
gcctccctgc ctattgtcgg ggccggaggc gagccgacgc agcatcagct cgtcaacggg    23220
aaggaagatg cctccctgca cgcccgccgc gcacagagca taagaatct gcgctgagga    23280
ggcaggagaa gaaagccggt gagtcggggg catctccccc gtggattttc cgcgccccg    23340
gggccgggcc agccgtgctg caggccctgt gcgtgcggag gacggtgccc gagtcagcat    23400
tttgggtctg agtcccggcg ttgccgctgc ctgtgcgctg cacagatgct ccgggcagca    23460
acacggctgg tgccacggcc cggggaaggc gtgcggctgc agcagctccc agcaatgtca    23520
ggggaaacgc agtgagaggc tgttgttttg cgggtgacag atttttagaa aaataaggct    23580
gtggagggac cttctgagcg aggcaggggc tgctggaggg acatgctcac cccgaggacg    23640
gatggtgtgt ggcccaggcc tggtggatgc gtggcggtgg ctgtggaggg ctggggccg    23700
gggggcttgg ggaaatcgtc ttgggctcgt ctgcctgcct ggcccagggg agttgctggc    23760
tgttgggagt ttcactgtgg ccgatgcttt ttggttgtgg gtctgtgggt ctgtgggtct    23820
gtcgggccca ggacgatgg ccgcttcgtc tccattctgc attgctgcag gtgggcagat    23880
tgatgagacc acgggtgaag tctggagacc ccaggtgcca gggctggtag tggtaacagc    23940
```

```
cagcacctgt tccaggcctg cggtctttcc gtctcgagcc tgccctcccg cctgtctgag   24000
ccccgttttt gcattgacag tgttgggttg gagtctgggt ggcacggcca gggttaatgt   24060
gcacggctca ctccatcggg gtcctcggat ggtggcgagg agcggggctg cggcgtcctg   24120
ttttctattc tgaaatggtt ggaggtagac tcggaggggt ctggggctg catggtgttt    24180 ggcagggatg tgggaatgtg ggtgcttttc tgacgaccat tttgcaaggt gttttttta    24240 aaaaaaaaaa caacaaaaaa ccaaaacaac aaccagcctc cccagtcagg cttgtgggga   24300
gccgtgggcc tggggagact gggctgctga agtggggac tgggctgctg ggggaggcgg    24360 cttccctct cggggggtgc tggctgctgg ggaggctggc agcgcgcccc tcccccaggt    24420
gcgaagggac ctcagcagac gcagggctgc tccgcacagc cagcttgggc cgcaggggtc   24480
cttgagtgat gaagattctg tgttgatggg gtgagtggga gagagacgga gctggggtgg   24540
ttttcacacg tgcgcctgcc tgcgaggaga aacgtgctgt gtcatagttt cctcggtgcc   24600
tgggacggct tggcctctgc tttcgtgtga gcccacgctg gccatgcaca gctggcacga   24660
tccctcgcgg tgtgaataca ctgctggggt gggagcgccg tggccagggt caggattcga   24720
gcggttactg gcttttggtc tgatggccct cggtgggtga gtcagagctg ggatggggac   24780
agattggagg ggccaccggc tgccccccag aagctgtttc gtgttgatgc tgccggggcc   24840
agctgtggta cctgtgtctg tgtctcggcc agatcggcgc acatcttccg cgttcctgtc   24900
ccagctgcat cagccatcag tgggggccct ctccgaccg tcttcctaga cttcagagcc    24960
actggtggtt atgtaaggag ttgtgtgttc ctctgcccaa ctccgagctt ggtcccacct   25020
cccagactca cctctgggct ccgggctctg ctgcgatgtt tccgaggctc ccagttaatc   25080
agatctgtca gcccagtgtc cacagggtgc ctgagagccc agcccatcca cactgggtgc   25140
cccagacctt ccacggggtc tggtggggac ctgccagggc tgtcaatggc cccagtggag   25200
aggcccactg agcatcctga gaagttcctg tgcttgtgac ctgctctcgt gtgtgtagca   25260
gcgggggctg cgtctcatct gccacacgtt tctgatcgcc gaggactcag ccgggcacat   25320
ggaggttgaa ctgttggggg gcgggaggac catccatggg gtcaggcacc aacctctgct   25380
gaggatccca aaatgtgggg tagccatcct ttcttgtgct ggcgtggagc ttttcccagg   25440
agctgggcag ggagctgtca cagggccagg cccctgaatg ggctgtttgg ggccggggct   25500
gagggggtgc ccagtgccat cgaggggaag cctgtgggaa agtgtgatga catctgaaaa   25560
accaggagca ggtcccttgc tgtgctggtc gtggtgctcg agtgtgggct cggcaggtct   25620
ggtctcctgg cgcccactca ctccctggcc atctccccac ctccctcaca tggcaggggg   25680
aagtggaacg tgcggccact gctcccaccg tccctcacag cacaggctgg acaggcaccc   25740
tgaggcatcc ccatctccca gccctgggg ttggcatgat gctgggcctc cagaaatgtt    25800 tgtcattta tgcaaagggc agaaaaagct ttgttcaggc caggcacagt ggctcacgcc    25860
tgtattacca gcactttggg aggccgaggt ggggatcac ctgaggtcag gagttcaaga    25920
ccagcctggc caacatggag aaaccccggc tctactaaaa atacaaaaat tagctgggcg   25980
tggtggtgag cgcctgtaat cccagccatt caggggctg aggcaggaga atcgcttgaa    26040
tccgggaggc agaggtcaca gtgagtcaag attgcgccac cgcactccag cctgggcaac   26100
agagcgagac tccatcttga aaaaaaaaa aaaggaaaa gctttattca aaagaagcca     26160
cctgaaccag tcggtcgtcc agtgttcagc ttgttttgg tcataaagtg gtggcacttg    26220
tcactcatac aggagacgct gtggcagagc ccctccacgc atcggggccc ggcagctcat   26280
ttctaggatt ctcctgaaca cgcgaaggag ggcacccacc acgctcggga ctggctgctt   26340
```

```
ctctgtgagg cctccaggca gaaccagtga ttccaccgtc gtggggcagc cttggtgggc    26400
ccacaggtct gttgttcccc ctgagagagg atcagagtca ggagaggcga gacaccaagt    26460
tgacacgaac agatccctgc tgccggttgt tctggtggtg ctgtgagcac gtctgacggg    26520
tgtgagggtg ctgggcttc gtttcgtcca cgctcacgta tcgggcacac aggagagttt    26580
acacgcgctc tggtgggtgg aaggggcccct gacttgatgt tattttgaaa taggggttt    26640
gagtgtgtct ggtctttctg aagttttctt ttttaacgtc tcttctgtgg gaagtttgaa    26700
aagattcaac cgactgcaag acggagccgc cctgtgtctg ttggggctgt ggggacccag    26760
gtgcactggc agctcagccg catcgtgggc ccagatggct tcttctgttt gttcctcagc    26820
gaaccttgat tgttgaaaga atcccgtgag gctgtgtcaa gtgtagacag gccaggcctg    26880
gtgtcttgtc ctggtcagga aattgtgttg ttgcccttgt taaatggttg tgtataaagt    26940
ttgcattgta cattatattt aaaattttat tttgagtttt ccatatttc tattgtaagg    27000
tgttgatagt tctgtgggac tcacaaagag agaacaggtg tccctggtcc tccctgctgc    27060
cccagctcca ctccctggag gggatcacag cagtttcttt ttgacattta tttccagatt    27120
tctaaatgac acatttctgc tgctatttct agtcgtttcc atttaggatg ttacttccct    27180
actttctctg ggacacatca gctcatctct tccttccttg ttccatccct ctgatggagt    27240
tatgtcactg tttattgttt ttaatcattg agtgtttacc taattgcggg tgacgtgaat    27300
atgcatgagc taccatgatt gcattccctt gttggcacaa cttttgggtt tccttggagt    27360
taatacattg tgattgttta aatcagtttc ctagatgtct tgtctcaaat ttactccagt    27420
ttcctcttcc cagaagaggg gcagctccca ccgacgcctg cctcacctcc ctcctggtgc    27480
acctggcccc ccacacaaca tgccgtgggg cttccctgtg ccccgagctg gaacagtcc    27540
cctcctctct cctctgccta cagtcttgat ctctggctcc ctctcttcct ctttcttggc    27600
ttaatgtccg gttaagaccc tccagcagct gtctgagaaa gatggcgtgg gaggccagtt    27660
tgggggatct agttggaaaa tgcttttcct ccagccacac acttaaggat agtttagcta    27720
ggtatgaaat tctgtattgg aaagaatttt ccctctgcat ttcgaaggga tcgctctact    27780
gtcttctggc ttcttgtgtg accgagaagt caggtgccat tttgattttg tgtgtttttc    27840
tcctgaaagt cttgtagaat cttttgtctt cagggttctc aagtttcatg ataatgttcc    27900
ttgtcgtgga aacttctttg tctcttgtgc tgggaactcg tgctgtggaa ccttgcgaca    27960
tttggatgtg aggagcttta cacccagtta tttatcacat ggccgactcc ccgtctctga    28020
ctctctttta gagttaacgc tgattatttg ttggccctcc caggctggtc ctttaatttt    28080
cttctctatt ttccatttct ttgtttatgt tatatgctag gagacatctt caggtttctc    28140
tgtccaaacc atctgttaag tttgttagtt tgttgccttg ttcccgttct tgtctttcga    28200
tcttttttct ctgaaggtgg cttttttttt tttttttgag atggagtctt gctctgtcgc    28260
ccaggctgga gtgcagtggc gtgatttcgg ctcactgcaa cctccacctc ctgggttcag    28320
gccattctcc tgcctcagcc tcctgagtag ctgggactac aggcgcccgc caccacgccc    28380
agctaatttt ttgtagtttt agtagagacg gggtttcacc gtgttagcca ggatggtctc    28440
gatcttctga ccttgtgatc cgcccgcctc ggcctcccaa agtgccggga ttacaggcgt    28500
gagccactgc gcccggcctg aaggtgcctt tttaaggcag agtgccctgc ccttgtgtca    28560
aaggcatatc gcactttttc tctggggtta ttcgtcccgg ctgagaggca ccgcggtatc    28620
atgtggtgat tgagcagcac ccagcacatt catggctgcg aggcttcccg tgtgtgaact    28680
```

```
catttaatct tctcagttcc ttgtgggcac cattgttttc tttgttctgg gtagagatta   28740
gcactgaggc acagacaggt caagaaattt cccagaatcg cacagtttga gctgggactc   28800
aaacccaag ggctgggctt aagcccacgc tatttgccgc gtgccccagg gcctgaagct   28860
gcgtggtcag gccccagctc tgctgcccac cagccacgtg acctcggcca caacgctgtc   28920
caccgtgtcc cggaccctca taagtgagcg tgatggtaaa aggcttggct cccaaggcta   28980
tcatgggatt agccagtaac taagccacaa cgctggcccc gcggctgctg ctgatggcgg   29040
cacatggtgg gagcatgtgt gctggcagcg gttggtgata acgtctcctt ttggtgtttt   29100
cttttggcctc gtactcagct gttttcaccg agagtccctt tttgtgtttg tcctggcctt   29160
tgcggcttcc tgggcccctg gtgacccgca tttgtctgcc cacattgact cgtggggcac   29220
cacagagctg tggtggcgg aagtcccag gggagtgtcc tgcctgggag ggccgggcgt   29280
ctcaccccta gtaaggagtc tgctgccccc gcaagccctc tcgttccctg gctgctttgg   29340
gtgaggaagg gggtctgggg gtcgactcct cactgactgg gaccctgcac agcaggtgcc   29400
ccactttcct gctacctgga gcctctgact tggggcccctt ctttggggtt cggcccagta   29460
cagtctcctg gtgccacgg ggccctctgc cttccaggtc ccagggcatc cactacccgg   29520
cctgtcctcc tctttgctgt tacgggtttt ttggagtttt tcttccttg gtcttgggag   29580
ggagagtcag tcagtgatgt gtttgagctg ctgtgtccac ctggaaacca tcgtgatgac   29640
gctttctgaa ggctaaagta tgcaggaaaa ccagagttgg agaaggtctt taggtagggg   29700
cagtgcgcgt ggacgtggcg gtgcgcgtgg acgtggcggt gcgcgtggac gtggcggtgc   29760
gcgtggacgt ggcaggtgtg gaccagcacg tcccactgct ctgcatcctg aggggccgga   29820
gggtgtggtg caggggtttta aggagggcaa aggcccctct gtttgttttt ccttgatgct   29880
gccccccgtg cgacctgggg gcagttttca aatgcttgac ccaggtagtt tggttctgtc   29940
accccctcgt tcagtggggt ggtgggaaga ccagttttg gaacagtttt ggatttacag   30000
aaaaatcagg acaggagtag agcacaagca ttccctccct gctccctcct ggtcagcgta   30060
atgcgtgagt tacacttcac cagccagtct cggcaccttt ccagctaagg ctttattccg   30120
cttgcctcag tctccctcc tgccccttt ctgtcccagg atcccgtcca gggccccacg   30180
tggcacttgg ccgtcacgtc tccttaggtc cctctcactg tggcaggtct ctcagacttg   30240
cctcattttc aacgaccttc gtagttttaa ggagggctgg tcaggtgttt tgtgggacag   30300
cccttcgctg gggtttgcct catgttttc tcataaggac tggggccttg tgttttggga   30360
ggaggtgaag cctccttata tcgctgggtc cgggtccaca ccctcccacgc agcctgtccg   30420
tgctggcctt gcgtgtcacc tggccgcggt gtgtttgtcg gctcacacct gcccgtgcct   30480
cttcccccgt gctgtcctgt ctgcggagtg aggcgtgcgt ggcccacacc taagaggtga   30540
ggagctacat acgtgatgtc aagttttgca cgggacttgt acgtctgttc tcccattggt   30600
tatttaatta ttcctttctg ttcatgtgga ctcgcaggtc tcaatttcat acttgggtta   30660
gaatcggata ccgtgtcgct tacttattgc tcagattgtt ccagctttgg gcactggggc   30720
ccctgcaggc tggctgttgg ggcagcgatg aggccagaca ctgggtgggt tggggtggg   30780
tgctgacggg tctctggcag gaggggcag gctgcaggga cagggggaa gcaggtccca   30840
ggcccagagg tgggtctcgg gcgagtctgg gctgtgggca tggacccca gaaggggcct   30900
gtgtggccag gacgtcccat ggctgcagac cccggtgtgg ggtgtgggcc ctgggaggtg   30960
attggtactg cagccggagc tccagcatca tgccaaggtg gtgctgggtc gaggcgggga   31020
ggggagaagt caccacactg tgcccggact tggtggcgtg gtgatgtcgg ggctgcggtt   31080
```

```
gggggactga ccccgcatac tcttctccca gctgagttgg cagtgctgta gggtcagcag  31140
cccaggctct gcatggggct cgtgtgggac tcggcaggtc cctgcatcac ctggcaccaa  31200
gctcaggcac gccccccaca ccccaccact gccgccccgc cccccagcat ccccttcctg  31260
ctgccctctg tgctgcactg acttcctcag ttggtttgat gagaggtgac aaaggcagaa  31320
atgggcagag agcggcacca tcgctggccc ctcttgccca tttgtcccct gctgggtggg  31380
cagtcctctt ttttcggaaa tgtgttcagt tctcttgcat tgcataattt gttcatatta  31440
aagcaggctt gatccgggct gccgtggttc cgatcgactc cgaataggac accacacagt  31500
cgtgccaaga aggcgcctaa gtgtctttcc acacggccat ccgagggcgg acgtggtcag  31560
gggtgctgga cgcgtcagac gggttctttg cagcccttgg cagcgtcgcc cgctctgtcc  31620
cgcctgttgt gtgcgccttt tccctgctcc agggctgtgt atttggcaag agggaggctc  31680
cgtggcacga tcacacgtgc aggagctggg ggctgccaga gcggctgttc aagatggact  31740
tggcaaatca cctctttcaa gttgccggct acccggctgc cgtagacaga gtgaagtctg  31800
gtagtttgtg tttatttatt tatcttggcc agcagagaga attgagtttg catggagact  31860
gtaatttcat tctgtgagtg taagatcacg tccgcgttcc tagcgaccgg ttttgtgatg  31920
tgggcagtgc cgtgctggta aatgctctgt gaggaaggaa cgatggtggg atttgtcact  31980
cagtcgattt ccctggtgta aatgctccca ccacggccga tttcaggctg ccgaagtgga  32040
ggggttcagt gaaggtggag ttgggcaagg gcgtacacgg tcggcttctg agagttggtc  32100
cccccgccca accctcccct ggagatggga tgtcaggaga cctggttcca tttgtttttt  32160
tgcctgagcg tccggggtg gctttgagga cacctgtcct ccttcacagg ggcactccgg  32220
atgtagtagc agggagaggg tggaggggcg gccaagggcg tgaggagag ggtggagggg  32280 tggtgtgagg gtgcaaggga gagggtggag agggtggcag tgagggcgcg agagggtgga  32340
ggggcggcat gagggagcaa gccacctcgg gcacaggtga aggacaggtg tccacacctt  32400
gggtgccccc gtcctccctc tcctcatgtc ctaataggtc tgaacaggaa gttacattta  32460
gggcggctgt acagtgagtt ttaaatacct tggtccaaat tttcaaacac gtatcgttag  32520
cgtttcccct gttgctggcc ccagagtgtt cggttcactg ggtggagcat gctctgagcc  32580
cctggaggta cagggatttt acgggaggag ggtcgcttc gagggaggt ggctgcgtcc  32640 atgtctggac ggaattactc actgcctgtc cctccctgca gcctctgttc cctcctcacc  32700
agtctctgat tccagctctg ggctcagcca gtggtctcag gaccccccacc acattcatga  32760 aaattactgt ggtcctcaaa gagcttttgg gtacgtgggc tgtagctgcc agtgtgaact  32820
gtactgaaaa tttagaacga ggaatattta ttcctcatta actctaatta atgtatgatt  32880
aattagatta attctaaaat aacccatcgg ctgttaacat tttaatgaaa agtgactatt  32940
ttcccaaaca aaatattcgg caagagagtg gcaacatttt tgcatctggt tgagcagaac  33000
acggttgagc catcacacct gcctctgcgt tcaggctgct gcagtgttgg gttaagattg  33060
tgaggaaatc cagtgtgtga ggaggcttgg ggtgaattcc agtgtgtcag gaggcttggg  33120
gtgaattcca gtgtgtcagg aggcttgggg cgttttaaca gcttttcctc tggtaaacgt  33180
gggtattctt ctttgatatt tctctgaaac tcggcacgtg gtcatttctt acatgtcagt  33240
tgaaacatgg aatctgaaac tgtattggtg tcactttcct gcagttacct taaaaatccg  33300
ctggtctctt ttgcgctcga ataggtttct tacgcgtgcg tgtgttttaa aaatcgtatg  33360
ttggccgggc gcggtggctc acgcctgtag tcccagcact ttgggagacc gaagtgggca  33420
```

```
gatcacttga ggtcaggagt tcgagaccag cctggccaat gtgatgaaac cccatctcta   33480
ctaaaaatac aaaaattagc cgggcatgca tggtggcgga tgcctgtaat taatcctagc   33540
tactcgggag gctgaggcac gagaatcact tggacctggg aggcggaggt tgcggtgagc   33600
caagattgca ccactgcact ccagcctggg cgagagagcg aaactctgtc tcaaacagca   33660
acaacaaaaa acatcgcata ttggctgtta ggaaatattg ctccactggg ttctgcaggt   33720
cttcctaagc gcagtggaaa attcccccca cgctcatgag ggcgagtgtg aagaaggcag   33780
gtgctgtccg cttcggatta tggtcatagc ttgcactcgc ggctcccctg cctggtctct   33840
gggaccccca ggcatcccca gacctccctg gcctcagcca gttcccgccg cttcaccata   33900
tggcagaaca catgcgcggc cggccggctc acagatgggc gtccctgcgt ccggcccacc   33960
cgcctgcggt cctgtgtgct caccctgccc tggtctctgc ctggactgtg gatggggtg    34020 agtgggcat ggaggcgttc tgcacccacc agctgtcagt gccagccacc tgcctgccca    34080
gcatcgggtc tgtgtggcag caccttgtca gcaagtggag gtcagatgtg gggtcagctg   34140
ggcgcagtgg ctcacgcctg tcatcccagc acttcgggag gctagccgg gtggatcgcc    34200 tgagctcagg agttttcaag accagcctgg gcaacatggc aaaacccat ctctacaaaa    34260 aaatgtaaaa attagcctgg tgtagtggtg cacacctgtc gttccagctc ctcgggaagg   34320
ctgaggtggg aggatcgcct gagcccagga gttcgaggct gcagtgagct gagattgtgc   34380
cacttcactc cagcctgggt gacagagtga gaccctctta aaaaagaaa aaaaaaaag    34440 atgcaggtca ggcacagaag cccgacaggc tgctcccacc ccaacatgac cgacaaggtg   34500
ctgtgtccct gccctccctg tggctctgcg ggtaggggggc gattcctctg tcagctgggt  34560
gaggagtaga gaggcagctg agtgggtatt tatttaaagg gaagacaagg acgtagactg   34620
tacggctctc tgaaacttca gcaacttttc cgagacacgt tgtaccatcc gccctacctg   34680
gcgtgggcgt gaagctggta gcacacagaa ggtcccggag caggagctgg ccccgagcca   34740
gcagctttgt gccctgtgtt accggatctt cagaatgcgc ctccagcctg ttgaccatct   34800
tactgctcac ctgggtccgc agcccgccag ataccaggct tgactttact cctggcgggg   34860
ctagggccag aacccagact ggttgctgcg cacggtgctt tttgccaaac ctcacatttg   34920
ttggttgcgt ttttcacaac tcttgtcctc tgaagatgcc tgctcagagc ccatgcagcg   34980
ccacgctgga ggggctgagg atatggggg ccctgttctc agagcccgtg aggcaccgtg    35040 ctggagggc tgaggacgtc ggggggccct gttctcagag cccgtgaggc accgtgctgg    35100
aggggctgag gacgtcgggg ggccctgttc tcagagcccg tgaggcaccg tgctggaggg   35160
gctgaggacg tcggggggcc ctgttctcag agcccgtgag gtaccgtgct ggagggctg    35220 aggacgtcgg gggccctgt tctcagagcc cttgaggcac cgtgctggag gggctgagga    35280
cgtcgggggg ccctgttctc agagcccgtg aggcaccgtg ctggaggggc tgaggatatg   35340
gggggcccgg gccggctcc cctctcacag gcaggtctgc acccatgggt gggtttggga    35400
ggccccggtc ttactgtgtt gatgcagaga ggcacttctc tctttctctc gctcccttct   35460
cctgtctggg ttggcatcat cccaggagta agagctgtgt cttctcccct ccctgttgaa   35520
aggaatcttg atcctaatgt gaactcaagg attttctaaa aactgggttt attatcatcc   35580
tttttttttt tttttttaaa ttgagacgga gtcttgctct gtcgcccagg ctggaatgca   35640
gtggtgcaat cttggctcac tgcaacctct gcctcccagg tttaagtgat tctcccacct   35700
cagcctccca gtagctggg actacaggct cctgccacca cgcccagcta atttttgtgt    35760
tttgatagag acagggtttc tccatttttgc ccaggctgat cttgaactcc tggcctcaag   35820
```

```
cgatcctctt gcctcagcct ccctaagtgc tgggattaca ggtgtgagcc tccaggcctc   35880
agcctcccta agtgctggaa ttacagatgt gagcctccgc acctggcctg gaatcatcga   35940
tttctgtcat tgttcgtctt gaggctctgg tcctcccagg tttggctggc aggggccttg   36000
gcgagcggct ccccccatgc tacccgcttt ccatcaggt tttgtgtgtt gctcgcatcc    36060
gggcagcagg ctctggcatc ccctcggccc tttctgctcc aggctggacc tggccgtttc   36120
tccacggaac ttggcttcct tcggaggagg gtggacttca gaaactaacc tgcctgctgc   36180
tcctgggggc cgtgaggctg tgcccggtgg gcggtgggcc aggggctgca tggggattcg   36240
atgtgcagtt cccgcggcag ctcccagtgc cgcaggctct tctcttctcc acttctgagt   36300
ggggtctcca tctgcacagc gtgagcctgt tcgctcgtgt gctctgcctt cgaatgcgga   36360
tgacacagct tcagagccgc ggcatcgtca ccagggcagc agacccagcc aggccagggc   36420
ttctcagcat tcttttgtcc tcagaatgcc tcctgccatg cccatgccct ggagagcag    36480 tttccagaag ttaacttgga ttcgtttatt catttgttgt ctttcgtggg ttatgctgt    36540 cagtatgatg gtcagttggc tttatttgtt tctgtttgca tttgatttta gtgtatttcc   36600
ccattctttt atttattttt tttgagacag aatcttgctc tgtcacccag gctggagtgc   36660
agtggcgcga tctcagctca ctgtaaccac tgcctcccgg gttcaattga ttctcgcacc   36720
tcagcctcct gagtaactgg gattacaggc acccaccacc acacccagct aattttttgtg   36780 ttttttagtag agatggggtg tcaccatgtt ggccaggctg gtctcgaact cctgacctca   36840
agggatccac ccacctcggc ctcccaaagt gctgagatta taggtgtgag ctgttgcgcc   36900
cggcccccat tcttgtttat tttacttacc tttgggtggt gaggcgccac ggctcaccgt   36960
ggcaacagct ggcagtgcag ccccaccacg cagagagctg caccagcacc tgtggatggc   37020
atcccgaggt gccaggcgaa ccctgggggct tctgtgtctc tcctacaacc ttcgctccca   37080
agggttttta atgatgctct tattttgca ttaattggg tgtatcccat cacctggatg    37140
tgattaccga gaggagtata gcaggatacc cgagtaatat gtgtgcgatg ccagcagaaa   37200
gacgtgaaga gagtaaatga ataacaggtg gttttgctct gaagtgacct tttggtgggg   37260
gtggcggggg aggttaaaac cttcctgctc ccctaaccgg gtacccacta acagaaaatg   37320
cccgactctg gaaaggagtc cccggaggcc cctgaggagg accagcgtct ggcctgtccg   37380
ggcaccgggg gcagcatcca ggccctcggg agccaggcag gtcactgcct gcacccgggg   37440
aggcctggct tcgaggctgg gaacactggg acggcgtgag ggacaggctg ctggtgcctg   37500
gcgcgtgctg gccgcctgga cactcagtga agacggtctt tgttttgatg gcggcagagc   37560
ccatcctgaa tagcggcttt ctctgctgtg tgggtggggg cctcgggctc ggatgctgcc   37620
tgagttgggg ttttggtttt acagtttccc actcgtgtaa ctttaaggag gccactcagc   37680
agtgtcctca cctacctggc ccagactccg cctccctcat ctggataacg cccagcacac   37740
ctgagaagag gcacagctct gcccccgtct gtccctcgtc ctcctcactg ctccctcccc   37800
cttgcctgga tggtgcgccc catggggtct gcacgcccct ccctccgcct ccctgttcct   37860
cccctgcagt ctcagctcgg aggctgcccc tttccatcgt gggcttcctg ggaaccaaat   37920
ccctcagctt tggccctggt tgcatcctta gggctgaaaa tggtgcctgg acccagcag    37980 ggctccctgg acatttgctg aacgtcctcg agtccttgag tgaagatggc tgtggcgagt   38040
gattgccgcg tgactcagcc tctccatccc acgcccagag cggcttccgg aggtcccaga   38100
gcccgggctc caggatgagc ccagcagagt cttcccgtag acaccatcat cctgtgtgga   38160
```

```
atgtcacctc tcctttctag gtcaggctgt gggagcttcg gagcctgacc aaacccaggt    38220
catgtgtgca cagctcagct gcctggaggc ccctcccagt cggcggcgtc tcttcactca    38280
cagactccag ctggggctca gcgcaacata gcaagacccc atctgaaaaa aacacaaatc    38340
agtgtttctg gttgtgaaag caacacatgt tcactacaga aaacttgacc cataggycag    38400
gatgtcagaa aagctcaaat tgctcttgct tgtactccct ggtgagcctg tcacttttgt    38460
tttattttgt tttgttttcc gagagcatat cgttttaat ttcattctgg tcttctatac    38520
tattagtttt tatagaaaat actagtgata cgaggttaga atccctccct gtcatcagct    38580
aataatagca gtaacaatgg tgccagttct gttccgggct catcgtttct ttttaaaatg    38640
gtggagctta ctgcagtaga gtgttttcct tagccggggt cagctctggt tttagaactc    38700
atttccctgt tcgcgaggtc cctgggcaga gttcggccgg gcgatggcag acgccgatga    38760
ggaaggaccc agaggtctct gtttctgggg cctgcatggg tagaaacgtg ggggtgacgg    38820
tgtgagcatg aggatactca gagctgggaa gacttgaggg tcggggttgg ggacagagac    38880
ttccaggagg cagggccgtc tctggtccgt cggggtctgc gttcatttgc ttcagcctct    38940
gtgaggaggc accacgaggg gtggcctgta aacaaggacc ctgattgctc gagatgctga    39000
aggcggggaa gtccaggcaa ggtaccagca gatttggtgc ctggtaagga ctggttcaca    39060
gccagagcct tctcagagtc ttcttcacgt gataaagggg acgaacaaac actctggggt    39120 cccctttgaaa agcactatta atcccattcc ggaaggccac aaccttacca cctctcaaag    39180
gcctcctgac accgtcgcct gtgggtgagg atttcagcgt gtgaattcgg tgggacgtaa    39240
acactcaggt cacagtgctg gggccgctgt agcaacgtac cacagatggc ggctcacacg    39300
gcagaactca attctctctc agcttgtgtg gtgatcccag ctactccgga ggctgcggtg    39360
ggaggaccac ttgagtgcag gagtttgaat gtagccaggg caacatagcg agatcccatt    39420
aaaaaaaaat ccaaacaaaa agctttattc tctgtctgga gaccagcgtc cgagagctgg    39480
gtttcggcag ggctggttcc cggaggccgt gaggagcccg ggccaggcct gtccccttgg    39540 ctggtgagc cgtctcttct tcacccgggc ccttcctccc cgtgcggccg tgtccacgtt    39600
accctctgtt atgagaacag cagttgtttt ggatctaagt ctgctgtaat gacctcactc    39660
acttaactga ttcatctgc agtgtccat gtgtaaataa gggcatgttc tgagctcctg    39720
ggggtcagga cggcagcttg gattccgagg ggattcagtt gcactcatgc agaggccctg    39780
ggggctgcac cttggcaagg ggttcccatg gcctggccgg tctgcagtcc ttgtagtcag    39840
ctgcacccag ccctcctgca aaggggccc gtgcacccat ggttttgtag ccgtcaggga    39900
gcacctgttc agagggccct gctgaccgag gggcgtgggc tcagcactgc cagggcccgt    39960
gccctgtgtc cccacaggat ggtgctggcc gtctcaccac tgaggggatg cccccccagcc    40020 ccctcaccct cagctgctcc ttccaggagc ttaaggcccc taaagtctgc cccggtccct    40080
ggggtcagag cccaccctgg gctggttttg aagaaacacc agtgcttctc caaggaggcc    40140
ccgtgcacat gtaggaatga agccctcgtc ctcccacagc tgcatgcccc tcctgcgctg    40200
cgtgtgtggt tttgctcatg gcacctgcg tgggcgccct gggagcggca gccggggcg    40260 tctcggagag agccagtgca ggggggaccc cacaatctgg gaggccatgg atcctggttg    40320 tgggttttg gttttaacat ttggtttact tattttcaga cttttttcca aacaaatggt    40380
ttatccatat taatttagct ctccctgtgg aatttgtagg acctcagttt tcttgacatt    40440
atgatctaag cagattattg aacacacgtc ttaaatatca tcttttcaaa ctgccacatg    40500
taccatcata tagatgtgct ttaataaaga ggtcagagag ctgtggccca ctgtagttct    40560
```

```
tgtttgtttt tttgagctgg agtctcactc ttgttgccca ggctggactg cagtggtgca      40620
atctcggttc actgcgacct ccacctcctg ggttcaagca gtgctcctgc ctcagcttcc      40680
caagtagctg ggattacagg cgcttgccac catgcccggc taattttgt attttagta       40740
gagacgggtt ggggttttac catgttggcc aggctgctct cgaactcctg acctcaggtg      40800
atctgcccgt cttggcctcc caaagtgctg ggattataga agtgagccac cgcgcctggc      40860
ctgtttgttt tttaattgtg gtaaaatacc tataacataa aattcaccat tttaaccatt      40920
tctaagtgtg tagttcagta aagtaaattc atgctgcaca gccaatctcc agaatttcat      40980
cttgcacaac agaacctccg cagtcccacc tgcagcacac aggagttacg atgtctcgcc      41040
gtcctcgctg acactcccga ctttctgttc ctggccgtcc tcttggggcg aggcagtgcc      41100
cagtgtgggt ctagtttgcc tctcccggtg gttggtgatg ttgagcctct cacgcctgtg      41160
gccgcttgtg tgtcggcttt ggagaaacgt ctgcacaggt cctttgcccg ttttgtaatt      41220
gagttcctcg tttctgtggt tgcgttgtcc tgtggggtgg ttgacctgca cgcaccgtgt      41280
gaactgatcc cacttgttcc atgcggaccc accgattacc aggtgggagc agcaggggc      41340
gtccgagggc cctgacccca ggcgggagga cagatgcgcg tcctgtgttg gggccacgga      41400
gttgtgggca attgtttctt tttcttttac tttctttggt atcttccaaa tctttataaa      41460
atctttataa aaattattta aggagaagac tcatgtagaa tggaaagcgt cgtgccagac      41520
agtgcttggt acttgcaaga atggccgtgt ccccaggagc cggtggacga atctgtcctt      41580
gctgccaccc gtgcggccgc agagtgagac aggagggacc ggcaggcatc gcgcttctcc      41640
cctagatact ccggccatgc cagccgcccc cttggctccg gccccgtcca tccagcccct      41700
tcccagggct ttgtccccctc accccgccg ccctccccct gttttcctac gggaggcgaa      41760
tccttgatga gaggaggagg ccgggaaccc tgccccctct gtgtgaagag gagggcagcc      41820
cctgctgctt tgtagggaaa ccctgcccaa gagaagcccc agctcagcag gacggagccc      41880
ggcgttcccg cctcagggtg cccagagagg gcggggacac cctggctggg acaaagtgcg      41940
cagctctacc cctgctctga aatgcccggg actcggccgc gccctccccc tttttcagag      42000
caacctgtgg gccctggcaa ggataggcct caggcaaagg aaaaccaccc tcgttttctt      42060
agcttttaga ttttaaaagg agcagtgggg ccaggtggac ttgaagctcc gtgggtttgt      42120
ttaaggtata aattcattga gcttgaagat gttgtacgtg gaagtgaaca gaacacacat      42180
aatttattca tggattttag ctggcctgtt tttgtacaaa gggagctttt aaatttaatt      42240
attttttaagc attagaggat ggtgtatccg aggcagctgg aggccctggt cttcactgtg      42300
agcagggagg gcccttggga cagggctcgg gaggaggggc cggtggacc cctgcagggc      42360
tggaggacac tgagggcctc agatcaccac acagtgggcc cagctagggg gtgaccctga      42420
attccagtcc cagcggacac atctcttgcc ttcagcatag agggcccag gcctcgggcc      42480
ctgcctcagt tgcctccacg atgtcagctt ccaggtgtgg ggaccgggtg ccacctcacc      42540
ccccagttac acccacacga ggccgcggtg cccagtagca cagagatgcc acgtgatggg      42600
tggttttcaa caggaactca agagaaaagt tcatgcttgt gaggacagag ctgcagcttt      42660
agccctgaga gacctggcgg gagaggaggc agatggcgag ggcccaccg gcagagctgc      42720
tgccctgaaa agcacctcct cctggtggac accaggtgca tggtgtggtc aggtgtggag      42780
tgtgggcccg ctggcctcgc tgcttcctgc gccctgttta ccaccctca cccctggcc      42840
ccagccttgc tcttggcggg cggctagtgt cctctggccg ccctggggca ggtcagaccg      42900
```

```
ccggggtgtg gagtggggtg cttgcctttt tctgcctgac cctgcttcgt gtgggactc    42960
tgggacgctg tgacttggct ctggcctggt ccagccccca gtgtccactt ctctggaagg   43020
cgaaaggcag ggtggggtc tccttgatgt gggactggaa gctgctcagc cagtctccct   43080
ggaaaaggtc ctggtgacag tcactgctcg ctgcagtggc tggtgccttc ctcaaaggtg   43140
agggtgtccg ggtggctgtt ggtgcggggc cgctgggacc tgtaccctct aagttgggac   43200
ttcagccccg cctctgcccc caaacgtggt gggctgagat gggggaggcc cttggaaggg   43260
cccagaggaa ccccagggcc tcacagagga cgtgctgtgt acggtgcctc ctccctgcgg   43320
cctgccccgc ctgtgcttgg agctgcatcg ggcacagcct gccttggcgg gcacgggacg   43380
agccgaggat ccccgcgtcg acgtggaggt ccgcggccgt cagcgttgca gccctcggcc   43440
gggcactaag ggctgagtgt ggggccaggg cagagggagc caggccagca gctccaggcc   43500
caggtggagg aagtgctgcc tgacacgtgt gtctgctccc tgcggcacgt ccacagcacc   43560
tgccagccca ctttgggtga ccctcctgtt tgtcctgtcc tagcgcagcc acatcccttg   43620
ggagcctgct tgtctctaga accttctgcc tgatgcacaa cctcagagcc ctccgtcgcc   43680
atccctcccc cgtcccggga gcagccccc cacttccacc tgtcttggac gggagctgga   43740
agggacgtgg ttccagtcct gctgtgccaa gcctggtgac ccgagggtac ccttggcctc   43800
ccggcctgaa ctcttctcct accatgatgg tgcctgggat gctgtgtggt gcccgtgggc   43860
agtggcggag gcagtggccc cggctcgttg aaccttgggc actgcccatt ctgaggcgcc   43920
cgctgtgccc ggctcgttga accttgggcg ctgcccgttc tgaggcaccc gctgtgcccg   43980
gctcattgaa ccttgggcgc tgcccgttct gaggcgccct ctgtgcccgg ctcgttgaac   44040
cttgggcgct gcccgttctg aggcgccctc tgtgcccggc tcgatgaacc ttgggcgctg   44100
cccgttctga ggcgcccgct gtgcccggct cgttgaacct tgggcgctgc ccgttctgag   44160
gcgcccgctg tgcccggctc gttgaacctt gggcgctgcc cgttctgagg cgcccgctgt   44220
gcccggctcg ttgaaccttg gcgctgcccg ttctgaggc gcccgctgtg cccggctcgt   44280
tgaaccttgg gcgctgcccg ttctgaggcg tctgctgtgg cccttaccgt ctggcttctc   44340
tgctggctct tttggccttg gattcatttc tggagctgca gagtcacttc tcttagagcc   44400
tggttttggc cctctctctc ctgcctataa aaagccctgc cctgggttcc ctgctccatg   44460
ccagttctct ccctgccccc gccggcacga cacggacact ggtgcccgag tgatgcctgt   44520
gggtgatgca gacactgact gtcacccag cccccatgt gctgctccgc cacacccag    44580
gccccgtagc agggtggtgg tttgggcagc tgggtttgct ggtcccctgg gagtccaagc   44640
aacatcacca ctgggtccca gatatgccgt ctccctgggg cacctgtgct tctggtaccc   44700
agggtggagt ctggttgtct cctttccaga cccttctagg tctgcgttgg cctggctggt   44760
ttccctgagg ttccctctgt aggggagggc ctgccctcct ggcagggcc cttgtgtgcg    44820
tcctgagctc accgtggttt tggaggtggc tgggcagtgg cgggcagagc ccatgctgt    44880
cctctgcctt tgaggtgggc acggcacacg tgagagctga gcattggtgg aggaggccac   44940
aaccggtgcc cagtggttga gtcgctggtg cccaccgagg gcccagggag tgagggaccc   45000
cctgaagagg tagctgggag ccagaccctc ctcccgtgga tgccttttca agtccctgtc   45060
agttgttcag agaagagggg gaggattcgc gctttgcgtc agatgcgtgc gtcctgcatg   45120
ggtggtgccg gccggctgtg cccaaagtca tgccctgccc ctgtctcccg cagcctggca   45180
tgggctcacg tccgtgtgct tgtccagcct ccactcgcca cagctcccct cccctcccct   45240
ccttttccct cccctccttt ccgctcccct cctctcccct cctttccgct cccctcctct   45300
```

-continued

```
tccctcctct gccctctgct cccctctcct cccttcccct cctgtcccct ccc ctcccctt    45360
ctcctcttt cccctcccct ccctcccct cttttcctt cccctccct cct ttcccct         45420
cccctcctct cccctcctct cccctccctt cccctctcct cctttccct cccctcacct       45480
gtttgactct gctgtgccag gggccagggc agggctggcc cctcactctg cggagtaaat      45540
gggtgtgggg gccgggcctg tctgggatca gggcagccag gcagggtctc ctgcaggagc      45600
aggcatagtc ccagggagca ggcagctgcc taggaaggca gtcaagcaga tggggacctc      45660
ggctgcccca agactggccc ggggctggtc ctccctgcgt ctggcctctg ggtgggtggt      45720
ggtggcttcc ttgtgacttc atccctccga tcgggcaggt ggttttgtgc agtgtgtgcc      45780
tgggaggcgc acggcagcat gatcggtccc tgagtgtcac ggcagcatca gaggccagtt      45840
tggcatctgg agtagctgcc accgagagag gcccagccgc caggcagctg ggagcacagg      45900
tgtcggcatc ccactgggag cacggggtgag gtgcctccct tctctgggca gagtttcccc     45960
agttggtggt gtagacgcca ggaacgcggt tgtacggact tcgtgaggat ctaacacagc      46020
agtgtgtaaa aacagcgcca agcgtgtcct cggtgggcgc tcagaggcgg ttgtgagcag      46080
tgcagatgct gttggcctag ttctgacagg gtggcccagg ggtctccccg tggcatggca      46140
tggacggtgg cagctcctgt ggtcatcact gccatggtcc ggagcggccc tgggctctgc      46200
agcaaggcgg tgaatgtgga gctgagcggt ccgaatcagg gtctggggttg ctcgttcaac      46260
tcaggaactt ccccagattc ctgagttttc ctctagccga ggtcaggggc agccaaggga      46320
agggtcagcc agctcatcca gacctcgctc tgcaacagat ctccagcctg ggttgccatg      46380
aggcaccctg gggaggactc aggacgaggc cccttgaggc tgaacctgag acctaggaaa      46440
ctccaggtgg gtcctaacag ggcttgtcac tgagcgtagg cctggacacg gcctgtggt      46500
gtctcaccca cgggcaccag tccctgttga gcaaggtcca cgcagcccct tgttctggac      46560
ggagctgacg ctcaggccac agactccgac tccattcttc agaggcttca tcgcctgcac      46620
aggaagagag gcctggagat accaggttgt cttggggcca cagctggccc ttggcatggc      46680
tggggagcag caaagcagtt cattaggacc agggctgacc ataccagtgt ccatgcccag      46740
aggttctggg ttctgccctc ttgctgtcgt ccggtgcagg ccacatggcc acctgggaag      46800
gcctgggtcg tcgtcatatt ccgagtgtga ccaagagttc aggggcccag gtacctttct      46860
gggcccctct cagggtcttt ggaaaagtcc agaatgagct gggctggtgg agaattcagg      46920
aggtgtggcc agtgccccccc tgtgctctca gaagcagggg tcactggcga gagggctggg    46980
tggcccggcg atcaacctga aggcattcct tacctgccct tggacccggt gagccagtga      47040
ctggcgtagg ctttcaaacc tttcaaacca cttctcctgg agcccgtgt tgtgtgcgtc       47100
cctcagccca tgcaccccgg aaggcacgcc tcgcacccag ctgtagagcc ccatgttgtg      47160
tgcaccccca gcccatgcac cccggaaggc acgcctcgca ccgtgctcct ggtggggccc     47220
gtgccagggg ggcccaggct cctggggaca gtggcccagg acttgggatg ttagaaataa     47280
atttgggtg ccgcaaaaga aatagcactc gaacataaat ttaattttct cagcaaggca       47340
attttacttc tatagaaggg tgcgtcttgc agatggagca atggcgagag cacacctgaa      47400
cgagggaggt ggaggtctca tcctaacgca gccagtccct gctgctgtgt ggttcccctg     47460
ttggctaggg ttgaccgca cagtctaagc taattccgat tggctatttt aaagagagta      47520
gcagtacgag ccggagtggc ggggtgaata gtttgacggg aaggatggtt acagaacagg      47580
tgactcagga tgactaagaa cagagcaggt gacaaggatg actaaggtca gagcaggtga      47640
```

```
ccaggagtga ctaaggtgac caggggtgac taaggacaga gcaggtgata gaggctaggc    47700
aggggttgtt tactgaaact aggggcaagg atatgtaaag tacaaggaag ttaaacttta    47760
gaatgaagaa caaagaatgg ggatgtaacc atacgatac attgcttctt tggagaggag     47820
ctcagaattc attatactta acaatttaca ggctaaaacc tttgaagagg aatttattat    47880
gttctacagg agcggtgccg ctggcctgtg gcttctgcag ggacaagtag tggctgtggc    47940
cgggaggcgt tcggcagctg tgcttcagcc ccggccccag cttcagctct tcgagttgct    48000
ggcttctcta aggcctgtcc tgaagtggcc tggagactgc tgagttactt ctggaatctg    48060
caccgtgaaa gtgaaacctg gaccatgatg tgaggctggt gagagggtgc cctgccgtca    48120
cccccggcct tgtagaaaac tcattccaat ggccctctgg ttctcactca ggaccaaata    48180
gtgatggttt tttgtttgtt ttcgttttgt tttgttttgt tttgttttgt tttgtttttt    48240
tagacagagt ctcgctctgt cgcccaggct ggagtgcagt ggcgtgatct cggctcactg    48300
cgagctccac ctctcgggtt cacaccattc tcctgcctca gcctcccaag tagctgggac    48360
tacaggcgcc caccaccaca gttggctaat ttttttgtata tttagtggag atggggtttc    48420
accatgttag ccaggatggt cttgatttcc tgacctcgtg atccacccac ctcagcctcc    48480
caaagtgctg ggatgacagg cgtgagccac cgcgccgggc ccaatagtga tgtttttact    48540
gctctgggcc tgatcgcatg caccgttgtc tgtgctgtga cttccgtcgt tgtctgtgct    48600
gtgacttccg ttgttgtctg tgctgtgact tccgttgttg tctgtgttgc gacttctgtg    48660
ggatattcgt tggagaagga gccacacagc tgtgtgggac ccggcactcc ttcatcacca    48720
tcatccaggg ccacggacac ccctctcac aagtcgctgg gatatgaaat tagggaataa     48780
atgggaattt tcagtgcgat gcagctggcg ctaggatcct cctcagtgtg acgtctgaga    48840
ccttttccca gctggagccc tgtcattcat tcattcattc atcccatgcc aggctgggcg    48900
gctgccagag gcacaatccg gaaccgcccc ttgctaatgg gcggaccagt gaaagcaaag    48960
cgggctcgct gtgcagacca atgattgaca gttccagggt gtgatggaca caggcggctg    49020
ccaggaagga gcccttcag aagcagtggg cggggcgggg tggggaaggc cgtggggagg     49080
agtgacttcc agatgaggct cacaggactg tacccggagg gagggggcag caaggaccct    49140
gtgggcagcc gggggcacgg cacaggctgt ggctgtaggt gtgggtggtg cccaggcatt    49200
gacagagggg agctcactgg acgggcagc gtggaggtga gggtcgggtg agggcccctc      49260
gggagcccct ggccatgtta gttgcacatt tcatgactct ttaaggagtt agtgaggcct    49320
gggtgtgacc tatttcccgt tccaattaaa caggtcatta gtccgtgtcg tgctaaagca    49380
gatcactcgc aaggaatgga aaacccttga aatacgtttt ttaaatcggt gaaagtgaga    49440
aaccgatgcc tctgtgggaa aagaccagac tccaggtct gcaccctcag agtgatgagc      49500
tgcgtctgtt aggggtgacc tgaggtccct gctttgaacc agcttgttga aaccggaagc    49560
catttctcat cttctgtaag agcctgcagc ccctgtcaga tgccagccat tccccaggtc    49620
ttgctgacac tgtcattagg attcctatga gggccagtgg ggagacagct cagtctcggc    49680
cctgcttccg accccaccac cacccccaaa tgcatactgc tggcctttcc tgggtttaat    49740
tttattttgc agtggtagag gttgttttgc taaaattatt tcaaaatctg ccttgtggaa    49800
aaacgcccac gtcagggtga ccatctgtgg taaccgagaa ttccttggag gcagcgtctt    49860
caccgcctgg ctaagcggat ggcacaagct gccagccaga cctctgtctg tccctgccca    49920
gaggccccag ctgcccttc ctccaggcac ctccctgatc tctggagtcc aggttttgtt      49980
cccaaggtcc tacctttgta tctaaatgct gtgtcctctc cccggacgat ctcctccagg    50040
```

```
cactggctct caggggccag ctccccatgg gcgatgatgt ctctgataca ggaacttatg    50100
ggtaccttgc aagtttgcac agaaagtgga gcccgtctgt tccttctggg gtgtacgagc    50160
ggggcctcgg ggagcaggtg caggacaggg cacaggagga acaggcacgg ctggtggtgt    50220
gcagtgaaca gcagtggtca caccaggtgg tggctcccgt gggacttttg aggccggccc    50280
agccctgagc aggtggggtc tgcagaggcc tcgtgggttg gaggagactt attcagaggg    50340
agttttggtc ttgctagaaa ttgcatgaga tgaaagatga cattttaatt ctatcattga    50400
ggcatagtct ttccaacaca cccctgagg tgtgagggag ctgtccctat atgatgtgg     50460
tccccgctcc ttcaggctgg ggctcctggc cagttcatct ttcgtcctgt gtctgacttt    50520
ctctatcatt tctaaaatga ctaagacaat ttattttgtt aaaaaaaaaa aaaaaggcg    50580
ttaagatgat tctactttgt agagggatcc caagggagcg tctcctctgg gactggccct    50640
gtccccatc ttgttttccc tctaaacgac atgtgagttc ccaactcttg attttagttc     50700
tgacaactgg agactttatt cccataccttt tttaaaactt tttaaaaggt ttaacttcaa   50760
ggagatacca ttcctttgt gtatttggtt actaaagctg tcttgcatct caaatgtgat    50820
ttaagaaatc aagcaaaatg cactggccac gtcctctcag taggggagg ccagcgggca    50880
tctcccctcc tcgcccctc tctggtggtc tcactgatgt cccccggccc ccagccctcc     50940
ttcctttctt tcccttgact ttgtcctcag actccaggga caaccctgg tgcgagacat    51000
cctgttgctg atttacttgt tctctcattt gtttctgtgt ttgttccatt tctttcgttc    51060
attcattcat tcattcatac tcagctgcg agaccatcag ccagtctgcg ttcggcctgt     51120
gtctgccact ggctgcaggg cccggggcaa aggtcttcaa gtgccctggg cttcagttcc    51180
ccttcctgga gaatgagggt gggagagtac ctcccctggg ggtttgcgaa gatgacatga    51240
gcccgtgcat cctgggtctg gaccgcatct gatacttagc aggtacttag cagcaggtac    51300
tgagtagaca cagtgctcca cagcaaagat gtgtggcaga ggcgtagtgg atgcgtgatc    51360
gagacgcaca gtagacacgc aaggatacac ggcagagata cgtggtgggt atataatgga    51420
tacagcgggc gtggtggatt tataacagat atgtagcaga tatgtgatag gaaccaggca    51480
tgctaatgac aagtcaggaa tgtcacagag gactgtgtct tctgggggtc ctgggccttt   51540
ttcacgagga aggattgcag gtggggcttt ggaaaaattg tccaatttcc atcccctgtg    51600
tcctttcccc ggtcaccgct cctacccagt agcaggtgga gaaggtgact tccatactgg    51660
gggccaggat caggagcagc cacatgccag agcgggtagg cagcccctgg tgcctgcctg    51720
gccctgcccc gacctccaca ccagttcagc cctgtgtcct gcccaggatg gatgggtggg    51780
taatttattg attcattcat ttccagggtc tcgtgtgggc tttgtgaagc ctagtacacg    51840
ttttttattg cgttttttt gtttgtttgt tttgttttgt tttgtttttg agatgaagtc    51900
tcactgtgct gcccaggctg gagtgcagtg gtgcaatctt ggctcactgc aagcccgtc    51960
tcccaagttc acaccattct cctgcctcag cctcccgagt agctgggagt acaggcgccc    52020
accaccacgt cccgctaatt ttttgtattt ttagtagaga tggggtttca ccgtgttagc    52080
cgggatggtc tcgatctcct gacctcgtga tccgcccgcc ttggcctccc aaagtgctag    52140
gattacaggt gtgagccacc gtgcccggcc ctcgttttg tttgttttac tttgttatga    52200
gtaatgatag atttctagaa acttcgtgta ttttttctc cactttattt caactttgta    52260
gaaagagatc taaaaatgca agtctcctcc cccaacccccc aactctcctg cgtcacggat    52320
tggttcagaa ccaggagaca cagggcccag aaacctaggg gctggagggg ccttacccctt   52380
```

```
tggactcttg actgttttta tattctggcc cctccccccg tctgtctctc tctcaagaga   52440
cagggtcttg ctctgtcgcc caggctggag tacagtggta caatcacggc tcactgcagc   52500
tgggctcaag caagcctccc acctcagcct cccaactagc tgggacttca ggcgcgcacc   52560
accacgcttg gctaattttt tatttttagt agagttgggg gtcttgattt gttacccagg   52620
ctggtctgga atgccccaag tgattctccc acttcgcccg cccaaagtac tgggagccac   52680
cacgccgggc tagactgtgg ggttttgggg ggcaagaat tgtactcata tctctgtttc    52740
cacagtgggt cttacactgt ggacaaacag cagctgatgt tctcacccgg ccttgttcta   52800
agaggactcc aaaaagcaag tcgtagcccc agtgactggg aaaggcttcc ccgggagagc   52860
ggccgacaca gctgccgcag tagtaagggt ttatttatca aaactgattt atttatcagt   52920
tcaagacaca gttacacaga gtgtggggga tggttcatca gcagctggca cgtccagtgg   52980
cgcgtgtgcc tcgggaaggc ctgggagggg gacacaggtg ctccgcgggg aaagctgccc   53040
ccaccccagc ccaaagaagc cttccaagct ccatcagtca tgcagtcatg tactttcct    53100
catcagcaca aaccccgctt ccttgaagag aagcgtgagg ctgggcacgg tggcgcgtgt   53160
ctgtaggcct agctacgagg gaggatcgct tgagcccagg aggtcgaggc tgcagggcta   53220
tgattgcaac actgcactct ggcctgggca acagagaaag agagagagga ctgtctagaa   53280
gggaaaacag ggatagcaaa gtagatggga aggaagggcc tctggggcgg cgggtgagtg   53340
ctggccgctc ccctctccac aagctgctgt ggtctctggg ggctgcacct gaggcggcag   53400
tgggaggaga ggggtgaagg gcaacgcgcc cccgtttaaa cacctcctgg cctggacgcc   53460
agctgttcac ttgtaatcac tggtcaccct gaagagatgg gatggacccc tgcccaacat   53520
ttggctcagg tgtccacaca gatgacagca ccgcacgcag acgggaggga gcttctcacc   53580
acataatgag gttttctggg gagagcaggg gaggggggtc ttccaggatg gtccagaaag   53640
gtcttgagcg cgcctgtaag gagactgtct cggtttccgt ggcggctctg ggcaaggcg    53700
gggtgagcag gggctgaggc ttgcagggtt tgaactttcc ccagggccct catcacctca   53760
ctgggatgtg ggcgggaggg gagcgggtcg tctcaaacac ctccagcagt cgaacatcaa   53820
aaaggggtc caactcttgg ttgcgatttc tttggctgaa gcctggactc ctagccccac    53880
gggctgaggg aaggttacgg ctggtggttg gatagacgcc agtgcttgcc ccagagctgc   53940
aggggaagaa ggtggcctga acctcagggc ctctgtgtcc agttcagggg ccagtacagc   54000
agcatcggtc tgcgaggggt atgtgttcta gaggagtgag gggacagaca ggggagcccc   54060
agaggcatcc agtggcgcga atggtgggaa gggccctaag aggggaggct gggaggggac   54120
aatcccaggt ggcaggggat ggccgcgatg aggccctggg gtggagccca gcagggagc    54180
atccagggga agccagtgtg ggtgggggact gggaggagag agggaggctg ggcctgccct   54240
ggcgaggggt ggtcagaaca tcgctcggtg ccagacaggc aggacgcagc gggctggcct   54300
gcggggctca ctgctgcccc ccggggccga gcacgaaagg gagagttgga gggcgcttcc   54360
tcgccgggtg ttgcggtgtg agcggggact ggtgagtgtg tgctgtcttc agagagagaa   54420
gagcagtttt cagggtgagt agcctttatt cttcacacct cattacacag cacccaggcc   54480
ttttattcag gagggcgcgg ccggcctcac cccgacagcc accctggctt gttgaccttg   54540
atctgtgaca gctcccctgt gagttcagac ttctcaagga cgcttgcata gccaacattg   54600
ttgagaacga gtaaccccct tatcacagca acgtctgtcg tgccatgaag caatttccca   54660
tccctgtggc tttgaaggca taagtcactg cgtcactgcc atgctgttcc ttccaaacct   54720
gctcgtcagg agacagctct tgcgctgtgt accggcactg ccgcccagca ggtgaccccca  54780
```

```
gcagctggtt tgtccctgcc tgggggtgag ggcctgcagg gtgtttgtag acgcaactct    54840
tgaaaggccc tgaggttggg gcttggtcat gagggtgccc ggggcccatc cgggagtaga    54900
agtaagtgca ctaggcattt ggccaagggt cacgttaggc cttatttatt tattttttga    54960
gacagtctca ctcttttgcc caggctggag tgcagtggcg tgatctcagc tcactgcaac    55020
cttcgcctcc cgggttcaag cgattctctt gcctcggcct cccgagtagc tgggattaca    55080
ggcacctgcc accatgcgca gctaattttt gtattttag tagagacggg gtttcaccat    55140
gttggccagg ccgtctcaa actcctgacc tcaagtggtc cacccacctc agcctcccaa    55200
agtgctggga ttacaggcgt gagctgccac tcctggccag gtcttttttc aaataaatgt    55260
ctaagcaaaa tgaatttggg gtgaagtagt cacagagctg tcaggaggag cagggtggct    55320
gcgtgcccct gggagctgcc gtgggtgatg accaggtgat gccgggaagg tcactttcag    55380
acacatagtt gtcatcgtcg gatgagaatt attctcaggt ctcaggtggg agggctgcc    55440 caccaggcct ggatgaggcc ccaccccccc acacacacat gctgggacca cgagtggcac    55500
cccctgagga tgaggggct cctgcgtttg tgccctgtgt gggaggtgcc acctcatttg    55560
catgtggccc ttccacgtct cctggccatg ccagacaggt cctcaggatt gttgggagat    55620
gagggcctcg cccaggactt cgatggggtg tcccccagc ccctgtggc tgatggagca    55680 gcctgacatt ttgtggacac aaagcccct agagccaggg aaggacaggg ccggacccag    55740
agccagggaa gggaggtgga gctccagcca aggcatccaa acatcaaaag gcagaactga    55800
gcggcttggt acttgaaaag ttttattag gaaaaatgcc aaactgacag aagtagagag    55860
aattacatag tgaggcctcg tgcacaccct gcctggctcc tggcaacctg cactccagcc    55920
gatacctgtg actctcagca agcccctcta gtgggcgagg acctcacac gtgtcgccag    55980 gccaggcgac tctcagcaag cccctccggt gggcgaggac ctccacacgt gtcaccaggc    56040
caggtaactc tcagcaagcc cctccagtgg gcgaggacct ccacgtgtgt caccaggcca    56100
ggtgactctt cagcaggccc ctccggtggg cgaggacctc catgcgtgtc gccaggccag    56160
gtaactctca gcaagcccct ctggtgggcg aggacctcca cgtgtgtcac caggccaggt    56220
aactctcagc aagcccctct ggtgggcgag gacctccaca cgtgtcacca ggccaggcga    56280
ctcttcagca agcccctcca cacgtgtcac caggccaggt gactcttcag caggcccctc    56340
tggtgggcga ggacctccac acgtgtcacc aggccaggcg actcttcagc aagcccctcc    56400
acacgtgtca ccaggccagg tgactctcag caagcccctc cggtgggcga ggacctctgc    56460
acgtgtctcc agaggccaaa gcagaagaaa acgttagcac aggagtcact tgacttcacc    56520
aaacgcagcc aggattgcgg tttctccggc tcggctgtct cagttgttta agagagttca    56580
tgcttttgag atcaaagtta aagaaggcc tgtgcctcgc agggcctgct ctgcctcccc    56640
cgtgtttcct cggggttctg cgtctgtgac cggggtgcgg agcactggtg tgcagttctc    56700
tgtctcgtga ttcgtgtaac agtgagtgct gcctgcacca acagccagct gccttccgtg    56760
gctgtgtggg ctcctgtgcg gaggccgccc ctctccctgg ccaagcaaca ctgaggcggg    56820
attgcgtcct ccctctcctg aggcaggtcc tgctccagac ctgctttttt cccgcacgtc    56880
acgtgtcctg agacccctca gtggatgcgt cctctctcct tccacggccg cacacactcc    56940
cgtgcccgtt gggctgggct gactgatgca tgtgggggct ccgtcccatc tttttcaact    57000
acagatggag ctgcgtggg aaacgtgtg cagataccte ccattttact tttgtgctgg    57060
ggcttttttg ggatcagttc ctagaagtag gggactgggt gaaaggctga tcaccctcag    57120
```

-continued

```
acaccgaacc cctggaggaa acacaggag ggaggatgag ccctgcgagg tgcaggcctt    57180
cttttaacac tgaccttggg ttctcaggac tgccgaaatc ccctctaccc gggctgtgcc    57240
tctccggcct gtgcctctcc ggcccttcgg cagtgtcgag ggagccccca acacccagca    57300
gcatccaggg atttccccca gggcagtgtc gggagccccc aacaccccaa cagcgtccag    57360
ggattccccc cagggcagtg tcgagggagc cccaacacc ccggcagtgt ccagggattc    57420
cccccagggc agtgtcggga gcccccaac cccggcagtg tcaagggagc cctggcagt    57480
gtcaagggag cccccagaca gtgtcaaggg agccccccaa ccccggcagt gtcaagggag    57540
cctgcctccg tggggtgctg ccagccttag gcctgggcca gtcggggtgg ttggatgcct    57600
gttctggggg tagagaagtc aggtagccca gggcccgcac tctcaataga ccttcagaga    57660
aaaggcatcg aggtaaatgc cgcactcgag tacccgtgtg atctctgggt ggggccatga    57720
tccttctggg cgctggtcca agcgcgtggt gaggccgtcc tctcctgcag aaccccggcc    57780
tcttcgcccc tgcccgctca cctgttctgt cctgctcacc tcctccagga agcctgcctg    57840
gccttctcca tgctgatggg cgtggcccct tgtccctgca gccatgcatt gacctccgtg    57900
gctcctggag gccaggccac gtcctcatcc cctctgggtg agtgagaggc acagcctggg    57960
tgcgtggggc cgtggcggct ccgaggcgcc accgctgtgt cctctcatga gtgggtgccg    58020
tccaggtctg tcctgggctg gctgcgagga ggaggttggc ctcgcgcggc catgtgcgtg    58080
acagtggaga catcgccagc ctcctgcttg cacagctgac ggcagcccct ctctctccag    58140
ccatgtcccc aggactcttg agtagttggc ctggtggccg tgggagaagc aggccccgag    58200
tccccagggc tgtgagcgag gctgtctgat gtgctccctg gtcaccaccc cctgcctgtc    58260
cgtcttgcct gggcagatgg aggtggatga acttcctgcg gccgctgtaa cagtggccgc    58320
cactgggggg cttaaagcaa cacgcatttg ttagctcagc ggtctggagg gtgcgagtgc    58380
agatggagct cactgggcca aatttagtca aggcaccagc tgggtgggtt ctttctgggg    58440
gctccaggga gaccccgttt cccgccttct ccggcgtctg aagccgcctg cccccttggtg    58500
cagccctgag tcaccccagc ctctgcctcc gtctcacgtc accgcctctg atacagccgc    58560
cccccatcc ctcttgtgag gaccccgcaa tgacgtgggc ccacccagat catccaggaa    58620
catctcccca tccccacgtc cttcacttca tcgtctgcaa agtcccgtat gccacgaagg    58680
gtgacacagt cttgggtccc gggacttgca tgtggggctg tctgggtttt gcacagctga    58740
ccatgggtgc ttccggatgc ttggcattgg aggtttctgt cctctgctgg aaggattcct    58800
ggagtgaggg cagcagaggg cacccagatg gaggcactgc cggacgcgca ggggcgatgg    58860
tcgggggca cctgggagcc accttcccctt gtctctgggg ggtgaccctt gaccttggtg    58920
gcctcagttt tctcatctgt aaagtggtgc acacgatacc tgctccgtcc tcctcactga    58980
attgtcctga gatcaggtgt ggtcgtgaat attaaacatg tggattgcaa ccctagacag    59040
agctcccttg gacggttgag cagatgcagc caggtgtggg tccggctgtg gcggaggggg    59100
gtcacacggg gccgagtggc ttcagcgaga gtccatagga catggagagt cccggccgtg    59160
gtgaggacac ggggttgcgg cagctcacgc ccactgcagt gtccggaagg cggtgctagg    59220
tccacctcat ttacggggtc gggctctcat tctccccatt gtacagccca gcctgtagag    59280
gcaggtgagg tccaggccat gggcctgtgg gccgtgccac atcgctcaga ttttgtggtg    59340
tcggtggtgg gagccgccgg ggaaagccgt catcctggag ccgggcgaga gagggccagg    59400
gcagtggggt ggactccaga aatgtccagt agcagaattg ccagacctgg ccattggctg    59460
gggtgttgag ggagacgtct ccagggatgt ccagtgtctc ccagtctggg caagcggagg    59520
```

-continued

```
agccggccag catgggccat ttcatcgggg ccctccctgg gggcagccaa ggacctaaaa    59580
ccaatgggtc ccaaccaaga ggatcccaga ggtgagacac agaacggcca gggctgaatc    59640
cggggccctc cctgggggca gccaaggacc taaaaccaat gggtcccaac caagaggatc    59700
ccagaggtga gaaacagaac ggccagggct gaatctgcct ccagcggggg ccccgggcgt    59760
gatcagagca ggcaggacct tcttccctc tctgcagctc cggcactggc ttcctccgtt    59820
caggcttcat ccccggtcag ggggctcctg gtcccgtggc agcccgtgg ctcctgggtc    59880
gcagcttcat gggggaaaca gagactcctc tggtaccagg gtccctgaa tctccggagt    59940
cccccaagtc cattgagtcc actgggcccg aagagggaaa cagagactcc tctggtacga    60000
aggtccccca gtccctgga gtccctgag tccactgggc cctcgacacc cttgggtcac    60060
ttgtccaccc tcacaccatc gctggcccag ggaatggggg tttggatcgg ccttggtgac    60120
tgtgggcctc tgcctgaaac cctgtgagtg tgggtgggt gggctgggtc ctgagagagc    60180
tgggagcagc ggagtgaagg gggctggggt ggggctggtg acagtggagt ccctgtgggg    60240
ggcagggctg gtggacagta gagtcccctgt aggggctggt gacagtggac tctgtggggc    60300
cagggtgggg ctggtggacg gtgtagttcc tgagagaccg agccggaagg tgagggactg    60360
gaagcttgca cacgtccctg cggccttccc ctcgggtgcg aggcctgcca tcctgagctc    60420
ccccacccta ccccgtgccc gccctgaggg cgggacccag gccagttcac acagcatggc    60480
gaggtaaggg ctcaggatgg aaggcaggag gaaagttggg cctgctgcac ccatgggtat    60540
tgcggcaggg aaggcgagga ggagccgagg tgggtgctgg gagctgtggg gctggctgtg    60600
cgtgttgggc ctaactcggg ctgagctgag gttactgagc cctcaggagg gtgctgtggg    60660
aaaagaaaga ggcagagaag gtgtctttgg accacttagg ggacggggag ggaacccac    60720
ggcaactgtg aaggtctggg gcacagccag ggagggtccc aggttgacag ggacaggcgg    60780
ggtgggggtg caacatggag gcctgggggct gagcctccga gaagtgatgg gcaggatgag    60840
ggggccagag gggatcacgc aacaaggggt gcaccttggt ggtctgggtg tctccagaga    60900
agctggttgt caggactcaa gaggcggaca gggaggggct ggggttaggg aagagtgtgt    60960
ggcaggggga ggaagggagc ctggttgccg ggtcacctgg cattgggagc tgtcccctgc    61020
ctgctgcgcc ccgcctgcca ttgttggagt tctccagtct gggctggtct ggatgaggaa    61080
ctggcagggc tgctgccggc ctggactcag gaccctcacc ctccagcccg caccctcgac    61140
tccccaccag ccagaccctc tgtcctggtg tggacagcac ccacatcctg gctccaccct    61200
tgtttcttgc cctttgacct acagcctcag gacgtgcagg agggaggtac gtaggcactt    61260
gtgggtccgg cctcctgacc gaccgtccat ccaccaccag gcttctggat gttcacccat    61320
gtgggagaga cgggtgtcgg ggaagggacc acagcttcct ttcagaagac ccgggaaggg    61380
cagtgccgtg tgccagcctc ccagttggca ccttcctttc accttagtcg tcttcgaggc    61440
gatgtttcct cgggacaagt catttcatg aatctgctgt aaaacgtctc ccaaactcca    61500
agtgtttccc aaactgagtg aaaatcgctg cagaatgtgg tttccagcag agcttttccc    61560
ctctccttcc ttcacctctg cctgggttac agggtgcggg ttccaggagt ctgcctagaa    61620
ggcaaaaaac aggctttgct tagaatcccc taaattgctc ataaaacaca gtgtttgacg    61680
tttatgtgta gacatgatcc ttatgtgggt taagctgagg cccctgcccc agtgacacag    61740
aggcctcaaa cggcacagtg caccttctgt ctgaagcagc cggcgaggcg gcccgcgaac    61800
ctctgacgtg ctccattgca atgaggatga acgagcctca ggcggagggt cagcctgaa     61860
```

```
cccctgcccc gtgaacacca gccagcttca tgctgaggac ccctcagtcc aacccagagg   61920
cccatgctga ggtcccggca tgggggactg tggggtgcag ccgccgcttg gagtggaggt   61980
gaatgggacc ccacacgttt cctcctcgtt ctctggatgc ctgtaaccat cacagtactc   62040
aaacaaggaa gaagaaaaag gtccttgaaa cttgctggag ttgcagttcc gttttttgt    62100
ttgtttggtt ggttggttgg ttggtttttt tttttttgga gacagagtct tgctcttgtc   62160
gcccaggctg gagtgcagtg gcgtgatctc ggctcactgt aacctccacc tcctgggttc   62220
aagggatttt cctgcctcag cctcccaaat agctgggact acaggagctc gccaccatgt   62280
ctggctattt tttttctata tttggtagag gcggggtttc accgtgttgg ccaggctggt   62340
ctcgaactcc tgacctcagg cgatccgcct gccttggcct cccaaagtgc tgggattaca   62400
ggcttgagcc actgcgcccg gccccatttt ctttacattt gtgacttaca gtcatcagct   62460
gaaggaaaga cagtggcttg gctagggcct gcccactgct ggccgaggct ggccgggtca   62520
cccaggtgcc tgcccctcct gctctggagc cgggcactgc ctgagggcct gcagcaccag   62580
tcagggcccc ggggatccc tccagggtct cagttctgac tagcgagtac ctcgattcat     62640
gagtatgttt tttaatgtaa ggttttaacg taaggtttaa aaaggcagcc gccccgtttc   62700
ctccccactg gtctcgcctt cagcagtgat ttgtggtgac tgtgacgttc tcttcggtgg   62760
gctgcctgtg gatcgccaag tatgtgctcc tgctgcttct acctgatgtc tccccatctt   62820
gggctttgag gggggctcat ccggggcatt catattttct gcccgagttc gctcctgacc   62880
cagggcaggg ggaagccagc aggtgaggac caggtgtca gccagaaact cggaagtggc     62940
acagaggcag catccgatag ccccttttgtc agaggcgacc agggccttga gtgagctggg   63000
atggacttct cttatcctga catcctggaa ggggtgcag cctgcctgtc tgtgtcccag     63060
ttgagttggc aacatttttt gtctttcctc atgatgcacg aagtagtggt atctctgaga   63120
gccaatggca gcctagctgc cgtggagaat gctgggggt gggtgagagt tggggcacag     63180
aggactcatg gggcagaggc tgtggtccag tccttgtggg ggtgactcca gggatggcag   63240
gtgggtggtg tggccaagga ggagggaggt caaggcactg tgttgggggc agggagaagg   63300
gaccgcagtg cccatgtgtt tgagggaggg gagatgatga tgtgggagtg tagagagggc   63360
ggggccccgg ccaacagcat ccatgccctg gggattgggt gccaccggtc aagggctcca   63420
cgggctggc tctgggggag ggagagcggg cgccatgttg tgtgtgtggt gcgtgtggcg      63480
cgtgggtgag ggtatggccg gctgcgtaag tttgtggaag cgttcggaat gctcaggaga   63540
taaaaacagc agagggctgc acccccccac cctcccaccc cagctttttct ccaggaggac   63600
gctccgtcgt ggcctgggag gacgtggaag gagggacccc ggatgcaggg caggttcgtc   63660
ttgtgtgttg agaacgtgct ctccagggat ctgtgttaat acaggtagcc caagcacagt   63720
gtccaatgag ggaaggaaca tttgaaacag aagagatgac ttattttgtt ggacaaaaaa   63780
ggaatatggt ggacattaat tcttagaaga ggttttattt gaaacaagtc acaaaaataa   63840
tcaaacagca ggttgacttt ggagttcagc tcacgaaagt taagcttaca gagcaaataa   63900
aataagctga agaaaaagat aagatgactg ggcgcagtgg ctcacgcctg taatcccagc   63960
actttgggag gccgaggcgg gtagatcacg aggtcaggag tttgagacca tcctggctaa   64020
cacggtgaaa tccagtctct actaaaaata caaaaattag ccgagtgtgg tggtggacac   64080
ctgtagtccc agctgctcgg gaggctgagg caggagaatc gcttgaaccc gggaggtgga   64140
ggtggcagtg ggccgagatc gtgccactgc actccagcct ggtgacagag cgagactccg   64200
tctcaaaaaa aaaagaaaaa gaaaagaaa aagctaagat gcagcaggtg gagccgcctg     64260
```

```
ccgttgggtt tcagcttttc ttatggaaag aatgttacgg cctgggtgcc tccattctct    64320
gatttctttt tctttcttga cttttaaaa ttgaaacaaa actccctaaa acatgaaatc     64380
tgaagcgttc aactccacga gttttacaa agcaaactgc accgcgtcac atagctgatc    64440
cgtgtgtagc ttgtcctctg gacacgggc caccccaca ccccgaggtg accccaggcg     64500
taacctaccc gtccccggcc ttggtgcctg cagatagttt tgcttgtttc gagcttttgt   64560
cttgggatcc ggggccatcc accctgggtg tggccgctca gtcgggcccc tgtgtggggc   64620
tttcccgtgg tgtggggtgc ggttctgccg tgtccgtccc cactgcgggg ctgctctgct   64680
ggctgaattc tccacgtctt atgtatccac cctcatcttg cgaggcaccg gggtcccggc   64740
ttttggccac agacatccga gcgccttctg ttgcccgtag cgcatctttc atgtgggcac   64800
acccaggagt ggagtttccg ggaaacagac gtttccctcg cgtggccgca ccaggtcgca   64860
ctctgcactg tgtttctgcc tccagttatg tggggttttc tgcacccaca gccactctgg   64920
cgccagctgg ttgtcctgtg tttccattca gctctgacat caattacctg acgttagcgc   64980
agaccctgca gatgaagggc tcattcccac aagcctgccc ctacttgaga gccagctgca   65040
agtgccaggt gacaacctgg attctgacca actggctgtg aatcgggggt gtccgtgacc   65100
ccttcctgag gctcgggtgg gctagaatag ctcccggaac tcaggaaaac actttgctta   65160
gtgtacccgt ttattagaaa ggacagccac acggaggagc tgcacgggag gctgaggtat   65220
gggggggtgca gagcttccgt gccctctcca ggcacgccac cctccagcac cttggtatat   65280
tcaccaactc ggacactctc cagaccatgt cattgagggc ttttttgtgga ggcttcgtga   65340
caggcacggt tgattcaaca gccagccact gctgattacc tcagtctctc ctgtctcctc   65400
tctgaccgt gggctgtggg acggaaagtt ccaacccgct aggcattcct tggtcctgct    65460
gaagaccagc cgcatcctgg agctgtccgg gctcccggct cccgtcatc tcattagcat    65520
gcaaaaagac actcttacca cactccagga ttcctagggt cagaggggct gcgcgccggg   65580
aaactgagac aaaggctgaa tctgtgttga tggcacagtc actctgggtc gtgtgggaat   65640
tcccgatgca cctccttcca gcacatggac tgtcagagcc ctgcgttgtc gccagcacag   65700
cagatctgaa aggcactagg ctgtggcctc gcgacggctg aggtgagctg cttctccgag   65760
gctcccgggt tattggggac cctccttta aaggtgcctg ttccagtctt ttgccccatt    65820
tcaaaattgg gctgtcaaag aacaatgtca ttggggggtc cgtctttttt gttggttcct   65880
ggggggctgtg tgtgttttag agacaagtgc tttgattttt tgtgttgcaa acagcttctg   65940
tcactccgcg gctcgccttc cactccatgg atggtgtctt ctgatgaaca gaaagtaaaa   66000
gcttacttta taattagggc ttttgcgtcc tggctgtgtg tggggcctct ttctggactg   66060
atctgtcccc tttgtttttt gccccatgt cgtactgttc tgatttcttc tgctttataa    66120
tcaccattgg taacttgtgt tatgagtctc caatttgggg tttttagttt tcaaggttat   66180
cttggttatt ggcttttac atttccatac acatgggctt gttaataagc catttacagt   66240
tggcttattt gctttcaaaa tctccataag acatttggat tgcatttgga tttcttgatc   66300
agtatgggag attagcatct ttacaatact gaggtttcca atccgtgaac atatctttag   66360
gcctttgatt gggtttttt tggcagggga gttgcggggg gcagacagga cctcactctt    66420
gcccaggctg gagtgcagtg gcatgatcat ggctcactgc agccttgacc tcctgggctc   66480
aagcaatcct cccacctcag cctcccaagt agctgggact acaggtgtgc accaccatgc   66540
ccagctattt tggcatttttt ttgtagagac agggtctccc tatgttgccc aggctggtct   66600
```

```
tgaactcctg ggctcaagtg gtccttctgc ctcagcctcc taaggtgctg ggattacaga   66660
tgcaagccac tgcacccggc cttaaattct ttcaataata ttttgtagtc ttgtgtgtag   66720
cagtcatcca catttttttgt tcaaatgatt ccctggtatt tcagtgctta tgctgtttta   66780
agccgtatta cttttacagt ttttttttt ttatcttttt gtttatagca atgtgtaaag   66840
aagtgtgatt aactcatttg tcttggcctc tcctggtccc cgtagtttgt ctgtggttgc   66900
tccggaacct ctctgtgcgc tgccattttg tcagtgaccg gctgtttgtt tctgcctttc   66960
cttcagatgt tgccttgtta ccctggcact gttgatcctt ccaaaacagt atgggacaga   67020
agtggtgaca gccacatcct ctcgtgcctg atttcaggga aaagctttaa gaattccacc   67080
attaagggtg ctgtttgcgg aaatactgtt tttccttcgt aaatcccac caacaaatta   67140
aagaggttct attttattcc tagttgaaag ttgttaatat gaatggtgct gaattttttc   67200
agatgctttt tttccttcat ctattgatgt gacagaactt ttctccttta ttctgttcat   67260
acgatgaatt ctatggattg gctcttaatg gtagaccgat ggcattcctg tagtgtgcct   67320
cgtttggttg tgatgagttc gccttttttat attttgcttg attcagtttg ctattatttt   67380
gtttgttgtt tttgcaactg tatttatgag agagattagc ctattatttc cttttttttt   67440
tttttttttt ttttggagt ctcactctgt cacccaggct ggagtggagt tcagtggccc   67500
gatctgggct cactgcaacc tccgcctccc tggttcaagc gattctcctg cctgagcctc   67560
ctgagtagtt gggattacag gtgtgtgcca ccacgcctgg ctaattttg tattttagt   67620
agagacaggg tttcaccatg ttggccaagc tggtcttgaa ccctgaccct taggtgatcc   67680
gcccgccttg gcctcccaaa gtgctgggat tacaggtgtg agccaccatg cctggccata   67740
tcttcctttt gattgatgct tttatcatca tgaaatgttt ttgttttttt tttttttgag   67800
acagagtgtc gctctgtccc ccaggctgga gtgcagtggc accatctcca ctcactgcaa   67860
gctctgcctc ctgggttcac gccattctcc tgcctcagcc tcctgagtag ctgggactac   67920
aggtgcctgc caccgcgcct agctaatttt ttatatttt agtagagacg aggtttcacc   67980
gtgttagcca ggatggtctc gatctcctga cctcctgatc cgcctgcttc ggcctcccaa   68040
agtgctggga ttacaggcgt gagccactgt gcccggccaa atgttgctct ttagatgaaa   68100
atattattgt cattaacatc tgatctgtat gatgttagtg tgaccacacc agctctgtgt   68160
gtgtgtgtgt gtgtgtgtgt gtgtgtgtgt gtgtgtgtga tgaggggagg gagggaaggg   68220
gacttagtgt ttatatgctc tattttttca tccttcact ttcttttctg tatattttgg   68280
aaatgactct taaaagcaga agttagttat ttttaatcca gtctgaaaat ggctgtgttt   68340
taaatgaaag atttagtccg tttacattta atgtcattct gatgtgttac attgtagctt   68400
tgtcatcttg ctatgggtcc ttatttgtcc ggtctgttct ttgttttgtc cctctttctt   68460
gccttctttt ggtttaatca gatgtttta ttccactttc ctcccttta ttattatagc   68520
tttgttaagt aatacttctc ttaatgttat tttaatggct accttagaaa ttatgagtca   68580
catccttgga acgtagcata aactacttt accattttct tcaaaacctt ataacagttt   68640
aattcttatt ttttcctttt tttttttttt tttttgagatg gagtgtcact cttgttgccc   68700
aggctagagt gcaagggcgc gattttggct cactgcaacc tccacctcct gggttcaagt   68760
gattctgctg cctcagcctc ctgagtagct gggattacag gtgcccacca ccatgcccaa   68820
ctattttttg tatttttagt agaggcaggg tttcaccata ttgaccaggc tggtatcgaa   68880
ttcctggcct caagtgatct gtctgccttg gcctcccaaa gtgctgggat tacaggcatg   68940
agccactgtg cctggcctaa ttattcttct ttccttattg ttagtttgtg ctattatttt   69000
```

```
atcagtcttt gtgctgttat tatcatgcct gtaaattcta cgtgtatttc agacccacaa   69060
accaagtgtt gtcttagaca gtggtccttc agatttaccc ccaggttacc cttctagtct   69120
tcctgcagga cggcgcttac atggagacca gcttccttct gcctgaagta gtccctttag   69180
tattcctttc agcacagact tgtaattaat tcttttattt tcttttcttt tcttttttt    69240 ttttttttga gatggatttt tgctcttgtt gcccaggctg gagtgcagtg gtgtgatttt   69300
ggctcactgc agcctccacc tcccaggttc aagcgattct cctggctcag cctcctgagg   69360
agctaggatt gcaggtgtgc gccaccacgc ccagttgttt tttgtttgtg tgggaaatgt   69420
ctttggcatt ctttctggag ggtgttctcc actctgtgtg gagttctagg caggtagggg   69480
gtttccccca acaggttttt gtgttggctt ggagtgttgg tcatttctgt ggtgagggcg   69540
ccttccagcc tcactgccac ccctggaagg caacatctct tttctctgac tcctgttaaa   69600
agtgttttca tcacaacagc agccttgtga aggacagagg aatcgagaat ttctcctaat   69660
tgagattggt agagcttctt gaatcaggga catgatagct tttgtctctt ttggaaaata   69720
tcagcccttg acttttcgtt tttttttttt ttttttttt tttttggagt ctcgctcttg    69780
ttgcccaggc tggagtgcaa tggcgcgatc tcgactcact gcaatctcca cctccccggt   69840
tcaagtgatt ctcctgcctc agcgtcccga gtagctggga ttacaggcac ttgccaccat   69900
gaccggctaa tttttttgc atttatagga gagacagggg ttcaccatgt tgaccaggct    69960
ggtctggaac tcctgatcat acatccacct tggcctccca aagtgctggg attacaggtg   70020
tgagccaccg tgcccggcca gcccttggct tttcaaatag catcctgttc tctctccct    70080 gggaccccca cacttcacac ctgtgtgtct aatgtgctct ttttctggg tttcttctgc    70140 gttggttttt tcccgctttg tgcttcaatg tggattttt tctactgtta tctcttattt    70200
cacccaatct actcttaaat ctacccttta aattattaat ttcagtcact tcattttta    70260 cttttagaat ttccatttga ttctttttt tttttttg cccaggatgg caatggcacg     70320
ctctcggctc actgcaacct ccgcctccca ggttcaagca atattcctgc cccagcctcc   70380
caagcagctg ggattacagg gtcacactac cacgccccac taattttat gtttttatta    70440 gagacggggt tttgccatgt tggccaggct ggtctcgaac tcctgacctt gggtgatccg   70500
cttgcctcag cctcccaaag tgttgggatt acaggcgtga ccactgcgc ctggcatcgt    70560 agttctctct tctggggtgg aatgtctat tctgtgtcct tctcacgtgc aaaatactgt     70620
cattacatcc caatggcccc agaacccta actcctccca gtgtggcggg gcagtcttg     70680 tctgaacaag gcatggggga gcctggaggc ccattcctcc tgaggccaag ttcctccctg   70740
gctgtgggcc agcataagcg aacaaggcgt gtacttccgg aatgctatgg actgagtgtg   70800
tgtctcccca gaatccatat gttgaagccc taaccctcca gtgtgatggt gtttggagac   70860
gaagcctttg acaggtagtt agagtcatgg cggtagttag ttagagtcat ggcggtagtt   70920
agttagggtc acggtggtag ttagggtcat ggtggtactt aaggtcatgg tggtagttag   70980
ggttatggta gttagggtca tgcagtagt tagggttata tcagtagtta gggctatggc    71040
tgtagttagg gtgacggtgg tagttaaggt cacagcagta attagggtca tggtggtggt   71100
tagggtcgtg gtggtagtta gggtcacggc tgtagttagg gtcatggtgg tagttagggt   71160
cacggtggta gttagggtca tggtggtagt taggatcatg gctgtagtta gggtcatggt   71220
ggtagttagg gtcacggctg tagttagggt catggtggta gttagggtca cggctgtagt   71280
tagggtcatg gtggtagtta gggtcgtggt ggttaggttc atggtggtag ttagggtcac   71340
```

```
ggtggtagtt agggtcatgg tggtagttag ttagagtcat ggcggtagtt agttagggtc    71400
acggtggtag ttagggtcat ggtggtactt aaggtcatgg tggtagttag ggttatggta    71460
gttagggtca tggcagtagt tagggttata tcagtagtta gggctatggc tgtagttagg    71520
gtgacggtgg tagttaaggt cacagcagta attagggtca tggtggtggt tagggtcgtg    71580
gtggtagtta tttagggtca cggtggtagt tagggtcatg gtggtagtta ggatcatggc    71640
tgtagttagg gtcatggtgg tagttagggt cacggctgta gttagggtca tggtggtagt    71700
tagggtcacg gctgtagtta gggtcatggt ggtagttagg gtcacggctg tagttagggt    71760
catggtggta gttagggtca cggctgtagt tagggtcatg gtggtagtta gggtcacggc    71820
tgtagttagg gtcatggtgg tagttagggt cacggctgta gttagggtca tggtggtagt    71880
tagggtcacg gctgtagtta gggtcatggt ggtggttagg gtcgtggtgg ttaggttcat    71940
ggtggtagtt agggtcacgg tggtagttag ggtcatggtg gtagttaggg tcacggctgt    72000
agttagggtc atggtggtag ttagggtcac ggctgtagtt agggtcatgg tggtagttag    72060
ggtcacggct gtagttaggg tcatggtggt agttagggtc acggctgtag ttagggtcat    72120
ggtggtagtt agggtcacgg ctgtagttag gtcatggtg gtggtaggg tcgtggtggt    72180
taggttcatg gtggtagtta gggtcatggc tgtagttagg gtcatggtgg tagttggggt    72240
cacggctata gttggggtca tggtggtagt tagggtcacg gctgtagtta gcgtcatggt    72300
ggtagttagg gtcatggtgg tagttagggt catggtggta gttagggtca cggtggtggt    72360
tagggtcacg gtggtggtta gagtcacagg gtagaaccct tgtggtggga tttgtgccct    72420
ttataggatg agaggatgag acacaagaga ggttgtgctg cgcctgtgct ctctgctcca    72480
catgagaaca tggtgagcat gaggccgcca gcaagcaagg agatacccg ccctgcaggt    72540
tccgtcatcc tgactccagc ctcggaaaca tgagaaagtc aatgcctgtc acttaagccg    72600
cccagtctgt ggtattttgc tgtggtggct gagccgacgg agacagttcc ataggtcttg    72660
attgtcctgg tggccctgaa ccccagtttt tgtctccagt gagatgcctg gcccggcttt    72720
ctgtgtgacc tccgaagggt cagcagacgc cgtgcatgtg cagggcttgg gtggcgcatc    72780
tctctggcaa caccttctct tctgacgcac ttgtctggtc tcggatgcct ccaacgcggt    72840
ttttacttat tttccagctt tcgtcgattg ttcgtgggag gagggttaga ctcctcgcgt    72900
ggcgtccctg gccacatcct cagcgctgtg tcccctcgca gctcagttcc tggttctgag    72960
ttattgtgac tcagccgcac gtcctcccag gggccttgcc agcctggctc tgtgccgggc    73020
gctgggcaat ctctgcctcc agcctgggcc tttgggtctg tttgagggtg ggggacacgg    73080
agctcagcag tgaggaactc ggagcagctt cttgttgttg gtgttgatgt gttttgtttg    73140
ttttagtgaa tccagaaaaa aaatttctta catagaaagg agcggtattt ggtatgaatt    73200
tatttgcaac tgactgcttg gaagttggcg tacatctttc cacggaaact atgaaaatac    73260
cggtcagcct ctcagtcatt tcataaaatc ttgattttgt attacaacaa attaggatat    73320
tttcagtaga actgattgta aggccagact gttggaatgt aattccttcc caaacatctc    73380
tcaggggcac tttcctgaac ggctgctgac agcagcattt gaggacggtg gggcggagga    73440
catcctgggg ggcctggctt cttgggaact ggaggctttg gcccttgtcc caccctgct    73500
cccctgagga gggaggcgtg gggccctggg ctggctgcaa gacgtggagt gactgtgggt    73560
ccccgtggcc cctgacatgc tcccaggaa cccaagaaaa gactgagacc ctgtggtgcc    73620
tcccgctttc catccgcatt ccatggcagg tgagtctgat tattcgaagg aggctggagt    73680
gtgggcggag ggcagcgcca ggtttcccaa tcagatttgc tcagggtccc tccagcagtc    73740
```

```
catgccgcag aggctgtccc ttgggggccc acgcatccta gccacggcct cctcacgtcc    73800
atgcggggat ttgcgccctg aaggagccg cccggctgcc tctcgccaac atgcagcact    73860
tcccttcctt tccatggagc acggttcctg tcccgggggt ccatattggc cactgtggga    73920
gagagtcggg cagctgaatt cccgcaggtg ggaatgccag ggcccgagga tgttgcccct    73980
gtcctgaagg ctgtcgcccg atcgctctat ccaaggctgc cctggggcag cgtcacctgg    74040
gggtcctgcg ggggcttctc agcacagcat ccagcactgc cacctagtgt gttcccgtca    74100
cgtctcctcc ccccgcctgc accaggcacc agagacccag atgccaaggc ctgtcagctt    74160
cctcaatggg aaacttttct tcagtgaaca aagctctgtt ttatagactt tttaaatttt    74220
cagctcaaaa accaaagtct gccagtgttg gtggccttgg agggctggtc tgctgccctg    74280
ggctgcaggg gctgcccggc tggggtcgtg gtcggggcag gtgccgccca caggttgttt    74340
ggctgcaggt gatgggcagg tcccccatca cgtgtccaga ggtgggtgct gctggtgggt    74400
aatccagctc attacctgtc tcccccccagc cgccttgggc tggggaccct gccccgccga    74460
ccctgccatg cccacccccc tccagcctga ttgcgtgtct cagtcacatg accgccctgg    74520
gcccgtgatg tcactgggaa atgccctcgt ttgattggct tagaccccag atgaacaagc    74580
ccaaggtctt ggggcatcag agccacccat gagggcagct ggatgcagcg ccacagcct     74640 gtggttgggg aatggcattg cgcagctcca ccacgagggg acctgaggct tggactgtga    74700
gactggccca ggctcgccac ttgcccctca cccggggttg ccttcccgag ggccgcggac    74760
acctgagcag tccccatgcc actgcattgt ggcagggaca cggccgccca tccctcctgg    74820
gtcccttatc cacctgcctg tcccttcgta tcactgacac cctgataccc attgtgctgc    74880
gccgtgtggc ccggtgccca cagggccggg ttctgcctgt tcctgggggt ccgtgtgtcc    74940
cacgtgccta gacgtgagag gacggaagtc ggcagagctt ggctccctgt tcgcccgact    75000 ggcgcctcg ctgtgcctct tctgtctctc gagctcttct gtgccgtgtg gttgcactaa    75060
gcagctgtgg ggaaggggga ggttgttgcc tcagtgggag cctgggctgt ggctgccagt    75120
ccccaaaaca gaccctgcgc cccgggcaac catctgcttc ccgccacagt ggtgcccaaa    75180
accttttcca agtcgtcttc tgtgactta gtgttattct tcagtcacct ttaaaagcat    75240
agcatgtttt caatcacatg ttcagctggg aaatagatct gtggttagaa acggaagtt    75300 tgagttgcag gcttgcgatc cgggcaggtc cctcagatgg aggggctgca cctccactgc    75360
cccccccacc gccgccctg ccccacgcc accccagatc ctcagacgcc cctccctgtg    75420
ccttctcacc ctctggtcct ggctgggccc gtcccgcccc acgtcccgcc tcccactgcc    75480
ctcagcctct ggaacggtgc ctgcatggct ggcactatcc agcgcagaag gaatgaagga    75540
cttctgttca gacagctctg ctgggagcgt tctggcctga aatgcagtgg gagctctggt    75600
gcaggtgtag ccgaggctca ggggctccac accaggcaaa taggcgaacg gcgtctcccg    75660
cggctcccgg tggctttta ggactctgcg ttcgtgttct ccattgtccc tggcagcccc    75720
tggccagggt ggcccagtgc ccactataga gggtgcaggt cagtttgtgg accaatggcc    75780
aaccaggctg agtcaggtga ggtggggagt cccaccccaa accccaaact ccagtgtctg    75840
ggccacgggc agccctggga caccttagct ctggacacga atttgcggtc attgctgttc    75900
ttgtgtctct atttgcctag gacatgctgg cagctaactg ggtgctgggg aagcctggag    75960
aggaagccag gtggcccag gctcctggag ctcagaatct agtggaaatc gctgcccagg    76020
gaagaagctc cggagtctag aggtggcagc acccatttta cctgcaccct cagtgacagc    76080
```

```
tgcaccctgg cttctgggga cctctgggcc caagggcacc tcactgtctc cttgtcctcc   76140
tggtcactga cctgggccac catagaaggc acctggctat ctgcatgtgg cttgaccact   76200
gccttgcacc catccgggcc ccgcaggggc gtcctgtggc actgctttgg gctgtgctgg   76260
tcaccctgtg tagcggggcc atgtccagtg aacaggagag gcctcaagtg cccctgacc    76320 tgctgccagg gactcggccc ctccctcacc gccaccgcac ccaagggctg tcgcctgtcc   76380
cagcctgctg ctccgagttt agtgttttaa acgtgtttt ctacgtcttg tcagagtgct   76440
caaggcgcga gattgccatg gaaactgagc tccttagaat tcctgtggcc gtcctaatta   76500
tagaatctca aagacacgca cagagctcct tgaggttgtc ggagttaagg ctgaaagagg   76560
aggagcggcc cctgtgatcc ccacaatttt gttccctgct tgcttcagca gagcctggca   76620
cccagggagg tggcaggatg ggtccccaat gggcacgtga catcgagcca gctctgactc   76680
caaagcctga cccgtgtggc tgcaccgtcc actgtgcgct gtccactgca ggagacccca   76740
ggctgtgtcc acacgtaccc ccggaaggac ctcctgctaa cctgggcttg actttgagac   76800
cctgttccac agaggtagcc gggggactcg cggtgccagg cccacagcct cctcgccggt   76860
agtatctggg ggccaggggc cgtttccaga gcacactccc cagaagggct cccttctcct   76920
tttcacagcg ctgtctgtcg cttaggtcag aaataggccc atcgctttcc aagcagaaac   76980
ccaaacactg aaaattcgac tgtgactttt gaggggtggg gaccgccagg tcccccaac    77040 atccctgccc gcgggcccag aaaggcagag tggctgccgg cccgcgtgtc caggcccctt   77100
acactgaggg aaccttctag tcaattgcct gaagttcgaa ggtttgggg gttttcgtgg    77160 ttgcttccgt ttgttttggc agttgcagaa tcccccgaaa aggtgggaat gtggattttt   77220
caaggcaggt gctcctttga ttcagaagct aaggaggccc taagtgcagt ctcaccttga   77280
gaaaaatatc aggccagtcc taacggaggg gcgtcctgca gacacccagc ctgcactcag   77340
aactgtcacg gtcagaaagc acggtcagaa agtctgagaa agtcacggtg cagcagggcc   77400
cgagaggcaa gacggtgaca cgtgggctcc tggaagaggc aggatggtga cacgtgggct   77460
ccaggacagg accctggggc ggacgcagac agtgggtgaa aaccaaggaa aggtctgaat   77520
atcgcttaag gtagccatgg atcctgtctc attaattgta acagtgtagc aggcgggtgg   77580
aagatgagag ctgtggggag ccaggcaggg ggggtctctg ggaactctcc aatttaaagc   77640
tgttcttaaa aatagtctat taaaaaagac agttgagggc ggccctgcct acagctggag   77700
ttgaggttct agcaccaggc ttcctctcag cctccatagg cgagtaggga ccaggcaggg   77760
ccttggccac agggaggctt ctggttacca ggttctccac agcctttgca gtttccctgt   77820
gaatctgaaa ttaccccaa ataaaaagga tgggttttt tgtttgtttg ttttgttttg    77880
tttttgagac agggtctggc tctgttgccc aggctggaat acagtggtgt gatctctgct   77940
cagtgcagcc tccacctgcc aggctcaggt gatcctccca cctcagcctc ccgagtagct   78000
gggactatag gtgcacgcca ccacactcgg ctcattttt atatttttt tatagagacg     78060 gggtctcacc atattgccta ggctggattc aaattcctgg gctcaagtga tccacctgcc   78120
tcgacctacc gaggtagtgg ggttacaagc atgagccgcc acgcctggcc aaaaggtgta   78180
tttgttaagt acaggctgcc ctgctgtccg ttatcccctta taactcacct ggtccctgct   78240
ttccagctgg ggactggcat ggaccccatg gggcttcccc catttcactg aggcaagacc   78300
cagatgctgg gggtattggg tgtcctgccc aaccagggtc cccagggcca ggggctcctg   78360
gcgtgccttc ccgtgggact ccgcatgggg ggctgggagg gcgaggaaaa tgggaaacat   78420
gatgcctgcc caaaactccc acctcggaga ccctgtgcca gggttttcca gagagaccaa   78480
```

```
accaataggg tgtgcgtata gaaagatcta ttgtaaggaa ctggcttgtt catagagact    78540
tatgaagccc aaaatctaca gggggcccag caggctggag acctaggagg agccacagcc    78600
gcagcactgc tgcttaggga gctcagcctt tgctctgtgg aggcctttt  ctgcttgggt    78660 gaggcccacc tgcattgtgg tgggcagtct gcttccccca aagtcagctg atttaaatgt    78720
ttatctcatc catactcacc ctcatggaaa catccaggat aacatttgac cagccgtctg    78780
ggcaccatgg cccagccgcg tggacacata cagtgaacca ttgcaggccc ttccttggca    78840
cttggcatcc acgcatatcc ccttaagcca cactcagtct ccacacagca gtactcccgc    78900
ctgacacact cggtctccac acacagcagt actcccgcct gacacagttc gaccctcccg    78960
caagcagtgc cagcacactt ggccttccca gaagagggcc accatcatgg gctcggacct    79020
tccagctgga ctgcagtggg gtggggcgtg gcctcgcctc tgtggtcttt gggtcacttg    79080
aatccccgcc tctcactcat tttcctttgg tatttgcaaa tttgtccccg tggcgcctgg    79140
agctgactgc cgggtgccac atgtgtcctg cctcaagcca agctccaggc ggcacccgtg    79200
agcaggcagg gatgccagtg gtttctcacc tgggagtttc tttgcaggct cagagctctt    79260
tgttcctttt taaaaatctg atttgaaggc cgggcacagt ggctcacacc tgtaatctca    79320
gcactttggg aggccgaagt gggcatatcg cctgaggtca ggcgttggag accagcctgg    79380
gcaacacagg ttggggcaac tcccttccct aataaaagtt caaaaccaac ccttaaagtt    79440 taaaagtga gatgggatat ttgaaggagg caggtctgag ggaaatgctt gaaattatcc    79500
tctctgtccc tgtgctgcca ggtcatttag ttccattgtt attcaacata ccatttgaca    79560
catgctagga gcgcaggact cggcaatata aagcgtggta atcgatggac actgccccca    79620
gcagccagcc aggggcagga cttaagcccc acccaactgc aggctgtccc ccgccgctgc    79680
tagcctgaaa ttggattggt tactgctgcg gcctgaaatt ggattggtta tttgcttact    79740
ggaacatttt tgtcacatga ctgtgtattc taaaacaaga tgttgttttt gttttttgaga    79800 gagtctcgct ctgtcgccca ggctggagtg cagtggcgcg atcgcggctc actgcaagct    79860
ccacctcccg ggttcacgcc attcctctgc ctcagcctcc caagtagttg ggactacagg    79920
cgcccaccac cacacccgac taatttttg  tatttttagt agagacgggg tttcaccgtg    79980
ttagccagga tggtctggat ctcctgacct tgtgatctgc ccgcctcggc ctcccaaagt    80040
gctgggatta caggcgggag ccaccgtgcc tagtattggg tttgtttgtt tgttttttga    80100
cttacttgtt tggttctata gcaatggcac catgttctg  tcaccctagg gtttgatttt    80160
tggtgtttct aagacacctc tgggccactg cacatggctg aggtgggctt cgcactggct    80220
ctgtcttccg ttggacgccc acacatcggt ttatttatgc attctcttgt ccacagacct    80280
tgaggtcatc agacatcttg aatgctcccg agcccagggg cgagcgtttc tgagctttga    80340
cggagcagca gtgggctgc  cgggcccctag ggggagcaaa tggtcctcgt ttctgagctg    80400
cgaggctctc ccagagaata agccatttct ccggggcact cctgggcctc gaaggtgttt    80460
ggggctgcgg gggattgatt tgtgccgacc ccgcagtgta ggagacgcct gggcggcctt    80520
gcgggttgct tcgatggttc tcggggctga gatgcttgtg tctctctcgg gcgagacgcc    80580
tgctctgggc ttctgttcct attttgactg cttttttcctc atggattttt cagtccagca    80640
tccctagcca cgggccctt  gtctctcatg tgtgcaggtg actcacggtg actaaaatct    80700
tctgtaattc cttctaaaat gttttgccgc tttgctgtcc acgttccac  ccttagtctc    80760 tgaggggcct agtgtgtgta tggtgggaag cggggtcagc ccccgcctgg accgctgtga    80820
```

```
cagaacccca cagacagggt gacttacaca cgacagaaac gtcttttctc aagttctgga  80880
ggcgtgggga ccccatctcc aaatacagcc acattggggg ttagggctcc ccacgtgaat  80940
ttagggaca cttcagttcg tcccggcggg gactggggac gccgggctgt gtgctgtgtc  81000
ctgtgggaga gtttgttcac cctgctggag gctccctgat gagccctggc gtctgctagg  81060
acgtcattct ctttactgat tgaactcgaa ggatgtccag ttggcgcatt ttcagggttt  81120
cccaggcgca ctgggggtgg gtcctgtgtg tccccgctcc agccagcttc gaccccagc   81180
tgtgcgtcag tccctcagct ccgcccccca gctgcgcggc cgtccctcgg ctccgcccca  81240
cagctgtgtg accgccctgc ggctccgccc gcagctgcac gttcgtccct cggctccgcc  81300
cccagttgct cgtcggttcc ctcggctccg cccctcggc tgtgcgtctg ccctcagct    81360
ccaccccag ctgcgcgtcc gttcctcagc tcagtcccca agctgtgcgt ccttccctca   81420
gctctacccc cagctgtgcg cccgccccct tggttccacc ccctcccag ctgtgcgccc   81480
gccccttggt tccacccccc ccagctgtgc atccgtccct ggctccgcc ccgcactgtg   81540
cgtccatttt tgactccgcc ccggctgtg cgctcatccc tcggctccgc cccggctgt    81600
gcgtccgtcc ctcggttccg cccccggctg cgcgtctgtc cctcgactcg gcccctcagc  81660
tgtgcgccac tttctctgtg gcccacagta cctccgtctc cgccgcttca cacccttctc  81720
tttctttctc tcttcagaga gggttgttgg gcaggcagag catcccccga ggggacaagt  81780
caggcctacg gactcctgga gccaggacct gccgtaggct ggttagggca ggatgcgccc  81840
tgtcttcgtg ggtagagcca catggggct caccccgaccc cctcagggct gaggggcaca  81900
ggggccgaaa gtgtggccgc ccctgggggt ctgcgcctct tgtggagccc aggcctggcg  81960
cccaggtggg tggagtgtgg agggggcaca ggctgcacga ccccagcctg gcctcgggct  82020
tgctgggagt cgcgtctgtg gccggagggg cctttggtgt caccaggcct ctgtcaaacc  82080
ccaagccgca tcctgggagg gctgggtggg ctgagccgcc cgctgccgtg aggcctcttt  82140
gacctgcgct cctggaggac ccctgacttc ttggtttcgc tctgaatctt ccatttaaag  82200
gaagaggagc aggttttacc atccgtgtgg cctgatttca gcagtttcca gtcagggcta  82260
gtcatttgct tgttttaaaa acattccgtt acaatttcca cttcagtata tttgtggcac  82320
tttcatttgg ttcatgaaag tcgcttttat gatggaattt tataaaagca caaagcttcc  82380
cattgtacgt tccgtttctg aagattctgt ttacacacac atccgtttca aagagttttg  82440
gaggagcaaa gtgggacacg gtgttgagga aggacaagac cagccgtctg gttacaggct  82500
tggtgccgcc tttctcataa gaggcacagt ccgcatgggc tggactgtca aatgcatgtt  82560
ataaagatga tgttttggt aacttgcgaa tggaaacggg tgcacggtcg gtttggctct  82620
cctgccctga gatttattag gttaaaggaa actcgactgg agagcccggg gcctcgcgcc  82680
gcttgcgtct ggcgagttgt tgaagtgaag tcagtggcgc tctgcacctt agcctggccc  82740
aggctccact gtgcgtcca ctcttcctcc tctgacagtc atgtgtaaat attgaggccc    82800
gtttgaacta tccctgtgcg gaaaaaaagg cctgtttttc acagggctgc ctggggagga  82860
ggggggtgga aaggaaaaca ggcagggac agacggaccc ggcctgcgtt ggcctgggt    82920
gacttcacgg ctccactgtc agcaagcggc cgtcccgtgg tggatcctgt ccgccctgcg  82980
aggacacctg gctccatcca cacctgggcc tctgtctcca gccgcgagg ccgtgacacc   83040
atgaggatca tgtgaggagg ggcagagaga ggcctccggg aggccgtcat tccagccctg  83100
ccttccctgc ctgggaggac gctgcggccg ccaccacctg gacgggagtg gcctgtcgca  83160
gctgcaccct gcgtgggctc gtggctgcca cgctgtttct ttacacccttt ctcatatcct  83220
```

```
ttccagaatc tatctaccgc cggggagcca gaagatggag gaagctgtac cgtgccaacg    83280
gccacctctt ccaagccaag cgctttaaca gggtgagtgg ccccttgggg actagtccct    83340
caagggcct tttgttactt ttaaaagcaa agagagagga ggggaggcac gtcccgctga     83400
gcccaggctg ggctctttt ggcgcccgag ggcaaggtta cagaaatgct ttctctggtg     83460
caggatgagg cttgactag ggctgtctga ggcgggaagt gccctccggg cctttccctg     83520
cgtggtggct gcccagtgaa tgctgtctgt gtctgcctgg ctgtgtgact cttatcaggg    83580
ctcagggctc actggcctga ggccccagcc tgcctgcatc cagagtgggg cggccgcatt    83640
ccatccgcat gtagcgccag ggtgtgtgtt ttcagccgca cacagtgttg cctagtagct    83700
aagagtctcc gtgaaccctg gaagctcctt cagccccatc cctgcttggg cctctgtctt    83760
cccagcggcc acccacgggg gcccttccca gaggacactt agcttatttt ccttgtttct    83820
ctttatgatg ctttctctagt tcctatgaaa tgggtgattc agatgctttt gtaattgttc   83880
tgtttcacag tggaagggga ggtgtctggg tgtgccttgg tggccctgga gttggtccca    83940
cacagggagt gtcttggggg tgcgtggaag tatacagggc ctgtccccac tgcgggactc    84000
cacacagagc ccctgacagc ccctcacagg agcggtggcc ctggggctac cttttgcattc   84060
cacactcacc tgccacgtgg cctcacgtgt caacctccgc tgggtgtacg gcacctctgt    84120
ctcctggagc ggcctcaagt cacctgcccc tccttctact cccatggtct gccctctaga    84180
ccatcaggaa gttctgttca tgtgagccac tcctcctgcc cctgcgtgtg ctcggtccct    84240
gtcatgtggc aagagtgggt ctggactccc attcctcttg gggctaacac aggtgaggat    84300
gcaggacaag ctcctgagtg actgaagagg ggtgtggtgg gaactaggct ccaggagatg    84360
agcaggtcag cactaggaag acctggacat tgcctggaga gcccagagga cttcctggag    84420
gaggaggcat ctgatcatac tgcctgggag gtcagtgcag aggagatgcc aggagcaccg    84480
aggatgtggc aggcacggga gagtccagcc agtgtctggg aggccctgag gacgaggttg    84540
gggacaccag gaaatgggga gcctaggcgg ctgtgtgctt agggcaggtg ggtgtgggtg    84600
aacaggcagt ttggctcagg ctgggactca ggagagtgtg gctggaggtg gccacattgg    84660
gaatatctgt ggagtatggt gccagggagt gttgcagcac agagatcccg tccgcacccc    84720
agcccaccct ggccgccttt tctgaggaca cacgttgtga gtcttctggg gctgcagaac    84780
acagcaccac taactggcag cttaaacaat ggaaacttgc tctccggcag tctggggctg    84840
gaagtccaaa acgaaggtgt ctttatgagt cagggttctc cagagggatg gtaccaatgg    84900
gatgcatgta catgaaaggg agttgattag ggagaactgg ccctcgggcg cacaagacga    84960
agtcttacga taggccagct gcaggctggg gaagaaagaa gccagtagtg gctcactccg    85020
agtccaaaag cctcagaagc agggaagccg acagtgcagc cttcagcctc tgccagaggc    85080
tccagagccc ccggcaaacc actaataagt cccggagtct aaaggcccaa gaacctggaa    85140
tctgatgtcc cagggtagga cgagtggcag gaagcatcca gcatgggaga aagatgaaag    85200
ccagaagacc caggaaaact gcttctccca cctgcttccg cctgctttgc cccagccgca    85260
ctggcagctg attggacgcc accgcccacc cacattgagg gtgggtcttg ccctcccagt    85320
ccactgactc aaataccagt ctcagggcag cgccctcata cacacaccca gatgcaatac    85380
ttcaccagtt ctctaggcat ccttcaaccc agtcaagtcg cgcctggtg ttacccatta     85440
cagtgccaca gggctgcgcc ctccttccc cgcagccact ggtagctgcg ggcagccttg     85500
ttcctgtgct ggcagaggaa ccactcacct ctgtttccgt ctccacatgg cctcctctgt    85560
```

```
atctgtctct tctgtcattc tgcatgacgg attagcccag agtgaaccct acccacccag    85620
tgacatgggc cagggctccg ggcagcacag ggtgtggcct ctcactgtgc agctttgagg    85680
agaaaagtcc attctgccga tggcaggtgc agaccataag tgaccctccc cctccccacc    85740
accaccagtg agcaaaagct tttcctttcc ttcctgcaga cactggagga aagggtggca    85800
ggtggaccca ccacagcccc gctctgctgt ggaggtacag cccttctggg cgtgtgaacg    85860
agccagtttc acaaacacag aggccaaggc gagagtggcc cgaaagcctg caacctgact    85920
gctcagggag ggcggctgcc ctgcagttca gcctgtccga ttcccgccta attgtgcccg    85980
ggctctgatc tcgccacctg ctcgtaacgt tctctgtccg gacctcagag ccgctccatg    86040
tagtgctcac ttcatgttaa ttgcaggacc actcagatca cctctgctgt cacttaaaag    86100
gggcatttca ggaggaaagc acttggtttt gtgtgaatca gtaagactta aaggggaaca    86160
agcacccagg agaagagaga cttttccgtc ctctttgttg gtgaagcgag gatgaaagag    86220
tgggcatccg tcgctgggga ctgggctccc cgcccagctc tttctgtgca cttgaaagca    86280
ctgcccttgg actttgagaa ggaagcgttc agtgggggag ccaaagggag agagccagcg    86340
aggttctgaa gaaggaggtg aggaggggct gcctcctcca tgaaggatgg tgccgggggt    86400
ggcagggaag cccactcagt ggaacagaac tgctgggtca gagctggccc agggctgagc    86460
acttcttgca gaggagggaa gggatcctcc agtaaatcct gaggaggtga ttggttaatt    86520
atcagcccag gaatgggggg tgaggtgggt aggaatccag gctgctggct cccatcacag    86580 taaacgcag gtggattgag gttaaaaaaa aatcacaggg cccggcgcag tggctcacgc    86640
ctgtaatccc agcactttgg gaggccgaga tgggtgatcg cttgaggcca ggagttcaag    86700
atccatctgg ccaacatggt gaaacccatc tgtactaaaa atacaaaaat tagccaggcg    86760
tggtggcacg tgcctgtaat cccagctact caggagtctg aggcaggaga atcacttgaa    86820
cccaggaggc gggggttgcg gtgagccgag attgtgccac tgggcgacag agtgagactc    86880
cgtctcaaat aaataaaaag aagaaaccta gaagctgtgc agatctctgg agaaaaaccg    86940
ggcagtgagg accagagggt ctttagactc agccacacag aattttcaga ttttttcagt    87000
ttccaaatta aatgcaaaaa acatacagga aaggggtttg tagcacgtaa aacccagaag    87060
agatccagac atctcacact tagaattgaa gagctcctac acaaaggctt ttggtaaatg    87120
ctgggaccga gaagctgaga accggtgtga atggttaatg aagtaagact gtaattgttt    87180
agagatgagg acagcatgac ctccacaggt gatcagggaa acacaagaca tttctctgt    87240 caacatcaaa gatgttaaaa gtaattaaag ccggccgggc gtggtggctc acgcctgtaa    87300
ttccagcact ttgggaggcc gaggtgggtg gatcacgagg tcagcagttc aagaccagcc    87360
tggccaagtt ggtgaaaccc cgtgtctact aaaaatacaa aaaagtagc caggcgtggt    87420 ggtgggttcc tctaatccca gctactcggg aggctgaggc agagaattgc ttgaacccgg    87480
gaggcagagg ttgtagtgag ccgagatggc accactgcac tccagcctgg cgacagagc    87540 aggactctgt ctcaaaacaa cacaaaacaa aaacaaaaca acaaaaaagt aattaaagcc    87600
cagggttgct gtcatggggt ctgccaaccc tggggatgtg ggacaggcat ggaccctact    87660
ctctggaaat cacgcagaaa tgtgcagcga tgttcccatc ctgcctctct tcaaaagaaa    87720
tcacccgtca ttcggaggtt tgtgtatggg gaagatcagc tcagcattat ttttacaagc    87780
aagagtggga atcgtgtctg gagttagcta ctccctttgc tgtgaacaac ccactccacc    87840
acgtggggta taaccatgg tagggacacg tctctgagct gtggctgctg gagagccctc    87900
tgctggtggc acatagggca caagtgccgc agggacagct gggtggatgg cccaagactt    87960
```

```
tggcctttat catgagtgga cagaggagtg accacttggg tccctggaga agaggctata   88020
gagagtgagg gtggggaagg gagatcagaa gatgccatcc atgagcagca gtgcctgtca   88080
ggtttggtcc aagcagtgcc ctcaggtggc tggcagaggc caatgcaatt ccttttcaag   88140
ccagcatcaa agaattcctg atgataaata aatcaggcat ctgagctcgc aatggaaaac   88200
cacaaaacac agtgggaagc aggatatcct gagtccaagc tggtaaaagc ccagacagag   88260
gctccaacca tcagaatagg taagggtgtg gcaggtctaa acatgaaaaa tgggcgattg   88320
aaaatatgag caggaggccg ggcgcggtgg ctcacgcatg taatcccagc actttgggag   88380
gccgaggcag gcggagtgcc tgaggtcagg agttcgagac cagcctggtc aacatagtga   88440
aacactgtct ctactaaaaa tacaacaaaa atttagccag gcgtggtggt gggtgcctgt   88500
aatcccaggt actcggtagg ctgaggcagg ggaatggctt gaaccaggga gctggaggtt   88560
tcagtgagct gagaacatgc cactgtactc cagcttgggt gacagagtga gactccgtct   88620 caaaaaaaa gaaagaaaat gtgagcaggg aggccaggtg cagtagctca cacctgtaat   88680
cccagcactt tgggaggctg gagcgggcag atcacctgag gtcaggggtt cgagacgagc   88740
ctggccaaca tggcgaaact ttgtctctac taaaaataaa aaatcagccg gacgtggtgg   88800
caggtgccta taatcccagc tactcaggag gctgagacag gagaatcgct tgaacccagg   88860
aggcggaggc tgcagtgagc caagatcgta ccactgcact ccagcctggg aacagagcg   88920 aggcgcgagg ctgtcggagg gagggaatat gagcaaggaa caagttggca gcatgtaaga   88980
cgtacttaaa acgttttac ccattaatct atgaattcct ctgagtttct gagaatggaa   89040 acttgggtt taggttttat ttttttaatg tcacatttcc tgaaatgtta ctattcaaat   89100
atagatttga aacaagagct tttgacagag cttgggcagc ctcacttaca aagcacacac   89160
gtgaggtctc tgtggtgggt gccaacccett ggcagattca cactgcccett gtcagcagat   89220 gtcctggcct gaccccaggt aagggtggct ccccacggaa aggaacccttg gtcaatttgt   89280 tttttgtttg tttgtttgtt tttctttttc tttttttttt tttttgaga cacagtctca   89340 ctctgttgcc caggctggag tgcagtggcg tgatcttgac tcactgcaac ctctgcctcc   89400
tgggttcaag tgattctcct gcttcagcct cccgagtagc tgggattaca gatgtgcgcc   89460
accacgccca gctaatttt tgtacttttag tggagatggg gtttctccat gttggtcagg   89520
ctggtctcga actcctgacc gcaagtgatc cgcccgcctt ggcctcccaa agtgctggga   89580
ttacaggcat gagccactgc gcctggccaa tcttggttaa tttgtaaaga tacctggtgg   89640
ctgtgaattt ggtcttaact aggaccgtag tgttgcagag taagatgtta aatggtgacc   89700
tagagaaagc caaacacatt aggcacatta taccaaaaga acttgacttt taaataatgg   89760
ttttagaaat ggaagctggt gttcttctgc gctgtggacg cggaggagaa tggagcaggt   89820
ctgcacagcc aaagtgcctc ctttcactcc agggtccagg catccagcag ccgaagcgcc   89880
tcctttcact ccagggtcca cacatccagc agccgaagcg cctcctttca ctccagggtc   89940
cacacatcca gcagccgaag cgcctcttt cactccaggg tccacacatc cagcagccga   90000
agcgcctcct ttcaatccag gtccacaca tccagcagcc gaagcgcctc ctttcactcc   90060
agggtccaca catccagcag ccgaagcgcc tcctttctct ccagggtcca cacatccagc   90120
agccgaagcg cctcctttca ctccagggtc cacacatcca gcagccgaag cgcctccttt   90180
cactccaggg tccacacatc cagcagccga agcgcctcct ttcactccag gtccacaca   90240 tccagcagcc gaagcgcctc ctttcaatcc agggtccaca catccagcag ccgaagcgcc   90300
```

```
tcctttcact ctagggtcca ggcatccagc agccgaagcg cctcctttca atccagggtc    90360
cacacatcca gcagccgaag cgcctccttt caatccaggg tccacacatc cagcaggtgc    90420 cgactgggc aaaactccca atgccggcat taagctagat tggcccggaa tcagaggtct     90480
tgggtgggat gcccctctc acccatccct ccttcgaata gagcccacgg tcctggtgtg     90540
gctctgtcat ggctgggctg atgtaggtag catgtgcaga ggatgtggag tcggctcctt    90600
tttcctgtga cgaagttgaa agcgatgatg catgtgtgtt ttcttacccg atgcccactg    90660
tgtgctgggc actgtcctag gtgctggtca tccggcccca cccaaacaag tgggctgtgt    90720 gggcggggg agggtccccg ggccctgacg tcccgagcag gctcttctga tgagcaggag     90780
agtcccgtag agggtctgga ccccctttgc tcagccgcac ctgatgccca catgtgctga    90840
gggtcccggt tcctcacgtg aactcagtgc tgtatttct cttcagtccc gtttcctcac     90900
gtgaattcag tgcaggcggt tcacagtaca ctgtatttcc tcttcttttt ttttttttt    90960 tttttgaga tggagtctca ctctgtcgcc caggctggag tgcagtgacg caatctcggc    91020
tcactgcaag ctccgcctcc ggggttcacg ccattctcct gcctcagcct cccgagtacc    91080
tgggactaca ggtgcccgcc accacacctg gctaattttt tgtatttgt agtagagacg     91140 gggtttcacc gtgttagcca ggatggtctc aatctcctga cctcctgatc cacccgcctc    91200
ggcctcccca agtgctggga ttacaggcgt gagccaccac gcccggccta tatttcctcg    91260
tcttaactca ggtgtgaggt gagctctgta ataggaagga aatttgtgaa aaatggtaaa    91320
agagggaaaa gcatatgaaa gggctgtgtc tggaaagaat ctgaattgga ggctctgggc    91380
acatggtgac agtgcagatg caccccttta ctcccaggaa cactttgggc acttaggcaa    91440
ggcagaaaat gtccaagcag gtcccgacaa cattcattct catgcctttt gtaacattta    91500
aacgttcatg aaaacatcgc caaacaagct gataattacc atcattttgg aattgttcag    91560
aaccatgaag aataaagaag gatcatttaa aatcttgaaa aatactgaac aaagaatact    91620
aagataattg caggctgcca tgtagcagtt caagatgttc atgagtccga gttccccttc    91680
tctgaggctg tcaggaggag gttctgtttg aatgaaggtc aggcaggggg tgccccaca    91740 cactctgctt agccctagac gggaccccag gctgctctac gcagagcgca gcaggagctg    91800
cagcccccca gcccctgcaa gccacggggc cttgcctgaa gcagcacctc gtcacccctg    91860
cccgatggca cctcccctgt gtcccctcat gcagagcagg gttccaggcc tctccttggg    91920
gccactggtt cccccaacct tgggatagac ccaagaggag gctctcaagc ttgggcaagc    91980
ctggcgcccg gaagggacaa ggtgccgggg ccacctgttg cccggctcag tgtcctcttt    92040
tgagaaggta taggtgtgga aggccctgcc tgtcctctcc gctggcccct cagtgtggcc    92100
tgggcctgac gctctgttcc cacctgcaga gagcgtactg cggtcagtgc agcgagagga    92160 tatgggcct cgcgaggcaa ggctacaggt gcatcaactg caaactgctg gtccataagc     92220
gctgccacgg cctcgtcccg ctgacctgca ggaagcatat ggtgagtggc agggctgggg    92280
aggcccgggg ggcacgggcg ggtcgggc gtggcagcca gcccattgtc caagcagacc      92340
ttggtgaccc tgggttcttc aagagggggcc gtggtgccgt cctagctctg ggctgcagcg    92400
tgagactcag gcggcagtct tggataggac ccatcttcct gagccccac aagcccccgg     92460 cacactctgc tcattgggc atgaggctca ggcagcaggc tcaggtagga cgtggtacgc     92520
tctgctcagt gggtcggagg taaggttcat tcatacccca gtcttgaacc agctcttaag    92580
gactgtggag gtgaaagcca ggtctgacct agtagcattg ggcacgctga ggctccgaac    92640
atctggagcc tctccctggc atccccctg ggaagccatg cccagcctgt gatgagggcg     92700
```

```
gcaccttccc tccgccatcc ccgagtgctt ggacttgaag catccaggcc tttgggggcc    92760
ttattgactt ttgcttattg aaggctgcct ctggcatttc cgtgtggccc cctgcatccc    92820
actgaaccac gggggtgagg cctggactga acattcaact ccctgggccc tgctgcagcg    92880
tgcagtgggt gtgtctgggg agggtggctt gtctgcatct tgctgtggca tgggaggaaa    92940
ggcgcctgtg gcagtgacgt gccctctcct ctgttacggg ataaagacag agtctggatc    93000
agggtgtcac cccaggatca ccagccacag ggatggggga ccacgcaggc tggtgcatgc    93060
gttggcacag tccttccaga ggtccttcag ctgcatctgc caaaaagcct gtaatgccct    93120
ttgacctcat aggtccactt tagcgtaagc aaatgagacc ggccccagaa atgtggtcag    93180
ctagaggcgg agggaggcca gagcctgcca cccagctgac cgccagtact ggtggctcca    93240
ttatgacata tctgcaggcg gaacccagag gcccttagaa tggcccctg atgcttggtt     93300 actgacagga tgcagctttg ggacagggga gatgaccaag cattgtgcaa aatatcccgt    93360
tgtataaagc acttggtgga aaggtcatgg cctgcagtac cgagtggcca cctccgtctg    93420
cagaatcata ggtaatgttt atgttcttta tctaattcag taaatagca taacaattag     93480 attttatat actatattac agtatacca ttgtaatgtg taaatatgta aatcataaat      93540
agtcttgaag tggccaggtg cagaggctca cacctgtaat cccaacactt tgggaggcca    93600
aggtgggaag atcacttgag gccaggagtt caagaccagc ctgagcaata tggtgagacc    93660
ccatctctac aaaaaaaata caaaaattag ccaggcatgg tggtgcgcac ctgtagtgcc    93720
cgctgctctg gaagctgagg cgggaggatt gctcgagctc aggaggttga agctgcagtg    93780
agccgtgatc gcgccactgc tctccagcct ggatgatgac agactgtgac cctgtctgta    93840
aaaaaaagtt cttaatttta aaagtcaca aagtgtttac agaagctaca ttgtaacacc     93900
tgctctagca cttggtcatg ctgccatctc tgtgtctctc cggcaggatt ctgtcatgcc    93960
ttcccaagag cctccagtag acgacaagaa cgaggacgcc gaccttcctt ccgaggagac    94020
agatggaagt aggcgctgct ttcttccggc cgggtagagc ctgggcatca cctcaccctg    94080
ctcacctctg ccttctagcc acgagtcctt tctcagtccc atctgctctg caggggtcat    94140
tgtcttcaag cctggccacc cttccctggg gctggggatg aggctctcca gggcctcctc    94200
tcaatccccg gcagagatga gcagggtgag ctggccctcc ctggaggctg ctgggcaggg    94260
atgcctccgt gaagtgctgt tgtggttgcc caggggtgca gagcctcttc ctctaaccag    94320
ctccgggagt tctcgaaggc acttagtgca gcagccacca tggccgggca cctcccacaa    94380
tctggctgct gcacagagct gagccctatc tggggaaagc ctggcgaggt ggctgctgca    94440
cacacagcgt ggcagtggca tggtccttgg atttttgtga gggtttgttt gttgtgggga    94500
aggacttgtt ttattgctat gaagcattca gagagagaac tctaaccacc atttgactta    94560
caggtccgtg tttgaagcct cacacccagc cccctcacc ggggggggg gagcacctt      94620 tatttgttgc atgtgggtgg tggggagggt gggaacaata aacaagcgac tgatgatgat    94680
tttcactcga gccttttggc actgatatgc ggactcagtg gctgacgata ctaatagtct    94740
attaccggtc gttgttttta ccgcttacag ttcagatgga ggtatatata cccacatcag    94800
nnnnnnnnnn nnnnnnnnnn nnnnnnnnnn nnnnnnnnnn nnnnnnnnnn nnnnnnnnnn    94860
nnnnnnnnnn nnnnnnnnnn nnnnnnnnnn nnnnnnnnnn nnnnnnnnnn tctcttttgg aaaatatcag    94920
cccttgactt ttcgtttttt tttttttttt tttttttttt tggagtctcg ttttgttgc     94980 ccaggctgaa gggcaagggc gcaatctcaa ctaattgaaa tctccacctc ccgggttaaa    95040
```

```
gggattttcc tgcctaagcg ccccgagtag ttggaataac aggcatttgc caccatgacc    95100
ggttaatttt ttttgcatta ataggaaaaa cagggtttca ccatgttgac caggttggtc    95160
tgaaactcct gataatacat ccaccttggc ctcccaaagg gctggaatta cagggggag    95220 ccaccgggcc cggccagcct ttggttttta aaaagcatc ctgttttttt tcccctggaa     95280
cccccacatt taacacctgg gggtcaaagg ggcttttttt ttggggtttt ttttgcgtgg    95340
gttttttccc gttttgggct taaagggga ttttttttcta cggtaatctt taattcaacc   95400
caatttactt taaaatctac ctttaaaatt ataaattcca gccacttaat ttttaacttt    95460
aaaaattccc attggatttt tttttttttt ttttcccca gaatggaaag ggcacctttt    95520
gggttcattg aaacctccgc ctccaaggtt aaagaaatat tcctgcctca gcctcctgag    95580
tagctgggat tacggggcca cattaccacc ccccattaat ttttatgttt taattaaaaa   95640
ggggtttcac catgttggcc aggctggtct caaactcctg acctcaggtg atccgcccgc   95700
cttggccttc caaagtgctg cgtatattta aagatacagt tagataactt ttgatgtatg    95760
caaacacata taaaacatgt ataaaaccct cgctgccgtc cagatgatga acctgtccgt    95820
cacccagaag ctctctccta cccacacccc tttctcccca ggctgcagca gtctgctttt    95880
gggcctgtag attcgttgcc ttccttagag ctttgtctaa atgaaatcct acaatatgtt    95940
cttcttttgg tctggcttcc ttccctcagc gtcattattt tgggctcctt ggatgcgtgg   96000
cgtgtgctgg gcagtgttcc cctgcgtgga tgtcgcgttt gttcctccat ttgcccgttg   96060
gagcgtgtgg agtgtttcca gttcttgact gtcacaaaga aagcggctgt gaacaattcg    96120
gtacaagttg ttgtcgggat acaccgtttt atttccctgg atagatacct aggtgtggaa   96180
tggctggatc atatagtcgg agctgatgtt caactttgga gaactgccag gctatgtgca   96240
aggtgtgggt ggcatttgtt gacctaccag gggaaagtgt atatatctat tgttactcct   96300
atcacccgtc tgtgcaccct tccgtaccct ctctccctcc cccccctcagt tcacccttt   96360 cccctagccc ccttccctt acactccggt tttgccccct gttgtgctca ccaccccgat    96420
ttttccccct ctcctctttc gcctcgtctc tcagtcacca cccctttttt ccttattctt    96480
catctcttag attacgctat caatgtaann nnnnnnnnnn nnnnnnnnnn nnnnnnnnnn   96540
nnnnnnnnnn nnnnnnnnnn nnnnnnnnnn nnnnnnnnnn nnnnnnnnnn nnnnnnnnnn   96600
nnnnnnnnca gttttcttga cattatgatc taagcagatt attgaacaca cgtcttaaat   96660
atcatctttt caaactgcca catgtaccat catatagatg tgctttaata aagaggtcag    96720
agagctgtgg cccactgtag ttcttgtttg ttttttttgag ctggagtctc actcttgttg   96780
cccaggctgg actgcagtgg tgcaatctcg gttcactgcg acctccgcct cctgggttca   96840
agcagtgctc ctgcctcagc ttcccaagta gctgggatta caggcgcttg ccaccatgcc    96900
cggctaattt ttgtattttt agtagagacg ggtttgggtt ttaccacgtt ggccaggctg   96960
ctctcgaact cctgacctca ggtgatctgc ccgtcttggc ctcccaaagt gctgggatta    97020
tagaagtgag ccaccgcgcc tggcctgttt gttttttaat tgtggtaaaa tacctataac   97080
ataaaattca ccatttttaac catttctaag tgtgtagttc agtaaagtaa attcatgctg   97140
cacagccaat ctccagaatt tcatcttgca caacagaacc tccgcagtcc cacctgcagc   97200
acacaggagt tacgatgtct cgccgtcctc gctgacactc ccgactttct gttcctggcc   97260
gtcctcttgg ggcgaggcag tgcccagtgt gggtctagtt tgcctctccc ggtggttggt    97320
gatgttgagc ctctcacgcc tgtggccgct tgtgtgtcgg ctttggagaa acgtctgcac    97380
aggtcctttg cccgttttgt aattgagttc ctcgtttctg tggttgcgtt gtcctgtggg   97440
```

```
gtggttgacc tgcacgcacc gtgtgaactg atcccacttg ttccatgcgg acccaccgat    97500
taccaggtgg gagcagcagg gggcgtccga gggccctgac cccaggcggg aggacagatg    97560
cgcgtcctgt gttggggcca cggagttgtg ggcaattgtt tcttttctt ttactttctt    97620 tggtatcttc caaatcttta taaaatcttt ataaaaatta tttaaggaga agactcatgt    97680
agaatggaaa gcgtcgtgcc agacagtgct tggtacttgc aagaatggcc gtgtccccag    97740
gagccggtgg acgaatctgt ccttgctgcc acctgtgcgg ccgcagagtg agacaggagg    97800
gaccggcagg catcgcgctt ctcccctaga tactccggcc atgccagccg ccccctthggc    97860 tccggccccg tccatccagc cccttccag ggctttgtcc cctcacccc gccgccctcc    97920 ccctgttttc ctacgggagg cgaatccttg atgagaggag gaggccggga accctgcccc    97980
ctctgtgtga agaggagggc agcccctgct gctttgtagg gaaaccctgc ccaagagaag    98040
ccccagctca gcaggacgga gtccgacgtt cccgcctcag ggtgcccaga gagggcgggg    98100
acaccctggc tgggacaaag tgcgcagctc tacccctgct ctgaaatgcc cgggactcgg    98160
ccgcgccctc cccctttttc agagcaacct gtgggccctg gcaaggatag gcctcaggca    98220
aaggaaaacc accctcgttt tcttagcttt tagattttaa aaggagcagt ggggccaggt    98280
ggacttgaag ctccgtgggt ttgtttaagg tataaattca ttgagcttga agacgttgta    98340
cgtggaagtg aacagaacac acataattta ttcatggatt ttagctggcc tgttttgta    98400 caaagggagc ttttaaattt aattattttt aagcattaga ggatggtgta tccgaggcag    98460
ctggaggccc tggtcttcac tgtgagcagg gagggccctt ggacagggc tcgggaggag    98520 gggccaggtg gaccctgca gggctggagg acactgaggg cctcagatca ccacacagtg    98580
ggcccagcta gggggtgacc ctgaattcca gtcccagcgg acacatctct tgccttcagc    98640
atagagggcc ccaggcctcg ggccctgcct cagttgcctc cacgatgtca gcttccaggt    98700
gtggggaccg ggtgccacct cacccccag ttacacccac acgaggccgc ggtgcccagt    98760
agcacagaga tgccaatgtg atgggtggtt ttcaacagga actcaagaga aaagttcatg    98820
cttgtgagga cagagctgca gctttagccc tgagagacct ggcgggagag gaggcagatg    98880
gcgagggccc caccggcaga gctgctgccc tgaaaagcac ctcctcctgg tggacaccag    98940
gtgcatggtg tggtcaggtg tggagtgtgg gccgctggc ctcgctgctt cctgcgccct    99000
gtttaccacc cctcacccc tggccccagc cttgctcttg gcgggcggct agtgtcctct    99060
ggccgccctg gggcaggtca gaccgccggg gtgtggagtg gggtgcttgc cttttttctgc    99120 ctgaccctgc ttcgtgcggg gactctggga cgctgtgact tggctctggc ctggtccagc    99180
ccccagtgtc cacttctctg gaaggcgaaa ggcagggtgg gggtctcctt gatgtgggac    99240
tggaagctgc tcagccagtc tccctggaaa aggtcctggt gacagtcact gctcgctgca    99300
gtggctggtg ccctcctcaa aggtgagggt gtccgggtgg ctgttggtgc ggggccgctg    99360
ggacctgtac cctctaagtt gggacttcag ccccgcctct gccccaaaac gtggtgggct    99420
gagatggggg aggcccttgg aagggcccag aggaacccca gggcctcaca gaggacgtgc    99480
tgtgtacggt gcctcctccc tgcggcctgc cccgcctgtg cttggagctg catcgggcac    99540
agcctgcctt ggcgggcacg ggacgagccg aggatcccg cgtcgacgtg gaggtccgcg    99600
gccgtcagcg ttgcagccct tggccgggca ctaagggctg agtgtggggc cagggcagag    99660
ggagccaggc cagcagctcc aggcccgggt ggaggaagtg ctgcctgaca cgtgtgtctg    99720
ctccctgcgg cacgtccaca gcacctgcca gcccactttg ggtgaccctc ctgtttgtcc    99780
```

```
tgtcctagcg cagccacatc ccttgggagc ctgcttgtct ctagaacctt ctgcctgatg    99840
cacaacctca gagccctccg tcgccatccc tcccccgtcc cgggagcagc ccccccactt    99900
ccacctgtct tggacgggag ctggaaggga cgtggttcca gtcctgctgt gccaagcctg    99960
gtgacccgag ggtaccctcg gcctcccggc ctgaactctt ctcctaccat gatggtgcct   100020
gggatgctgt gtggtgcccg tgggcagtgg cggaggcagt ggccccggct cgttgaacct   100080
tgggcactgc ccattctgag gcgcccgctg tgccccggctc gttgaacctt gggcgctgcc   100140
cgttctgagg cacccgctgt gcccggctcg ttgaaccttg ggcgctgccc gttctgaggc   100200
gccctctgtg cccggctcgt tgaaccttgg gcgctgcccg ttctgaggcg ccctctgtgc   100260
ccggctcgat gaaccttggg cgctgcccgt tctgaggcgc cgctgtgccc ggctcgatg   100320
aaccttgggc gctgcccgtt ctgaggcgcc cgctgtgccc ggctcgttga accttgggcg   100380
ctgcccgttc tgaggcgccc gctgtgcccg gctcgttgaa ccttgggcgc tgcccgttct   100440
gaggcgcccg ctgtgcccgg ctcgttgaac cttgggcgct gcccgttctg aggcgtctgc   100500
tgtggccctt accgtctggc ttctctgctg gctcttttgg ccttggattc atttctggag   100560
ctgcagagtc acttctctta gagcctggtt ttggccctct ctcctgcc tataaaaagc    100620
cctgccctgg gttccctgct ccatgccagt tctctccctg cccccgccgg catgacacgg   100680
acactggtgc ccgagtgatg cctgtgggtg atgcagacac tgactgtcac cccagccccc   100740
catgtgctgc tccgccacac cccaggcccc gtagcagggt ggtggtttgg gcagctgggt   100800
ttgctggtcc cctgggagtc caagcaacat caccactggg tcccagatat gccgtctccc   100860
tggggcacct gtgcttctgg tacccagggt ggagtctggt tgtctccttt ccagacccttt   100920
ctaggtctgc gttggcctgg ctggtttccc tgaggttccc tctgtagggg agggcctgcc   100980
ctcctggcag gggcccttgt gtgcgtcctg agctcaccat ggttttggag gtggctgggc   101040
agtggcgggc agagcccat gctgtcctct gcctttgagg tgggcacggc acacgtgaga    101100
gctgagcatt ggtggaggag ccacaaccg gtgcccagtg gttgagtcgc tggtgcccac    101160
cgagggccca gggagtgagg gacccccctga agaggtagct gggagccaga ccctcctccc   101220
gtggatgcct tttcaagtcc ctgtcagttg ttcagagaag agggggagga ttcgcgcttt   101280
gcgtcagatg cgtgcgtcct gcatgggtgg tgccggccgg ctgtgcccaa agtcatgccc   101340
tgcccctgtc tcccgcagcc tggcatgggc tcacgtccgt gtgcttgtcc agcctccact   101400
cgccacagct cccctcccct ccctccttt ccctcccca ctttccgct ccctcctct      101460
cccctccttt ccgctccct cctcttccct cctctgccct ctgctcccct ctcctcccct   101520
cccctcctgt cccttcccct cccttctcct cttttcccct cccttcccct cccttctttt   101580
cctttcccct cccctccttt cccctcccct cctctccct cctctcccct cccttcccct   101640
ctcctccttt cccctcccct cacctgtttg actctgctgt gccagggcc agggcagggc    101700
tggcccctca ctctgcggag taaatggtgt gggggccgg gcctgtctgg gatcagggca    101760
gccaggcagg gtctcctgca ggagcaggca tagtcccagg gagcaggcag ctgcctagga   101820
aggcagtcaa gcagatgggg acctcggctg ccccaagact ggcccggggc tggtcctccc   101880
tgcgtctggc ctctgggtgg gtggtggtgg cttccttgtg acttcatccc tccgatcggg   101940
caggtggttt tgtgcagtgt gtgcctggga ggcgcacggc agcatgatcg gtccctgagt   102000
gtcacggcag catcagaggc cagtttggca tctggagtag ctgccaccga gagaggccca   102060
gccgccaggc agctgggagc acaggtgtcg gcatccact gggagcacgg gtgaggtgcc   102120
tcccttctct gggcagagtt tccccagttg gtggtgtaga cgccaggaac gcggttgtac   102180
```

```
ggacttcgtg aggatctaac acagcagtgt gtaaaaacag cgccaagcgt gtcctcggtg   102240
ggcgctcaga ggcggttgtg agcagtgcag atgctgttgg cctagttctg acagggtggc   102300 ccagggtct ccccgtggcg tggcatggac ggtggcagct cctgtggtca tcactgccat    102360
ggtccggagc ggccctgggc tctgcagcaa ggcggtgaat gtggagctga gcggtccgaa   102420
tcagggtctg ggttgctcgt tcaactcagg aacttcccca gattcctgag ttttcctcta   102480
gccgaggtca ggggcagcca agggaagggt cagccagctc atccagacct cgctctgcaa   102540
caaatctcca gcctgggttg ccatgaggca ccctggggag gactcaggac gaggcccctt   102600
gaggctgaac ctgagaccta ggaaactcca ggtgggtcct aacagggctt gtcactgagc   102660
gtaggcctgg acacggccct gtggtgtctc acccacgggc accagtccct gttgagcaag   102720
gtccacgcag ccctttgttc tggacggagc tgacgctcag gccacagact ccgactccat   102780
tcttcagagg cttcatcgcc tgcacaggaa gagaggcctg gagataccag gttgtcttgg   102840
ggccacagct ggcccttggc atggctgggg agcagcaaag cagttcatta ggaccagggc   102900
tgaccacacc agtgtccatg cccagaggtt ctgggttctg ccctcttgct gtcgtccggt   102960
gcaggccaca tggccacctg gaaggcccg gtcgtcgtc atattccgag tgtgaccaag     103020
agttcagggg cccaggtacc tttctgggcc cctctcaggg tctttggaaa agtccagaat   103080
gagctgggct ggtggagaat tcaggaggtg tggccagtgc cccctgtgc tctcagaagc    103140 aggggtcact ggcgagaggg ctgggtggcc cggcgatcaa cctgaaggca ttccttacct   103200
gcccttggac ccggtgagcc agtgactggc gtaggctttc aaacctttca aaccacttct   103260
cctggagccc cgtgttgtgt gcgtccctca gcccatgcac cccggaaggc acgcctcgca   103320
cccagctgta gagccccatg ttgtgtgcac ccccagccca tgcaccccgg aaggcacgcc   103380
tcgcaccgtg ctcctggtgg ggcccgtgcc aggggggccc aggctcctgg ggacagtggc   103440
ccaggacttg ggatgttaga aataaattt gggtgctgca aaagaaatag cactcgaaca    103500
taaatttaat tttctcagca aggcaatttt acttctatag aagggtgcgt cttgcagatg   103560
gagcaatggc gagagcacac ctgaacgagg gaggtggagg tctcatccta acgcagccag   103620
tccctgctgc tgtgtggttc ccctgttggc tagggttgga ctgcacagtc taagctaatt   103680
ccgattggct attttaaaga gagtagcagt acgagccgga gtggcggggt gaatagtttg   103740
acgggaagga tggttacaga acaggtgact caggatgact aagaacagag caggtgacaa   103800
ggatgactaa ggtcagagca ggtgaccagg ggtgactaag gacagagcag gtgatagagg   103860
ctaggcaggg gttgtttact gaaactaggg gcaaggatat gtaaagtaca aggaagttaa   103920
actttagaat gaagaacaaa gaatgggat gtaaccatac ggatacattg cttctttgga    103980
gaggagctca gaattcatta tacttaacaa tttacaggct aaaacctttg aagaggaatt   104040
tattatgttc tacaggagcg gtgccgctgg cctgtggctt ctgcagggac aagtagtggc   104100
tgtggccggg aggcgttcgg cagctgtgct tcagcccgg ccccagcttc agctcttcga    104160
gttgctggct tctctaaggc ctgtcctgaa gtggcctgga gactgctgag ttacttctgg   104220
aatctgcacc gtgaaagtga aacctggacc atgatgtgag gctggtgaga gggtgccctc   104280
tgccgtcacc cccggccttg tagaaaactc attccaatgg ccctctggtt ctcactcagg   104340
accaaatagt gatggttttt tgtttgtttt cgttttgttt tgttttgttt tgttttgttt   104400
tgttttttta gacagagtct cgctctgtcg cccaggctgg agtgcagtgg cgtgatctcg   104460
gctcactgcg agctccacct ctcgggttca caccattctc ctgcctcagc ctcccaagta   104520
```

```
gctgggacta caggcgccca ccaccacagt tggctaattt tttgtatatt tagtggagat 104580
ggggtttcac catgttagcc aggatggtct tgatttcctg acctcgtgat ccacccacct 104640
cagcctccca aagtgctggg atgacaggcg tgagccaccg cgccgggccc aatagtgatg 104700
tttttactgc tctgggcctg atcgcatgca ccgttgtctg tgctgtgact tccgtcgttg 104760
tctgtgctgt gacttccgtt gttgtctgtg ctgtgacttc cgttgttgtc tgtgttgcga 104820
cttctgtggg atattcgttg gagaaggagc cacacagctg tgtgggaccc ggcactcctt 104880
catcaccatc atccagggcc acggacaccc cctctcacaa gtcgctggga tatgaaatta 104940
gggaataaat gggaattttc agtgcgatgc agctggcgct aggatcctcc tcagtgtgac 105000
gtctgagacc ttttcccagc tggagccctg tcattcattc attcattcat cccatgccag 105060
gctgggcggc tgccagaggc acaatccgga accgcccctt gctaatgggc ggaccagtga 105120
aagcaaagcg ggctcactgt gcagaccaat gattgacagt tccagggtgt gatggacaca 105180
ggcggctgcc aggaaggagc cccttcagaa gcagtgggcg gggcggggtg gggaaggccg 105240
tggggaggag tgacttccag atgaggctca caggactgta cccggaggga ggggcagca 105300
aggaccctgt gggcagccgg gggcacggca caggctgtgg ctgtaggtgt gggtggtgcc 105360
caggcattga cagaggggag ctcactggac ggggcagcgt ggaggtgagg gtcgggtgag 105420
ggcccctcgg gagcccctgg ccatgttagt tgcacatttc atgactcttt aaggagttag 105480
tgaggcctgg gtgtgaccta tttcccgttc caattaaaca ggtcattagt ccgtgtcgtg 105540
ctaaagcaga tcactcgcaa ggaatggaaa acccttgaaa tacgtttttt aaatcggtga 105600
aagtgagaaa ctgatgcctc tgtgggaaaa gaccagactc cagggtctgc accctcagag 105660
tgatgagctg cgtctgttag gggtgacctg aggtccctgc tttgaaccag cttgttgaaa 105720
ccggaagcca tttctcatct tctgtaagag cctgcagccc ctgtcagatg ccagccattc 105780
cccaggtctt gctgacactg tcattaggat tcctatgagg gccagtgggg agacagctca 105840
gtctcggccc tgcttccgac cccaccacca cccccaaatg catactgctg gcctttcctg 105900
ggtttaatttt tatttgcag tggtagaggt tgtttgcta aaattatttc aaaatctgcc 105960
ttgtggaaaa acgcccacgt cagggtgacc atctgtggta accgagaatt ccttggaggc 106020
agcgtcttca ccgcctggct aagcggatgg cacaagctgc cagccagacc tctgtctgtc 106080
cctgcccaga ggccccagct gccccttcct ccaggcacct ccctgatctc tggagtccag 106140
gttttgttcc caaggtccta cctttgtatc taaatgctgt gtcctctccc cggacgatct 106200
cctccaggca ctggctctca ggggccagct ccccatgggc gatgatgtct ctgatacagg 106260
aacttatggg taccttgcaa gtttgcacag aaagtggagc ccgtctgttc cttctggggt 106320
gtgcgagcgg ggcctcgggg agcaggtgca ggacagggca caggaggaac aggcacggct 106380
ggtggtgtgc agtgaacagc agtggtcaca ccaggtggtg gctcccgtgg gacttttgag 106440
gccgccccag ccctgagcag gtggggtctg cagaggcctc gtgggttgga ggagacttat 106500
tcagagggag ttttggtctt gctagaaatt gcatgagatg aaagatgaca ttttaattct 106560
atcattgagg catagtcttt ccaacacacc ccctgaggtg tgagggaggc tgtccctata 106620
tgatgtggtc cccgctcctt caggctgggg ctcctggcca gttcatcttt cgtcctgtgt 106680
ctgactttct ctatcatttc taaaatgact aagacaattg attttgttaa aaaaaaaaa 106740
aaaaaaaggc gttaagatga ttctactttg tagagggatc ccaagggagc gtctcctctg 106800
ggactggccc tgtcccccat cttgttttcc ctctaaacga catgtgagtt cccaactctt 106860
gattttagtt ctgacaactg gagactttat tcccataacct ttttaaaact ttttaaaagg 106920
```

```
tttaacttca aggagatacc attccttttg tgtatttggt tactaaagct gtcttgcatc   106980
tcaaatgtga tttaagaaat caagcaaaat gcactggcca cgtcctctca gtaggggag    107040
gccagcgggc atctcccctc ctcgccccct tctggtggt ctcactgatg tcccccggcc    107100
cccagccctc cttcctttct ttcccttgac tttgtcctca gactccaggg acaaccctg    107160
gtgcgagaca tcctgttgct gatttacttg ttctctcatt tgtttctgtg tttgttccat   107220
ttctttcgtt cattcattca ttcattcata ctcagctgcg gagaccatca gccagtctgc   107280
gttcggcctg tgtctgccac tggctgcagg gcccggggca aaggtcttca agtgcccctg   107340
gcttcagttc cccttcctgg agaatgaggg tgggagagca cctcccctgg gggtttgcga   107400
agatgacatg agcccgtgca tcctgggtct ggaccgcatc tgatacttag caggtactta   107460
gcagcaggta ctgagtagac acagtgctcc acagcaaaga tgtgtggcag aggcgtagtg   107520
gatgcgtgat cgagacgcac agtagacacg caaggataca cggcagagat acgtggtggg   107580
tatataatgg atacagcggg cgtggtggat ttataacaga tatgtagcag atatgtgata   107640
ggagccaggc atggtaatga caagtcagga atgtcacaga ggactgtgtc ttctgggggt   107700
cctggggcct tttcacgagg aaggattgca ggtgggctt tggaaaaatt gtccaatttc    107760
catcccctgt ctcctttccc cggtcaccgc tcctacccag tagcaggtgg agaaggtgac   107820
ttccatactg ggggccagga tcaggagcag ccacatgcca gagcgggtag gcagcccctg   107880
gtgcctgcct ggccctgccc cgacctccac accagttcag ccctgtgtcc tgcccaggat   107940
ggatgggtgg gtaattattt gattcattca tttccagggt ctcgtgtggg ctttgtgaag   108000
cctagtacac gttttttatt gcgttttttt ttttgtttgt tttgtttgt tttgttttg    108060
agatgaagtc tcactgtgct gcccaggctg gagtgcagtg gtgcaatctt ggctcactgc   108120
aagccccgtc tcccaagttc acaccattct cctgcctcag cctcccgagt agctgggagt   108180
acaggcgccc accaccacgt cccgctaatt ttttgtattt ttagtagaga tggggtttca   108240
ctgtgttagc cgggatggtc tcgatctcct gacctcgtga tccgcccgcc ttggcctccc   108300
aaagtgctag gattacaggt gtgagccacc gtgcccggcc tcgttttg tttgttttac     108360
tttgttatga gtaatgatag atttctagaa acttcgtgta ttttttttctc cactttattt  108420
caactttgta gaaagagatc taaaaatgca agtctcctcc cccaaccccc aactctcctg   108480
cgtcacggat tggttcagaa ccaggagaca cagggcccag aaacctaggg gctggagggg   108540
ccttacccctt tggactcttg actgttttta tattctggcc cctcccccg tctgtctctc   108600
tctcaagaga cagggtcttg ctctgtcgcc caggctggag tacagtggta caatcacggc   108660
tcactgcagc tgggctcaag caagcctccc acctcagcct cccaactagc tgggacttca   108720
ggcgcgcacc accacgcttg gctaattttt tatttttagt agagttgggg gtcttgattt   108780
gttacccagg ctggtctgga atgccccaag tgattctccc acttcgcccg cccaaagtac   108840
tgggagccac cacgccgggc tagactgtgg ggtttttggg gggcaagaat tgtactcata   108900
tctctgtttc cacagtgggt cttacactgt ggacaaacag cagctgatgt tctcacccgg   108960
ccttgttcta agaggactcc aaaaagcaag tcgtagcccc agtgactggg aaaggcttcc   109020
ccgggagagc ggccgacaca gctgccgcag tagtaagggt ttatttatca agactgattt   109080
atttatcagt tcaagacaca gttacacaga gtgtggggga tggttcatca gcagctggca   109140
cgtccagtgg cgcgtgtgcc tcgggaaggc ctgggagggg gacacaggtg ctccgcaggg   109200
aaagctgccc ccacccccagc ccaaagaagc cctccaagct ccatcagtca tgcagtcatg  109260
```

```
tacttttcct catcagcaca aacccccgctt ccttgaagag aagcgtgagg ctgggcacgg   109320
tggcgcgtgt ctgtaggcct agctacgagg gaggatcgct tgagcccagg aggtcgaggc   109380
tgcagggcta tgattgcaac actgcactct ggcctgggca acagagaaag agagagagga   109440
ctgtctagaa gggaaaacag ggatagcaaa gtagatggga aggaagggcc tctgggcgg    109500 cgggtgagtg ctggccgctc ccctctccac aagctgctgt ggtctctggg ggctgcacct   109560
gaggcggcag tgggaggaga ggggtgaagg gcaacgcgcc cccgtttaaa cacctcctgg   109620
cctggacgcc agctgttcac ttgtaatcac tggtcaccct gaagagatgg gatggacccc   109680
tgcccaacat ttggctcagg tgtccacaca gatgacagca ccgcacgcag acgggaggga   109740
gcttctcacc acataatgag gttttctggg gagagcaggg gaggggggtc ttccaggatg   109800
gtccagaaag gtcttgagcg cgcctgtaag gagactgtct cggtttccgt ggcggctctg   109860 ggcaaggcg gggtgagcag gggctgaggc ttgcagggtt tgaactttcc ccagggccct    109920
catcacctca ctgggatgtg ggcgggaggg gagcgggtcg tctcaaacac ctccagcagt   109980
cgaacatcaa aaggggggtc caactcttgg ttgcgatttc tttggctgaa gcctggactc   110040
ctagccccac gggctgaggg aaggttacgg ctggtggttg gatagacgcc agtgcttgcc   110100
ccagagctgc aggggaagaa ggtggcctga acctcagggc ctctgtgtcc agttcagggg   110160
ccagtacagc agcatcggtc tgcgaggggt atgtgttcta gaggagtgag gggacagaca   110220
ggggagcccc agaggcatcc agtggcgcga atggtgggaa gggccctaag aggggaggct   110280
gggaggggac aatcccaggt ggcagggat ggccgcgatg aggccctggg gtggagccca    110340
ggcagggagc atccagggga agccagtgtg ggtgggact gggaggagag agggaggctg    110400
ggcctgccct ggcgaggggt ggtcagaaca tcgctcggtg ccagacaggc aggacgcagc   110460
gggctggcct gcgggctca ctgctgcccc ccggggccga gcacgaaagg gagagttgga    110520
gggcgcttcc tcgccgggtg ttgcggtgtg agcggggact ggtgagtgtg tgctgtcttc   110580
agagagagaa gagcagtttt cagggtgagt agcctttatt cttcacacct cattacacag   110640
cacccaggcc ttttattcag gagggcgcgg ccggcctcac cccgacagcc accctggctt   110700
gttgaccttg atctgtgaca gctcccctgt gagttcagac ttctcaagga cgcttgcata   110760
gccaacattg ttgagaacga gtaaccccctt atcacagcac acgtctgtcg tgccatgaag   110820
caatttccca tccctgtggc tttgaaggca taagtcactg cgtcacggcc atgctgttcc   110880
ttccaaacct gctcgtcagg agacagctct tgcgctgtgt accggcactg ccgcccagca   110940
ggtgacccca gcagctggtt tgtccctgcc tgggggtgag ggcctgcagg gtgtttgtag   111000
acgcaactct tgaaaggccc tgaggttggg gcttggtcat gagggtgccc ggggcccatc   111060
cgggagtaga agtaagtgca ctaggcattt ggccaagggt cacgttaggc cttatttatt   111120 tatttttga acagtctca ctcttttgcc caggctggag tgcagtggcg tgatctcagc     111180
tcactgcaac cttcgcctcc cgggttcaag cgattctctt gcctcggcct cccgagtagc   111240
tgggattaca ggcacctgcc accatgcgca gctaatttt gtattttag tagagacggg     111300 gtttcaccat gttggccagg ccggtctcaa actcctgacc tcaagtggtc cacccacctc   111360
agcctcccaa agtgctggga ttacaggcgt gagctgccac tcctggccag gtctttttc    111420 aaataaatgt ctaagcaaaa tgaatttggg gtgaagtagt cacagagctg tcaggaggag   111480
cagggtggct gcgtgcccct gggagctgct gtgggtgatg accaggtgat gccgggaagg   111540
tcactttcag acacatagtt gtcatcgtcg gatgagaatt attctcaggt ctcaggtggg   111600
aggggctgcc caccaggcct ggatgaggcc ccaccccccc acacacacat gctgggacca   111660
```

```
cgagtggcac cccctgagga tgagggggct cctgcgtttg tgccctgtgt gggaggtgcc 111720
acctcatttg catgtggccc ttccacgtct cctggccatg ccagacaggt cctcaggatt 111780
gttgggagat gagggcctcg cccaggactt cgatggggtg tcccccccagc ccctgtggc 111840 tgatggagca gcctgacatt ttgtggacac aaagccccct agagccaggg aaggacaggg 111900
ccggacccag agccagggaa gggaggtgga gctccagcca aggcatccaa acatcaaaag 111960
gcagaactga gcggcttggt acttgaaaag tttttattag gaaaaatgcc aaactgacag 112020
aagtagagag aattacatag tgaggcctcg tgcacaccct gcctggctcc tgcaacctg 112080 cactccagcc gatacctgtg actctcagca agccctcta gtgggcgagg acctccacac 112140
gtgtcgccag gccaggcgac tctcagcaag cccctccagt gggcgaggac ctccacacgt 112200
gtcaccaggc caggtaactc tcagcaagcc cctctggtgg gcgaggacct ccacacgtgt 112260
caccaggcca ggtaactctc agcaagcccc tccagtgggc gaggacctcc acacgtgtca 112320
ccaggccagg taactctcag caagcccctc tggtgggcga ggacctccac gtgtgtcacc 112380
aggccaggta actctcagca gcccctccg gtgggcgagg acctccatgc gtgtcaccag 112440
gccaggtaac tctcagcaag cccctctggt gggcgaggac ctccacacgt gtcaccaggc 112500
caggtgactc ttcagcaggc ccctctggtg ggcgaggacc tccacacgtg tcaccaggcc 112560
aggcgactct tcagcaagcc cctccacacg tgtcaccagg ccaggtgact ctcagcaagc 112620
ccctccggtg ggcgaggacc tctgcacgtg tctccagagg ccaaagcaga agaaaacgtt 112680
agcacaggag tcacttgact tcaccaaacg cagccaggat gcggtttct ccggctcggc 112740 tgtctcagtt gtttaagaga gttcatgctt ttgagatcaa agttaaaaga aggcctgtgc 112800
ctcgcagggc ctgctctgcc tccccgtgt ttcctcgggg ttctgcgtct gtgaccgggg 112860
tgcggagcac tggtgtgcag ttctctgtct cgtgattcgt gtaacagtga gtgctgcctg 112920
caccaacagc cggctgcctt ccgtggctgt gtgggctcct gtgcggaggc cgcccctctc 112980
cctggccaag caacactgag gcgggattgc gtcctccctc tcctgaggca ggtcctgctc 113040
cagacctgct tttttcccgc acgtcacgtg tcctgagacc cctcagtgga tgcgtcctct 113100
ctccttccac ggccgcacac actcccgtgc ccgttgggct gggctgactg atgcatgtgg 113160
gggctccgtc ccatctttt caactacaga tggagctgcg gtgggaaaac gtgtgcagat 113220
acctcccatt ttacttttgt gctggggctt ttttgggatc agttcctaga agtaggggac 113280
tgggtgaaag gctgatcacc ctcagacacc gaacccctgg aggaaacaca gggagggagg 113340
atgagccctg cgaggtgcag gccttctttt aacactgacc ttgggttctc aggactgccg 113400
aaatcccctc tacccgggct gtgcctctcc ggcctgtgcc tctccggccc ttcggcagtg 113460
tcgagggagc ccccaacacc cagcagcatc cagggatttc ccccagggca gtgtcgggag 113520
cccccaacac cccaacagcg tccagggatt ccccccaggg cagtgtcgag ggagccccca 113580
acaccccggc agtgtccagg gattccccccc agggcagtgt cgggagcccc caacccccgg 113640
cagtgtcaag ggagccctg gcagtgtcaa gggagccccc agacagtgtc aagggagccc 113700
cccaaccccg gcagtgtcaa gggagcctgc ctccgtgggg tgctgccagc cttaggcctg 113760
ggccagtcgg ggtggttgga tgcctgttct ggggtagag aagtcaggta gcccaggggcc 113820 cgcactctca atagaccttc agagaaaagg catcgaggta aatgccgcac tcgagtaccc 113880
gtgtgatctc tgggtggggc catgatcctt ctgggcgctg gtccaagcgc gtggtgaggc 113940
cgtcctctcc tgcagaaccc cggcctcttc gcccctgccc gctcacctgt tctgtcctgc 114000
```

-continued

```
tcacctcctc caggaagcct gcctggcctt ctccatgctg atgggcgtgg cccttgtcc   114060
ctgcagccat gcattgacct ccgtggctcc tggaggccag gccacgtcct catcccctct   114120
gggtgagtga gaggcacagc ctgggtgcgt ggggccgtgg cggctccgag gcgccaccgc   114180
tgtgtcctct catgagtggg tgccgtccag gtctgtcctg ggctggctgc gaggaggagg   114240
ttggcctcgc gcggccatgt gcgtgacagt ggagacatcg ccagcctcct gcttgcacag   114300
ctgacggcag cccctctctc tccagccatg tccccaggac tcttgagtag ttggcctggt   114360
ggccgtggga gaagcaggcc ccgagtcccc agggctgtga gcgaggctgt ctgatgtgct   114420
ccctggtcac caccccctgc ctgtccgtct tgcctgggca gatggaggtg gatgaacttc   114480
ctgcggccgc tgtaacagtg gccgccactg gggggcttaa agcaacacgc atttgttagc   114540
tcagcggtct ggagggtgcg agtgcagatg gagctcactg ggccaaattt agtcaaggca   114600
ccagctgggt gggttctttc tgggggctcc agggagaccc cgtttcccgc cttctccggc   114660
gtctgaagcc gcctgcccct tggtgcagcc ctgagtcacc ccagcctctg cctccgtctc   114720
acgtcaccgc ctctgataca gccgcccccc catccctctt gtgaggaccc cgcaatgacg   114780
tgggcccacc cagatcatcc aggaacatct ccccatcccc acgtccttca cttcatcgtc   114840
tgcaaagtcc cgtatgccac ggaaggtgac acagtcttgg gtcccgggac ttgcatgtgg   114900
ggctgtctgg gttttgcaca gctgaccatg ggtgcttccg gatgcttggc attggaggtt   114960
tctgtcctct gctggaagga ttcctggagt gagggcagca gagggcaccc agatggaggc   115020
actgccggac gcgcagggc gatggtcggg gggcacctgg gagccacctt cccttgtctc   115080
tgggggtga cccttgacct tggtggcctc agttttctca tctgtaaagt ggtgcacacg   115140
atacctgctc cgtcctcctc actgaattgt cctgagatca ggtgtggtcg tgaatattaa   115200
acatgtggat tgcaaccccta gacagagctc ccttggacgg ttgagcagat gcagccaggt   115260
gtgggtccgg ctgtgggcgg aggggtcac acgggccga gtggcttcag cgagagtcca   115320
taggacatgg agagtcccgg ccgtggtgag gacacggggt tgcggcagct cacgcccact   115380
gcagtgtccg gaaggcggtg ctaggtccac ctcatttacg gggtcgggct ctcattctcc   115440
ccattgtaca gcccagcctg tagaggcagg tgaggtccag gccatgggcc tgtgggccgt   115500
gccacgtcgc tcagattttg tggtgtcggt ggtgggagcc gccggggaaa gccgtcatcc   115560
tggagccggg cgagagaggg ccagggcagt ggggtggact ccagaaatgt ccagtagcag   115620
aattgccaga cctggccatt ggctggggtg ttgagggaga cgtctccagg gatgtccagt   115680
gtctcccagt ctgggcaagc ggaggagccg gccagcatgg gccatttcat cggggccctc   115740
cctgggggca gccaaggacc taaaaccaat gggtcccaac caagaggatc ccagaggtga   115800
gacacagaac ggccagggct gaatccgggg ccctccctgg gggcagccaa ggacctaaaa   115860
ccaatgggtc ccaaccaaga ggatcccaga ggtgagacac agaacggcca gggctgaatc   115920
cggggccctc cctgggggca gccaaggacc taaaaccaat gggtcccaac caagaggatc   115980
ccagaggtga gaaacagaac ggccagggct gaatctgcct ccagcggggg ccccgggcgt   116040
gatcagagca ggcaggacct ttcttccctc tctgcagctc cggcactggc ttcctccgtt   116100
caggcttcat ccccggtcag ggggctcctg gtcccgtggc agcccgtgg ctcctgggtc   116160
gcagcttcat gggggaaaca gagactcctc tggtaccagg gtcccctgaa tctccggagt   116220
cccccaagtc cattgagtcc actgggcccg aagagggaaa cagagactcc tctggtacga   116280
aggtccccca gtccctgga gtcccctgag tccactgggc cctcgacacc cttgggtcac   116340
ttgtccaccc tcacaccatc gctggcccag ggaatggggg tttggatcgg ccttggtgac   116400
```

```
tgtgggcctc tgcctgaaac cctgtgagtg tgggtggggt gggctgggtc ctgagagagc    116460
tgggagcagc ggagtgaagg gggctggggt ggggctggtg acagtggagt ccctgtgggg    116520
ggcagggctg gtggacagta gagtccctgt aggggctggt gacagtggac tctgtggggc    116580
cagggtgggg ctggtggacg gtgtagttcc tgagagaccg agccggaagg tgagggactg    116640
gaagcttgca cacgtccctg cggccttccc ctcgggtgcg aggcctgcca tcctgagctc    116700
ccccacccta ccccgtgccc gccctgaggg cgggacccag gccagttcac acagcatggc    116760
gaggtaaggg ctcaggatgg aaggcaggag gaaagttggg cctgctgcac ccatgggtat    116820
tgcggcaggg aaggcgagga ggagccgagg tgggtgctgg gagctgtggg gctggctgtg    116880
cgtgttgggc ctaactcggg ctgagctgag gttactgagc cctcaggagg gtgctgtggg    116940
aaaagaaaga ggcagagaag gtgtctttgg accacttagg ggacggggag ggaaccccac    117000
ggcaactgtg aaggtctggg gcacagccag ggagggtccc aggttgacag ggacaggcgg    117060
ggtgggggtg caacatggag gcctggggct gagcctccga gaagtgatgg gcaggatgag    117120
ggggccagag gggatcacgc aacaaggggg gcaccttggt ggtctgggtg tctccagaga    117180
agctggttgt caggactcaa gaggcggaca gggaggggct ggggttaggg aagagtgtgt    117240
ggcaggggga ggaagggagc ctgcttgccg ggtcacctgg cattgggagc tgtcccctgc    117300
ctgctgcgcc ccgcctgcca ttgttggagt tctccagtct gggctggtct ggatgaggaa    117360
ctggcggggc tgctgccggc ctggactcag gaccctcacc ctccagcccg caccctcgac    117420
tccccaccag ccagaccctc tgtcctggtg tggacagcac ccacatcctg gctccaccct    117480
tgtttcttgc cctttgacct acagcctcag gacgtgcagg agggaggtac gtaggcactt    117540
gtgggtccgg cctcctgacc gaccgtccat ccaccaccag gcttctggat gttcacccat    117600
gtgggagaga cgggtgtcgg ggaagggacc acagcttcct ttcagaagac ccgggaaggg    117660
cagtgccgtg tgccagcctc ccagttggca ccttcctttc accttagtcg tcttcgaggc    117720
gatgtttcct cgggacaagt cattttcatg aatctgctgt aaaacgtctc ccaaactcca    117780
agtgtttccc aaactgagtg aaaatcgctg cagaatgtgg tttccagcag gcttttcccc    117840
ctctccttcc ttcacctctg cctgggttac agggtgcggg ttccaggagt ctgcctagaa    117900
ggcaaaaaac aggctttgct tagaatcccc taaattgctc ataaaacaca gtgtttgacg    117960
tttatgtgta gacatgatcc ttatgtgggt taagctgagg cccctgcccc agtgacacag    118020
aggcctcaaa cggcacagtg caccttctgt ccgaagcagc cggcgaggcg gcccgcgaac    118080
ctctgacgtg ctccattgca atgaggatga acgagcctca ggcggagggt cagcctggaa    118140
cccctgcccc gtgaacacca gccagcttca tgctgaggac ccctcagtcc aacccagagg    118200
cccatgctga ggtcccggca tgggggactg tggggtgcag ccgccgcttg gagcggaggt    118260
gaatgggacc ccacacgttt cctcctcctt tctctggatgc ctgtaatcat cacagtactc    118320
aaaaaaggaa gaagaaaaag gtccttgaaa cttgctggag ttgcagttcc gttttttttgt    118380 ttgtttggtt ggttggttgg tttttttttt ttttggagac agagtcttgc tcttgtcgcc    118440
caggctggag tgcagtggcg tgatctcggc tcactgtaac ctccacctcc tgggttcaag    118500
ggattttcct gcctcagcct cccaaatagc tgggactaca ggagctcgcc accatgtctg    118560
gctatttttt ttctatattt ggtagaggcg gggtttcacc gtgttggcca ggctggtctc    118620
gaactcctga cctcaggcga tccgcctgcc ttggcctccc aaagtgctgg gattacaggc    118680
ttgagccact gcgcccggcc ccattttctt tacatttgtg acttacagtc atcagctgaa    118740
```

```
ggaaagacag tggcttggct agggcctgcc cactgctggc cgaggctggc cgggtcaccg   118800
aggtgcctgc ctctcctgct ctggagccgg gcactgcctg agggcctgca gcaccagtca   118860
gggccccggg ggatccctcc agggtctcag ttctgactag cgagtacctc gattcatgag   118920
tatgtttttt aatgtaaggt tttaacgtaa ggtttaaaaa ggcagccgcc ccgtttcctc   118980
cccactggtc tcgccttcag cagtgatttg tggtgactgt gacgttctct tcggtgggct   119040
gcctgtggat cgccaagtat gtgctcctgc tgcttctacc tgatgtctcc ccatcttggg   119100
ctttgagggg ggctcatccg gggcattcat attttctgcc cgagttcgct cctgacccag   119160
ggcaggtgga agccagcagg tgaggaccag ggtgtcagcc agaaactcgg aagtggcaca   119220
gaggcagcat ccgatagccc ctttgtcaga ggcgaccagg gccttgagtg agctgggatg   119280
gacttctctt atcctgacat cctggaaggg ggtgcagcct gcctgtctgt gtcccagttg   119340
agttggcaac atttttttgtc tttcctcatg atgcacgaag tagtggtatc tctgagagcc   119400
aatggcagcc tagctgccgt ggagaatgct gggggtggg tgagagttgg ggcacagagg   119460
actcatgggg cagaggctgt ggtccagtcc ttgtgggggt gactccaggg atggcaggtg   119520
ggtggtgtgg ccaaggagga gggaggtcaa ggcactggtg ttgggcagg gagaaggac    119580
cgcagtgccc atgtgtttga gggaggggag atgatggtgt gggagtgtag agagggcggg   119640
ggcccagccc acagcatcca tgccctgggg attgggtgcc accggtcaag ggctccacgg   119700
ggctggctct gggggaggga gagcgggcgc catgttgtgt gtgtggtgcg tgtggcgcgt   119760
gggtgagggt atggccggct gcgtaagttt gtggaagcgt tcggaatgct caggagataa   119820
aaacagcaga gggctgcacc cccccacccct cccacccag cttttctcca ggaggacgct   119880
ccgtcgtggc ctgggaggac gtggaaggag ggaccccgga tgcagggcag gttcgtcttg   119940
tgtgttgaga acgtgctctc cagggatctg tgttaataca ggtagcccaa gcacagtgtc   120000
caatgaggga aggaacattt gaaacagaag agatgactta ttttgttgga caaaaaagga   120060
atatggtgga cattaattct tagaagaggt tttatttgaa acaagtcaca aaaataatca   120120
aacagcaggt tgactttgga gttcagctca caaaagttaa gcttacagag caaataaaat   120180
aagctgaaga aaaagataag atgactgggc gcagtggctc acgcctgtaa tcccagcact   120240
ttgggaggcc gaggcgggta gatcacgagg tcaggagttt gagaccatcc tggctaacac   120300
ggtgaaatcc agtctctact aaaaatacaa aaattagccg agtgtggtgg tggacacctg   120360
tagtcccagc tgctcgggag gctgaggcag gagaatcgct tgaacccggg aggtggaggt   120420
ggcagtgggc cgagatcgtg ccactgcact ccagcctggt gacagagcga gactccgtct   120480
caaaaaaaaa agaaaaagaa aagaaaaag ctaagatgca gcaggtggag ccgcctgccg    120540
ttgggtttca gcttttctta tggaaagaat gttacggcct gggtgcctcc attctctgat   120600
ttctttttct tcttgacttt ttaaaattg aaacaaaact ccctaaaaca tgaaatctga    120660
agcgttcaac tccacgagtt tttacaaagc aaactgcacc cgcgtcacata gctgatccgt   120720
gtgtagcttg tcctctggac gcggggccac ccccacaccc cgaggtgacc ccaggcgtaa   120780
cctaccgtc cccggccttg gtgcctgcag atagttttgc ttgtttcgag cttttgtctt    120840
gggatccggg gccatccacc ctgggtgtgg ccgctcagtc gggcccctgt gtgggcttt    120900
cccgtggtgt ggggtgcggt tctgccgtgt ccgtccccac tgcggggctg ctctgctggc   120960
tgaattctcc acgtcttatg tatccaccct catcttgcga ggcaccgggg tcccggcttt   121020
tggccacaga catccgagcg ccttctgttg ccgtgtgcgc atctttcatg tgggcacacc   121080
caggagtgga gtttccggga aacagacgtt tccctcgcgt ggccgcacca ggtcgcactc   121140
```

```
tgcactgtgt ttctgcctcc agttatgtgg ggttttctgc acccacagcc actctggcgc 121200
cagctgggtg tcctgtgttt ccattcagct ctgacatcaa ttacctgacg ttagcgcaga 121260
ccctgcagat gaagggctca ttcccacaag cctgcccta cttgagagcc agctgcaagt 121320
gccaggtgac aacctggatt ctgaccaact ggctgtgaat cgggggtgtc cgtgacccct 121380
tcctgaggct cgggtgggct agaatagctc ccggaactca ggaaaacact ttgcttagtg 121440
tacccgttta ttagaaagga cagccacacg gaggagctgc acgggaggct gaggtatggg 121500
gggtgcagag cttccgtgcc ctctccaggc acgccaccct ccagcacctt ggtatattca 121560
ccaactcgga cactctccag accatgtcat tgagggcttt tgtggaggc ttcgtgacag 121620 gcacggttga ttcaacagcc agccactgct gattacctca gtctctcctg tctcctctct 121680
ggaccgtggg ctgtgggacg aaagttcca acccgctagg cattccttgg tcctgctgaa 121740
gaccagccgc atcctggagc tgtcccggct cccggctccc cgtcatctca ttagcatgca 121800
aaaagacact cttaccgcac tccaggattc ctagggtcag aggggctgcg cgctgggaaa 121860
ctgagacaaa ggctgaatct gtgttgatgg cacagtcact ctgggtcgtg tgggaattcc 121920
cgatgcacct ccttccagca catggactgt cagagccctg cgttgtcgcc agcacagcag 121980
atctgaaagg cactaggctg tggcctcgcg acggctgagg tgagctgctt ctccgaggct 122040
cccgggttat tggggaccct cctttaaag gtgcctgttc cagtcttttg ccccatttca 122100
aaattgggct gtcaaagaac aatgtcattg gggtccgt ctttttttgtt ggttcctggg 122160 ggctgtgtgt gttttagaga caagtgcttt gattttttgt gttgcaaaca gcttctgtca 122220
ctccgcggct cgccttccac tccatggatg gtgtcttctg atgaacagaa agtaaaagct 122280
tactttataa ttagggcttt tgcgtcctgg ctgtgtgtgg ggcctctttc tggactgatc 122340
tgtccccttt gttttttgcc cccatgtcgt actgttctga tttcttctgc tttataatca 122400
ccattggtaa cttgtgttat gagtctccaa tttgggggttt ttagttttca aggttatctt 122460
ggttattggc tttttacatt tccatacaca tgggcttgtt aataagccat ttacagttgg 122520
cttatttgct ttcaaaatct ccataagaca tttggattgc atttggattt cttgatcagt 122580
atgggagatt agcatcttta caatactgag gtttccaatc cgtgaacata tctttaggcc 122640
tttgattggg gttttttttgg cagggagtt gcggggggca gacaggacct cactcttgcc 122700
caggctggag tgcagtggca tgatcatggc tcactgcagc cttgacctcc tgggctcaag 122760
caatcctccc acctcagcct cccaagtagc tgggactaca ggtgtgcacc accatgccca 122820
gctattttgg cattttttttg tagagacagg gtctccctat gttgcccagg ctggtcttga 122880
actcctgggc tcaagtggtc cttctgcctc agcctcctaa ggtgctggga ttacagatgc 122940
aagccactgc acccggcctt aaattctttc aataatattt tgtagtcttg tgtgtagcgg 123000
tcatccacat tttttgttca aatgattccc tggtatttca gtgcttatgc tgttttaagc 123060
cgtattactt ttacagtttt tttttttta tcttttttgtt tatagcaatg tgtaaagaag 123120
tgtgattaac tcatttgtct tggcctctcc tggtccccgt agtttgtctg tggttgctcc 123180
ggaacctctc tgtgcgctgc cattttgtca gtgaccggct gtttgtttct gccttcctt 123240 cagatgttgc cttgttaccc tggcactgtt gatccttcca aaacagtatg ggacagaagt 123300
ggtgacagcc acatcctctc gtgcctgatt tcagggaaaa gctttaagaa ttccaccatt 123360
aagggtgctg tttgcggaaa tactgttttt ccttcgtaaa tccccaccaa caaattaaag 123420
aggttctatt ttattcctag ttgaaagttg ttaatatgaa tggtgctgaa ttttttcaga 123480
```

```
tgcttttttt ccttcatcta ttgatgtgac agaactttc tcctttattc tgttcatacg   123540
atgaattcta tggattggct cttaatggta gaccgatggc attcctgtag tgtgcctcgt   123600
ttggttgtga tgagttcgcc tttttatatt ttgcttgatt cagtttgcta ttattttgtt   123660
tgttgttttt gcaactgtat ttatgagaga gattagccta ttatttcttt tttttttttt   123720
tttggagtct cactctgtca cccaggctgg agtggagttc agtggcccga tctgggcgca   123780
ctgcaacctc cgcctccctg gttcaagcga ttctcctgcc tgagcctcct gagtagttgg   123840
gattacaggt gtgtgccacc acgcctggtt aattttgta ttttagtag acagggtt      123900 tcaccatgtt ggccaagctg gtcttgaacc cctgaccttta ggtgatccgc cgccttggc   123960 ctcccaaagt gctgggatta caggtgtgag ccaccatgcc tggccatatc ttccttttga   124020
ttgatgcttt tatcatcatg aaatgttttt gttttttttt ttttgagaca gagtgtcgct   124080
ctgtccccca ggctggagtg cagtggcacc atctccactc actgcaagct ctgcctcctg   124140
ggttcacgcc attctcctgc ctcagcctcc tgagtagctg gactacagg tgcctgccac    124200 cgcgcctagc taattttta tattttagt agagacgagg tttcaccgtg ttagccagga    124260
tggtctcgat ctcctgacct cctgatccgc ctgcttcggc ctcccaaagt gctgggatta   124320
caggcgtgag ccactgtgcc cggccaaatg ttgctcttta gatgaaaata ttattgtcat   124380
taacatctga tctgtatgat gttagtgtga ccacaccagc tctgtgtgtg tgtgtgtgtg   124440
tgtgtgtgtg tgtgtgtgtg tgtgagatga ggggagggag ggaaggggac ttagtgttta   124500
tatgctctat ttttcatcc tttcactttc ttttctgtat attttggaaa tgactcttaa    124560
aagcagaagt tagttatttt taatccagtc tgaaaatggc tgtgttttaa atgaaagatt   124620
tagtccgttt acatttaatg tcattctgat gtgttacatt gtagctttgt catcttgcta   124680
tgggtcctta tttgtccggt ctgttctttg ttttgtccct cttcttgcc ttcttttggt    124740 ttaatcagat gttttattc cactttcctc cctttattat tatagctttg ttaagtaata   124800
cttctcttaa tgttatttta atggctacct tagaaattat gagtcacatc cttggaacgt   124860
agcataaact acttttacca ttttcttcaa aaccttataa cagtttaatt cttatttttt   124920 ccttttttt ttttttttt gagatggagt gtcactcttg ttgcccaggc tagagtgcaa     124980
gggcgcgatt ttggctcact gcaacctcca cctcctgggt tcaagtgatt ctgctgcctc   125040
agcctcctga gtagctggga ttacaggtgc ccaccaccat gcccaactat ttttgtatt    125100 tttagtagag gcagggtttc accatattga ccaggctggt atcgaattcc tggcctcaag   125160
tgatctgtct gccttggcct cccaaagtgc tgggtttaca ggcatgagcc actgtgcctg   125220
gcctaattat tcttctttcc ttattgttag tttgtgctat tatttatca gtctttgtgc    125280 tgttattatc atgcctgtaa attctacgtg tatttcagac ccacaaacca agtgttgtct   125340
tagacagtgg tccttcagat ttaccccag gttaccttc tagtcttcct gcaggacggc    125400
gcttacatgg agaccagctt ccttctgcct gaagtagtcc ctttagtatt cctttcagca   125460
cagacttgta attaattctt tttatttctt ttcttttctt ttttttttt ttgagatgga    125520 ttttgctct tgttgcccag gctggagtgc agtggtgtga ttttggctca ctgcagcctc    125580
cacctcccag gttcaagcga ttctcctggc tcagcctcct gaggagctag gattgcaggt   125640
gtgcgccacc acgcccagtt gttttttgtt tgtgtgggaa atgtctttgg cattcttcct   125700
ggagggtgtt ctccactctg tgtggagttc taggcaggta gggggtttcc cccaacaggt   125760
ttttgtgttg gcttggagtg tttgtcattt ctgtggtgag ggcgccttcc agcctcactg   125820 ccaccccctgg aaggcaacat ctctttctc tgactcctgt taaaagtgtt ttcatcacaa   125880
```

```
cagcagcctt gtgaaggaca gaggaatcga gaatttctcc taattgagat tggtagagct  125940
tcttgaatca gggacatgat agcttttgtc tcttttggaa aatatcagcc cttgactttt  126000 cgttttttt  ttttttttt  ttttttttt  tgagtctcgc tcttgttgcc caggctggag  126060
tgcaatggcg cgatctcgac tcactgcaat ctccacctcc ccggttcaag tgattctcct  126120
gcctcagcgt cccgagtagc tgggattaca ggcacttgcc accatgaccg gctaattttt  126180
tttgcattta taggagagac agggtttcac catgttgacc aggctggtct ggaactcctg  126240
atcatacatc caccttggcc tcccaaagtg ctgggattac aggtgtgagc caccgtgccc  126300
ggccagccct tggcttttca aatagcatcc tgttctctct cccctgggac ccccacactt  126360
cacacctgtg tgtctaatgt gctctttttt ctgggtttct tctgcgttgg ttttttcccg  126420
ctttgtgctt caatgtggat ttttttctac tgttatctct tatttcaccc aatctactct  126480
taaatctacc ctttaaatta ttaatttcag tcacttcatt ttttacttt  agaatttcca  126540 tttgattctt ttttttttt  ttttgccca ggatggcaat ggcacgctct cggctcactg  126600
caacctccgc ctcccaggtt caagcaatat tcctgcccca gcctcccaag cagctgggat  126660
tacagggtca cactaccacg ccccactaat ttttatgttt ttattagaga cggggttttg  126720
ccatgttggc caggctggtc tcgaactcct gaccttgggt gatccgtttg cctcagcctc  126780
ccaaagtgtt gggattacag gcgtgagcca ctgcgcctgg catcgtagtt ctctcttctg  126840
gggtgggaat gtctattctg tgtccttctc acgtgcaaaa tactgtcatt acatcccaat  126900
ggccccagaa cccttaactc ctcccagtgt ggcggggca  gtcttgtctg aacaaggcat  126960
gggggagcct ggaggcccat tcctcctgag gccaagttcc tccctggctg tgggccagca  127020
taagcgaaca aggcgtgtac ttccggaatg ctatggactg agtgtgtgtc tccccagaat  127080
ccatatgttg aagccctaac cctccagtgt gatggtgttt ggagacgaag cctttgacag  127140
gtagttagag tcatggcggt agttagttag agtcatggcg gtagttagtt agggtcacgg  127200
tggtagttag gatcatggtg gtacttaagg tcatggcagt agttagggtt atatcagtag  127260
ttagggctat ggctgtagtt agggtgatgg tggtagttaa ggtcacagca gtaattaggg  127320
tcatggtggt ggttagggtc acagtggtag ttagggtcac ggtggtggtt agggtcgtgg  127380
tggtggttag ggtcacggtg gtggttaggg tcacggtggt agttagggtc acggcggtac  127440
ttagggtcac ggcggtggtt agggtcacgg cggtggttag ggtcacggtg gtggttaggg  127500
tcacggcggt ggttagggtc acggtggtgg ttagggtcgt ggtagttagg ttcatggtgg  127560
tggttagggt cgtggtggtt agggtcacgg tggtggttag ggtcacggtg gtagttaggg  127620
tcacggctgt agttagcgtc atggtggtgg ttagggtcac ggcggtggtt agggtcacgg  127680
tggtggttag ggtcacggcg gtggttaggg tcacggtggt ggtagggtc  gtggtagtta  127740 ggttcatggt ggtggttagg gtcgtggtgg ttagggtcac ggtggtagtt agggtcgtgg  127800
tggttagggt catggtggtg gttagggtca cggtggtggt tagggtcgtg gtggttaggg  127860
tcgtggtggt tagggtcgtg gtggttaggg ttgtggtggt tagggtggtg gtggttaggg  127920
tcgtggcggt ggttagggtc gtggcggtgg ttagggttgt ggtggttagg gtcacggtgg  127980
tggttagggt cacggtggtg gttagggtca cggtggtagg gtcgtggtgg ttagggtcgt  128040
ggcggtggtt agggtcgtgg cggtggttag ggttgtggtg gttagggtca cggtggtggt  128100
tagggtcacg gtggtggtta gggtcacggt gtagggtcg  tggtggttag ggtcgtggcg  128160
gtggttaggg tcgtggcggt ggttagggtt gtggtggtta gggtcacggt ggtagttagg  128220
```

```
gtcacggtgg tggttagggt catggtggtg gttagggtca cggtggtggt tagggtcgtg  128280
gtggttaggg ttgtggtggt tagggtcgtg gcggtggtta gggtcacggt ggtgttagg   128340 gttgtggtgg ttagggttgt ggtgttaggg tcgtggcgg tggttagggt tgtggtggtt   128400
agggttgtgg tggttagggt tgtggtggtt agggtcgtgg tggttagggt cgtggcgtg   128460 gttaggggttg tggtgttag ggttgtggtg gttagggtcg tggcggtggt tagggtcgtg   128520
gcggtggtta gggtcgtggc ggtggttagg gttgtggtg ttagggttgt ggtggttagg    128580
gtcacggtgg tggttagggt cacggtggta gttagggtca cggtggtggt tagggtcacg   128640
gcggtggtta gggtcacggt ggtagttagg gtcatggtgg tggttagggt cacggtgta   128700 gggtcgtggt ggttagggtc gtggcggtgg ttaggttcat ggtggtggtt agggtcgtgg   128760
tggttagggt cacggtggta gttagggtca cggtggtggt tagggtcacg gtggtggtta   128820
gggtcacggt ggtagttagg gtcacggtgg tggttagggt cacggcggtg gttagggtca   128880
cggtggtagt tagggtcacg gtggtggtta gggtcacggt ggtagggtcg tggtggttag   128940
ggtcgtggcg gtggttaggt tcatggtggt ggttagggtc gtggtggtta gggtcacggt   129000
ggtagttagg gtcacggtgg tggttagggt catggtggtg gttagggtca cggtggtggt   129060
tagggtcgtg gtggttaggg ttgtggtggt tagggtcgtg gcggtggtta gggtcacggt   129120
ggtggttagg gttgtggtgg ttagggtcgt ggcggtggtt agggtgtgg tggttagggt   129180 tgtggtggtt agggttgtgg tggttagggt cgtggcggtg gttagggtcg tggcggtggt   129240
tagggttgtg gtggttagggt tgtggtggt tagggtcacg gtggtagtta gggtcacggt   129300
ggtagttagg gtcacggtgg tggttagggt cacggcggtg gttagggtca cggtggtagt   129360
tagggtcacg gtggtggtta gggtcacggc ggtggttagg gtcacggtgg tagttagggt   129420
ggtggtggtt agggtcacgg tggtggttag ggtcacggtg gtagttagg gtcacggtggt   129480 ggttagggtc gtggcggtgg ttagggttgt ggtggttagg gtcacggcgg tggttagggt   129540
cacggtggtg gttagggttg tggtggttag ggtcacggtg gcggttaggg tcacggcggc   129600
ggttagggtc acggcggcgg ttagggtcac ggcggtggtt agggtcacgg cggtggttag   129660
ggtcacggcg gtggttaggg tcacggcggt ggttagggtc gtggtggtta gggtcacggt   129720
ggcggttagg gtcacggcgg cggttagggt cacggcggcg gttagggtca cggcggcggt   129780
tagggtcacg gcggcggtta gggtcacggc gacggttagg gtcacggcgg tggttagggt   129840
cacggtggtg gttagggtca cggcggtggt tagggtcacg gcggtggtta gggtcacggc   129900
tgtagttagg gtcacggctg tagttagcgt cacggtggtg gttagggtca cggtggtggt   129960
tagggtcatg gcggtagtta gggtcacggc tgtagttagc gtcacggtgg tagttagggt   130020
cacggtggtg gttagggtca cggtggtggt tagggtcacg gcggtggtta gggtcacggc   130080
ggcggttagg gtcacggcgg tggttagggt cacggtggtg gttagggtca cagggtagaa   130140
cccttgtggt gggatttgtg cccttttatag gatgagagga tgagacacaa gagaggttgt   130200
gctgcgcctg tgctctctgc tccacatgag aacatggtga gcatgaggcc gccagcaagc   130260
aaggagatac cccgccctgc aggttccgtc atcctgactc cagcctcgga aacatgagaa   130320
agtcaatgcc tgtcacttaa gccgcccagt ctgtggtatt tgctgtggt ggctgagccg    130380 acggagacag ttccataggt cttgattgtc ctggtggccc tgaacccag ttttgtctc     130440 cagtgagatg cctggcccgg ctttctgtgt gacctccgaa gggtcagcag acgccgtgca   130500 tgtgcaggggc ttgggtggcg catctctctg gcaacaccct tcttctgac gcacttgtct   130560 ggtctcggat gcctccaacg cggtttttac ttatttccca gctttcgtcg attgttcgtg   130620
```

```
ggaggagggt tagactcctc gcgtggcgtc cctggccaca tcctcagcgc tgtgtcccct   130680
cgcagctcag ttcctggttc tgagttattg tgactcagcc gcacgtcctc ccaggggcct   130740
tgccagcctg gctctgtgcc gggcgctggg caatctctgc ctccagcctg ggcctttggg   130800
tctgtttgag ggtgggggac acggagctca gcagtgagga actcggagca gcttcttgtt   130860
gttggtgttg atgtgttttg tttgttttag tgaatccaga aaaaaatttt cttacataga   130920
aaggagcggt atttggtatg aatttatttg caactgactg cttggaagtt ggcgtacatc   130980
tttccacgga aactatgaaa atactggtca gcctctcagt catttcataa aatcttgatt   131040
ttgtattaca acaaattagg atattttcag tagaactgat tgtaaggcca gactgttgga   131100
atgtaattcc ttcccaaaca tctctcaggg gcactttcct gaacggctgc tgacagcagc   131160
atttgaggac ggtggggcgg aggacatcct gggggggcctg gcttcttggg aactggaggc   131220
tttggccctt gtcccacccc tgctcccctg aggaggagg cgtggggccc tgggctggct   131280
gcaagacgtg gagtgactgt gggtccccgt ggcccctgac atgctcccag ggaacccaag   131340
aaaagactga gaccctgtgg tgcctcccgc tttccatccg cattccatgg caggtgagtc   131400
tgattattcg aaggaggctg gagtgtgggc ggagggcagc gccaggtttc ccaatcagat   131460
ttgctcaggg tccctccagc agtccatgcc gcagaggctg tcccttgggg gcccacgcat   131520
cctagccacg gcctcctcac gtccatgcgg ggatttgcgc cctggaagga gccgcccggc   131580
tgcctctcgc caacatgcag cacttccctt cctttccatg gagcacggtt cctgtcccgg   131640
gggtccatat tggccactgt gggagagagt cgggcagctg aattcccgca ggtgggaatg   131700
ccagggcccg aggatgttgc ccctgtcctg aaggctgtcg cccgatcgct ctatccaagg   131760
ctgccctggg gcagcgtcac ctgggggtcc tgcgggggct tctcagcaca gcatccagca   131820
ctgccaccta gtgtgttccc gtcacgtctc ctccccccgc ctgcaccagg caccagagac   131880
ccggatgcca aggcctgtca gcttcctcaa tgggaaactt ttcttcagtg aacaaagctc   131940
tgttttatag actttttaaa ttttcagctc aaaaaccaaa gtctgccagt gttggtggcc   132000
ttggagggct ggtctgctga cctgggctgc aggggctgcc cggctggggt cgtggtcggg   132060
gcaggtgccg cccacaggtt gtttggctgc aggtgatggg caggtccccc atcacgtgtc   132120
cagaggtggg tgctgctggt gggtaatcca gctcattacc tgtctccccc cagccgcctt   132180
gggctgggga ccctgccccg ccgaccctgc catgcccacc ccctccagc ctgattgcgt   132240
gtctcagtca catgaccgcc ctgggcccgt gatgtcactg ggaaatgccc tcatttgatt   132300
ggcttagacc ccagatgaac aagcccaagg tcttgggca tcagagccac ccatgagggc   132360
agctggatgc agcggccaca gcctgtggtt gggaatggc attgcgcagc tccaccacga   132420
ggggacctga ggcttggact gtgagactgg cccaggctcg ccacttgccc ctcacccggg   132480
gttgccttcc cgagggccgc ggacacctga gcagtcccca tgccactgca ttgtggcagg   132540
gacacggccg cccatccctc ctgggtccct tatccacctg cctgtccctt cgtatcactg   132600
acaccctgat acccattgtg ctgcgccgtg tgcccggtg cccacagggc cgggttctgc   132660
ctgttcctgg gggtccgtgt gtcccacgtg cctagacgtg agaggacgga agtcggcaga   132720
gcttggctcc ctgttcgccc gactggcgcc tcggctgtgc ctcttctgtc tctcgagctc   132780
ttctgtgccg tgtggttgca ctaagcagct gtggggaagg gggaggttgt tgcctcagtg   132840
ggagcctggg ctgtgctgc cagtccccaa aacagaccct gcgcccggg caaccatctg   132900
cttcccgcca cagtggtgcc caaaaccttt tccaagtcgt cttctgtgac tttagtgtta   132960
```

```
ttcttcagtc acctttaaaa gcatagcatg ttttcaatca catgttcagc tgggaaatag    133020
atctgtggtt agaaacggga agtttgagtt gcaggcttgc gatccgggca ggtccctcag    133080
atggaggggc tgcacctcca ctgcccccc caccgccgcc cctgcccac ggccacccca    133140 gatcctcaga cgcccctccc tgtgccttct caccctctgg tcctggctgg gccgtcccg    133200 ccccacgtcc cgcctcccac tgccctcagc ctctggaacg gtgcctgcat ggctggcact    133260
atccagcgca gaaggaatga aggacttctg ttcagacagc tctgctggga gcgttctggc    133320
ctgaaatgca gtgggagctc tggtgcaggt gtagccgagg ctcagggct ccacaccagg    133380 caaataggcg aacggcgtct cccgcggctc ccggtggctt tttaggactc tgcgttcgtg    133440
ttctccattg tccctggcag cccctggcca gggtggccca gtgcccacta tagagggtgc    133500
aggtcagttt gtgaccaat ggccaaccag gctgagtcag gtgaggtggg gagtcccacc    133560
ccaaacccca aactccagtg tctgggccac gggcagccct gggacacctt agctctggac    133620
acgaatttgc ggtcattgct gttcttgtgt ctctatttgc ctaggacatg ctggcagcta    133680
actgggtgct ggggaagcct ggagaggaag ccaggtggcc ccaggctcct ggagctcaga    133740
atctagtgga aatcgctgcc cagggaagaa gctccggagt ctagaggtgg cagcacccat    133800
tttacctgca ccctcagtga cagctgcacc ctggcttctg ggacctctg gcccaaggg    133860 cacctcactg tctccttgtc ctcctggtca ctgacctggg ccaccataga aggcacctgg    133920
ctatctgcat gtggcttgac cactgccttg cacccatccg ggccccgcag ggccgtcctg    133980
tggcactgct ttgggctgtg ctggtcaccc tgtgtagcgg ggccatgtcc agtgaacagg    134040
agaggcctca agtgcccct gacctgctgc cagggactcg gccctccct caccgccacc    134100 gcacccaagg gctgtcgcct gtcccagcct gctgctccga gtttagtgtt ttaaaacgtg    134160
ttttctacgt cttgtcagag tgctcaaggc gcgagattgc catggaaact gagctcctta    134220
gaattcctgt ggccgtccta attatagaat ctcaaagaca cgcacagagc tccttgaggt    134280
tgtcggagtt aaggctgaaa gaggaggagc ggccctgtg atccccacaa ttttgttccc    134340
tgcttgcttc agcagagcct ggcacccagg gaggtggcag gatgggtccc caatgggcac    134400
gtgacatcga gccagctctg actccaaagc ctgacccgtg tggctgcacc gtccactgtg    134460
cgctgtccac tgcaggagac cccaggctgt gtccacacgt accccgaa ggacctcctg    134520 ctaacctggg cttgactttg agaccctgtt ccacagaggt agccggggga ctcgcggtgc    134580
caggcccaca gcctcctcgc cggtagtatc tggggccag gggccgtttc cagagcacac    134640
tccccagaag ggctcccttc tcctttcac agcgctgtct gtcgcttagg tcagaaatag    134700
gcccatcgct ttccaagcag aaacccaaac actgaaaatt cgactgtgac ttttgagggg    134760
tggggaccgc caggtccccc caacatccct gcctgcgggc ccagaaaggc agagtggctg    134820
ccggcccgcg tgtccaggcc ccttacactg agggaacctt ctagtcaatt gcctgaagtt    134880
cgaaggtttg gggggttttt gtggttgctt ccgtttgttt tggcagttgc agaatccccc    134940
gaaaaggtgg gaatgtggat ttttcaaggc aggtgctcct ttgattcaga agctaaggag    135000
gccctaagtg cagtctcacc ttgagaaaaa tatcaggcca gtcctaacgg aggggcgtcc    135060
tgcagacacc cagcctgcac tcagaactgt cacggtcaga aagcacggtc agaaagtctg    135120
agaaagtcac ggtgcagcag ggcccagag gcaagacggt gacacgtggg ctcctggaag    135180
aggcaggatg gtgacacgtg ggctccagga caggacctg gggcggacgc agacagtggg    135240
tgaaaaccaa ggaaaggtct gaatatcgct taaggtagcc atggatcctg tctcattaat    135300
tgtaacagtg tagcaggcgg gtggaagatg agagctgtgg ggagccaggc aggggggtc    135360
```

```
tctgggaact ctccaattta aagctgttct taaaaatagt ctattaaaaa agacagttga  135420
gggcggccct gcctacagct ggagttgagg ttctagcacc aggcttcctc tcagcctcca  135480
taggcgagta gggaccaggc agggccttgg ccacagggag gcttctggtt accaggttct  135540
ccacagcctt tgcagtttcc ctgtgaatct gaaattaccc ccaaataaaa aggatgggtt  135600
tttttgtttg tttgttttgt tttgttttttg agacagggtc tggctttgtt gcccaggctg  135660
gaatacagtg gtgtgatctc tgctcagtgc agcctccacc tgccaggctc aggtgatcct  135720
cccacctcag cctcccgagt agctgggact ataggtgcac gccaccacac tcggctcatt  135780
ttttatattt tttttataga gacggggtct caccatattg cctaggctgg attcaaattc  135840
ctgggctcaa gtgatccacc tgcctcgacc taccgaggta gtggggttac aagcatgagc  135900
cgccacgcct ggccaaaagg tgtatttgtt aagtacaggc tgccctgctg tccgttatcc  135960
cttataactc acctggtccc tgcttttccag ctggggactg gcatggaccc catgggcttt  136020
cccccatttc actgaggcaa gacccagatg ctgggggtat tgggtgtcct gcccaaccag  136080
ggtccccagg gccaggggct cctggcgtgc cttcccgtgg gactccgcat gggggggctgg  136140 gagggcgagg aaaatgggaa acatgatgcc tgcccaaaac tcccacctcg gagaccctgt  136200
gccagggttt tccagagaga ccaaaccaat agggtgtgtg tatagaaaga tctattgtaa  136260
ggaactggct tgttcataga gacttatgaa gcccaaaatc tacaggggggc ccagcaggct  136320 ggagacctag gaggagccac agccgcagca ctgctgctta gggagctcag cctttgctct  136380
gtggaggcct ttttctgctt gggtgaggcc cacctgcatt tggtgggca gtctgcttcc  136440 cccaaagtca gctgatttaa atgtttatct catccatact caccctcatg gaaacatcca  136500
ggataacatt tgaccagccg tctgggcacc atggcccagc cgcgtggaca catacagtga  136560
accattgcag gcccttcctt ggcacttggc atccacgcat atccccttaa gccacactca  136620
gtctccacac agcagtactc ccgcctgaca cactcggtct ccacacacag cagtactccc  136680
gcctgacaca gttcgaccct cccgcaagca gtgccagcac acttggcctt cccagaagag  136740
ggccaccatc atgggctcgg accttccagc tggactgcag tggggtgggg cgtggcctcg  136800
cctctgtggt ctttgggtca cttgaatccc cgcctctcac tcatttttcct ttggtatttg  136860 caaatttgtc cccgtggcgc ctggagctga ctgccgggtg ccacatgtgt cctgcctcaa  136920
gccaagctcc aggcggcacc cgtgagcagg cagggatgcc agtggtttct cacctgggag  136980
tttctttgca ggctcagagc tctttgttcc tttttaaaaa tctgatttga aggccggggca  137040 cagtggctca cacctgtaat ctcagcactt tgggaggccg aagtgggcat atcgcctgag  137100
gtcaggcgtt ggagaccagc ctgggcaaca caggttgggg caactccctt ccctaataaa  137160
agttcaaaac caacccttaa agtttaaaaa gtgagatggg atatttgaag gaggcaggtc  137220
tgagggaaat gcttgaaatt atcctctctg tccctgtgct gccaggtcat ttagttccat  137280
tgttattcaa cataccattt gacacatgct aggagcgcag gactcggcaa tataaagcgt  137340
ggtaatcgat ggacactgcc cccggcagcc agccaggggc aggacttaag ccccacccaa  137400
ctgcaggctg tcccccgccg ctgctagcct gaagttggat tggttactgc tgcggcctga  137460
aattggattg gttatttgct tactggaaca tttttgtcac atgactgtgt attctaaaac  137520
aagatgttgt ttttgttttt gagagagtct cgctctgtcg cccaggctgg agtgcagtgg  137580
cgcgatcgcg gctcactgca agctccacct cccgggttca cgccattctc ctgcctcagc  137640
ctcccaagta gttgggacta caggcgccca ccaccacacc cgactaattt tttgtatttt  137700
```

```
tagtagagac ggggtttcac cgtgttagcc aggatggtct cgatctcctg accttgtgat   137760
ctgcccgcct cggcctccca aagtgctggg attacaggcg ggagccaccg tgcctagtat   137820 tgggttttgtt tgtttgtttt ttgacttact tgtttggttc tatagcaatg gcaccatgtt   137880
tctgtcaccc tagggtttga ttttttggtgt ttctaagaca cctctgggcc actgcacatg   137940
gctgaggtgg gcttcgcact ggctctgtct tccgttggac gcccacacat cggtttattt   138000
atgcattctc ttgtccacag accttgaggt catcagacat cttgaatgct cccgagccca   138060
ggagcgagcg tttctgagct ttgacggagc agcagtgggg ctgccgggcc ctaggggag   138120 caaatggtcc tcgtttctga gctgcgaggc tctcccagag aataagccat ttctccgggg   138180
cactcctggg cctcgaaggt gtttggggct gcggggatt gatttgtgcc gaccccgcag   138240
tgtaggagac gcctgggcgg ccttgcgggt tgcttcgatg gttctcgggg ctgagatgct   138300
tgtgtctctc tcgggcgaga cgcctgctct gggcttctgt tcctattttg actgcttttt   138360
cctcatggat ttttcagtcc agcatcccta gccacgggcc ctttgtctct catgtgtgca   138420
ggtgactcac ggtgactaaa atcttctgta attccttcta aaatgttttg ccgctttgct   138480
gtccacgttt ccacccttag tctctgaggg gcctagtgtg tgtatggtgg aagcggggt   138540 cagcccccgc ctggaccgct gtgacagaac cccacagaca gggtgactta cacacgacag   138600
aaacgtcttt tctcaagttc tggaggcgtg gggacccat ctccaaatac agccacattg   138660
ggggttaggg ctccccacgt gaatttaggg gacacttcag ttcgtcccgg cggggactgg   138720
ggacgccggg ctgtgtgctg tgtcctgtgg gagagtttgt tcaccctgct ggaggctccc   138780
tgatgagccc tggcgtctgc taggacgtca ttctctttac tgattgaact cgaaggatgt   138840
ccagttggcg cattttcagg gtttcccagg cgcactgggg gtgggtcctg tgtgtccccg   138900
ctccagccag cttcgacccc cagctgtgcg tcagtccctc agctccgccc cccagctgcg   138960
cggccgtccc tcggctccgc cccacagctg tgtgaccgcc ctgcggctcc gcccgcagct   139020
gcacgttcgt ccctcggctc cgcccccagt tgctcgtcgg ttccctcggc tccgcccct   139080 cggctgtgcg tctggccctc agctccaccc ccagctgcgc gtccgttcct cagctcagtc   139140
cccaagctgt gcgtccttcc ctcagctcta ccccagctg tgcgcccgcc ccttggttcc   139200 accccctcc ccagctgtgc gcccgcccct tggttccacc cccccagct gtgcatccgt   139260 cccttggctc cgccccgcac tgtgcgtcca ttttttgactc cgccccggc tgtgcgctca   139320 tccctcggct ccgccccgg ctgtgcgtcc gtccctcggt tccgccccg gctgcgcgtc   139380 tgtccctcga ctcggcccct cagctgtgcg ccactttctc tgtggcccac agtacctccg   139440
tctccgccgc ttcacaccct tctctttctt tctctcttca gagagggttg ttgggcaggc   139500
agagcatccc ccgaggggac aagtcaggcc tacggactcc tggagccagg acctgccgta   139560
ggctggttag ggcaggatgc gccctgtctt cgtgggtaga gccacatgag gggtcacccg   139620 acccctcag ggctgagggg cacagggcc gaaagtgtgg ccgcccctgg gggtctgcgc   139680
ctcttgtgga gcccaggcct ggcgcccagg tgggtggagt gtggagggg cacaggctgc   139740 acgaccccag cctggcctcg ggcttgctgg gagtcgcgtc tgtggccgga ggggcctttg   139800
gtgtcaccag gcctctgtca aaccccaagc cgcatcctgg gagggctggg tgggctgagc   139860
cgcccgctgc cgtgaggcct cttttgacctg cgctcctgga ggaccctga cttcttggtt   139920 tcgctctgaa tcttccattt aaaggaagag gagcaggttt taccatccgt gtggcctgat   139980
ttcagcagtt tccagtcagg gctagtcatt tgcttgtttt aaaaacattc cgttacaatt   140040
tccacttcag tatatttgtg gcactttcat ttggttcatg aaagtcgctt ttatgatgga   140100
```

```
attttataaa agcacaaagc ttcccattgt acgttccgtt tctgaagatt ctgtttacac   140160
acacatccgt ttcaaagagt tttggaggag caaagtggga cacggtgttg aggaaggaca   140220
agaccagccg tctggttaca ggcttggtgc cgcctttctc ataagaggca cagtccgcat   140280
gggctggact gtcaaatgca tgttataaag atgatgtttt tggtaacttg cgaatggaaa   140340
cgggtgcacg gtcggtttgg ctctcctgcc ctgagattta ttaggttaaa ggaaactcga   140400
ctggagagcc cggggcctcg cgccgcttgc gtctggcgag ttgttgaagt gaagtcagtg   140460
gcgctctgca ccttagcctg cccaggctc cactgtggcg tccactcttc ctcctctgac    140520
agtcatgtgt aaatattgag gcccgtttga actatccctg tgcggaaaaa aaggcctgtt   140580
tttcacaggg ctgcctgggg aggagggggg tggaaaggaa acaggcagg ggacagacgg    140640 acccggcctg cgttggcctg ggtgacttc acggctccac tgtcagcaag cggccgtccc    140700
gtggtggatc ctgtccgccc tgcgaggaca cctggctcca tccacacctg gcctctgtc    140760 tccagccgcc gaggccgtga caccatgagg atcatgtgag gaggggcaga gagaggcctc   140820
cgggaggccg tcattccagc cctgccttcc ctgcctggga ggacgctgcg gccgccacca   140880
cctggacggg agtggcctgt cgcagctgca ccctgcgtgg gctcgtggct gccacgctgt   140940
ttctttacac ctttctcata tccttttccag aatctatcta ccgccgggga gccagaagat   141000
ggaggaagct gtaccgtgcc aacggccacc tcttccaagc caagcgcttt aacagggtga   141060 gtggcccct tgggactagt ccctcaaggg gccttttgtt acttttaaaa gcaaagagag     141120
aggaggggag gcacgtcccg ctgagcccag gctgggctct ttttggcgcc cgagggcaag   141180
gttacagaaa tgctttctct ggtgcaggat gaggctttga ctagggctgt ctgaggcggg   141240
aagtgccctc cgggcctttc cctgcgtggt ggctgcccag tgaatgctgt ctgtgtctgc   141300
ctggctgtgt gactcttatc agggctcagg gctcactggc ctgaggcccc agcctgcctg   141360
catccagagt ggggcggccg cattccatcc gcatgtagcg ccagggtgtg tgttttcagc   141420
cgcacacagt gttgcctagt agctaagagt ctccgtgaac cctggaagct ccttcagccc   141480
catccctgct tgggcctctg tcttcccagc ggccacccac gggggcccctt tccagaggac   141540 acttagctta ttttccttgt ttctctttat gatgcttttc tagttcctat gaaatgggtg   141600
attcagatgc ttttgtaatt gttctgtttc acagtggaag gggaggtgtc tgggtgtgcc   141660
ttggtggccc tggagttggt cccacacagg gagtgtcttg ggggtgcgtg gaagtataca   141720
gggcctgtcc ccactgcggg actccacaca gagcccctga cagcccctca caggagcggt   141780
ggccctgggg ctacctttgc attccacact cacctgccac gtggcctcac gtgtcaacct   141840
ccgctgggtg tacggcacct ctgtctcctg gagcggcctc aagtcacctg cccctccttc   141900
tactcccatg gtctgccctc tagaccatca ggaagttctg ttcatgtgag ccactcctcc   141960
tgcccctgcg tgtgctcggt ccctgtcatg tggcaagagt gggtctggac tcccattcct   142020 cttgggcta acacaggtga ggatgcagga caagctcctg agtgactgaa gagggtgtg    142080 gtgggaacta ggctccagga gatgagcagg tcagcactag gaagacctgg acattgcctg   142140
gagagcccag aggacttcct ggaggaggag gcatctgatc atactgcctg ggaggtcagt   142200
gcagaggaga tgccaggagc accgaggatg tggcaggcac gggagagtcc agccagtgtc   142260
tgggaggccc tgaggacgag gttggggaca ccaggaaatg gggagcctag gcggctgtgt   142320
gcttagggca ggtgggtgtg ggtgaacagg cagtttggct caggctggga ctcaggagag   142380
tgtggctgga ggtggccaca ttgggaatat ctgtggagta tggtgccagg gagtgttgca   142440
```

```
gcacagagat cccgtccgca ccccagccca ccctggccgc cttttctgag gacacacgtt   142500
gtgagtcttc tggggctgca gaacacagca ccactaactg gcagcttaaa caatggaaac   142560
ttgctctccg gcagtctggg gctggaagtc caaaacgaag gtgtctttat gagtcagggt   142620
tctccagagg gatggtacca atgggatgca tgtacatgaa agggagttga ttagggagaa   142680
ctggccctcg ggcgcacaag acgaagtctt acgataggcc agctgcaggc tggggaagaa   142740
agaagccagc agtggctcac tccgagtcca aaagcctcag aagcagggaa gccgacagtg   142800
cagccttcag cctctgccag aggctccaga gcccccggca aaccactaat aagtcccgga   142860
gtctaaaggc ccaagaacct ggaatctgat gtcccagggt aggacgagtg gcaggaagca   142920
tccagcatgg gagaaagatg aaagccagaa gacccaggaa aactgcttct cccacctgct   142980
tccgcctgct ttgccccagc cgcactggca gctgattgga cgccaccgcc cacccacatt   143040
gagggtgggt cttgccctcc cagtccactg actcaaatac cagtctcagg gcagcgccct   143100
catagacaca cccagatgca atacttcacc agttctctag gcatccttca acccagtcaa   143160
gtcggcgcct ggtgtgaccc attacagtgc cgcagggctg cgccctcctt cccccgcagc   143220
cactggtagc tgcgggcagc cttgttcctg tgctggcaga ggaaccactc acctctgttt   143280
ccgtctccac atggcctcct ctgtatctgt ctcttctgtc attctgcatg acggattagc   143340
ccagagtgaa ccctacccac ccagtgacat gggccagggc tccgggcagc acagggtgtg   143400
gcctctcact gtgcagcttt gaggagaaaa gtccattctg ccgatggcag gtgcagacca   143460
taagtgaccc tcccccctccc caccaccacc agtgagcaaa agcttttcct ttccttcctg   143520
cagacactgg aggaaagggt ggcaggtgga cccaccacag ccccgctctg ctgtggaggt   143580
acagcccttc tgggcgtgtg aacgagccag tttcacaaac acagaggcca aggcgagagt   143640
ggcccgaaag cctgcaacct gactgctcag ggagggcggc tgccctgcag ttcagcctgt   143700
ccgattcccg cctaattgtg cccgggctct gatctcgcca cctgctcgta acgttctctg   143760
tccggacctc agagccgctc catgtagtgc tcacttcatg ttaattgcag gaccactcag   143820
atcacctctg ctgtcactta aaagggcat ttcaggagga aagcacttgg ttttgtgtga   143880
atcagtaaga cttaaagggg aacaagcacc caggagaaga gagactttc cgtcctcttt   143940 gttggtgaag cgaggatgaa agagtgggca tccgtcgctg gggactgggc tccccgccca   144000
gctctttctg tgcacttgaa agcactgccc ttggactttg agaaggaagc gttcagtggg   144060
ggagccaaag ggagagagcc agcgaggttc tgaagaagga ggtgaggagg ggctgcctcc   144120
tccatgaagg atggtgccgg gggtggcagg gaagcccact cagtggaaca gaactgctgg   144180
gtcagagctg gcccagggct gagcacttct tgcagaggag ggaagggatc ctccagtaaa   144240
tcctgaggag gtgattggtt aattatcagc ccaggaatgg ggggtgaggt gggtaggaat   144300
ccaggctgct ggctcccatc acagtaaacg gcaggtggat tgaggttaaa aaaaaatcac   144360
agggcccggc gcagtggctc acgcctgtaa tcccagcact ttgggaggcc gagatgggtg   144420
atcgcttgag gccaggagtt caagatccat ctggccaaca tggtgaaacc catctgtact   144480
aaaaatacaa aaattagcca ggcgtggtgg cacgtgcctg taatcccagc tactcaggag   144540
tctgaggcag gagaatcact tgaacccagg aggcggggt tgcggtgagc tgagattgtg   144600
ccactgggcg acagagtgag actccgtctc aaataaataa aaagaagaaa cctagaagct   144660
gtgcagatct ctggagaaaa accgggcagt gaggaccaga gggtctttag actcagccac   144720
acagaatttt cagatttttt cagtttccaa attaaatgca aaaaacatac aggaaagggg   144780
tttgtagcac gtaaaaccca gaagagatcc agacatctca cacttagaat tgaagagctc   144840
```

```
ctacacaaag gcttttggta aatgctggga ccgagaagct gagaaccggt gtgaatggtt 144900
aatgaagtaa gactgtaatt gtttagagat gaggacagca tgacctccac aggtgatcag 144960
ggaaacacaa gacattttct ctgtcaacat caaagatgtt aaaagtaatt aaagccggcc 145020
gggcgtggtg gctcacgcct gtaattccag cactttggga ggccgaggtg ggtggatcac 145080
gaggtcagga gttcaagacc agcctggcca agttggtgaa accccgtgtc tactaaaaat 145140
acaaaaaaag tagccaggcg tggtggtggg ttcctctaat cccagctact cgggaggctg 145200
aggcagagaa ttgcttgaac ccgggaggca gaggttgtag tgagccgaga tggcaccact 145260
gcactccagc ctgggcgaca gagcaggact ctgtctcaaa acaacacaaa acaaaaacaa 145320
aacaacaaaa aagtaattaa agcccagggt tgctgtcatg gggtctgcca accctgggga 145380
tgtgggacag gcatggaccc tactctctgg aaatcacgca gaaatgtgca gcgatgttcc 145440
catcctgcct ctcttcaaaa gaaatcaccc gtcattcgga ggtttgtgta tggggaagat 145500
cagctcagca ttatttttac aagcaagagt gggaatcgtg tctggagtta gctactccct 145560
ttgctgtgaa caacccactc caccacgtgg ggtataaacc atggtagggc cacgtctctg 145620
agctgtggct gctggagagc cctctgctgg tggcacatag ggcacaagtg ccgcagggac 145680
agctgggtgg atggcccaag actttggcct ttatcatgag tggacagagg agtgaccact 145740
tgggtccctg gagaagaggc tatagagagt gagggtgggg aagggagatc agaagatgcc 145800
atccatgagc agcagtgcct gtcagatttg gtccaagcag tgccctcagg tggctggcag 145860
aggccaatgc aattcctttt caagccagca tcaaagaatt cctgatgata aataaatcag 145920
gcatctgagc tcgcaatgga aaccacaaa acacagtggg aagcaggata tcctgagtcc 145980
aagctggtaa aagcccagac agaggctcca accatcagaa taggtaaggg tgtgacaggt 146040
ctaaaacatg aaaatgggcg attgaaaata tgagcaggag gccgggcgcg gtggctcacg 146100
catgtaatcc cagcactttg ggaggccgag gcaggcggag tgcctgaggt caggagttcg 146160
agaccagcct ggtcaacata gtgaaacact gtctctacta aaaatacaac aaaaatttag 146220
ccaggcgtgg tggtgggtgc ctgtaatccc aggtactcgg taggctgagg caggggaatg 146280
gcttgaacca gggagctgga ggtttcagtg agctgagaac atgccactgt actccagctt 146340
gggtgacaga gtgagactcc gtctcaaaaa aaagaaaga aatgtgagc agggaggcca 146400 ggtgcagtag ctcacacctg taatcccagc actttgggag gctggagcgg gcagatcacc 146460
tgaggtcagg ggttcgagac gagcctggcc aacatggcga aactttgtct ctactaaaaa 146520
taaaaaatca gccggacgtg gtggcaggtg cctataatcc cagctactca ggaggctgag 146580
acaggagaat cgcttgaacc caggaggcgg aggctgcagt gagccaagat cgtaccactg 146640
cactccagcc tggggaacag agcgaggcgc gaggctgtcg gagggaggga atatgagcaa 146700
ggaacaagtt ggcagcatgt aagacgtact taaaacgttt ttacccatta atctatgaat 146760
tcctctgagt ttctgagaat ggaaacttgg ggtttaggtt ttatttttt aatgtcacat 146820 ttcctgaaat gttactattc aaatatagat ttgaaacaag gcttttgac agagcttggg 146880 cagcctcact tacaaagcac acacgtgagg tctctgtggt gggtgccaac ccttggcaga 146940
ttcacactgc ccttgtcagc agatgtcctg gcctgacccc aggtaagggt ggctccccac 147000
ggaaaggaac cttggtcaat tgttttttg tttgtttgtt tgttttttctt ttcttttttt 147060 tttttttttt ttgagacaca gtctcactct gttgcccagg ctggagtgca gtggcgtgat 147120
cttgactcac tgcaacctct gcctcctggg ttcaagtgat tctcctgctt cagcctcccg 147180
```

```
agtagctggg attacagatg tgcgccacca cgcccagcta attttttgtac ttttagtgga  147240
gatggggttt ctccatgttg gtcaggctga tctcgaactc ctgaccgcaa gtgatccgcc  147300
cgccttggcc tcccaaagtg ctgggattac aggcatgagc cactgcgcct ggccaatctt  147360
ggttaatttg taaagatacc tggtggctgt gaatttggtc ttaactagga ccgtagtgtt  147420
gcagagtaag atgttaaatg gtgacctaga gaaagccaaa cacattaggc acattatacc  147480
aaaagaactt gactttttaaa taatggtttt agaaatggaa gctggtgttc ttctgcgctg  147540
tggacgcgga ggagaatgga gcaggtctgc acagccaaag tgcctccttt cactccaggg  147600
tccaggcatc cagcagccga agcgcctcct ttcactccag gtccacaca tccagcagcc  147660
gaagcgcctc ctttcactcc agggtccaca catccagcag ccgaagcgcc tcttttcact  147720
ccagggtcca cacatccagc agccgaagcg cctcctttca atccagggtc cacacatcca  147780
gcagccgaag cgcctccttt cactccaggg tccacacatc caacagccga agcgcctcct  147840
ttctctccag gtccacaca tccagcagcc gaagcgcctc ctttcactcc agggtccaca  147900
catccagcag ccgaagcgcc tccttttcact ccagggtcca cacatccagc agccgaagcg  147960
cctccttttca atccagggtc cacacatcca gcagccgaag cgcctccttt cactctaggg  148020
tccaggcatc cagcagccga agcgcctcct ttcaatccag gtccacaca tccagcagcc  148080
gaagcgccct cctttcaatc cagggtccag gcatctagca gccgaagcgc ctcctttcaa  148140
tccagggtcc acacatccag cagccgaagc gcctcctttc aatccagggt ccacacatcc  148200
agcaggtgcc gactgggggca aaactcccaa tgccggcatt aagctagatt ggcccggaat  148260
cagaggtctt gggtgggatg cccctctca cccatccctc cttcgaatag agcccacggt  148320
cctggtgtgg ctctgtcatg gctgggctga tgtaggtagc atgtgcagag gatgtggagt  148380
cggctccttt ttcctgtgac gaagttgaaa gcgatgatgc atgtgtgttt tcttacccga  148440
tgcccactgt gtgctgggca ctgtcctagg tgctggtcat ccggcccac ccaaacaagt  148500
gggctgtgtg ggcggggggga gggtccccgg gccctgacgt cccgagcagg ctcttctgat  148560
gagcaggaga gtcccgtaga gggtctggac ccccttttgct cagccgcacc tgatgcccac  148620
atgtgctgag ggtcccggtt cctcacgtga actcagtgct gtattttctc ttcagtcccg  148680
tttcctcacg tgaattcagt gcaggcggtt cacagtacac tgtatttcct cttcttttt  148740
tttttttttt tttttgtctc ctgcctcagc ctcccgagta cctgggacta caggtgcccg  148800
ccaccacacc tggctaattt tttgtatttt gtagtagaga cggggttttca ccgtgttagc  148860
caggatggtc tcaatctcct gacctcctga tccacccgcc tcggcctccc caagtgctgg  148920
gattacaggc gtgagccacc acgcccggcc tatatttcct cgtcttaact caggtgtgag  148980
gtgagctctg taataggaag gaaatttgtg aaaaatggta aaagagggaa aagcatatga  149040
aagggctgtg tctggaaaga atctgaattg gaggctctgg gcacatggtg acagtgcaga  149100
tgcaccccctt tactcccagg aacactttgg gcacttaggc aaggcagaaa atgtccaagc  149160
aggtcccgac aacattcatt ctcatgcctt ttgtaacatt taaacgttca tgaaaacatc  149220
gccaaacaag ctgataatta ccatcatttt ggaattgttc agaaccatga agaataaaga  149280
aggatcattt aaaatcttga aaatactgaa acaaagaata ctaagataat tgcaggctgc  149340
catgtagcag ttcaagatgt tcatgagtcc gagttcccct tctctgaggc tgtcaggagg  149400
aggttctgtt tgaatgaagg tcaggcaggg ggtaccccca cacactctgc ttagccctag  149460
acgggacccc aggctgctct acgcagagcg cagcaggagc tgcagccccc cagcccctgc  149520
aagccacggg gccttgcctg aagcagcacc tcgtcacccc tgcccgatgg cacctcccct  149580
```

```
gtgtccctc atgcagagca gggttccagg cctctccttg gggccactgg ttcccccaac 149640
cttgggatag acccaagagg aggctctcaa gcttgggcaa gcctggcgcc cggaagggac 149700
aaggtgccgg ggccacctgt tgcccggctc agtgtcctct tttgagaagg tataggtgtg 149760
gaaggccctg cctgtcctct ccgctggccc ctcagtgtgg cctgggcctg acgctctgtt 149820
cccacctgca gagagcgtac tgcggtcagt gcagcgagag gatatgggc ctcgcgaggc 149880 aaggctacag gtgcatcaac tgcaaactgc tggtccataa gcgctgccac ggcctcgtcc 149940
cgctgacctg caggaagcat atggtgagtg caggctgg ggaggcccgg ggggcacggg 150000
cggggtcggg gcgtggcagc cagcccattg tccaagcaga ccttggtgac cctgggttct 150060
tcaagagggg ccgtggtgcc gtcctagctc tgggctgcag cgtgagactc aggcggcagt 150120
cttggatagg acccatcttc ctgagccccc acaagccccc ggcacactct gctcattggg 150180
gcatgaggct caggcagcag gctcaggtag gacgtggtac gctctgctca gtgggtcgga 150240
ggtaaggttc attcataccc cagtcttgaa ccagctctta aggactgtgg aggtgaaagc 150300
caggtctgac ctagtagcat tgggcacgct gaggctccga acatctggag cctctccctg 150360
gcatcccccc tgggaagcca tgcccagcct gtgatgaggg cggcaccttc cctccgccat 150420
ccccgagtgc ttggacttga agcatccagg ccttttgggg ccttattgac ttttgcttat 150480
tgaaggctgc ctctggcatt tccgtgtggc ccctgcatc ccactgaacc acgggggtga 150540
ggcctggact gaacattcaa ctccctgggc cctgctgcag cgtgcagtgg gtgtgtctgg 150600
ggagggtggc ttgtctgcat cttgctgtgg catgggagga aaggcgcctg tggcagtgac 150660
gtgccctctc ctctgttacg ggataaagac agagtctgga tcagggtgtc accccaggat 150720
caccagccca agggatgggg gaccacgcag gctggtgcat gcgttggcac agtccttcca 150780
gaggtccttc agctgcatct gccaaaaagc ctgtaatgcc ctttgacctc ataggtccac 150840
tttagcgtaa gcaaatgaga ccggccccag aaatgtggtc agctagaggc ggagggaggc 150900
cagagcctgc cacccagctg accaccagta ctggtggctc cattatgaca tatctgcagg 150960
cggaacccag aggcccttag aatggccccc tgatgcttgg ttactgacag gatgcagctt 151020
tgggacaggg gagatgacca agcattgtgc aaaatatccc gttgtataaa gcacttggtg 151080
gaaaggtcat ggcctgcagt accgagtggc cactccgtc tgcagaatca taggtaatgt 151140
ttatgttctt tatctaattc agtaaaatag cataacaatt agatttttat atactatatt 151200
acagtatacc cattgtaatg tgtaaatatg taaatcataa atagtcttga agtggccagg 151260
tgcagaggct cacacctgta atcccaacac tttgggaggc caaggtggga agatcacttg 151320
aggccaggag ttcaagacca gcctgagcaa tatggtgaga ccccatctct acaaaaaaaa 151380
tacaaaaatt agccaggcat ggtggtgcgc acctgtagtg cccgctgctc tggaagctga 151440
ggcgggagga ttgctcgagc tcaggaggtt gaagctgcag tgagccgtga tcgcgccact 151500
gctctccagc ctggatgatg acagactgtg accctgtctg taaaaaaaag ttcttaattt 151560
taaaaagtca caaagtgttt acagaagcta cattgtaaca cctgctctag cacttggtca 151620
tgctgccatc tctgtgtctc tccggcagga ttctgtcatg ccttcccaag agcctccagt 151680
agacgacaag aacaggacg ccgaccttcc ttccgaggag acagatggaa gtaggcgctg 151740
ctttcttccg gccgggtaga gcctgggcat cacctcaccc tgctcacctc tgccttctag 151800
ccacgagtcc tttctcagtc ccatctgctc tgcaggggtc attgtcttca agcctggcca 151860
cccttccctg gggctgggga tgaggctctc cagggcctcc tctcaatccc cggcagagat 151920
```

```
gagcagggtg agctggccct ccctggaggc tgctgggcag ggatgcctcc gtgaagtgct 151980
gttgtggttg cccaggggtg cagagcctct tcctctaacc agctccggga gttctcgaag 152040
gcacttagtg cagcagccac catggccggg cacctcccac aatctggctg ctgcacagag 152100
ctgagcccta tctggggaaa gcctggcgag gtggctgctg cacacacagc gtggcagtgg 152160
catggtcctt ggattttgt gaggttttgt ttgttgtggg gaaggacttg ttttattgct 152220
aagaagcatt cagagagaga tctcaaacac cagttggact tacagcccag gtttgagcct 152280
ccacacctgc acctctgcac gggggtgtga gagcctcact ttcacttgat gcatgtgagt 152340
tctgtctcat tgggagacca cagaaacataa agcacttatg agaccacaga acataaagca 152400
cttagttcac acagtgcctc acgcaaaaga gatgcctcac aaacaactgc ctgcccacct 152460
gctcctccac ccacctatcc tctatacaga tattcatccg tacatcatcc attcaccac 152520
ctagccaacc aaccagccct catccagcca accagccatc ctccaccgc ccattctcca 152580
tccatccacc acctatccat ctatccacga tccatccatc tcgtcatcca gccagccagc 152640
cagccatcct ccacccaccc atcctccagc tatcttccat tcgttcatct gttgtccact 152700
gacctctcca tctatccatg tatctattgt ccactgacct ctccatctat ccatctattg 152760
tccactgacc tctccgtcta tccgtctatt gtccactgac ctctccatcc aacgtctat 152820
tgtccactga cctctccatc tatccatcca tcttttgtcc actgacgtct ccatctatcc 152880
atctgtctgt tgtccactga cctctccacc catctatctg ttgtccactg acctctccat 152940
ctttccatct gttgtccact gacctctcca tctatccatc tattgtccac tgacctctct 153000
atctatccat ctattgttca ctgacctctc cttccatcta tctgttgtcc actgacctct 153060
ccatctatcc atctatcttg tccactgacg tctccatcta ccacacatc tgttgtccac 153120
tgacgtctcc atctgttcat ctatctgttg tccactgacc tctccaccca tctgtctgtt 153180
gtccactgac ctctccatct ttccgtctat tgtccactga cctttccatc tatccagcta 153240
ttgtccactg acctctccat ctatccatcc atctattgtc cactgacgtc tccatctgtc 153300
catctatctg ttgtccactg acctgtccac ccatctgtct gttgtccact gacctctcca 153360
tctatccatc cactgtccac tgacctctcc atctatccat ccattgtcca ctgacctctc 153420
catctatcca tccatctatt gtccactgac gtctccatct gtccatctat ctgttgtcca 153480
ctgacctgtc cacccatctg tctgtagtcc actgacctct ccatcttttcc gtctgttgtc 153540
cactgacctc tccgtctatc catctatcta ttgtccactg acctctccat ctatccatct 153600
attgtccact gacctctcca tctatccatc catctattgt ccactgacct ctccatctat 153660
ccatccactg tccactgacc tctccatcta tccatccatc tattgtctac tgacctctcc 153720
atctatccat ccatctattg tccactgacg tctccatcta tccatctgtc tgttgtccac 153780
tgacctgtcc acccatctgt ctgttgtcca ctgacctctc catctttccg tctgttgtcc 153840
actgacctct ccgtctatcc atctatctgt tgtccactga cctctccatc tatccatcta 153900
ttgtccactg acctctccat ctatccatcc atctattgtc cactgacctc tccatctgtc 153960
catccactgt ccactgacct ctccatctat ccacctattg tccactgacc tctccgtcta 154020
tccatccatc tattgtccac taacctctcc atctatccat ccatctattg tccactgacc 154080
tctccatcta tccatccatt gtgcactgac ctctccatct atccgtcttc tatccaggcc 154140
tccattcatc ccccatctag tcatcctcca tccatccacc agacatccac tcctgcccct 154200
acccacccat tcactagaca ccaaaatccg gtgacgaatt atttgcagat ggacccctgg 154260
ggacgtatgt cacgaatgta catccccagg tcccatggtc agagtcggca ggtgtgagtg 154320
```

```
gggcccagga aactgcattt tcagaagact ctaaattaga atcagacatg gctgctgtgt  154380
ggattcaccc ttcaccgtca ccctgcagag gagcaaggtc cacagggtcg ctgtgttccc  154440
agtgcgttcc tgaccacacc gtaacgcccc ttccttcctc cctctctcac cagttgctta  154500
catttcctca tcccggaagc atgacagcat taaagacgac tcggaggtga gtgtgtggag  154560
cagctcgctg ccatttccga cgtcctctgg aaagtctgtg agcctgtctc tggggtagtc  154620
acggaaatct agatgtgaaa tagacatggt ccggggtgtt gctaactaat cttcacgggt  154680
gtggatgtct agaaggaagt ccttattctt gggtcttact tcaggcatgt ccttgatgaa  154740
tacctgcagg cagctgtccc cgcaggtggt ctggggacca caccctgcgg gggaagccgt  154800
gccccacatc ctctccattc aggtggtaca gtgcccaggg gctggctttt tgagctgcaa  154860
tttttatcaa gttgtgtctg caccatgcct tccgaattgt gttgcctcat ttggccatcc  154920
tggcaaaccc tctgaagccc tttcatgtcc ttccccaact tgagccaaga ggctcaactg  154980
agcctcacgt ctgtggccag ctctgcacca taaaccctga aagggaaca gaagagcttg  155040
ctgcgttctc agcctctgct cgtaaaaccc agggaaggac tgcactagcg aagcccactc  155100
cttttccagag caccaacaag tgtcaccctc acaactcgtg ctccttcctg gccatcctgt  155160
gtctggaggg aggccggggc acttagaaag cagaatctga ggctgagcac ggcgactcac  155220
acctccaatc ccagcatttt gggaggctgc gcacatcgct tgagtccagg agctcgagaa  155280
cagcctgggc agcatagcga daccctgttc ctacaaaaat aaatacaaaa taattagctg  155340
ggcatggtgg cacgggcctg tggtcctagc tgcttgggag gctgaggtgg gaggatcgcc  155400
tgagcctggg aggtggaggc tgcagtgagc tgagatcgca ccactgcact ccagcctggg  155460
cgacagagga agagtctgtc tcaaaaaaag cagaatccgg ctgggcgcgg tggctcacgc  155520
ctgtaatccc agcactttgg gaagctgagg cgggcagatc acgaggtcag gagatggaga  155580
ccatcctggc taacacggtg aaaccccgtc tctactaaaa atacaaaaaa aaaaaaagct  155640
gggcgtggtg gcgggcgcct gtagtcccag ctactgggga ggctgaggca ggagaatggc  155700
gtgaacccgg gaggtggagc ttgtagtgag tcgagatcgt gccactgcac tccagcctgg  155760
gcgacagagc cagactccgt ctcaaaaaaa aaaaaaaaa aaaagcagaa tccattttgc  155820
cgcacagaac agcacctccc aaggaaccgc ctcctccacc ccgacctcct tgccaggtgt  155880
agcttgcggg aggcagaggc ttctgttctt cctcggagcg cctttctcct gggtatttct  155940
aataattatt tctaataatg tgtgcctgcc ggtttgggag ctcttggcag gcattagctg  156000
cattcgcttt accttccttc ccctgaggga gggcactgat caggaaggat gggcccaggc  156060
cctgggccac atgtccctgt ggccacctct tcagccccac tgatagggct gagggcctgg  156120
gggtccctcc cacctgcagc tgtgaccaga gccatggtct gtggaacgaa cagcttctag  156180
cttctagca ccttcctcag aagcacacag ccttaaattc ttacctttca tgccccagtt  156240
tagatgggag tttgggggtg ggatatgtgg gacgcagaac tgagactcga atcatgaggc  156300
cctgggctct gaggagcagg tctctgttgg gaccgcatga gtgatgcgtg gtcctctgag  156360
tctcccggga acccccctct cactttctgg ggtcttgttc tccctcccta ggaccttaag  156420
ccagttatcg atgggatgga tggaatcaaa atctctcagg ggcttgggct gcaggacttt  156480
gacctaatca gagtcatcgg gcgcgggagc tacgccaagg ttctcctggt gcggttgaag  156540
aagaatgacc aaatttacgc catgaaagtg gtgaagaaag agctggtgca tgatgacgag  156600
gtaggtgccg cttctcatgg ggcccggggg cccgggaacg cgctgccctg gggcctcctc  156660
```

```
cgggctttag cggaattaat ccatgcacga gagacctagc ctcacgttga cggagtttgt   156720
gcaaaatcaa tagtcatgca tcgtgtaatg accaggatgt gttctggaaa gtgcctggtt   156780
aggtaatggc actgttgtgt gaacatcaca gtgtgcactc cacaaaccca aacagcacag   156840
ccaactccac agccaagatg cacagtgcag ctcctgctcc caggctgcaa gcccgtacgg   156900
ctgttagtgc actgcacact gcaggcagtg aggggaccac cacgagagca ctcacgtgtc   156960
taagcttaga aaaggtgaag atgggtatcg tggtctctgc aaccttctca tgtatggcca   157020
accactgata cgttgccttc cagcagactg cggttgagtt ttaggatgtc atcacccttg   157080
ttaggaaatc tctggggttg agctgaactg gacgggtgat ggggtgggac aggaagctgc   157140
ccagaggcac tgccctgctc cgtcctgcac aaggccccag ctttgcagta catgctgagc   157200
tgccgtggct ctgtgtagca gatcttccca caccagctgt ttctagggga gaagtttgtt   157260
gattatagga tcaatggttt atttgttgaa atcttttttt ttggaaacgg tcttactctg   157320
tcacccagac tggagtggct tgatcacagc ccactatagc ctcaaagtcc ccagctcagg   157380
tgatcctccc acttcagcct ctggagtgtt gggactacag gcatgagcca cccccccag   157440
ctgtataatt tttgtatttt ttgtagaggc agtgtctcat tctgttaccc aggctggagg   157500
gcagagcatg atcacggttc acctcctgca gcctccacct cctcctgcag cctccacctc   157560
ctgctaggct gaggtgatcc tcttgcctca gcctccagag gaaccaggac tacaggcatg   157620
caccaccatg cccagctatt ttttgtgttt tttgtagaga cggggttcca ctatattgcc   157680
caggctggtc tagaattcct gcgctcatgc actctgcccg cctcagcctg ctagagtgct   157740
gggattacag gcatgagtca ctatgcctgg cctgtttgtt gaaatcttaa ttctgacttc   157800
atagaccttt ttcttttaat taaagtaaaa tacacatgac atagaatttg ccattttaaa   157860
gtgtacagtt agggccgggc gcggtggctc acacctataa tcccagcact tgggaggct   157920
gagacaggtg gattacctga ggtcaggagt tcaagaccag cctgaacaat atggtgaaac   157980
cccaactcta ctaaaaatac aaaaattagc caggtgtggt ggcgcacacc tctaatccca   158040
gctactcaga ggctgagaca ggagaatcgc ttgaaccagg gaggcggaga ttgcagtgag   158100
ccgagatcac gctactgcac tccagtctgg gcgaccaaat gagactctgt ctttaaaaaa   158160
taataaaata tgcaaacaaa gtgtacagtt aggcggcttt tagcatattg agatacagag   158220
ttgagcagct atcacctctc tgattccaga acattttcct caccccaaaa ggagacccca   158280
tacccactcc ctgcttctgc tctgcgtcag ccccatggcc tccaatctgc cttcttcctc   158340
tgcggacttc cgtcttctgc acgcttgaca gaacggagtt gtgtgtgagc ttttggtgtc   158400
tggcttctcc agtgtccgtc catgtggccg ctcgctcagg ccttcctctc tctgcctggc   158460
cgggtaatgt tccgttgtcc agtggaggcc ccacgtttgt gcgtgcacct gccaggggc   158520
attatagtgt tcccacccctt ggctgttgtg agtggtgcca ctgtgaaggt tcgcgtacaa   158580
gaatctgttt gagtctatt ccagttcttt tgagtgcaaa cctagcagta cagttgctgg   158640
gtcacatggt agttctctgt tcaactgatg gggacctgcc aggctgcttc ccacgcagcc   158700
gcgccgtttc acctccccgc caacaccaca cgggcctgtt tctgcaggtc ctcagtgacg   158760
cgtgtgattg tgatgatcgc tatcctggca ggtgtgcagt ggtggctttg actcccatgt   158820
ctctgatgac tgcagtgtt cagcatcttt catgcacctg ttggcttctg gtattttgg   158880
tcttttgctt tcattcctga atgcaggttg cgtctctcag gattagataa aaggccaacg   158940
tgtgggtggc agtaatgctg ttgtcaccaa gtgctgctag cacagaaggc aactggctgc   159000
tcgtcgagcc ccgatgggcc acagagggg tccctcctcg ccagccatgc tcggggctgg   159060
```

```
gagggcagag ctggggctgg ggctgagcct ctactacctc ccagcagggc gtgtctgtgc  159120
agtgcacagg ctgtccaact ggcccctcat ccctgggtgc agaactcaaa agtgggtggc  159180
agcgtccatg ccctgcgccg aggaacagag gccccaagag gtgtggtgcc ctgctgacag  159240
ccccgctgct ggccagcggc agcacaggag gattccagcc cccttttgcag cacgtcccgg  159300
tcagctggaa agttaatgcc acgtatgaga gcaggtttgc gggaccctga gaaaagacat  159360
ttggaagagt cgctgctgcg gttttgttct gtcttgaaat catcctctgt gggccgggat  159420
gccgaggtgg ggactctggg gttgtctttc gagaagagcc tgattgcagg agttgttgaa  159480
tgcttggatg gtttctagaa atttctttct ccccacaaaa agactgcact ctctggggcc  159540
aggcttgcct cttgttcccc caggagtcac tggcaagccc cttcccaccg attctgcagc  159600
gccagcccca cgcagggcct tgaactcagc agtgctgtgt ccaggaggtt ccactcagtt  159660
tgggtgctga gtgatatgtg ggtcatgatg ccaacgccga cgtccctgcg ggccacagt   159720
gggtgggtgc tgctggtgag ggccactggg ggacgggtgg tggcaggtga ggggtggagg  159780
agtcaccgcc gacccactag gtcttcagcc actggagatg ggaggagatg cgggctggcg  159840
aggagctcgg cttgtggcct ggggtggcgt gagatacccg ggtgcacatg ttgagcagcc  159900
gtcgggggc aggtctgcag ctcagggaga ggccgggctg ggagctctcg gcgtggaaag   159960
atgagactcg aagccactcc attggatctg cctccgaaga gaagggaggg tggccgagga  160020
ccaagcctcg aggaggagga gggcgctgag gaggaatgac acagtctcag aggctaaata  160080
gatactcact aatggtttgt tgatttgttt ccacgaaact tccgggagtg ggggcaggca  160140
acacagtaag accctgcctc tacaaaaaat aaaattgcca agtgtggcat gtatctgtag  160200
tcccagctcc tctggaggct gaggtgggag gatcgctgga gctccagagg tcgaggctgc  160260
agtgagcagt aatcgcaccc ctgtgatcca gcctattttg acgcatttct ttcactgtca  160320
tttttctaac cccgaagaca aggggttgac ctaggaaggc ttgagaactt cgtccagctc  160380
tactttctgg ggtcaagatg agaccaagct gttggatctt tgtcactcta aagttgactt  160440
tgaccttgca gcattttgct gaactgcagc atgaattggg agggtgacag tcctatggct  160500
gaagctagtg ctctggtgat gggtgtgggc ttatcactcg gtagcgctgg gaccttgggg  160560
aatctgctta gccctccacc tcaatttcct tgtgtcctaa ctggagataa taatacctgc  160620
ctcctggaac tgttagggca aagcctggag gccagaggcc agtataccac cagaggccag  160680
catacaacca gagctggtag ctttggtgat cgtggtgaag atgatggtga tgatgatggt  160740
gacaatgatg gtgacgatga tggtgatgat ggtgatgatg gtgaggtagt ggtgatgacg  160800
tggtggtggt gatgaagatg ttgatgatgg cggtgatgat ggtgatggcg atgactgtga  160860
tggtggtggt agtgatgaca ttgaggatga cggtggtggt gatgatgatg gtagtggtga  160920
tgacaatggt ggtgatgaca gtgatgatgg tagtggtgat gacaatggtg gtgatgacg   160980
tgatgatggt gatgacagtg gtgatgatgg agatggtgat gacggtgatg atggcagtgg  161040
tgatgacagt gacggttgtg atggtgatga tggtggtggt gatggtgatg atgacggtgg  161100
tgatgaaggt gatggtaaca gcgacagtga tggtggtggg ggtagatggt gccaatggtg  161160
atggtggtgg tggtgatggt gatgacagtg atgatgcaga tggtgatgac ggtggtggtg  161220
atgatgacag tgacggtgat gatgacagtg gtggtgaagg tgatgtgac agcaacaatg   161280
atggtggtgg gtggaggtgg gagggatggt gacaatgatg acggtaatgg tgacagtgac  161340
gatgatagtg ggggtgggg gtagggtgta tggtgacagt ggtgtgacgg tggtgatgat   161400
```

```
gacagtgaca atgatgatga tggtggtggt ggtggtagag gtggggtgga tggtgacaat  161460
ggtggtaatg cagttcctaa tgggtgtttt cttttcctgt ctgcattgtc ttcctgaaag  161520
cggaggaaag agactcctcc cttgcctccc ccttgcccag gatgcctgtg aggagcattc  161580
gggagcctca ttaccactcc ctggtttcta tttcaggata ttgactgggt acagacagag  161640
aagcacgtgt ttgagcaggc atccagcaac cccttcctgg tcggattaca ctcctgcttc  161700
cagacgacaa gtcggtaaga aaagaaggg tatttctgat attctgcaga tttcagatgt  161760
gaactgcaca gaagctaagt ctggtgtgat gtgtcaactg tcacctgtaa ggttctccca  161820
gttgctgtac gggtgttttc aggccagcag actctctttg ttgttctcct tggttggtgt  161880
catattaagt acatttcatg atctgaagtt atttaattcc atttacgaaa tacttactgg  161940
aggtatccca ctgagtgcag gcattgggtc aggtgctggg gctacaaaag taagcaaaag  162000
aggtggattt ctgtgcttat taaaatatgt acagcttcac cttcaagctt tatatatact  162060
ggaattctgt ggctttgaat acatttgaaa gctgatgatc taggatatta aatgtatgcc  162120
ctgtttaaaa ttttggggc cagttgactt tgacctacct gatttgttta tttgaagagt  162180
tattaagtat gttctgcatt gagtcctcaa gaccatcccc aggttcgatg attggctagg  162240
aggactgctg ggatcaatca tggccgcact gggggccaca gctggcatac tgcactgggg  162300
agataaagga gacttggcca aggaaaaagg cacatgggga aaattccaga agaaaccagt  162360
cacaagctcc caagagccct ctcccagttc ctccagcaat gaattgtgac aactcatggt  162420
ttttgtcaag ggctggtcat gcaggctgca cacgaaccaa aattccagac tcccagtgga  162480
gagcaggtgt tcagcattgc gttagtcagg gttctcctga gaaacagaac cagttgtgtg  162540
cacgtgtgtg tgtgtgtgta aagagattta ttataagata ctggttcatg ggattatgga  162600
ggctgagaaa tcctataatc cgccatctgc aggctggagg cccaggagag ccagtggcac  162660
agcttgaagg cctgagagcc aggagctgat ggggtcgctt ccagtccggg tctgaaggcc  162720
tcagagctag gagcaagggg gccagaaggt ggatagctcg gtagtcaggg aaacgcagcc  162780
ttcctcctcc ttcttgttct cttcacgtcc ccagggggcct ggatgatgcc agtctacttc  162840
agggagggcc gtctgcttac tcttccagaa gccccctcaa caggcatgcc cggaagtcat  162900
gtacagccag ctactagggc gtcccgtgcc cagtcaaggt gaccgttgaa ttcaccatca  162960
cgagcataag gcatcctgtt caggcacaca cagtttgggc acagcaagca gctcttattc  163020
caaagctttt ttttttaat gtgcttttct tgttttttgag atggagtctc gctctatcac  163080
ccaggctgga gtgcagtggc aacatcttgg ctcactgcag tcaccacctc ctgggttcaa  163140
gcaattctcc tgcctcagcc tcctgagtag ctgggattac aagcacctgc caccacacct  163200
ggctaatttt tgtatttta gtactctgtg ttggccaggc gggtctcgaa ctcctgacct  163260
caagccatct gccctctgca gcctcccaaa gtgttgggat tacaggcatg agtgactgag  163320
ccccgcctcc agagtttttt tttttttttt tttaaataaa gatagggtct tgctctgtcg  163380
ccccaggctg gtctcaaact cctgggctcc tgcctcagcc tcccaaagtg ctgggattac  163440
aggtgtccac cactctgcct ggcggtcatg cagaagcatg ttatatccgt gtagggaact  163500
gtttgcagtt cacgttccca gccccagctc cgggccagct ttgcgggcca ggcttcctaa  163560
gcacagcggt cctaggccct gggtgcaacc ctctgctgct cggttcttag ctgtacatct  163620
ggcgacttgc tctcctccgc tgcactcttg gctctcctga ccgcagggtc ctgctcttgc  163680
ctgtgcttgg cagccacctc tgtctgtcgg aagagccggc gtgacccggc cgttcccga   163740 cctgctctac gtgcggtgcc gtcctggtca agggttcctg ttttctggct gcttacgcct  163800
```

```
cctaagtgtg tttcagggtc ccccaccctc cccacctgac cccagggctc cccagtgttg  163860
gcttccccat gttgggcctg agccatattt gagaaacaca gatctgaagt cttttttcctg  163920 cctcaaagct cctctgattc ctcctcccca gttgcttctg gggtaaattc caagcttcct  163980
gtgcgtgtgg acgaggcttg tggtgaccag gccccagtgc cccatcgtgt gcttcagcgt  164040
ggcgccctcg cccgcaccgc ctgcgcctga cggctctgtc ccctttcctt ctgctcccct  164100
gcttcccgga gtgagtcaat gcctcccttt gtgcattccc attgcgcttt tccaggcctc  164160
tttccgccct gactgccatc ccttgcgatt tgggaatacg cccaggggaa ggcagcccgg  164220 cccccacac ttcctaaatg gtgaggttcc aagaagggtt ttgttttgct ttggttcttc  164280
ttcatatgtg aacttgtagg gatgtagatg tataagggt ccgatatccc accctcactt  164340
cccctgagtg gcccaaagct cagccccttc tgcacttgtg tctttggact cttctgtcaa  164400
gtcacaagtt cccagatgcg taaacctgaa cttaaagaat tgtcgtctgt ggggtgtctg  164460
tgggatcccc gcagcggcac caatcactgt cctgtgggag cattcggcat tcacagttgg  164520
gaataattcc tatgcatgtc tgatttttttt gccttttttt tttttgagac ggagtcttgc  164580
tctgtcaccc aggctggagt gcagtggcac gatctcggct cactgcaact tccacctccc  164640
tggttcacgc cattctcctg cctcagcctc ctgagtagct gggactacag gcgcctgcca  164700
ctacacctgg ctaatttttt gtattttttag tagaaacggg gtgagctccg ggttgggggg  164760
aggaccggca gctgccttag tccaatagct gggggctgt gaaaactgcc cacaaattct  164820
tactgaccac acagcaccag acaccacgt gaagcaaagc caacatcggc aaggcggcca  164880
cgcgtccggg tggcggaaaa gtctggcctg gcccaggtgg gtgtgctcgg ctgtgccgcc  164940
tctgctccct ggtcactgga ggtgactgca ggctttatga ggacttcctc tttgtgcgtt  165000
ggttctgctg gaacatccag ctgaggtttt gcgtgggccc cttgctgagg gccaggtgaa  165060
taacacgcag aacaggacac tccttcgctc tgggcggcct cacagctccc gggccatatc  165120 caggggggaac ctggccgatg aaactgcaga ggtttccaca caagtttggt tcccataaag  165180
ggtctgtgag tggggaagaa tcagaattgc tttctttcca ccccaaatct ggtcttgcct  165240
cttctggccg gccatgttcg tgtccactgg gcggctacag ggaattcctg aatgttacag  165300
ttcaacatta gtctcacctc gtgtgtccag atggagagaa acaattcatt cgcagtttta  165360
agacacaata agcacctgct ttatggacaa accataccccc atatctacac agacagccca  165420
ccttttccag acagcagcca aaattgaaat gagccataaa gtctccaaaa cgagaaatcg  165480
cttcagttta agctatttca ggaaaaccag gtaactagag atttagctga aatgactact  165540
ttcagcgtcc cccgccccat tcaactggag tcggaggaca cttctcact aaggcacggt  165600 gatctcagat ggtaggtgag caaactaccc ttaaaatacg cccattcact cgctgttcta  165660
aaataaaatc tcttactgtt tgccacggtt gattatttta cattcattca cactcaatgt  165720
ttctttaaaa agaacaaaca cacaccttg cttatctgtg gaagcgcttc tcaggccgtg  165780
cactgactga gacacttgag taagctcttc ttggtcaaac tgacttctag acatgaaaag  165840
cacttcaccc agcagtgtgc gtgtgtgtgt gtgtgtgtgt gtgtgtgtgt gtgtcagtta  165900
tgctttgaaa cctgcccgaa gctctggaga gggagacagc tttactaaca gcagagagtg  165960
acgtccctgg aactggtcac cagcgtcagg aggcgtggca cccggggagg gtccgcaggg  166020
agcagagtgg gactccgtgg agaggggggc aggcaagggt tgggtcacgt aggaggggct  166080 catggggggac aggcctgtgg gaaggacgag ggcaatggtg tgtgtcaggg acagaagaga  166140
```

```
accaggcctg aaggtgccag gggctttcga agctggactt ggccaagagg ccctgggatg  166200
cggaggcccc agggattctc agtgcagtgc tggtgttggg caggcactcg tgtgaggagt  166260
aggatctggg ccgcagaagc cagagggacc tgctgggcct gtcatggcct ggagggaagc  166320
cttagggggt ggggaggagg ggcctgtccc catgtggggg agtcaccccg gttcgcagaa  166380
gtcagggcag tgctggccag acaggcacag agcggagcca gcctggacgt ggaggactcg  166440
ggggtgctgt ggcctgggat ggagacgccc cgccccgccg gggtgattg  tggttgtggg  166500 tgtgtgagaa agaggtgagg gtgtgacggg gtctgaccct ggggtgctgc ctcctcaggg  166560
ctgcaggagg aggcgccgcc gtcgggtgg  aggcagtaga gggaagggct cagtgggtgc  166620
cacagcaagg acagcctcgg ccgcgacctt gggaagggca ggtgcctctt cttggggaac  166680
atgagtcacc tcccttttcaa aacccatccg tgtgctggag tcatgggagc tcagaacaga  166740
aggagagatc ctgactgaca cccgtagggc ccagcgtggg cgcagccgcc tcagcctttg  166800
ttctgccgac acacggtgac ggctcagcgg cccctgatt  tgctcactt  tcatcggggt  166860 tgcctaaaat ggtaaaagtg ccaccctaaa ccctagcact tccggagcag gacgcttggg  166920
cctgtggccc ccacaaggct gtgcacggga gaaggggctc ttcccagcat caggggcctg  166980
gcaggagcca ggggcttggt ttgcctttg  cattgcgagg gcgtcctgca ctcttcggga  167040
acactgcgga cagctgcgca tgcatcctcc cagagccctg ggcagtgagg ggccctcggg  167100 gaccccagg  acatgggctt tgggacacac ctgcagtgta caggggccc  tgctgtttcc  167160 tgatgtggtg tcacaggcca cacaggactg tgcagaacac gggagaaagg gatgcgttgt  167220
ctgtagttct aatcggagg  cactggccgc tcttagaaca ggtcaggggg caggtgtcat  167280
tgccattcgg ggtcacgtta ggaccggggg acctccactg caggcttgga gatgattttg  167340
ctagtagtga gcagagatga ggtcatggca tctccccttc tccatccaga cccgaacgtc  167400
ccatgccact gcgccctgca tggttcccag gatgagcagg gatagggtg  gcagccctgg  167460 agccacctgg agtctcctta gttgaaggaa cttcaggac  cggtcctgaa attgtgcctt  167520
tgctgcttaa ctactagata acgacagaga ccacataaaa caagagcctc tttataaact  167580
tgtatcccat tttaacgtgc aggaaagaac cttcgtccgc actccaaaga cccttgacta  167640
accagcgtca ccatccagac agttttgcct cgttttcct  tttctcttgt ttatttttcc  167700
atgtggactt tataatcaac ccgtctgcct ccagaaagaa aaagaaactg ggattttctt  167760
ttcttttctt tgagaagggg tcttgctctg tcacccaggc cggagtgcag tggcgcaatc  167820
ttggctcact gcaacctccg ccccctgggt tcgaggaatt ctcatgcctc aaccccccga  167880
gtagctggga atacaggccc ctgccaccac acccagttaa tctttgtatt tttagtagag  167940 acggggttc  accctgttgg ccaggctggt ctcaaactcc caacctcaag tgatccacct  168000
gcctgggcct cccaaagtgc tgggattaca ggtgtaagcc actgggcctg gcccgaaact  168060
ggcattttca ttgggatttg ttaagttcac acattacctg gggcgaaatt gacatccttc  168120
taagtgttgg atcttcccat tcaggaaccc ggtttacctt tcattcact  cacatcctct  168180 ttcaggagac tcttgaagtc ttcatgtggt tttcttcact tccttgtcta attattatta  168240 ttatttttt  tacagatggg ggtcttgcta tgttgcccaa tctggtctca aactcctggg  168300
ctcaaacgat tctcccacct cagcttccca gagtgctggc atttcaggcg tgagccacg  168360 tgcctggcca cttccttgtt taattttgtc ttgagtgttt catctcgttt ctgttataaa  168420
cgaggtattt tttcttctct cagagcatcc agcagcaggc agcttggtct ctgcgtggta  168480
actgtgggcc ccatggcttc tgagttctct tccttgtagt aactttcatg gcttctgagt  168540
```

```
tctcttcctt gtagtaactt tcatggcttc tgagttcttc cttgtagtaa ctttcaggtg 168600
gttttctggg gctttggatg cacagggtta gcatctgcag gtggggcagc atcacccacc 168660
tcagccgctg caaccaggtc gtgccgtctc tgttcatctt cctctctggt gacagtggcc 168720
agcacctgcc tcactggggt gacgttgaca ctggacggcc ctgtcctatt cctgacccca 168780
gctggaacac tttgcaccgg aagcgcagtg ccatcctcaa ggcagaacgg aagcatttac 168840
ccatctcggg caggcagcat ttgccctggc atgtgcaaag ggtgttggga gggccacagg 168900
ggagaggaga gacaggggct ctgcctgcag ccgtggaact gggttctgga gcccacagag 168960
gagctgtccc tgcctgagct gttggagacg ggaacggacc ctcccagttc ctgggcccat 169020
catctggtct ctgaggacac ctgctggcaa aggccctggc aatgatacat acagcctctc 169080
agcccccagc cactgggaga aggttctaga aaggctgagc agcagcgtga agctgagaga 169140
agatgaccga taactgcatg cagaggtgtg acttgtccta ttaagggact ttccacccat 169200
ttctgttttg ctatcaagaa aaaacactga ggccgggtgc ggtggctcac gcctgtaatc 169260
ccagcactct gggaggccga ggcgggtaga tcacgaggtc aggagatcaa gaccatcctc 169320
gctaacacag tgaagccccg tctctactaa aaatacaaaa aaaaaaaaa attagccagg 169380 tgtggtggtg ggtgcctgta gtctcagcta cttgggaggc tgaggcagga gaatggcgtg 169440
aacccgggag gcggagcttg cagtgaacgg agattgcacc actgcactcc aacctgggcg 169500
agagagcgag actccatctc aaaaaaaaga aaaaaaaaag aagaacactg caagttgtgc 169560
aggggcctcc ttgccatttg tggagatcat tgttacgatt tttactcctt agggcctcct 169620
ggaatgaatg gtgtcatcgt aatgtagctg ctggtattga accatcctta gattcctggg 169680
gaaaaccgtg cctgtctta gtgtgctact ctgttaatgt gcttctgaat tcaatttgct 169740 gatatttat ttaggatttt ttttggttga tattcatatt gttttagttt agaatcttca 169800
ggacacagag ctactgctcc agtgatcaag ggagacacag gatggaaaca cacctttgt 169860 caccacagg ccttgggggt acacaacctg ctgggaggcc agggagcgta aagagagaca 169920
gggacccttt attgggtcca gggtgttctg cacacaggtt tcccatggga agttttaact 169980
gatggactta aagcaagcag gcctgagctc cgtggggcca cactgtgact gtcggggac 170040 tctgcagtgt ggctgcacag tccatgttgg gtgtggtatc agtggggctg cagggaagtc 170100
accagggggc agttgcatag ggtgggtgtc tggatgggcc agctcgagga atgggggatg 170160
tggaactgga aactgtcagg gcgacagccc tgcttctggt gggagaaagt ccagcttaga 170220
tccagaatgg atgccgaggc agcctaaaac catgagcgtt ccctgcacac tctggcgtct 170280
gatctctagc ttccctttct tgtgcaagct tcattggatt tttaaatttt cctaattttt 170340
caattcccgg gaacattcta aattgcgtta ttacctcttg gcgggatccc tgtgcgattg 170400
ccgggccttg ggtgtcgtgg agggcagctg cctcgctccg ccctggcttt cgtgatgttg 170460
tgagctttac cctgccgagg ctgggtgttc tcacccagtc ccacggctgc accctgcctt 170520
gccttctcct ctgctcaact tcaccccagg ccgtgtctcc tggctccagg aaggtgaggg 170580
gctgcctccc atgcgtcctt tcatgttgag gacacccgtg tttgcctttg cacgtgagcc 170640
ccattgtcgc tgggacacac tgccctccag tgctcgagtg catttcctgg gcactttctg 170700
gccttttatc tttgatggag aaatccgagg cctgccagca tccccaccag tagatttctt 170760
tggacgaagt aaaatccttc tgtggattca gctttaccgc cttttcctcat ctgctggtgt 170820 cttcctcaga gctttaatgt ccgtcctgct ctccgagtca ggaatctgat tttccagcgt 170880
```

```
gccctgtaat gacggtgctg tcaccgctgt gatgtccgct gtgaggtggg gacaggacct    170940
ggaagtgggg tttccaagtg agggttctgg gcccgcccga gtcatctgat gttgggtctg    171000
acaagccagg agctgtgtga gccggagaac gtcccctaac ctgtctgtgc ctcggcttcc    171060
ccatctgtaa aatggcgaga gctgaactta cttcctggtg atgggtcaa gtgcgttaac     171120
acagagggac ttggagactg acgcttactg agggccacac cagcggtcag caaaggttgt    171180
cttaaagggt caggcagtaa atatttccac ctttgtgggc catgcggcct ctgtggcaac    171240
tatgcgttct aaaacagaag cagccttaga cactgcgtga agggacgcgt gtggccgtgt    171300
tccaccagaa ctttctgtac acacatggtg gtgggcccgcc cggacccatc tggttaattc   171360
ttgactctca gggcagcgtc tcctgtgcct ccaggagagg gctgtggttc ctccctctga    171420
gccgggcacc ttgcattcct ggaagggggtg ggggagtgg cgaggagggg gcggcaccaa    171480
ggacagggcc cacctcctag gaggttttgt gagcttccct cagcccccgg ccgcccccta    171540
ggaggtttcg tgagcttcca gcatcccct gcggccactg tccctccatt tcccatgtct     171600
gttggatggt gccggttcca gggcagggtc agggactgga tccggctgcg gtctgcgtct    171660
cgcctggttc ctgagagctg cactttgtct ttggttgttg atgaatccat ttttgctggc    171720
gttcttcacg tttgtgtatt tgattaagta tcatggacag gcatgtgcag tggctcacac    171780
ctgtaatccc agccctttgg gaggctgagg ccggaggatc acttgaggcc aggggttcaa    171840
gaccagcctg ggaaatatct cgagacccctt tctctacaaa aaatttaaaa attagctggc   171900
ggtggtggtg caagcatgtg gtcccagctc ctcgggaggc tgaagccgga ggattgcctg    171960
agcctgggag gtcgaggctg cagtgagcca tgatcacacc actgcactcc agcctgagtg    172020
acagagtgag atcttgtctc agaaaaacag ccccgagggc acgtgtctca tgactcccgc    172080
ctcccgcctc ccatctgggc tctgcttgct cctctcccct tgcaaacatg agaggagcgt    172140
taatgccagg acagggagca gggaggggca tccccagcgc ctccaggcca caacatggcg    172200
agtgtggcta ccaggacacg gaggggcagc ctcagccccc tccccaggc cacgacatgg     172260
cgagtgtggc taccaggaca cggaggggca gcctcagccc ccccaggcc acgacatgg      172320
gagtgtggct accaggacat ggaggggcac cttcagcccc ccaccccac ccccaggctg     172380
tgcttcccag catcccttgg ggtcaggact gtgtgtgtca ctgagggct acgggtgaag     172440
ccacacacgc ccctggcctg gccttgcgcc cctgcctgag agcctctatg caggacagcg    172500
cctgtgggc acccaagtgg gccgagccca tgtggattac aggtgcacac caccagcgtg     172560
aggagaggag tgggctcgga gcatgctcag ccatggtccc aggcatcttg tcagcagcca    172620
gctcagcttg tgtcacgcag agtcgcctta gagtgaattg acaccagatt gtcctggtgg    172680
gttttgctc tgaagaaatg tcaaaagtag cattaaggtt tttctgtaga caaaaaaacc     172740
ccaccatcat tgcagcttga gcagttgcaa attaaataaa ttccttcctc agcaagctgc    172800
ctgggtccta ggccttgggc agagagaact ggctttcagc acagttcccg tgattggctt    172860
ttctctggag aagaagggga agcggcctcc gcctctacct ctctaagtgt ttaaatgtcc    172920
cccaaattct ctcagcctcc tgaggcattg tattgatgct tttctctaga attcatgtat    172980
ttctttattt tctctggaaa tggcattggc tttgtccccg tcctatgggc cgtgatagct    173040
taaagttagg atgaacccac agaggccgtg gaggcccttc ccaggcgccg cagcagcact    173100
gttggggtga acgtggctcc tctcgggggg acaggtggaa gggaccagca cccattgggg    173160
cgtgtaactc ctggtggcaa aaaatgtgcg gtgaagtcac cctaagggtt tttgtggttt    173220
tttgtatttt tattttattc tttgagacag agtcttgctc tgtcgcccag gctggagtgc    173280
```

```
agtggcgcaa tctcagctca ctgcagcctg tgcctcctgg gttcaggcga ttctcctgcc 173340
ctcagcctcc cgagtagctg agattacagg tgcacaccac cagccctggg tcattttttgt 173400
atctttagta gagatgaggt ttcaccatgt tggccaggat ggtctcgaac tcctgacctc 173460
aggtgatctg cttgccttgg cctcccagaa tgctgggatt acaggcctcg tgagccacca 173520
cgcccaggca ctctaagggt tttgaataaa ttctttctta acgttttctg accgactctt 173580
aggtcgtggg tgtcctccag gggttggagg ccttcatgga gcttcgttcc gtggggttga 173640
cgttactgaa cgagtccctc cacgggtgca ctgaggacgt tcctgcacat cgagggcacc 173700
ctcagagctg ctctttctgt cattgctatt ttgtttatac cggggattgg caaacttttt 173760
cttgaagggc caagagtag acatttttgg cttttgcggcc acagggtctc tgttagcaac 173820
tccctctgcc acggtggctg gaaagcagac atagaaaata gatgcaccag tgagcatagc 173880
ctcgttccaa taaaacttta tttacaaaac agggagcagt ggaccagcga gtccccaagg 173940
acaagggcca ggttaccaga gaatttccag gcacatccgt tggaggcagg ggagacaaca 174000
aaagccgagg aacgagcctt ccccagccgc tccccaaagg cacggcttat tcttcagggt 174060
gcccgactgg ccacgtggac gtctctccag ctcctcactt ggggcccagg gctctttcga 174120
tttttaggag tttgttttcca atcagaaact tcacagatga tttgcagcca gttcacctgc 174180
cctgtgtaaa ctggcctctg tcctctctgg cttaattctg ggagcttgtg gagggcagga 174240
gcagggacag gtgccttgag gcgtaacagt ggcggtggtg tgggagcttg cgtgggatcg 174300
aaggaaacgg gcagagtcac cacacgcttc cctccttcac tccccgctcc acgagggggca 174360
gccaggagca gccaccagtc ggaagcaaat aaacaattca ggtgccagag gagccgctga 174420
cctaaaaaaa cccgccacag ggtatttctg ggagattgta tgagaattta attttgaaaa 174480
ttgagtctca tgaaatgtag gaaaagatct tattaggaag agaaaccatg tggcccagtc 174540
cctgagacgg gaagggcctg cgtggtcctg atgacatctg cggatctttt aaaatcatac 174600
gatcatgtct gcgaaaccgg gatgccactt cccacctggc ttctccctga ccccagcttg 174660
ttcccttgga gggccggtgg actcctcagc cttgcagcaa tgaaatcagg ccttgaggcc 174720
accccacccg tgacctgcgg tgctgtcccc atgcaagaaa ctgcctcgct ccagccccca 174780
gcagatcctg tcccagcccc cagccctggt ccaagccacc tccactccca cctggtgacg 174840
ggccacctcc ttcattccgg ggcccaccca cacttcccaa gtccacacac agtggccaag 174900
agtgaaggcc ggcgaggccc ccgcatgact ccctcacctg cacccttcac gagcggcccc 174960
gcagcccgtc cccaccagcc cctctctgct gccagggtgc tcctgctgct cttttgctctt 175020
tgcaagactaa aacctgcggg aggttcggg cccacgaagg ccgcttctgt ggggcttctg 175080
tctaaggagg ccgccgtctg ccgaggtgac tgcagcctcc ggcgcctctc tccctgcagg 175140
ttgttcctgg tcattgagta cgtcaacggc ggggacctga tgttccacat gcagaggcag 175200
aggaagctcc ctgaggagca cgccaggtgg gtgcgcgtgg acggggccgg gtgggtgcgc 175260
ccggagttgg ggatgggtgg gtgcgtgcgg tgttggggggg ctgggtgggt gcgcacagag 175320
ggatgacggg tgggtgcgcg cggagttggg gggccgggtg ggtgtgcgca gagggaggt 175380
ggctgggtgg ggtgtgcacg gagggggtat gacgggggcg ggggggcgg ggtgcacgtg 175440
gagggggccg gggaccttct ccaggggtca gcagggagct caagggaggg aagtccaggt 175500
aggatggcag agggcatcat gtcccccaca gtgtgacgtc ccctgcattg tgacacattc 175560
catatttgct ccagagtcac aacatttggg aggtctcctg agttatggtg cctcagacca 175620
```

```
gtcccccagg ccccacccct gaagcagcac catgcctcat ccgagagaag tgagagtctc 175680
ctgggattgt gctgtcttca tggtggctct gccctggttc tgctcttcac cctgttagtg 175740
gcacagcatg gccagcattt cctcagcgtt aggagcagaa cgagagtggt ctgtttctag 175800
agtgacctga gagactcctt cctgcccttc cctttcatct ctgatatctt cgggcctccc 175860
ctggcagccg aggggcctcc agcatggttc aggagcctcc cccggcagcc gcgggacctc 175920
caggaccgtt tggggctta tttcagctcc ctggacctt cctgtctttt gtagtttctc 175980
cttttcctca tttccttact taagaacgtt gcatgcagtt ttgtgagtca ccttagattg 176040
tttctggcaa taggacagta ggcaataaat ctagaacagt acacttccca caacgctgtt 176100
tttaaaaact gtggcaacac acaacataaa aggtagcatt ttggggcatg gaattcagtg 176160
gcgttgaatg caccccatgc tttgcagcca ctgctggccc ccgtctcatc tccagagcac 176220
gccctcttc cctgctgaag cttggcccat cagacactcc ctccctgtcc ccgccccag 176280
cctcacatcc tcaccccaga cgggcacgtc ccactttctg tccctctgat tcgaggactc 176340
tagggacctc atcggagtgg aatcacagtg ttggtccttc ggtggctcat tttcctgagc 176400
atagcgtcct caagattcat ccgtgctgtg gcctgtctca gaattgcctt ccttttttcag 176460
gctggataat gccccgttgg atggagggc cacactttgc ttatccgtcc atccctcggg 176520
gggcacttga gtggcatcca catgttggcc atggtgaaca gtgctgctgt gaacatgggt 176580
gtgaagtaat ctcttgaaca ccctgcttcc ggttctttgg ggtatacacc cagaaactga 176640
attgctaacc acataagaat tccatattta ggccgggcgt ggtggctcac gcctgtaatc 176700
ccagcacttt gagaggccaa ggcgggcgga tcacgaggtc aggagatcga ccatcctg 176760
gctaacacgg tgaaataaca cagtgaaacc ctgtctctac taaaaataca aaaaattatc 176820
caggtgtggt ggcgggcgcc tgtagtccta gctactcggg aggctgaggc aggagaatgg 176880
cgtgaacctg tgggcagagc ttacagtgag ccaagatcgc gccattgcac tccagcctgg 176940
gtgacagagt gaaactctgt ctcaaaaaaa aaaaaaaaa ggtcatattt aattttttttt 177000
tttttttgat ggagtctcgc tctgtcaccc aggctggaat gcagtggtgg gatctcagct 177060
cactgcagcc tctgcctccc aggttcaagt gattctcctg cctcagcccc cagagtagct 177120
gggactacag gtgtgcgcca ccatacccgg ctaatttttt tgtatttta gtagagacgg 177180
agtttcgcca tgttgcccag gctggtcttg aattcctgac ctcaggtgat ctgcctgcct 177240
cgacctcccg aagtgctggg attacaggtg tgagccacca agcctggcac cgtgtttaat 177300
tttcgaggac ctgccggact gtcttccgca gcagcggcgc tgttctgcac tcctaccaca 177360
acgtgccatg gctccggtct ttcccgcatg gaagctgtcg tgttatttgc ccgctcctcc 177420
ccttgtggag gctgccacat cgttctctgt gtctttgaca gcaggccatc ctaaggcgca 177480
tgggtggtg tcctggagct ttcattggca tttccctccc tggccctgtg cactgcactt 177540
tcaaatcctg ggcctggtca ttgagaggat gccgggccg tggtggggca acgggagtg 177600
tgtggccccc aggctggagc tgttggcgca gcctctggca caggcactgc ccccatgacg 177660
gcatccccac cccaggttc tacgcggccg agatctgcat cgccctcaac ttcctgcacg 177720
agaggggat catctacagg gacctgaagc tggacaacgt cctcctggat gcggacgggc 177780
acatcaagct cacagactac ggcatgtgca aggtgcgtgc cttggaccgc ctccctgac 177840
catcccgcat gtgcgtctcg gggcgcctgt cccgcggggt agtgtctaca agaaccctct 177900
cccagtaact ttgcccccac aggaaggcct gggcctggt gacacaacga gcactttctg 177960
cggaaccccg aattacatcg ccccgaaat cctgcgggga gaggagtacg gtgagtgccg 178020
```

```
ctgccctggc ccctctcgga gcacacaggg ccagagatgg cttcgggcct ggcccagcag   178080
ccagggagag gtgtccttga ccatcttaca cccaaaagcc acacactgtc tttcccagcc   178140
ggatgtcatc atctggcctc agcccttat ttgaattctg gaaaacctcc catgtccact    178200
tgagcagctc cttggggagg gcactgcaca ggattcctcc tgccagggag ccccggggca   178260
cagggagggg aaagacacag aaagcggggg tgggacaggg tgcagcacct gagtcccgt    178320
gctgcacgag tggctggggg agaagctgtt gtctggggag ccccagggg tgcaggagcg   178380
tgtggacagg accccacagg ccctgcggct gaggacgccg tgcacaccag agtgtttctg   178440
ctcctctccc ctctctgggc gtgaaacggg gacatgggca cgcgtgtgca gccgtgtgtg   178500
cgtgtgtgaa acgggacgt gggcacgcgt gtgcagccgt gtgtgcgtgt gtgaaacggg    178560
gatgtgggca cgcgtgtgca gccgtgtgtg cgtgtgtgaa acgggacgt gggcacgcgt    178620
gtgcagccct gtgtgcgtgt gtgccgttgg gctgagtgtt cgtgtgtcgg gcatccatgt   178680
gtgttgtgtg cacatgcata ctgtgtttgt acacactcca cccacttctg catcctggtg   178740
ttttcaatga ggcatgcatg gtgtgccttc agacattttt acacattttt tttgccatca   178800
gaatgggtgt ggggcaggca gggcgggcag gtcactcgcc gctgggataa ctgggctccc   178860
cagcggccac aatggaagtc tcagtagcca gagaaggaca gacagcagat tggaggactg   178920
gaatatagtc tagaacccag cttgggatgg ggattccgtg tgggacagcg gcagcgtctc   178980
acctcagcag ggaccagggg gacttccggg gacgcagaga cagctgctgt ccttgggcaa   179040
aacgggtcag ggtctcccac ccctcattcg ctggaacaca ttcccaacag gttgactact   179100
tgaacctttt taaaaaacaa aatggctgta gaaggaaaca caggagagta tttccgttac   179160
tgcagcgaaa gggcttcttc aagcttagtt ctgtagaagc agaaacgaga gaggaggtc    179220
gtccgcaggt tccaccagtg cctcgtgccg gtgtggtcac aggtgccctg gcaggaccga   179280
cagcccagag gcagcctggg agacctccgt agtgtcaggg acggtggcag ggaggccgag   179340
ctgccaggtg gaggtgctgg ttctgtttgg gaagtggaag tcacagaggc ctgtgtgccg   179400
cctgctcaag cctggctcac actcgtgtca actgggcatg aaaaccaacg ccagccaggt   179460
tcgtcctgct gccggcccat gtggccccac tcggtgatgg ctgtgtgctc tccccagggg  179520
ttcagcgtgg actggtgggc gctgggagtc ctcatgtttg agatgatggc cgggcgctcc  179580
ccgttcgaca tcatcaccga caacccggac atgaacacag aggactacct tttccaaggt  179640
gcgtgccccg ctgtgcgttc gtaccctca cctgcacgac tgtcttcctt ccttttcaaa   179700
ggtgcaggtg gaggggtccc gcgggtgcct ggagcggcag tgccatgcaa agcgtaccgg  179760
gaaccattcc tcctggccag accctgtgtc acatgccact ccccgggccg tggggtgggg   179820
ttaccacacc tgtgggtcag caggaaagag aacctgtccc cattcagctc caactccctc   179880
ctgccctggc cagcagcaca tgctggagcc ccagcatgtc cttgaccgag gctgtaccga   179940
gctgaaagca cagcccccac cccaaaacc cacagccacc atcatgggct ccttcccacc    180000
tggaggcccc gggacctgct cctggtctgg aattcagtgc tgtggggatg tgggatctgg   180060
gaacgcggct gtctccgcgg tgccctctgg tggccagcct gcagaggcac ccgtgtacct   180120
gcgatcttgg ggctgaggaa ggggagctgc tggttcacgt ccgatcctac gacacgtgcc   180180
agcgcatgta accaggaggc ccaggaggga cccggcggga ctccgggtta tagatattgc   180240
tgggctgtag gaagggaggg gctccggggc cccaaggctg agctcccaaa gctcttgctc   180300
agagtcagag tctgggcggc actgggcaaa tggcacacaa cacaggcaag tcctcaccag   180360
```

```
gctccgccct tgcagtgatc ctggagaagc ccatccggat ccccggttc ctgtccgtca    180420 aagcctccca tgttttaaaa ggatttttaa ataaggtacg tttctggcca tgctgacaaa    180480
atctcgtttg tggcctcggt gttggtgggc agagggccag gcacggctgt tggccatttt    180540
ttcatgtcgg ctgctgtgta tcgggtgtgt gggttgattt tccgcttcag tatttgagct    180600
ctgtgttctg tgaatcgtcc gttttactc acacctaaca aaatgagaat gtgtgcccaa    180660
ggaaaatgga acggagctta acgtacgggg aaggaacttt caataaagga aacatctgat    180720
ttccaccacc tgggtcagag catcggggga gggcttgtca gcactgggag tggccaccaa    180780
ggagaggggg tcatggggct tccgggatgg ggctgacttg tccttgtttg aactctgacc    180840
tccaggaccc caaagagagg ctcggctgcc ggccacagac tggattttct gacatcaagt    180900
cccacgcgtt cttccgcagc atagactggg acttggtaaa gcatcacaaa gcctatttgc    180960 accccatcc ccatcccaac cccaaatcta cccaacccc atcccaaccc caaccccaat    181020
attcacccaa ccccaccccc acccatccg aaccccaata tccatcccaa ccccaaattc    181080
atccaaccct caccccacca ccaacccaac cccagccca actccaccc caaccccaa    181140 ctcaaccccc accccaatat ccacccaacc ccactccaac ccctacaccc caaccctc    181200 caaccctat aatctggtgg acagagccgg ggctgtgtgg gcctggtggg ctgtgtgagc    181260
tcgcgcaccg ccgggctggt cttttgacatg gccccacttg cgtggagcca aggtcctgt    181320 ctcccagaag ggtcagctgg gaatgggga ccaccctcca gggccccgag gagggatggg    181380
gagacacatt tcgtcctccg gagccaggag agtgaggggc cggacgagct cggcccatgg    181440
cgcttcctgg caaccctcga ctgtgctggc ttggtgccgc caggagctag cggcacatgc    181500
gtcctgacct gtgagcacat tggctgttgg ttccacaggg atctgatagt gggggccggc    181560
ctagagaagg gcgtttgctt tggtttcatg gccggtttta tcagcagtta ctggacagga    181620
ccagcagtcg cagcgttcac ggcttgagct ttagcgtcgg gtattgaagg agagtgagtc    181680
tgtggacagg gtgcgacgta cactggctcg atttaggaat ctgatttcgg tggtgtgtga    181740
gcagggtgca ttcggtagaa actactttga gttttgaccg ttccccagct ggccgtatga    181800
ggtcagtact ctcctgtgat gaggggcggt gactgcagcc ccagcgggcc acgtgatcag    181860
gagggggccg aatgtcccga ggggctctgc gtgcagggg ttttgccgga ctgtaggctg    181920
gcgtgtgtct gtcaggttaa ggcaggtaag gctgcgccgc ttggtcgtgg gttctgtgtg    181980
gaagtgcagt ctccacccag gatgtttcca gcgccgctcg gtcgtgggtt ctgtgtggga    182040
agcgcagtct ccacctagga tgtttccagc acatggaggg tttattggga ggtgaccttg    182100
tctgaagctg aggagcgtct gtggaatttg tttccagctg tgtaaatggt tgcagagcta    182160
ctgaaataaa acctttaaaa tacactctca aggaaaaaag cagattggat agctcgttca    182220
gtgcattttg gaggaggttg aactgaatca ggagaaagcc cagctctagc tctgtcctcc    182280
accccaccca acttttccag gcagcctcgg ccagcgtggg aggtcactcc ctggcccctg    182340
tggtcagtgg gggcccttgt ccacacagcc caacaagtca ctttctagtc gaaggccttg    182400 cttttgcctgt gcatgtgtgg gaccgtgggg gaaggtgggg agtgaagtgg tcagaacgtg    182460
cccacacccc ttcctacata cagcccttcc agagcccagc tgggctgctg ccaaactagg    182520
acggggccat tctctgtcgt gcggttgtca gatgcacaca cttagaaatg ttctgagcat    182580
aggcacctgc cacggaatca ccttcgcaaa ttcttcattt aaatttatgc ctctggtagc    182640
ataagggaga agagatctgc ctttggttct aactgtcagt catcctcacg cccaggccgg    182700
ggttagaggt ggcgtcccttt ttctctggct caggcacccc tggcctagtg gggttactgg    182760
```

```
tggcgttccc ctatctcagg ccacacctgg cctagctggt gttagtggtg gcatcccctt 182820
gtctctggcc cacagaaccc ctccggtcca cacacacact caggtccagg taccacccgg 182880
ctgaacccgt agcaggtgct tagtagaatt acgtgaggag ccagcatccc cgctcccagc 182940
cacctcccct cgcccgtctc agctcagtct ccccgtgcc tttcccaccc tctctcttcc 183000
aagcccacca ccgtatgggg cccaccagca ccatgggatc cagggagagc ccgatcctgg 183060
gtgcagcctt ggtgccagcc gggcccctga tcttgtctct caaccactct tggtttaccg 183120
ggagtggaca gatgaggaca gatggctgcc tgtggagtga cgggctcctt ctcttcggag 183180
cactgtctaa tctgagtgtg agtccaaccc tgcccgagcc ggaactcaag gagaccatga 183240
agccacccctt ggcctctagc tgggagaggt ctgcgtccct gcagcgagca cgccaggtga 183300
tctctggcac acacttgccg cgggctgtct ctcggaaggt agtcagcggc cctggcttcc 183360
cacctgggtc ccaccactgc agaatcaccc ccgtggctgc ccacaggggc ggcttccatc 183420
accctgcttc ttcctggctg ctgcgggctg tgttgtgact tccatcccag cctgagaggc 183480
ctgcgaaggg cttgccaccg actgccagcc ctgcctctgc caccgaccgc cggccctgcc 183540
tctgccaccg accgccgacc ctgcctctgc cgtttccttg ccacccatca gctcttgagg 183600
cttttaggaa gaagtgtggc tgttttggcc agattgcttt agctgtcctc agcagggttg 183660
gtgtggggtc accaccaccc ccatgtgacc ttggcagaag gaaggtcctc ctcccattca 183720
cccaacgcct gcaactcagt ggttctgagc aatcccagag ttacatgacg tcatcgcgat 183780
cactttcatc accctgtacc cagagaagac ccgaacccac tccagcctct ccccacaccc 183840
tgcagtggct gctccgccag gctgtgtggc tctgcctggt ctgcacatgt catggaagtg 183900
gacctgggca caccgcggcc tttcgtgcct gccctcccct cagcattgtc tccacaagct 183960
gcacccacac agtagcacgt ggcactgcct ccttcctgcg ctgaaccccca cccactgcgt 184020
ccactgcgtg gagactgcac ctctgcatcc gtcctcagtg gacatagggt ggcctccact 184080
ttctggccat tgtgaattgt gctgccgtga cacctgtga accgcttct gggtggactc 184140
gtgctgctgt gagcacctgt gaacccgctt ctgggtggac acgtgtttat ttctcttggg 184200
cacgtgctca gggcgcagtt gcaggtccgg tggtctcagt ctagcctttc aggggggcca 184260
cctgttcctg cagcggctgc tttctggtcc ctttgggggc cccctcagtc tgtgctggac 184320
ttagttccat ggctgtagtg ggcacagctt gagaacagtc cctcggtggg tgtcagctcc 184380
atgtgggagt ggggcacgtg tgaggccttg gtccccacct gtggactcag ggtctctttc 184440
acggactgcg gggaaggcag tgggagcagc aggaatggat ggtgaaagga cacagtgccc 184500
gcccccgag tgtccgaggg tagagctggg acagggtcac agtcacccca aagccgcccc 184560
ctccttgcct atccccagct gaaccagcac cactcaggca gtcgccgcca ctggggtgtg 184620
actctggggc ccggcaccgg gtccccaaca ctgctttcct cctggagcct ggcctctgca 184680
cactgccctg gagaagagag gcagtgtgtg tgcagagggc cccgtcagcc aggcagatcc 184740
acctgccttg cccctgcact gggaggtggc gctcatcttg tcgggggctc ccatgggccg 184800
tgtctagacc ccacccctccg ccggtccagg cacatcctca ggctcctaat cctgagtcct 184860
ccggtttggc tgtgggagca aaggccgtgg ggaagttgct gggcctgtcc cgggtgagct 184920
ttgagtgatg gacaggctca ttctgaagga actgggtcca gacagcacgt cctggcctgg 184980
tggctggggc tgccactcta agagggtccc catccccgca ggatcccggg tacttggcac 185040
actgcaaagc ctgagtattt gtggatcacg tgatctgtgc tagtgactat caggagtctg 185100
```

```
agatttgaag cgatggattt cccagcatgg tcccagctcc ccactgatgt gaaaggtggt   185160
ggtgagttaa cagctgagcc accacctgct gcccaacccc acgtgtccca catggccggg   185220
cggtgctgcg ctaactcatc tcccctgga tggaaacgtt tgcgtggtga cagccgattc    185280
tcttgagagt catttgctgc ccatgttgct ggggagattc tgcctcaggg ccaggagtgg   185340
tttgctcctc ccaccccggg cccagggctg ctggtgggag ccccaggga ggagcaagga    185400 ctctaatgct tcgtgtggtg ggagcctcag gactttccca cgtgcgacag gcacgttcct   185460
gggagctcgg tgggaggaac ccagccacgt tgtgtgctgc gcaaggagcc ggcggcaggg   185520
aggggaaaac ggaaagacgc agaggagggc aggtgacaag aggcccacag agagatggct   185580
gggtctgggc agcgggtggg agcaggaggg aggcggttat gggagacgtg gagcagtgga   185640
ggccgtcaga agtggggatc acagctgtga cctcatggag agggacaagc cccacagctg   185700
ggctggtgcc agctccacta cccagggcca acctgtgtgg ccgtaaaatt ctcaagcctg   185760
gagtgtgtag aaggcagcag tgccctggcc tggccacccg cgaacccctc tgtccacccc   185820
atgctgcgtg gcacagggca ggcgtggggc ctctagctgg agccttgagt gggtggatcc   185880
tcggtggggc tttaaggcca acctgtttat gaaaatgcat ggggactgac tgcagatgca   185940
cagacaactc agatgcacag acgcccggac gacgtggaca cccagacgat gtggacgcac   186000
agacgacatg gacgcacaga cgatgtggat gcacggacga cgtagacaca cggatgactc   186060
atccacagat gactcagatg cacggacacc cagacgacgc ggacgcacag acgacgcgga   186120
cgcacagatg acgtggacgc acagatgacg tggacgcacg gacgacgtgg atgcatggac   186180
gacgtggacg cacagatgac ctggacgcac ggacgacgtg gacgcacgga tgactcagat   186240
ccccagacga ctcagatgca cggacaccca gatgacatgg atgcacggac gactcagatc   186300
cacagatgac tcaaacgcac agatgactgg gatgctcaga tgaccgctgc tgtgctgcca   186360
ccccagggct ctctgggcgt ttcctgtggt ttgggcacca ggagcctggg agtcccatgc   186420
tgcccccagg gcactacctc ctgggcccag ccctgcatcc ggtggcaggg ctcaccgtca   186480
tcaccccaac agtgcagggt ggtctcaggg acctcctctc atcattgcca agaactggct   186540
ccaggatgtt tccatgtggc cggctagtat ggccaaagtg gaccctggcg tgctgtcccc   186600
ttggacgcct ccaggccctg cccagcacgt ggggctcgtc catcctgtgc ctgaccatgc   186660
tctgccatgc ggggcctagc ccagccccc agccctgctg cttctcccca ccccacccc    186720 gccacctcca ccaagccacc agcatcctgc ctggccctac ggacagcagg gtcgtcctgt   186780
gtccaaaagc ctcctccccc tcagcccctt cactcgggtc tcatggggcc cctctgtggc   186840
ccccagcgca caaggcacac acccactatg gggcctttgc acagctgtgc cctccccagg   186900
ctccagccct cacctccccc aggctatttc tcagatgtcc cttcagaact agagcccttg   186960
ggcccccagc cccattgaca cggaacgggc cccctgttgt atctcaggtc actgctgtgg   187020
ttgcagccac aggggcaaca cctgttactg ccacagcgtc cgacctgggg ccagcgtgca   187080
ttcaaacgca ctgctctgag aggccaggac gtccatgggt tgggcgcagg gggcggcggt   187140
gggaaaaggt gtcaggcacc atgggtcccg acctggagcc cacgtgccag ctgcagagat   187200
gggcactgaa ggcttttgag caagaggagg aggtaacgct ggcccctggg gatgctgtca   187260
gggaaactga gcaatcttg agccctcgga gcagagaacg ggctgggcca ggggctgag    187320 gaccctgggc cagctccagc tgggtcctgc tctgttccca cccctgctgc ttattaaacc   187380
cttgtaaagc agcacaggac taaggtaggg aaagtacttt aggaaatgcc ccttttcac    187440 attttatcgg caggtgtttc atacaaagaa tacaagtaac tgatgaatga aggggcatc    187500
```

```
ttgtgtcccc acaatcctgc tgtgcgcaca ccacaggtga gccgttctgc ctaagggaac   187560
agccccggcc cctccctccg gctcctcccc agcaccgtct cctccaccca gtggcctggc   187620
cgtggatgct gcctgtggcc cagctttgag acaccgccct gacacgtgtc cagccttacg   187680
tggaaggatt tgtctgtttt gtggcatcct agtagatgcc acgttagtag atgccatgtt   187740
agtagaatgg atgtgggcat ttctttgtaa gttcccaaaa gcctatgagg gttttttcca   187800
cgattccgtt cccagtttgg cttttgttgt tgttgtggct gttcttggcc ccctgggcc    187860
ctgcagtgga gtgggggct gcacctggga gcctcgagct gaggcccagc ccctcctgcc    187920
ctgcattttc ctgccaagca gcacctgaga ctctgaagcc gatgcctata caggcagaaa   187980
cctgccaatt ccagcttgaa cgactggagg gtcctgagga tgggggtccc tgggtgcca    188040
tcatgggcag ggtgcatctg tttgggtatg ctgcccccca gctggcgggg caccggggac   188100
aggcacagcc acactggggg catttctggt cttggaagcc ttcttggctc ttccggaggg   188160
aaggcggctg ctgggtgccc tgtgatccac ccgcgagctg ggctgttcgg cttggtctgc   188220
aggggctggg gggctgcatt tcttttcacc agctgcaccc accggcccc atcctggctg    188280
gcaccgaagg gagcagcgcg ccgtgacatc ctcccctcaa gcctggtgaa tggtggttcc   188340
atgaggctgg agtcagtggg tgcctgttgt gacagctgga tttcagtgtt ggtacaggag   188400
cacacaccta aggggcgggc cagtgaatga gtgtgcgagg gtgggctaga aacgagcaa    188460
gggaatgaga gagagtgggt tagagagtga gtgagccagt gaatgagtga gtgagcagga   188520
gtgggttaga gagcgaggga gtgagtgaat gagtgggcta agagggccg ggcgcggtgg    188580
ctcacgcctg taatcccagc actttgggag gccgaggagg gcagatgatc tgaggtcagc   188640
agttcgggag cagcctggtc aacatggtga accctgcct ctactaaaaa tacaaaaaca    188700
aaattagcca ggcgtggtgg cgggcgcctg tactcccagc tactcagaag gctgaggcgg   188760
gagaatggtg tgaacctggg aggtggagct tgcagtgagc cgagatcgtg ccactgcact   188820
tcagcctggg agacagagcg agtctcaaaa caaaaacaaa aacaaaatt agctgggcat    188880
ggtggtgcat gcctgtagtc ccggctactc aggagactga ggcaggagaa tagcttgaat   188940
cggagtcaga ggttgcagtg agccgagatc gcgccactgc actccagcct gggcaacaga   189000
gcaagactcc atctcaaaaa aaagtgggc tagagagta gtgagtgaat gagtgaatgg     189060
gagtgggtta gcgagggagt gagagggtga atgggagtgg gttagagagg gagtgagagg   189120
gtgaatggga gtgggttaga gagtgaggga gtaagcgagt gaatgtctct tggtgctgct   189180
gtaacagaat acctgagcga gcctgggtaa tttctaggga gcagagttct ttcccagctg   189240
tggaggttgg gagtccaggg tcatggtgcc agcaggcttg gtgtctggtg aggcctgatc   189300
tctgcttcca agatggcgcc caaacactgc attccccgga ggagagaggg gaggaaggcc   189360
acgtgtccac atggcagaag gcagagagga atccatgccc aagctgtctt gacagctaca   189420
ggagtttgtc tgtgagggcg gggctcccat caggttccac ctctctacac tgttgctctg   189480
gggaatgagt ttctcactgt gaatctgggg ggcacattca gaccctattg tgggtgagtg   189540
ggagagcatg gctgtgtcac tgggacaagt ggccatgagt cgggggaact gagggtttt    189600
cagtgtcctc acccgtatgt gttgtggcac ctgtgccagg caccagcgtt ctgccctccc   189660
cggcacaggc gcatcaccga gtcccaggcc cgcctgctgg gcattttcct gccaagcagc   189720
acctgagatt ctgaagtcga tgcctggata ggcagaaatg ggccggcagg aggctcctga   189780
cagacgggtc tgtgcagtgc cagcgcaggc agggtgctgt ggccaggtcc tacacctta    189840
```

-continued

```
tggtcagggt tccaagacgt catgagacgg cttgttcagc cagttagttg tcggtgcccc    189900
tctgaacaag gaccccccca aggaaggggg tggcctcgca tgggtggctg gggatcctgc    189960
tccgtcccac atgtgccag catggccgac actggcattt ctcagctcga caacaatttt    190020
tctgactttg gatattttct agattttgtg ttgtaagaaa aaacacttgg cagtcaaata    190080
ctaggcagat tgaaatgctg actttctcac tgtttcattt tgtgattgaa gtgcgtgcaa    190140
aacactcaat ctggtaggga tgatgcccgc gcggagctga cccttctcct attgtttttc    190200
caagctggag aagaagcagg cgctccctcc attccagcca cagatcacag acgactacgg    190260
tctgacaaac tttgacacac agttcaccag cgagcccgtg cagctgaccc cagacgatga    190320
gtgagtccca ctgggtgcgg gtccctggag caccctcgg gcagcccat ggcaggccgg     190380 caccttgggc agctggtgac ccagcctgcc cttgagtccc acccgcctgg tgtcatctct    190440
ccagtgggcg ttgggggagg attcttatgc gaacgtgact ccgcttcccc caagggaatg    190500
aacacacggt cacccccctc cccctgcca ccttgccca cagggatgcc ataaagagga     190560
tcgaccagtc agagttcgaa ggctttgagt atatcaaccc attattgctg tccaccgagg    190620
agtcggtgtg aggccgcgtg cgtctctgtc gtggacacgc gtgattgacc ctttaactgt    190680
atccttaacc accgcatatg catgccaggc tgggcacggc tccgagggcg gccagggaca    190740
gacgcttgcg ccgagaccgc agagggaagc gtcagcgggc gctgctggga gcagaacagt    190800
ccctcacacc tgggcccggg caggccagct tcgtgctgga ggaacttgct gctgtgcctg    190860
cgtcgcggcg gatccgcggg gaccctgccg aggggggctgt catgcggttt ccaaggtgca    190920
cattttccac ggaaacagaa ctcgatgcac tgacctgctc cgccaggaaa gtgagcgtgt    190980
agcgtcctga ggaataaaat gttccgatga                                     191010
```

<210> SEQ ID NO 8
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 8

Gly Xaa Gly Xaa Xaa Ala
1               5

<210> SEQ ID NO 9
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 9

Gly Xaa Gly Xaa Xaa Gly
1               5

```
<210> SEQ ID NO 10
<211> LENGTH: 14
<212> TYPE: PRT
<213> ORGANISM: Homo sapiens

<400> SEQUENCE: 10

Ser Ile Tyr Arg Arg Gly Ala Arg Arg Trp Arg Lys Leu Tyr
1               5                   10

<210> SEQ ID NO 11
<211> LENGTH: 592
<212> TYPE: PRT
<213> ORGANISM: Homo sapiens

<400> SEQUENCE: 11

Met Pro Ser Arg Thr Gly Pro Lys Met Glu Gly Ser Gly Gly Arg Val
1               5                   10                  15

Arg Leu Lys Ala His Tyr Gly Gly Asp Ile Phe Ile Thr Ser Val Asp
                20                  25                  30

Ala Ala Thr Thr Phe Glu Glu Leu Cys Glu Glu Val Arg Asp Met Cys
            35                  40                  45

Arg Leu His Gln Gln His Pro Leu Thr Leu Lys Trp Val Asp Ser Glu
        50                  55                  60

Gly Asp Pro Cys Thr Val Ser Ser Gln Met Glu Leu Glu Glu Ala Phe
65                  70                  75                  80

Arg Leu Ala Arg Gln Cys Arg Asp Glu Gly Leu Ile Ile His Val Phe
                85                  90                  95

Pro Ser Thr Pro Glu Gln Pro Gly Leu Pro Cys Pro Gly Glu Asp Lys
            100                 105                 110

Ser Ile Tyr Arg Arg Gly Ala Arg Arg Trp Arg Lys Leu Tyr Arg Ala
        115                 120                 125

Asn Gly His Leu Phe Gln Ala Lys Arg Phe Asn Arg Arg Ala Tyr Cys
    130                 135                 140

Gly Gln Cys Ser Glu Arg Ile Trp Gly Leu Ala Arg Gln Gly Tyr Arg
145                 150                 155                 160

Cys Ile Asn Cys Lys Leu Leu Val His Lys Arg Cys His Gly Leu Val
                165                 170                 175

Pro Leu Thr Cys Arg Lys His His Met Asp Ser Val Met Pro Ser Gln Glu
            180                 185                 190

Pro Pro Val Asp Asp Lys Asn Glu Asp Ala Asp Leu Pro Ser Glu Glu
        195                 200                 205

Thr Asp Gly Ile Ala Tyr Ile Ser Ser Ser Arg Lys His Asp Ser Ile
    210                 215                 220

Lys Asp Asp Ser Glu Asp Leu Lys Pro Val Ile Asp Gly Met Asp Gly
225                 230                 235                 240

Ile Lys Ile Ser Gln Gly Leu Gly Leu Gln Asp Phe Asp Leu Ile Arg
                245                 250                 255

Val Ile Gly Arg Gly Ser Tyr Ala Lys Val Leu Leu Val Arg Leu Lys
            260                 265                 270

Lys Asn Asp Gln Ile Tyr Ala Met Lys Val Val Lys Lys Glu Leu Val
        275                 280                 285

His Asp Asp Glu Asp Ile Asp Trp Val Gln Thr Glu Lys His Val Phe
    290                 295                 300

Glu Gln Ala Ser Ser Asn Pro Phe Leu Val Gly Leu His Ser Cys Phe
305                 310                 315                 320

Gln Thr Thr Ser Arg Leu Phe Leu Val Ile Glu Tyr Val Asn Gly Gly
```

```
                    325                 330                 335

Asp Leu Met Phe His Met Gln Arg Gln Arg Lys Leu Pro Glu His
            340                 345                 350

Ala Arg Phe Tyr Ala Ala Glu Ile Cys Ile Ala Leu Asn Phe Leu His
            355                 360                 365

Glu Arg Gly Ile Ile Tyr Arg Asp Leu Lys Leu Asp Asn Val Leu Leu
            370                 375                 380

Asp Ala Asp Gly His Ile Lys Leu Thr Asp Tyr Gly Met Cys Lys Glu
385                 390                 395                 400

Gly Leu Gly Pro Gly Asp Thr Thr Ser Thr Phe Cys Gly Thr Pro Asn
                405                 410                 415

Tyr Ile Ala Pro Glu Ile Leu Arg Gly Glu Glu Tyr Gly Phe Ser Val
            420                 425                 430

Asp Trp Trp Ala Leu Gly Val Leu Met Phe Glu Met Met Ala Gly Arg
            435                 440                 445

Ser Pro Phe Asp Ile Ile Thr Asp Asn Pro Asp Met Asn Thr Glu Asp
            450                 455                 460

Tyr Leu Phe Gln Val Ile Leu Glu Lys Pro Ile Arg Ile Pro Arg Phe
465                 470                 475                 480

Leu Ser Val Lys Ala Ser His Val Leu Lys Gly Phe Leu Asn Lys Asp
                485                 490                 495

Pro Lys Glu Arg Leu Gly Cys Arg Pro Gln Thr Gly Phe Ser Asp Ile
            500                 505                 510

Lys Ser His Ala Phe Phe Arg Ser Ile Asp Trp Asp Leu Leu Glu Lys
            515                 520                 525

Lys Gln Ala Leu Pro Pro Phe Gln Pro Gln Ile Thr Asp Asp Tyr Gly
530                 535                 540

Leu Asp Asn Phe Asp Thr Gln Phe Thr Ser Glu Pro Val Gln Leu Thr
545                 550                 555                 560

Pro Asp Asp Glu Asp Ala Ile Lys Arg Ile Asp Gln Ser Glu Phe Glu
                565                 570                 575

Gly Phe Glu Tyr Ile Asn Pro Leu Leu Leu Ser Thr Glu Glu Ser Val
            580                 585                 590

<210> SEQ ID NO 12
<211> LENGTH: 20
<212> TYPE: DNA
<213> ORGANISM: Homo sapiens

<400> SEQUENCE: 12
ccatgcccag caggaccacc                                              20

<210> SEQ ID NO 13
<211> LENGTH: 24
<212> TYPE: DNA
<213> ORGANISM: Homo sapiens

<400> SEQUENCE: 13
ccttctatta gatgcctgct ctcc                                         24

<210> SEQ ID NO 14
<211> LENGTH: 25
<212> TYPE: DNA
<213> ORGANISM: Homo sapiens

<400> SEQUENCE: 14
tgaaggaagg tctacaccat cgttc                                        25
```

```
<210> SEQ ID NO 15
<211> LENGTH: 18
<212> TYPE: DNA
<213> ORGANISM: Homo sapiens

<400> SEQUENCE: 15
acatggtcta catgttcc                                                18

<210> SEQ ID NO 16
<211> LENGTH: 19
<212> TYPE: DNA
<213> ORGANISM: Homo sapiens

<400> SEQUENCE: 16
cagatccaca acggaatac                                               19
```

ATYPICAL PROTEIN KINASE C ISOFORMS IN DISORDERS OF THE NERVOUS SYSTEM AND CANCER

The invention described in the present application is supported by Grants from National Institute on Aging (grant number AG000959) and National Institute of Health (grant number MH057068). The government may have some interests in the present invention.

FIELD OF INVENTION

The present invention relates to atypical isoforms of protein kinase C (aPKC) and their role in the intracellular mislocalization of gene products in nervous system disorders. In particular, the present invention relates to the discovery that aPKC isoforms are altered in neurodegenerative disorders, such as Alzheimer's disease (AD) and Parkinson's disease (PD). The present invention is further directed to the use of aPKC in diagnosis, drug screening and treatments, including gene therapy, for neurological and psychiatric disorders.

The present invention also relates to the atypical isoforms of protein kinase C and their role in cancer. In particular, the present invention relates to the discovery that the atypical PKCζ gene is commonly altered in numerous forms of cancer. The present invention is further directed to the use of aPKC in diagnosis, treatment and development of treatments for cancer.

BACKGROUND OF INVENTION

Protein kinase C (PKC) consists of a heterogeneous family of isozymes derived from nine genes divided into three classes: conventional, novel and atypical. The atypical class of isoforms (aPKC), e.g., PKCζ (PKCζI/II) and PKCι/λ, is distinguished from the conventional and novel classes by their insensitivity to calcium and diacylglycerol (DAG), the classical activators of PKC (Newton, 2003, Biochem J, 361-71). Together with the proteins encoded by par3 and par6 genes, aPKC has been shown to play a critical role in cell polarity (Ohno, 2001, Curr Opin Cell Biol, 13(5): 641-48). Recently, the par3 and par6 genes were also shown to play a role in the formation of neuronal axons (Shi et al., 2003, Cell, 112(1): 63-75). Loss of function of any of par3, par6 and aPKC proteins can result in disruption of cell polarity.

In addition, a role for aPKC in synaptic plasticity, learning and memory has been established (Sacktor et al., 1993, Proc Natl Acad Sci USA 90:8342-46; Osten et al, 1996, Neurosci Letter 221:37-40; Drier et al, 2002, Nat Neurosci 5:316-24; Ling et al, 2002, Neurosci 5:295-96). In long-term potentiation (LTP), a widely studied model for memory, aPKC plays an important role in the two distinct temporal phases. While full-length aPKC forms are activated during the LTP induction phase, a truncated form of aPKC, termed PKMζ (i.e., PKCζII), is activated during the maintenance phase of LTP. PKMζ is identical to PKCζI, except that it lacks an autoinhibitory regulatory domain (Hernandez, et al., 2003, J Biol Chem 278, 40305-16 and Hirai et al., 2003, Neurosci Lett 348, 151-54). Although all of the PKC isoforms can theoretically have PKM forms (i.e., truncated or independent catalytic domains of PKC), the only PKM form that is consistently observed in the normal brain is PKMζ (Sacktor et al., 1993). Recent work has shown that PKMζ is both necessary and sufficient for long-term potentiation (LTP) maintenance (Ling et al). Furthermore, expression of PKMζ prolongs memory in an odor avoidance task in *Drosophila melanogaster* (Drier et al). Thus, the role of PKMζ in memory appears conserved in widely divergent species. Consistent with this notion, the human form of the PKMζ mRNA has been identified (Hernandez, et al).

Alzheimer's disease (AD) is a neurodegenerative disorder characterized by progressive impairment in memory and cognitive functions. Imbalances in neuronal signal transduction pathways have been implicated in AD's pathogenesis (Shimohama et al., 1990, J Neural Transm Suppl 30:69-78). Several studies have demonstrated abnormalities of protein kinase C (PKC) function in brain tissue of AD patients (Cole et al., 1988, Brain Res 452:165-174; Clark et al., 1991, Lab Invest 64, 3544; Horsburgh et al., 1991, J Neurochem 56:1121-1129; Masliah et al., 1990, J Neurosci 10:2113-24; Masliah et al., 1991, J Neurosci 11:2759-2767; Saitoh et al., 1990, Adv Exp Med Biol 265:301-10; Saitoh et al., 1993, Acad Sci 695:34-41; Shimohama et al., 1993, Neurology 43:1407-1413; Lanius et al., 1997, Brain Res 764:75-80; Wang et al., 1994, Neurobiol Aging 15:293-298).

Microscopically, the two major features of AD are the presence of β-amyloid (A β) containing senile plaques (SP) and tau containing neurofibrillary tangles (NFT). Amyloid angiopathy, defined as amyloid deposition in blood vessels, also occurs to a varying extent. Other changes include granulovacuolar degeneration (GVD) and Hirano body (HB) formation.

The NFT are abnormal structures, composed mainly of paired helical filaments (PHFs) consisting of a hyperphosphorylated form of the microtubule-associated protein tau (Buee et al., 2000, *Brain Res Brain Res Rev* 33, 95-130). The distribution of tau is largely restricted to axons, where it functions mainly to stabilize microtubules (MT) and promote MT polymerization. In NFT-containing neurons, however, tau-associated PHFs can be found throughout the cytoplasm and dendrites. Other components of the NFT include microtubule-associated protein 2 (MAP2) and ubiquitin. A "ghost tangle" is a type of NFT, where the surrounding neuron has completely degenerated. Ghost tangles can contain deposits of Aβ that accumulate after cell death. PHFs also exist in dystrophic neurites surrounding the senile plaques as well as in other neurites, where they are termed neuropil threads.

In addition to AD, at least 20 different diseases have tau-based neurofibrillary pathology as a feature and are collectively known as tauopathies (Lee et al., 2001, *Annu Rev Neurosci* 24, 1121-59). This group includes AD, Pick's disease (PiD), frontotemporal dementia with Parkinsonism linked to chromosome 17 (FTDP-17), progressive supranuclear palsy (PSP) and corticobasal degeneration (CBD). Considerable heterogeneity exists between the tangles found in the various tauopathies. For example, NFT in AD are composed principally of PHFs with a diameter of 8-20 nm; some straight filaments are also seen in AD. In contrast, the tangles of FTDP-17 are twisted and straight, but not paired and helical. Nevertheless, the tau protein in all these disorders is hyperphosphorylated.

It has been argued that tau-based tangle formation is not the primary pathological event in AD since tangles appear in a number of other disorders. This apparent lack of specificity suggests that the NFT is a final endpoint of a number of pathophysiologic processes rather than an initiating event. Contrary to this view, it has been discovered that a mutation in the tau gene itself in multiple FTDP-17 family lineages can lead to tau dysfunction and degeneration in the absence of Aβ accumulation (Lee et al., 2001).

NFT develop through stages (Braak et al., 1994, *Acta Neuropathol* 87, 554-67). The earliest form of NFT is the pre-NFT, where PHFs begin to form, but the full tangle has not yet developed. The next is the intracellular stage, where the cytoplasm becomes filled with hyperphosphorylated tau. The final stage is the "extracellular" NFT, where cell death has occurred, the membrane and organelles cleared away, but the cytoskeletal remnants remain. The final stage is also referred to as "ghost" tangles. Using phosphospecific tau antibodies, it was discovered that the pattern of tau phosphorylation varies between these three different stages (Augustinack et al., 2002, *Acta Neuropathol* (Berl) 103, 26-35). Theoretically, if one knows which residues on tau are phosphorylated first, then one can have a better chance at identifying the kinase responsible for the tau phosphorylation. It was demonstrated that T153, S262 and T231 were among the first residues in tau to become phosphorylated stages (Augustinack et al., 2002).

Despite extensive research, the particular kinase that phosphorylates tau in AD has not been clearly identified (Buee et al., 2000). The longest tau protein isoform contains 79 possible serines and threonines, with phsophorylation of least 30 of them occurring in AD. Numerous kinases have been shown to phosphorylate tau in vitro, but leading candidate kinases have been shown to phosphorylate tau in vivo. These are glycogen synthase kinase 3β (GSK3β) and cyclin-dependent kinase 5 (cdk5). Both are members of a group of proline-directed kinases that prefer serine/threonine residues directly followed by a proline. Abnormal tau from an AD brain contains a mixture of hyperphosphorylated serine and threonine residues with and without a trailing proline. Indeed, researchers have postulated multiple kinases phophorylating tau at different sites, which can be proline directed and non-proline directed protein kinases.

The conventional PKCα isoform can phosphorylate the cytoskeletal protein tau. It is not the full-length form of PKCα, but the truncated PKMα form of the enzyme which is selectively capable of phosphorylating tau (Cressman et al., 1995, M. *FEBS Letter* 367, 223-27). The only PKM isoform that is consistently overserved in the brain is PKMζ (Naik et al., 2000, J Comp Neurol., 426(2):243-58).

The present invention, for the first time, shows that PKMζ directly phosphorylates tau. For this reason, increases in aPKC will cause NFT formation. Furthermore, aPKC phosphorylates GSK3β, a kinase well known to phosphorylate tau, leading to inactivation of GSK3β (Lavoie et al., 1999, *J Biol Chem* 274, 28279-85). For this reason, decreases in aPKC activity constitute a removal of the negative regulation of GSK3β activity and indirectly causes NFT formation. The present invention provides that apkc and gsk3b, both known regulators of cell polarity, are present in a complex. Alterations in the signaling or activity of these two kinases leads to mislocalization of gene products within the intracellular and extracellular compartments as well as abnormal posttranslational modifications of gene products and subsequent pathology including neurological dysfunction and cancer.

While the etiology of cancer is heterogenous, and largely depends on the tissue type, there is a consensus among those skilled in the art that human cancer cells show a markedly increased genetic mutation rate (genetic instability). The mutations can manifest themselves as chromosomal abnormalities (e.g. deletions, insertions, amplifications, mutations and rearrangements) and point mutations. The effects of such genomic alterations are varied; but some of these alterations are direct contributors to cancer development. Cancer develops through stages. The early stages tend to be more benign, with a better prognosis. In contrast, the later stages are more malignant, and tend to metastasize to a larger extent. Late stage cancers tend to have accumulated more chromosomal alterations. The present invention utilizes alterations in the aPKC genes and their RNA or protein products to diagnose, stage, treat, and develop treatments for cancer.

One example of a chromosomal alteration associated with cancer development is deletion of the short arm of chromosome 1 (1p). Chromosome 1p deletions have been observed in a wide variety of cancers. It has been estimated that over one half of solid tumors are associated with chromosome 1p deletions. The current method for determining the status of chromosome 1p in tumors involves fluorescence in situ hybribization (FISH). While highly sensitive, FISH has numerous drawbacks including the fact that it is not routinely used in pathology laboratories, is costly and time consuming. The present invention provides a new way to determine the status of chromosome 1p in tumors using probes to the PKCζ gene, such as antisera. Antisera based methods are routinely used in pathology laboratories, are robust and inexpensive. For this reason, PKCζ gene status is by far superior to FISH in determining cancer status.

The PKCζ gene lies on the short arm of the first chromosome (1p36.33). The gene lies a relatively short distance, about 2 million base pairs, away from the telomere. The proximity of the PKCζ gene to the telomere should theoretically make it susceptible to chromosomal deletion and rearrangement. It is demonstrated by the present invention that the presence or absence of aPKC in cancers is useful for their diagnosis and staging.

The effect of deletion of chromosome 1p varies depending on the tumor type. For example, deletion of 1p in oligodendroglioma is a favorable prognostic indicator. In contrast, chromosome 1p deletion in neuroblastoma is considered unfavorable. As demonstrated by the present invention, one skilled in the art can now determine the status of chromosome 1p using specific probes to PKCζ. Examples of such probes include antisera, complimentary DNA or RNA sequences to aPKC, or PCR primers. The presence or absence of PKCζ is effective in determining the variety, stage or grade of the tumor.

SUMMARY OF THE INVENTION

The present invention demonstrates that an increase or a decrease in aPKC activity can lead to the development of pathological changes in cells, leading to nervous system dysfunction and cancer. It is contemplated by the presented invention that alteration in aPKC signaling contributes to the pathogenesis of nervous system disorders, such as Alzheimer Disease (AD). Accordingly, the localization of aPKC in NFT and the fact that disruption in aPKC signaling causes tau phosphorylation establish that aPKC alterations participate in pathogenesis of nervous system disorders. The present invention thus provides aPKC as a novel target for rational drug design useful for modulating aPKC activity for the purpose of treating nervous system disorders. The present invention further provides methods for diagnosis of nervous system disorders.

Specifically, it has been discovered by the present invention that PKMζ, a key molecule in the maintenance of long-term potentiation (LTP) and memory formation, e.g., in *Drosophila*, colocalizes with the NFT. Accordingly, disruption in PKMζ signaling contributes to the pathogenesis of nervous system disorders, such as AD. The presence of PKMζ protein in the human brain is also demonstrated by the present invention.

In accordance with the present invention, one aspect of the present invention is the identification of atypical isoforms of protein kinase C (aPKC), e.g. PKMζ, and their role in nervous system disorders, such as AD.

Another aspect of the present invention provides a method for diagnosing nervous system disorders, such as AD.

According to the present invention, a method for diagnosing neurological dysfunctions or nervous system disorders in a subject, using an aPKC specific probe, is provided. The diagnostic method of the present invention includes the steps of:
  a. contacting a sample from the subject, e.g. a tissue biopsy, cerebrospinal fluid (CSF), or a blood sample, with an aPKC specific probe,
  b. detecting the binding of the probe to the sample to determine the amount, localization or activity of the aPKC in the sample,
  c. contacting a control sample with the aPKC specific probe,
  d. detecting the binding of the probe to the control sample, e.g. a tissue biopsy, CSF, or a blood sample, to determine the amount, localization or activity of the aPKC in the control sample, and
  e. comparing the amount, localization or activity of the aPKC in Step b with the amount, localization or activity of the aPKC in Step d, whereby if the amount, localization or activity of the aPKC in Step b is different from the amount, localization or activity of the aPKC in Step d, a nervous system disorder in the subject is present.

Still another aspect of the present invention provides methods for screening drugs or molecular compounds useful for modulating the amount or activity of the aPKC. According to the present invention, a method for screening molecular compounds, e.g. peptides and small molecules, using cells and aPKC specific probes is provided. Such method includes:
  a. providing cells wherein aPKC gene is expressed,
  b. incubating the cells with a candidate compound for a sufficient time to induce a change in the amount, localization or activity of aPKC in the cells,
  c. incubating the cells as in Step b, in the absence of the candidate compound,
  d. contacting the cells from Step b and Step c with an equal amount of an aPKC-specific probe,
  e. detecting the binding of the probe to the cells to determine the amount, localization or activity of the aPKC in the cell from Step b and Step c, and
  f. comparing the amount, localization or activity of the aPKC in the cells, wherein if the amount, localization or activity of the aPKC in the cells from Step b is different from the amount, localization or activity of the aPKC in the cells from Step c, the candidate compound is identified as a compound that modulates aPKC.

An alternate method for screening molecular compounds for use in treatment of brain disorders involves the overexpression or deletion of genetic elements containing atypical PKC sequences in cells or animals, e.g. mice, and assaying said cells or animals for atypical PKC activity or levels.

In a further aspect of the present invention, an in vitro cell-free method for screening drugs or molecular compounds useful for modulating the amount, localization or activity of the aPKC, using aPKC and a substrate, is provided. Such method includes:
  a. incubating an aPKC in a first container with adenosine triphosphate (ATP), preferably radioactively labeled ATP, a substrate of the aPKC, e.g. protein tau, with a candidate compound, for a sufficient time to induce a change in the amount or activity of the aPKC in the first container,
  b. incubating the aPKC in a second container with ATP, preferably radioactively labeled ATP, and the substrate of said aPKC, e.g. protein tau, for a sufficient time to induce a change in the amount or activity of aPKC in the second container,
  c. quantifying the amount of incorporation of the phosphate into the substrate in the first container and the second container, and
  d. comparing the amount of incorporation in the first container and the second container, whereby a difference in the amount of incorporation in the first container and the second container indicates that the candidate compound is identified as a compound modulating aPKC amount, localization or activity.

A variation of this method involves using a phospho-specific antisera to quantify phosphate incorporation into the substrate.

In still a further aspect of the present invention, methods, including gene therapy, for treating and/or preventing neurological disorders are provided. According to the present invention, a method for treating and/or preventing neurological dysfunction is provided which employs a sequence corresponding to an aPKC, e.g. PKMζ (or an antisense sequence of aPKC) and an expression vector. This method includes the steps of:
  a. inserting the aPKC sequence, e.g. PKMζ, into the expression vector, and
  b. administering the vector to a subject, e.g. a patient, whereby the vector treats and/or prevents a neurological dysfunction.

The methods of the present invention can be employed in the treatment and/or prevention of a variety of neurological disorders characterized by abnormal aPKC activity, such as phosphorylation of protein tau and co-localization with NFT. Such tau-associated filamentous aggregates are neuropathological hallmarks of Alzheimer's disease (AD), Pick's disease (PiD), progressive supranuclear palsy (PSP), and corticobasal degeneration (CBD), Parkinson's Disease (PD), for example.

In yet a further aspect of the present invention provides antibodies against PKMζ for detection, treatment and/or prevention of neurological disorders, e.g. AD.

Thus, an object of the present invention is to detect, treat and/or prevent neurological disorders, such as Alzheimer's disease.

A further aspect of the present invention provides a method for constructing transgenic animals, such as a knock-out mouse lacking aPKC or a mouse that overexpresses the wild type or a mutant aPKC, that are useful as animal models of neurological dysfunction. The method includes:
  a. constructing a transgenic animal having an altered aPKC amount, localization or activity, e.g., by deleting an aPKC gene in the animal using knock-out techniques known to one skilled in the art,
  b. treating the transgenic animal from Step a with a candidate treatment process,
  c. treating the transgenic animal from Step a with a control treatment process,
  d. assaying the transgenic animals from Steps b and c for a biochemical or behavioral change, and
  e. comparing the results of the assay of the transgenic animals from Steps b and Step c, wherein a difference is indicative the efficacy of the candidate treatment process in alleviating the neurological dysfunction.

A variation of the method involves over-expression of either wild-type or mutated aPKC in a transgenic animal, alone or in combination with one or more other transgenes expressing mutations or polymorphisms in genes associated with neurodegeneration, e.g. superoxide dismutase, tau, β-amyloid, α-synuclein, and apolipoprotein E.

Still a further aspect of the present invention involves the genetic screening of DNA for mutations or polymorphisms in the DNA sequence of the aPKC genes, e.g. PKCζI/II and PKCι/λ, and regions regulating the expression of these genes including promoter regions, enhancer regions and negative regulatory regions. A method for such screening includes:
  a. isolating DNA from a sample of a subject,
  b. sequencing an aPKC gene or its regulating region of the DNA from Step a and,
  c. comparing the DNA sequence from Step b to a reference DNA sequence, wherein the reference DNA is a known normal DNA sequence of the same region as sequenced DNA in Step b but without any mutation, whereby a difference between the DNA sequence from Step b and the reference sequence is indicative of genetic susceptibility to a neurological or psychiatric disorder.

A particular aspect of the present invention is directed to the use of a known aPKC interacting protein for all of the above methods.

In a further aspect, the present invention is directed toward the treatment of other abnormal protein aggregates including α-synuclein seen in PD, multisystem atrophy (MSA) and dementia with Lewy bodies (DLB) and β-amyloid in AD and normal aging.

In another aspect, the present invention provides methods for diagnosing various forms of cancer, such as neuroblastoma. According to the present invention, a method for diagnosing and/or staging a tumor is provided. The diagnostic method of the invention includes the steps of:
  a contacting an aPKC specific probe, preferably a PKCζ specific probe, with a tumor sample, e. g. a human biopsy sample, from a subject,
  b. detecting the binding of the probe to the tumor sample to quantify the level, amount or activity of said aPKC in said tumor sample,
  c. contacting the aPKC specific probe with a control sample,
  d. detecting the binding of the probe to the control sample to quantify the level, amount or activity of the aPKC in the control sample, and
  e. comparing the level, amount or activity of the aPKC in Step b with the level, amount or activity of the aPKC in Step d, wherein the difference of the level, amount or activity of the aPKC is indicative of the type and the staging of the tumor.

Still another aspect of the invention provides methods for drug screening for the purpose of treating and/or preventing cancer, e. g. neuroblastoma. According to the present invention, a method for screening molecular compounds, e. g. peptides and small molecules, is provided.

Yet another aspect of the present invention provides methods for treating cancer with gene therapy.

BRIEF DESCRIPTION OF THE FIGURES

FIG. 4A: Representative Western blots on total protein homogenates from a representative control and AD case. FIG. 4B: Histogram showing mean and standard deviation. * indicates statistical significance.

FIG. 5A: Representative Western blots on total protein homogenates from a representative control and AD case. FIG. 5B: Histogram showing mean and standard deviation. * indicates statistical significance.

FIG. 9A: Immunohistochemical stain using z-C2 of paraffin embedded hippocampal cortex from case of AD. FIG. 9B: Silver stain from a non-adjacent section. Large arrows indicate SP; small arrows indicate neuropil threads. bar=100 μm.

FIG. 11A: Reverse-transcription polymerase chain reaction (RT-PCR) using specific primers reveal that PKMζ mRNA is abundant only in brain; PKCζ mRNA is abundant in many other tissues. FIG. 11B: RNase protection reveals levels of PKMζ mRNA and PKCζ mRNA in different tissues. FIG. 11C: Northern blot to quantify levels of PKMζ mRNA and PKCζ mRNA in different tissues.

FIG. 12A: Control culture untreated has low levels of PKMζ. FIG. 12B: Stimulation with high potassium results in an increase in PKMζ.

DETAILED DESCRIPTION OF THE INVENTION

The present invention is directed to the atypical isoforms of protein kinase C (aPKC) and their participation in intracellular localization and mislocalization of cellular components, particularly in human diseases, e.g. Alzheimer's disease (AD) and cancer.

By "Activity" is meant the ability of an enzyme to act as a catalyst to induce chemical changes in other substances, including the ability to transfer phosphate to substrate molecules as well as to aggregate molecules. "Activity of aPKC" or "aPKC activity" used herein includes, for example, inhibition of aPKC, co-localization of aPKC with neurofibrillary tangles (NFT) or Hirano body (HB) and phosphorylation of protein tau by aPKC. "Activity" used herein can be also referred to the level, amount or localization of the enzyme.

By "control" is meant a normal subject or unchanged chemical, or a subject or a chemical in its normal state. "Control" can also be referred to as a chemical with known properties, for example, in the case of a "positive control." Thus, a "control" can be referred to as comparison to a reference range which is the normal value.

The PKC gene family consists of at least 10 distinct isoforms with diverse cellular functions (Newton, 2003).

Although all of the PKC isoforms can theoretically have truncated PKM forms, the only PKM form that is consistently observed in the brain is PKMζ, an atypical member of the PKC family (APKC) (Sacktor et al). Specifically, it has been discovered by the inventors that PKMζ, a key molecule in the maintenance of long-term potentiation (LTP) and memory formation in *Drosophila*, colocalizes with the NFT. Accordingly, disruption in PKMζ signaling may contribute to the pathogenesis of neurological disorders, such as AD.

By "disruption in PKMζ signaling" is meant increases or decreases in the level, location or activity of the kinase or its effectors, substrates and associated molecules.

"Modulating" or "modulate" used herein also include inhibiting or inhibit and activating or activate.

Figure 1:
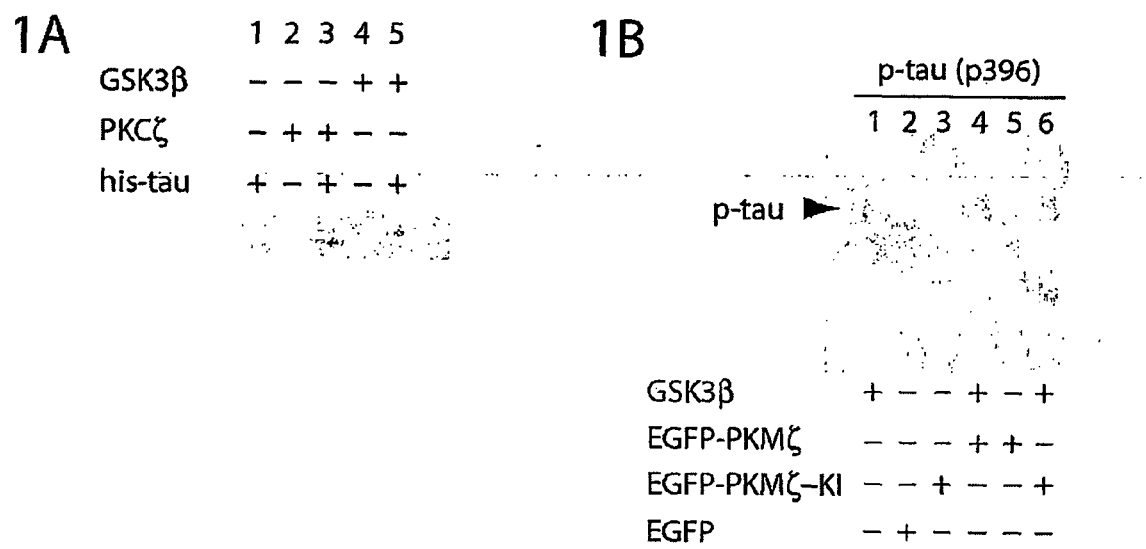
FIG. 1A illustrates that PKCζ phosphorylates the cytoskeletal protein tau. Autoradiogram showing incorporation of radioactive phosphate into tau Lane 1 shows that tau, in the absence of kinase, shows little incorporation of phosphate. Lane 2 and 4 show that in the absence of tau, there is no phosphorylarion. Lane 3 demonstrates that when tau is incubated with PKCζ phosphate is incorporated into tau. Lane 5 was included as a control, since GSK3β is well known to be able to phosphorylate tau.
FIG. 1B illustrates that cotransfection of PKMζ with GSK3β into neuroblastoma cells decreases tau phosphorylation. Western blot on protein extracts from neuroblastoma cells (IMR-32) transfected with full-length human tau and the indicated constructs were probed with a phosphospecific anti-tau (p396) antisera. Lane 1 shows that cotransfection of GSK3β results in a prominent degree of phosphorylation of tau on p396. Lane 2 shows that cotransfection with EGFP alone does not result in an increase in phosphorylated tau. Lane 3 shows that transfection with an EGFP-tagged kinase inactive mutant of PKMζ (EGFP-PKMζ-KI, K281W) also fails to result in increased tau phosphorylation. Lane 4 shows that transfection of GSK3β and EGFP-tagged PKMζ results in less phosphorylation of tau than GSK3β alone (compare with lane 1). Lane 5 shows that EGFP-tagged PKMζ is capable of phosphorylating tau (compare with lane 2 and 3) but not to the same degree as GSK3β (compare with lane 1). Lane 6 shows that cotransfection of EGFP-PKMζ-KI with GSK3β also results in decreased tau phosphorylation (compare to lane 1).
Figure 2:
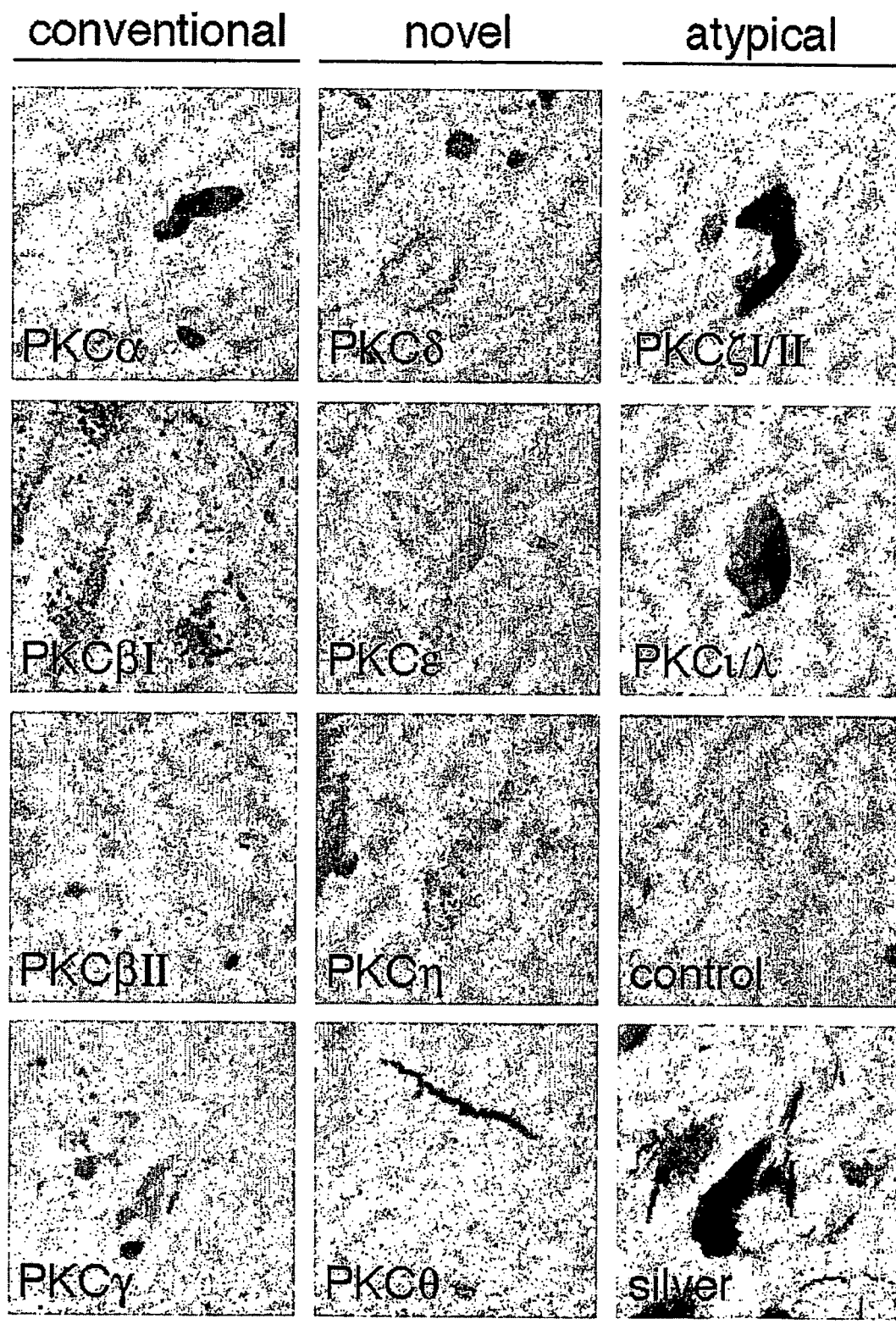
FIG. 2 illustrates that aPKC co-localizes with NFT. Using specific antisera to all known PKC gene products, immunohistochemistry reveals that only PKCζ and PKCι/λ are present in NFT. Silver stain confirms the presence of NFT in this tissue, and omitting primary antisera fails to label NFT.

According to the present invention, alteration in aPKC function can lead to hyperphosphorylation of the cytoskeletal protein tau, see FIG. 1. Also in accordance with the present invention, aPKC colocalizes with the NFT, see FIG. 2.

Phosphorylation of tau at sites clustered around the MT binding regions inhibits tau binding to MT. Indeed, the tau found in AD brain and NFT is hyperphosphorylated at many sites not normally phosphorylated in adult human brain. The present invention recognizes that phosphorylation of tau causes its dissociation from MTs and buildup in the cytoplasm, which in turn could lead to the formation of tau aggregates and ultimately NFT.

In accordance with the present invention, the localization of aPKC to the NFT and the ability of aPKC to phosphorylate tau confirm that aPKC is altered in nervous system disorders, such as AD. Accordingly, co-localization of aPKC, especially PKMζ, with NFT strongly suggests aPKC is involved in tau phosphorylation. Accordingly, the present invention employs the activity of aPKC, especially PKMζ, and provides compositions and methods that are useful for diagnosis, drug screening and treatment of neurological disorders, such as AD.

"Psychological disorder" refers to a diseases of the mind in the context of human and animal behavior. "Neurological disorder" refers to diseases of the nervous system. "Neurodegenerative disorder" refers to diseases characterized by progressive degeneration of neurons in the nervous system.

Accordingly, the present invention can be employed in detection, diagnosis, treatment, prevention or prognosis of nervous system disorders that include, but are not limited to, Acquired Epileptiform Aphasia, Acute Disseminated Encephalomyelitis, Adrenoleukodystrophy, Agenesis of the corpus callosum, Agnosia, Aicardi syndrome, Alexander disease, Alpers' disease, Alternating hemiplegia, Alzheimer's disease, Amyotrophic lateral sclerosis, Anencephaly, Angelman syndrome, Angiomatosis, Anoxia, Aphasia, Apraxia, Arachnoid Cysts, Arachnoiditis, Arnold-Chiari malformation, Arteriovenous malformation, Asperger syndrome, Ataxia Telangiectasia, Attention Deficit Hyperactivity Disorder, Autism, Autonomic Dysfunction, Back Pain, Batten disease, Behcet's disease, Bell's palsy, Benign Essential Blepharospasm, Benign Focal Aiyotrophy, Benign Intracranial Hypertension, Binswanger's disease, Blepharospasm, Bloch-Sulzberger syndrome, Brachial plexus injury, Brain abscess, Brain injury, Brain tumor, Spinal tumor, Brown-Sequard syndrome, Canavan disease, Carpal tunnel syndrome, Causalgia, Central pain syndrome, Central pontine myelinolysis, Cephalic disorder, Cerebral aneurysm, Cerebral arteriosclerosis, Cerebral atrophy, Cerebral gigantism, Cerebral palsy, Charcot-Marie-Tooth disease, Chiari malformation, Chorea, Chronic inflammatory demyelinating polyneuropathy (CIDP), Chronic pain, Chronic regional pain syndrome, Coffin Lowry syndrome, Coma, including Persistent Vegetative State, Congenital facial diplegia, Corticobasal degeneration, Cranial arteritis, Craniosynostosis, Creutzfeldt-Jakob disease, Cumulative trauma disorders, Cushing's syndrome, Cytomegalic inclusion body disease (CIBD), Cytomegalovirus Infection, Dancing eyes-dancing feet syndrome, Dandy-Walker syndrome, Dawson disease, De Morsier's syndrome, Dejerine-Klumpke palsy, Dementia, Dermatomyositis, Diabetic neuropathy, Diffuse sclerosis, Dysautonomia, Dysgraphia, Dyslexia, Dystonias, Early infantile epileptic encephalopathy, Empty sella syndrome, Encephalitis, Encephaloceles, Encephalotrigeminal angiomatosis, Epilepsy, Erb's palsy, Essential tremor, Fabry's disease, Fahr's syndrome, Fainting, Familial spastic paralysis, Febrile seizures, Fisher syndrome, Friedreich's ataxia, Gaucher's disease, Gerstmann's syndrome, Giant cell arteritis, Giant cell inclusion disease, Globoid cell Leukodystrophy, Guillain-Barre syndrome, HTLV-1 associated myelopathy, Hallervorden-Spatz disease, Head injury, Headache, Hemifacial Spasm, Hereditary Spastic Paraplegia, Heredopathia atactica polyneuritiformis, Herpes zoster oticus, Herpes zoster, Hirayama syndrome, Holoprosencephaly, Huntington's disease, Hydranencephaly, Hydrocephalus, Hypercortisolism, Hypoxia, Immune-Mediated encephalomyelitis, Inclusion body myositis, Incontinentia pigmenti, Infantile phytanic acid storage disease, Infantile Refsum disease, Infantile spasms, Inflammatory myopathy, Intracranial cyst, Intracranial hypertension, Joubert syndrome, Kearns-Sayre syndrome, Kennedy disease, Kinsbourne syndrome, Klippel Feil syndrome, Krabbe disease, Kugelberg-Welander disease, Kuru, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Lewy body dementia, Lissencephaly, Locked-In syndrome, Lou Gehrig's disease, Lumbar disc disease, Lyme disease-Neurological Sequelae, Machado-Jdseph disease, Macrenicephaly, Megalencephaly, Melkersson-Rosenthal syndrome, Menieres disease, Meningitis, Menkes disease, Metachromatic leukodystrophy, Microcephaly, Migraine, Miller Fisher syndrome, Mini-Strokes, Mitochondrial Myopathies, Mobius syndrome, Monomelic amyotrophy, Motor Neurone Disease, Moyamoya disease, Mucopolysaccharidoses, Multi-Infarct Dementia, Multifocal motor neuropathy, Multiple sclerosis, Multiple system atrophy with postural hypotension, Muscular dystrophy, Myasthenia gravis, Myelinoclastic diffuse sclerosis, Myoclonic encephalopathy of infants, Myoclonus, Myopathy, Myotonia congenita, Narcolepsy, Neurofibromatosis, Neuroleptic malignant syndrome, Neurological manifestations of AIDS, Neurological sequelae of lupus, Neurological Sequelae of Lyme disease, Neuromyotonia, Neuronal ceroid lipofuscinosis, Neuronal migration disorders, Niemann-Pick disease, O'Sullivan-McLeod syndrome, Occipital Neuralgia, Occult Spinal Dysraphism Sequence, Ohtahara syndrome, Olivopontocerebellar Atrophy, Opsoclonus Myoclonus, Optic neuritis, Orthostatic Hypotension, Overuse syndrome, Pain-Chronic, Paresthesia, Parkinson's disease, Paramyotonia Congenita, Paraneoplastic diseases, Paroxysmal attacks, Parry Romberg syndrome, Pelizaeus-Merzbacher disease, Periodic Paralyses, Peripheral Neuropathy, Persistent Vegetative State, Pervasive Developmental Disorders, Photic sneeze reflex, Phytanic Acid Storage disease, Pick's disease, Pinched Nerve, Pituitary Tumors, Polymyositis, Porencephaly, Post-Polio syndrome, Postherpetic Neuralgia, Postinfectious Encephalomyelitis, Postural Hypotension, Prader-Willi syndrome, Primary Lateral Sclerosis, Prion diseases, Progressive Hemifacial Atrophy, Progressive multifocal leukoencephalopathy, Progressive Sclerosing Poliodystrophy, Progressive Supranuclear Palsy, Pseudotumor cerebri, Ramsay-Hunt syndrome, Ramsay Hunt syndrome Type I, Ramsay Hunt syndrome Type II, Rasmussen's Encephalitis, Reflex Sympathetic Dystrophy syndrome, Refsum disease-Infantile, Refsum disease, Repetitive Motion Disorders, Repetitive Stress Injuries, Restless Legs syndrome, Retrovirus-Associated Myelopathy, Rett syndrome, Reye's syndrome, Saint Vitus Dance, Sandloff disease, Schilder's disease, Schizencephaly, Septo-Optic Dysplasia, Shaken Baby syndrome, Shingles, Shy-Drager syndrome, Sjogren's syndrome, Sleep Apnea, Soto's syndrome, Spasticity, Spina bifida, Spinal Cord injury, Spinal Cord Tumors, Spinal Muscular Atrophy, Stiff-Person syndrome, Stroke, Sturge-Weber syndrome, Subacute Sclerosing Panencephalitis, Subcortical Arteriosclerotic Encephalopathy, Sydenham Chorea, Syncope, Syringomyelia, Tardive Dyskinesia, Tay-Sachs disease, Temporal arteritis, Tethered Spinal Cord syndrome, Thomsen disease, Thoracic Outlet syndrome, Tic Douloureux, Todd's Paralysis, Tourette syndrome, Transient ischemic attack, Transmissible Spongiform Encephalopathies, Transverse myelitis, Traumatic Brain injury, Tremor, Trigeminal Neuralgia, Tropical Spastic Paraparesis, Tuberous Sclerosis, Vasculitis including Temporal Arteritis, Von Hippel-Lindau Disease (VHL), Wallenberg's syndrome, Werdnig-Hoffinan disease, West syndrome, Whiplash, Williams syndrome, Wilson's disease, Zellweger syndrome.

The present invention can also be employed in detection, diagnosis, treatment, prevention or prognosis of tauopathies (i.e., disorders involving protein tau based pathology), such as, Aging, Alzheimer's disease (familial, sporadic), Amyotrophic lateral sclerosis/Parkinsonism dementia complex of Guam, Argyrophilic grain disease, British type amyloid angiopathy, Corticobasal degeneration, Dementia pugilistica/autism with self-injury behaviour, Down's syndrome, Frontotemporal Dementia with Parkinsonism linked to chromosome 17 (FTDP-17), Gerstmann-Straussler-Scheinker disease, Hallenvorden-Spatz disease, Inclusion body myositis, Multisystem atophy, Myotonic dystrophy, Niemann-Pick disease type C, Parkinson with dementia of Guadeloupe, Pick's disease, Presenile dementia with tangles and calcifications, Prion protein cerebral amyloid angiopathy, Progressive supranuclear palsy, Post-encephalitic parkinsonism, Subacute sclerosing panencephalitis, Tangle only dementia.

It is also encompassed by the present invention for detection, diagnosis, treatment, prevention or prognosis of psychiatric disorders including Academic Problem, Acculturation Problem, Acute Stress Disorder, Adjustment Disorder Unspecified, Adjustment Disorder With Anxiety, Adjustment Disorder With Depressed Mood, Adjustment Disorder With Disturbance of Conduct, Adjustment Disorder With Mixed Anxiety and Depressed Mood, Adjustment Disorder With Mixed Disturbance of Emotions and Conduct, Adult Antisocial Behavior, Adverse Effects of Medication NOS, Age-Related Cognitive Decline, Agoraphobia Without History of Panic Disorder, Alcohol Abuse, Alcohol Dependence, Alcohol Intoxication, Alcohol Intoxication Delirium, Alcohol Withdrawal, Alcohol Withdrawal Delirium, Alcohol-Induced Anxiety Disorder, Alcohol-Induced Mood Disorder, Alcohol-Induced Persisting Amnestic Disorder, Alcohol-Induced Persisting Dementia, Alcohol-Induced Psychotic Disorder, With Delusions, Alcohol-Induced Psychotic Disorder, With Hallucinations, Alcohol-Induced Sexual Dysfunction, Alcohol-Induced Sleep Disorder, Alcohol-Related Disorder NOS, Amnestic Disorder, Amnestic Disorder NOS, Amphetamine Abuse, Amphetamine Dependence, Amphetamine Intoxication, Amphetamine Intoxication Delirium, Amphetamine Withdrawal, Amphetamine-Induced Anxiety Disorder, Amphetamine-Induced Mood Disorder, Amphetamine-Induced Psychotic Disorder, With Delusions, Amphetamine-Induced Psychotic Disorder, With Hallucinations, Amphetamine-Induced Sexual Dysfunction, Amphetamine-Induced Sleep Disorder, Amphetamine-Related Disorder NOS, Anorexia Nervosa, Antisocial Personality Disorder, Anxiety Disorder, Anxiety Disorder NOS, Asperger's Disorder, Attention-Deficit/Hyperactivity Disorder NOS, Attention-Deficit/Hyperactivity Disorder, Combined Type, Attention-Deficit/Hyperactivity Disorder, Predominantly Hyperactive-Impulsive Type, Attention-Deficit/Hyperactivity Disorder, Predominantly Inattentive Type, Autistic Disorder, Avoidant Personality Disorder, Bereavement, Bipolar Disorder NOS, Bipolar I Disorder, Most Recent Episode Depressed, In Full Remission, Bipolar I Disorder, Most Recent Episode Depressed, In Partial Remission, Bipolar I Disorder, Most Recent Episode Depressed, Mild, Bipolar I Disorder, Most Recent Episode Depressed, Moderate, Bipolar I Disorder, Most Recent Episode Depressed, Severe With Psychotic Features, Bipolar I Disorder, Most Recent Episode Depressed, Severe Without Psychotic Features, Bipolar I Disorder, Most Recent Episode Depressed, Unspecified, Bipolar I Disorder, Most Recent Episode Hypomanic, Bipolar I Disorder, Most Recent Episode Manic, In Full Remission, Bipolar I Disorder, Most Recent Episode Manic, In Partial Remission, Bipolar I Disorder, Most Recent Episode Manic, Mild, Bipolar I Disorder, Most Recent Episode Manic, Moderate, Bipolar I Disorder, Most Recent Episode Manic, Severe With Psychotic Features, Bipolar I Disorder, Most Recent Episode Manic, Severe Without Psychotic Features, Bipolar I Disorder, Most Recent Episode Manic, Unspecified, Bipolar I Disorder, Most Recent Episode Mixed, In Full Remission, Bipolar I Disorder, Most Recent Episode Mixed, In Partial Remission, Bipolar I Disorder, Most Recent Episode Mixed, Mild, Bipolar I Disorder, Most Recent Episode Mixed, Moderate, Bipolar I Disorder, Most Recent Episode Mixed, Severe With Psychotic Features, Bipolar I Disorder, Most Recent Episode Mixed, Severe Without Psychotic Features, Bipolar I Disorder, Most Recent Episode Mixed, Unspecified, Bipolar I Disorder, Most Recent Episode Unspecified, Bipolar I Disorder, Single Manic Episode, In Full Remission, Bipolar I Disorder, Single Manic Episode, In Partial Remission, Bipolar I Disorder, Single Manic Episode, Mild, Bipolar I Disorder, Single. Manic Episode, Moderate, Bipolar I Disorder, Single Manic Episode, Severe With Psychotic Features, Bipolar I Disorder, Single Manic Episode, Severe Without Psychotic Features, Bipolar I Disorder, Single Manic Episode, Unspecified, Bipolar II Disorder, Body Dysmorphic Disorder, Borderline Intellectual Functioning, Borderline Personality Disorder, Breathing-Related Sleep Disorder, Brief Psychotic Disorder, Bulimia Nervosa, Caffeine Intoxication, Caffeine-Induced Anxiety Disorder, Caffeine-Induced Sleep Disorder, Caffeine-Related Disorder NOS, Cannabis Abuse, Cannabis Dependence, Cannabis Intoxication, Cannabis Intoxication Delirium, Cannabis-Induced Anxiety Disorder, Cannabis-Induced Psychotic Disorder, With Delusions, Cannabis-Induced Psychotic Disorder, With Hallucinations, Cannabis-Related Disorder NOS, Catatonic Disorder, Child or Adolescent Antisocial Behavior, Childhood Disintegrative Disorder, Chronic Motor or Vocal Tic Disorder, Circadian Rhythm Sleep Disorder, Cocaine Abuse, Cocaine Dependence, Cocaine Intoxication, Cocaine Intoxication Delirium, Cocaine Withdrawal, Cocaine-Induced Anxiety Disorder, Cocaine-Induced Mood Disorder, Cocaine-Induced Psychotic Disorder, With Delusions, Cocaine-Induced Psychotic Disorder, With Hallucinations, Cocaine-Induced Sexual Dysfunction, Cocaine-Induced Sleep Disorder, Cocaine-Related Disorder NOS, Cognitive Disorder NOS, Communication Disorder NOS, Conduct Disorder, Conversion Disorder, Cyclothymic Disorder, Delirium Due to [Indicate the General Medical Condition], Delirium NOS, Delusional Disorder, Dementia Due to Creutzfeldt-Jakob Disease, Dementia Due to Head Trauma, Dementia Due to HIV Disease, Dementia Due to Huntington's Disease, Dementia Due to Parkinson's Disease, Dementia Due to Pick's Disease, Dementia Due to [Indicate the General Medical Condition], Dementia NOS, Dementia of the Alzheirner's Type, With Early Onset, Uncomplicated, Dementia of the Alzheiner's Type, With Early Onset, With Delirium, Dementia of the Alzheimer's Type, With Early Onset, With Delusions, Dementia of the Alzheimer's Type, With Early Onset, With Depressed Mood, Dementia of the Alzheimer's Type, With Late Onset, Uncomplicated, Dementia of the Alzheimer's Type, With Late Onset, With Delirium, Dementia of the Alzheimer's Type, With Late Onset, With Delusions, Dementia of the Alzheimer's Type, With Late Onset, With Depressed Mood, Dependent Personality Disorder, Depersonalization Disorder, Depressive Disorder NOS, Developmental Coordination Disorder, Diagnosis Deferred on Axis It, Diagnosis or Condition Deferred on Axis I, Disorder of Infancy, Childhood, or Adolescence NOS, Disorder of Written Expression, Disruptive Behavior Disorder NOS, Dissociative Amnesia, Dissociative Disorder NOS, Dissociative Fugue, Dissociative Identity Disorder, Dyspareunia (Not Due to a General Medical Condition), Dyssomnia NOS, Dysthymic Disorder, Eating Disorder NOS, Encopresis, With Constipation and Overflow Incontinence, Encopresis, Without Constipation and Overflow Incontinence, Enuresis (Not Due to a General Medical Condition), Exhibitionism, Expressive Language Disorder, Factitious Disorder NOS, Factitious Disorder With Combined Psychological and Physical Signs and Symptoms, Factitious Disorder With Predominantly Physical Signs and Symptoms, Factitious Disorder With Predominantly Psychological Signs and Symptoms, Feeding Disorder of Infancy or Early Childhood, Female Dyspareunia, Female Hypoactive Sexual Desire Disorder, Female Orgasmic Disorder, Female Sexual Arousal Disorder, Fetishism, Frotteurism, Gender Identity Disorder in Adolescents or Adults, Gender Identity Disorder in Children, Gender Identity Disorder NOS, Generalized Anxiety Disorder, Hallucinogen Abuse, Hallucinogen Dependence, Hallucinogen Intoxication, Hallucinogen Intoxication Delirium, Hallucinogen Persisting Perception Disorder, Hallucinogen-Induced Anxiety Disorder, Hallucinogen-Induced Mood Disorder, Hallucinogen-Induced Psychotic Disorder, With Delusions, Hallucinogen-Induced Psychotic Disorder, With Hallucinations, Hallucinogen-Related Disorder NOS, Histrionic Personality Disorder, Hypersomnia, Hypoactive Sexual Desire Disorder, Hypochondriasis, Identity Problem, Impulse-Control Disorder NOS, Inhalant Abuse, Inhalant Dependence, Inhalant Intoxication, Inhalant Intoxication Delirium, Inhalant-Induced Anxiety Disorder, Inhalant-Induced Mood Disorder, Inhalant-Induced Persisting Dementia, Inhalant-Induced Psychotic Disorder, With Delusions, Inhalant-Induced Psychotic Disorder, With Hallucinations, Inhalant-Related Disorder NOS, Insomnia, Intermittent Explosive Disorder, Kleptomania, Learning Disorder NOS, Major Depressive Disorder, Recurrent, In Full Remission, Major Depressive Disorder, Recurrent, In Partial Remission, Major Depressive Disorder, Recurrent, Mild, Major Depressive Disorder, Recurrent, Moderate, Major Depressive Disorder, Recurrent, Severe With Psychotic Features, Major Depressive Disorder, Recurrent, Severe Without Psychotic Features, Major Depressive Disorder, Recurrent, Unspecified, Major Depressive Disorder, Single Episode, In Full Remission, Major Depressive Disorder, Single Episode, In Partial Remission, Major Depressive Disorder, Single Episode, Mild, Major Depressive Disorder, Single Episode, Moderate, Major Depressive Disorder, Single Episode, Severe With Psychotic Features, Major Depressive Disorder, Single Episode, Severe Without Psychotic Features, Major Depressive Disorder, Single Episode, Unspecified, Male Dyspareunia, Male Erectile Disorder, Male Hypoactive Sexual Desire Disorder, Male Orgasmic Disorder, Malingering, Mathematics Disorder, Medication-Induced Movement Disorder NOS, Medication-Induced Postural Tremor, Mental Disorder NOS, Mental Retardation, Severity Unspecified, Mild Mental Retardation, Mixed Receptive-Expressive Language Disorder, Moderate Mental Retardation, Mood Disorder, Mood Disorder NOS, Narcissistic Personality Disorder, Narcolepsy, Neglect of Child, Neglect of Child (if focus of attention is on victim), Neuroleptic Malignant Syndrome, Neuroleptic-Induced Acute Akathisia, Neuroleptic-Induced Acute Dystonia, Neuroleptic-Induced Parkinsonism, Neuroleptic-Induced Tardive Dyskinesia, Nicotine Dependence, Nicotine Withdrawal, Nicotine-Related Disorder NOS, Nightmare Disorder, No Diagnosis on Axis II, No Diagnosis or Condition on Axis I, Noncompliance With Treatment, Obsessive-Compulsive Disorder, Obsessive-Compulsive Personality Disorder, Occupational Problem, Opioid Abuse, Opioid Dependence, Opioid Intoxication, Opioid Intoxication Delirium, Opioid Withdrawal, Opioid-Induced Mood Disorder, Opioid-Induced Psychotic Disorder, With Delusions, Opioid-Induced Psychotic Disorder, With Hallucinations, Opioid-Induced Sexual Dysfunction, Opioid-Induced Sleep Disorder, Opioid-Related Disorder NOS, Oppositional Defiant Disorder, Other (or Unknown) Substance Abuse, Other (or Unknown) Substance Dependence, Other (or Unknown) Substance Intoxication, Other (or Unknown) Substance Withdrawal, Other (or Unknown) Substance-Induced Anxiety Disorder, Other (or Unknown) Substance-Induced Delirium, Other (or Unknown) Substance-Induced Mood Disorder, Other (or Unknown) Substance-Induced Persisting Amnestic Disorder, Other (or Unknown) Substance-Induced Persisting Dementia, Other (or Unknown) Substance-Induced Psychotic Disorder, With Delusions, Other (or Unknown) Substance-Induced Psychotic Disorder, With Hallucinations, Other (or Unknown) Substance-Induced Sexual Dysfunction, Other (or Unknown) Substance-Induced Sleep Disorder, Other (or Unknown) Substance-Related Disorder NOS, Other Female Sexual Dysfunction, Other Male Sexual Dysfunction, Pain Disorder Associated With Both Psychological Factors and a General Medical Condition, Pain Disorder Associated With Psychological Factors, Panic Disorder With Agoraphobia, Panic Disorder Without Agoraphobia, Paranoid Personality Disorder, Paraphilia NOS, Parasomnia NOS, Parent-Child Relational Problem, Partner Relational Problem, Pathological Gambling, Pedophilia, Personality Change, Personality Disorder NOS, Pervasive Developmental Disorder NOS, Phase of Life Problem, Phencyclidine Abuse, Phencyclidine Dependence, Phencyclidine Intoxication, Phencyclidine Intoxication Delirium, Phencyclidine-Induced Anxiety Disorder, Phencyclidine-Induced Mood Disorder, Phencyclidine-Induced Psychotic Disorder, With Delusions, Phencyclidine-Induced Psychotic Disorder, With Hallucinations, Phencyclidine-Related Disorder NOS, Phonological Disorder, Physical Abuse of Adult, Physical Abuse of Adult (if focus of attention is on victim), Physical Abuse of Child, Physical Abuse of Child (if focus of attention is on victim), Pica, Polysubstance Dependence, Posttraumatic Stress Disorder, Premature Ejaculation, Primary Hypersomnia, Primary Insomnia, Profound Mental Retardation, Psychotic Disorder, With Delusions, Psychotic Disorder, With Hallucinations, Psychotic Disorder NOS, Pyromania, Reactive Attachment Disorder of Infancy or Early Childhood, Reading Disorder, Relational Problem NOS, Relational Problem Related to a Mental Disorder or General Medical Condition, Religious or Spiritual Problem, Rett's Disorder, Rumination Disorder, Schizoaffective Disorder, Schizoid Personality Disorder, Schizophrenia, Catatonic Type, Schizophrenia, Disorganized Type, Schizophrenia, Paranoid Type, Schizophrenia, Residual Type, Schizophrenia, Undifferentiated Type, Schizophreniform Disorder, Schizotypal Personality Disorder, Sedative, Hypnotic, or Anxiolytic Abuse, Sedative, Hypnotic, or Anxiolytic Dependence, Sedative, Hypnotic, or Anxiolytic Intoxication, Sedative, Hypnotic, or Anxiolytic Intoxication Delirium, Sedative, Hypnotic, or Anxiolytic Withdrawal, Sedative, Hypnotic, or Anxiolytic Withdrawal Delirium, Sedative-, Hypnotic-, or Anxiolytic-Induced Anxiety Disorder, Sedative-, Hypnotic-, or Anxiolytic-Induced Mood Disorder, Sedative-, Hypnotic-, or Anxiolytic-Induced Persisting Amnestic Disorder, Sedative-, Hypnotic-, or Anxiolytic-Induced Persisting Dementia, Sedative-, Hypnotic-, or Anxiolytic-Induced Psychotic Disorder, With Delusions, Sedative-, Hypnotic-, or Anxiolytic-Induced Psychotic Disorder, With Hallucinations, Sedative-, Hypnotic-, or Anxiolytic-Induced Sexual Dysfunction, Sedative-, Hypnotic-, or Anxiolytic-Induced Sleep Disorder, Sedative-, Hypnotic-, or Anxiolytic-Related Disorder NOS, Selective Mutism, Separation Anxiety Disorder, Severe Mental Retardation, Sexual Abuse of Adult, Sexual Abuse of Adult (if focus of attention is on victim), Sexual Abuse of Child, Sexual Abuse of Child (if focus of attention is on victim), Sexual Aversion Disorder, Sexual Disorder NOS, Sexual Dysfunction NOS, Sexual Masochism, Sexual Sadism, Shared Psychotic Disorder, Sibling Relational Problem, Sleep Disorder, Hypersomnia Type, Insomnia Type, Mixed Type, Parasomnia Type, Sleep Terror Disorder, Sleepwalking Disorder, Social Phobia, Somatization Disorder, Somatoform Disorder NOS, Specific Phobia, Stereotypic Movement Disorder, Stuttering, Tic Disorder NOS, Tourette's Disorder, Transient Tic Disorder, Transvestic Fetishism, Trichotillomania, Undifferentiated Somatoform Disorder, Unspecified Mental Disorder (nonpsychotic), Vaginismus (Not Due to a General Medical Condition), Vascular Dementia, Uncomplicated, Vascular Dementia, With Delirium, Vascular Dementia, With Delusions, Vascular Dementia, With Depressed Mood, Voyeurism.

"Label," "labeled" or "detectable labeled" refers to incorporation of a detectable marker, for example by incorporation of a radioactively labeled compound or attachment to a polypeptide of moieties such as biotin that can be detected by the binding of a section moiety, such as marked avidin. Various methods of labeling polypeptide, nucleic acids, carbohydrates, and other biological or organic molecules are known in the art. Such labels can have a variety of readouts, such as radioactivity, fluorescence, color, chemiluminescence or other readouts known in the art or later developed. The readouts can be based on enzymatic activity, such as beta-galactosidase, beta-lactamase, horseradish peroxidase, alkaline phosphatase, luciferase; radioisotopes such as $^3$H, $^{14}$C, $^{35}$S, $^{125}$I or $^{131}$I); fluorescent proteins, such as green fluorescent proteins (GFP); or other fluorescent labels, such as FITC, rhodamine, and lanthanides. Where appropriate, these labels can be the product of the expression of reporter genes, as that term is understood in the art. Examples of reporter genes are beta-lactamase (U.S. Pat. No. 5,741,657 to Tsien et al., issued Apr. 21, 1998) and green fluorescent protein (U.S. Pat. No.

5,777,079 to Tsien et al., issued Jul. 7, 1998; U.S. Pat. No. 5,804,387 to Cormack et al., issued Sep. 8, 1998).

A "test chemical" or "test compound" or "candidate compound" refers to a chemical, composition or extract to be tested by at least one method of the present invention to be a putative modulator. A test chemical can be of any chemical composition, such as inorganic, organic or a biomolecule. A biomolecule can be any molecule of biological origin that is found in or produced at least in part by a cell, and include, but are not limited to polypeptides, nucleic acids, lipids, carbohydrates or combinations thereof A test chemical is usually not known to bind to the target of interest. "Indentifying a compound" or "screening a drug" used herein refers to a process to determine the putative modulating or therapeutic function of a candidate compound.

"Control test chemical" or "control compound" refers to a chemical known to bind to the target (for example, a known agonist, antagonist, partial agonist or inverse agonist). Test chemical does not typically include a chemical added to a mixture as a control condition that alters the function of the target to determine signal specificity in an assay. Such control chemicals or conditions include chemicals that (1) non-specifically or substantially disrupt protein structure (for example denaturing agents such as urea or guandium, sulfhydryl reagents such as dithiotritol and beta-mercaptoethanol), (2) generally inhibit cell metabolism (for example mitochondrial uncouples) and (3) non-specifically disrupt electrostatic or hydrophobic interactions of a protein (for example, high salt concentrations or detergents at concentrations sufficient to non-specifically disrupt hydrophobic or electrostatic interactions). The term "test chemical" or "candidate compound" also does not typically include chemicals known to be unsuitable for a therapeutic use for a particular indication due to toxicity of the subject. Usually, various predetermined concentrations of test chemicals are used for determining their activity. If the molecular weight of a test chemical is known, the following ranges of concentrations can be used: between about 0.001 micromolar and about 10 millimolar, preferably between about 0.01 micromolar and about 1 millimolar, more preferably between about 0.1 micromolar and about 100 micromolar. When extracts are uses a test chemicals, the concentration of test chemical used can be expressed on a weight to volume basis. Under these circumstances, the following ranges of concentrations can be used: between about 0.001 micrograms/ml and about 1 milligram/ml, preferably between about 0.01 micrograms/ml and about 100 micrograms/ml, and more preferably between about 0.1 micrograms/ml and about 10 micrograms/ml.

"Macromolecule" refers to a molecule with a molecular mass greater than a one thousand daltons, such as a protein, nucleic acid, or polysaccharide.

"Treating" or "treatment" as used herein means to ameliorate, suppress, mitigate or eliminate the clinical symptoms after the onset (i.e., clinical manifestation) of a disease state, such as an AD, including, but not limited to inhibiting neuronal degeneration or neuronal death, promoting or stimulating neuronal growth such that the symptoms of the disease condition are prevented or alleviated. Such treatment can include chemicals, such as chemotherapeutic agents or test compounds and/or non-chemical treatment, such as electrical pules (such as electroinnovation), magnetic fields or radiation (such as radiation therapy) (see, for example, Buonanno et al., Nucleic Acids Res. 20:539-544 (1992)). An effective or successful treatment provides a clinically observable improvement.

By "candidate treatment process" is meant administration of a candidate compound to a subject, or modification of environment, diet, behavior of the subject. By "control treatment process" is meant that the nature status or state of a subject being maintained without any treating or modification, or a treatment process having known references or properties is performed.

By "prevent", "preventing" or "prevention" is meant that chances of regaining and/or worsening and/or progression of the symptoms of a neurological diseases, such as, for example, AD, are lowered, reduced or eliminated after the symptoms are ameliorated, suppressed, mitigated or eliminated by the treatment.

A "specific binding member" refers to a member of a group of two or more moieties that can specifically bind with each other rather than becoming non-specifically associated with each other, such as by precipitation. Examples of specific binding members include, but are not limited to, antigen-antibody, receptor-ligand and nucleic acid-nucleic acid pairs.

"Specific," "specifically," "specifically bind" or a "specific binding" in the context of the binding of first specific binding member with at least one other specific binding member refers to binding that is preferential and not non-specific. Preferably, a specific binding reaction is unique for the specific binding members, but that need not be the case.

"Detectably bind" or "detectable binding" refers to the specific binding of one specific binding member with at least one other specific binding member that can be detected. For example, one specific binding member can be detectably labeled such that the detectable presence of the label indicates a specific binding event. The detection limits of such detectable binding are related to the detectable label used and the detection method or device used.

An "antibody" refers to an immunoglobulin of any class or subclass, a portion thereof or an active fragment thereof, wherein an active fragment of an antibody retains its specific binding capability. An antibody can be a polyclonal antibody, a monoclonal antibody or a mixture thereof.

By "probe" is meant a substance, preferably a biomolecule, such as a fragment of DNA sequence or an antibody, which is labeled or otherwise marked and used to detect or identify another substance in a sample. An example of a probe can be a biomolecule that is labeled with radioactive isotopes or with a fluorescent marker that selectively binds to a specific gene so it can be isolated or identified or a strand of nucleic acid which can be labeled and used to hybridize to a complementary molecule from a mixture of other nucleic acids. The term "probe" used herein can be also referred to a single-stranded nucleic acid molecule with a known nucleotide sequence which is labeled in some way (for example, radioactively, fluorescently, or immunologically) and used to find and mark certain DNA or RNA sequences of interest to a researcher by hybridizing to it. A specific example of the probe used in the present invention is anti-aPKC antiserum.

A "specific probe" such as used in "aPKC specific probe" is referred to any probe that specifically binds to aPKC gene or gene product(s). Preferably, such specific binding is a detectable binding.

A "tissue" refers to a collection of cells as known in the art. A "culture" of cells is a collection of cells as known in the art and can be a clonal population of cells or a mixed population of cells. A "tumor tissue" is a collection of cells that includes at least one cell derived from at least one tumor.

A "tissue extract" refers to a preparation that is derived from at least one source of tissue that has been treated such that the tissue and/or at least one cellular component of the cells in the tissue is no longer in its natural state or environment. For example, a tissue extract can be made by rupturing tissue using methods known in the art.

A "sample" includes any physical sample that includes a cell or a cell extract from a cell, a tissue, a biopsy sample, a tissue extract, for example. A sample can be from a biological source such as a subject or animal or a portion thereof, or from a cell culture. Samples from a biological source can be from a normal or abnormal organism (such as an organism suffering from a condition or disease state, such as a neoplasm) or portion thereof and can be from any fluid, tissue or organ, including healthy or abnormal (such as diseased or neoplastic) fluids, tissues or organs. Samples from a subject or animal can be used in the present invention as obtained from the subject or animal, processed such as by sectioning, aspiration such as for bone marrow specimens or cultured such that cells from the sample can be sustained in vitro as a primary or continuous cell culture or cell line. For example, a sample in the present invention can be a tissue biopsy, cerebrospinal fluid (CSF), or a body fluid, such as blood, sample. In particular, a "tumor sample" is a sample that includes at least one cell derived from at least one tumor.

"Diagnosing" or "diagnosis" refers to the determination of whether a subject comprises a disease or condition, such as a nervous system disorder or cancer. "Diagnosing" also refers to distinguishing one cancer from another.

By "prognosing" or "prognosis" is meant the determination or prediction of the course of a disease or condition, such as cancer. The course of a disease or condition can be prognosed, for example, based on life expectancy or quality of life. Prognosing includes the determination of the time course of a disease or condition, with or without a treatment or treatments. In the instance where treatment(s) are contemplated, the prognosing includes prognosing the efficacy of a treatment for a disease or condition, such as cancer, or prognosing a malignancy.

A "control sample" refers to a sample that acts as a positive or negative control as they are known in the art and as appropriate for a particular assay. A control can be performed contemporaneously with an assay or be performed at a prior or later time. The results of an assay can be compared to a control to determine the validity of the assay. Controls can also be used to produce standard curves such that the results of an assay can be semi-quantitative or quantitative in nature. A reference range, i.e., a known range of normal values, can also be used as a control.

By "reference DNA" or "reference DNA sequence" is meant a DNA sequence, where its sequence is known and normal, i.e., without any mutation, and where it encompasses the same region in the genome of a species as a DNA molecule to be compared, assayed or analyzed.

By "promoter" or "promoter region" is meant a nucleic acid sequence that controls expression of a coding sequence or a gene of interest. By "control expresion" is meant controlling production of RNA (e.g., mRNA or non-coding transcripts) by providing the recognition site for RNA polymerase and/or other factors necessary for starting transcription at the correct site. A promoter or promoter region usually resides upstream (5') of a coding sequence. As contemplated by the present invention, a promoter or promoter region can include variations of promoters derived by means of ligation to various regulatory sequences, random or controlled mutagenesis, and addition or duplication of enhancer sequences.

By "tansgene" is meant any nucleic acid sequence non-native to a cell or an organism into which the nucleic acid sequence is transformed. "Transgene" also encompasses the component parts of a native gene of an organism modified by insertion of a non-native nucleic acid sequence by directed recombination.

The present invention is directed to the identification of the amount, localization and activity of atypical isoforms of protein kinase C (aPKC), e.g. PKMζ, and their role in disorders of the nervous system, such as Alzheimer's disease (AD).

Accordingly, one embodiment of the present invention is directed to diagnosis of AD. According to the present invention, a method for diagnosing neurological dysfunctions or nervous system disorders in a subject, using an aPKC specific probe, is provided. The diagnostic method of the present invention includes the steps of:

a. contacting a sample from the subject, e.g. a tissue biopsy, cerebrospinal fluid (CSF), or a blood sample, with an aPKC specific probe, b. detecting the binding of the probe to the sample to determine the amount, localization or activity of the aPKC in the sample, c. contacting a control sample with the aPKC specific probe, d. detecting the binding of the probe to the control sample, e.g. a tissue biopsy, CSF, or a blood sample, to determine the amount, localization or activity of the aPKC in the control sample, and e. comparing the amount, localization or activity of the aPKC in Step b with the amount, localization or activity of the aPKC in Step d, whereby if the amount, localization or activity of the aPKC in Step b is different from the amount, localization or activity of the aPKC in Step d, a nervous system disorder in the subject is present.

In accordance with the present invention, using probes to aPKC isoforms in the form of antibodies or nucleic acid, one can detect changes of aPKC in tissues from a subject through conventional techniques (Maniatis et al., *J Molecular Cloning*, a laboratory manual, 1987; Ausubel, F. M., *Current Protocols in Molecular Biology*, 1987), and thereby ascertain whether an individual has a neurological disease, such as AD, or is likely to develop one. These probes can be used on postmortem autopsy tissue, brain biopsy tissue or any other tissue, tissue extract or body fluid (e.g., blood). In accordance with the present invention, a preferred probe is the antisense probe described in Example 11. Also in accordance with the present invention, using gene analysis for mutations in the aPKCs, one can detect changes of aPKC in tissues from a subject through conventional techniques (Ausubel, F. M., *Current Protocols in Molecular Biology*, 1987), and thereby ascertain whether an individual has a neurological disease or is likely to develop one.

Thus, it is an object of the present invention to detect neurological disorders, such as AD, at an early stage in order to treat and/or prevent the disorder.

Another embodiment of the present invention is directed to a method for screening drugs or molecular compounds useful for modulating the amount or activity of the aPKC. According to the present invention, a method for screening molecular compounds, e.g. peptides and small molecules, using cells and aPKC specific probes is provided. Such method includes:

a. providing cells wherein aPKC gene is expressed, b. incubating the cells with a candidate compound for a sufficient time to induce a change in the amount, localization or activity of aPKC in the cells, c. incubating the cells as in Step b, in the absence of the candidate compound, d. contacting the cells from Step b and Step c with an equal amount of an aPKC-specific probe, e. detecting the binding of the probe to the cells to determine the amount, localization or activity of the aPKC in the cell from Step b and Step c, and f. comparing the amount, localization or activity of the aPKC in the cells, wherein if the amount, localization or activity of the aPKC in the cells from Step b is different from the amount, localization or activity of the aPKC in the cells from Step c, the candidate compound is identified as a compound that modulates aPKC.

An alternate method for screening molecular compounds for use in treatment of brain disorders involves the overexpression or deletion of genetic elements containing atypical PKC sequences in cells or animals, e.g. mice, and assaying said cells or animals for atypical PKC activity or levels.

In accordance with present invention, the aPKC isoforms are used as rational targets for drug design for the purpose of treating and/or preventing AD and other neurological disorders. There are numerous methods currently available for testing the ability of drugs to influence the activity of proteins (Enna, S. J., Current Protocols in Pharmacology, 1998). The present invention is directed to the discovery that aPKC plays a key role in neurological disease and that changes in aPKC can be used to screen for useful drugs.

According to the present invention, a preferred compound is chelerythrine chloride (a PKC inhibitor), the zeta-inhibitory peptide (ZIP), or a selective aPKC inhibitor. An example of ZIP is myristoylated PKCζ pseudosubstrate peptide, i.e., Myr-SIYRRGARRWRKLY (SEQ ID NO: 10). See, Standaert et al., 1999, J. Biol. Chem. 274(20):14074-78.

According to the present invention, drugs that modulate aPKC can be screened by employing methodologies and related reagents that are known to the persons skilled in the art. Three such conventional methodologies have been developed, in both in vivo and in vitro systems. The first is a kinase assay using recombinant expressed PKMζ in a baculovirus system. The second is a cell culture system using immunofluorescence. The third is using recombinant aPKC transfected into cultured cells. See, Ausubel, F. M., *Current Protocols in Molecular Biology*, 1987.

In accordance with the present invention, an aPKC, including PKMζ, contains a non-conventional ATP binding site motif GXGXXA (SEQ ID NO: 8), wherein G is amino acid glycine, X is any amino acid. This special characteristic of aPKC makes it less likely that drugs targeting these molecules will have harmful side effects comparing to other kinases or other PKC isoforms, which have ATP binding site hallmark motif GXGXXG (SEQ ID NO: 9).

In a particular embodiment of the present invention, an in vitro cell-free method for screening drugs or molecular compounds useful for modulating the amount, localization or activity of the aPKC, using aPKC and a substrate, is provided. Such method includes:

a. incubating an aPKC in a first container with adenosine triphosphate (ATP), preferably radioactively labeled ATP, a substrate of the aPKC, e.g. protein tau, with a candidate compound, for a sufficient time to induce a change in the amount or activity of the aPKC in said first container, b. incubating the aPKC in a second container with ATP, preferably radioactively labeled ATP, and the substrate of said aPKC, e.g. protein tau, for a sufficient time to induce a change in the amount or activity of aPKC in said second container, c. quantifying the amount of incorporation of the phosphate into the substrate in the first container and the second container, and d. comparing the amount of incorporation in the first container and the second container, whereby a difference in the amount of incorporation in the first container and the second container is indicative that the candidate compound is identified as a compound modulating aPKC amount, localization or activity.

A variation of this method involves using a phospho-specific antisera to quantify phosphate incorporation into the substrate.

Still another embodiment of the present invention is directed to a method, including gene therapy, for treating and/or preventing neurological disorders. According to the present invention, a method for treating and/or preventing neurological dysfunction is provided which employs a sequence corresponding to an aPKC, e.g. PKMζ (or an antisense sequence of aPKC) and an expression vector. This method includes the steps of:

a. inserting the aPKC sequence, e.g. PKMζ, into the expression vector, and b. administering the vector to a subject, e.g. a patient, whereby the vector treats and/or prevents a neurological dysfunction.

The methods of the present invention can be employed in the treatment and/or prevention of a variety of neurological disorders characterized by abnormal aPKC activity, such as phosphorylation of protein tau and co-localization with NFT. Such tau-associated filamentous aggregates are neuropathological hallmarks of Alzheimer's disease (AD), Pick's disease (PiD), progressive supranuclear palsy (PSP), and corticobasal degeneration (CBD), Parkinson's Disease (PD), for example.

According to the present invention, aPKC function is altered in AD and other neurological disorders. Thus, in accordance with the present invention, aPKC and mutated forms, e.g. inactivated form of kinase, can be introduced to treat and/or prevent AD and other neurological disorders. Using gene therapy, the aPKC cDNA, preferably PKMζ cDNA, sequences or the mutated aPKC sequences, can be introduced to treat these diseases.

Such sequences are preferably provided in an expression vector. Expression vectors for use in the present methods include any appropriate gene therapy vectors, such as nonviral (e.g., plasmid vectors), retroviral, adenoviral, herpes simplex viral, adeno-associated viral, polio viruses and vaccinia vectors. Examples of retroviral vectors include, but are not limited to, Moloney murine leukemia virus (MoMuLV), Harvey murine sarcoma virus (HaMuSV), murine mammary tumor virus (MuMTV), and Rous Sarcoma Virus (RSV)-derived recombinant vectors. Multiple teachings of gene therapy are available to those skilled in the art (Anderson, W. F., *Science*, 288: 627-629, 20001; Anderson, W. F., *Science*, 226: 401409, 1984; Anderson, W. F., *Science*, 256: 808-813, 1993; Friedmann, T., *Science*, 244: 1275-1281, 1989). Preferred vectors include neurotropic vectors such as herpes simplex viral vectors (U.S. Pat. No. 5,673,344 to Kelly et al.) and adenoviral vectors (Barkats et al., *Prog Neurobiol*, 55: 333-341, 1998).

In a further embodiment, present invention provides antibodies against PKMζ for detection, treatment and/or prevention of neurological disorders, e.g. AD.

The present invention further provides antibodies against PKMζ for detection, treatment and/or prevention of neurological disorders, e.g. AD. Those skilled in the art can use any of the well-known techniques and commercially available resources to generate such monoclonal or polyclonal antibodies (Harlow et al., Using Antibodies: A Laboratory Manual, 1999). Once an antibody is obtained, such antibody can be tested in assays to determine whether such antibody exhibits specific activity.

A still further embodiment of the present invention provides a method for constructing transgenic animals, such as a knock-out mouse lacking aPKC or a mouse that overexpresses the wild type or a mutant aPKC, that are useful as animal models of neurological dysfunction. The method includes:
a. constructing a transgenic animal having an altered aPKC amount, localization or activity, e.g., by deleting an aPKC gene in the animal using knock-out techniques known to one skilled in the art,
b. treating the transgenic animal from Step a with a candidate treatment process,
c. treating the transgenic animal from Step a with a control treatment process,
d. assaying the transgenic animals from Steps b and c for a biochemical or behavioral change, and
e. comparing the results of the assay of the transgenic animals from Steps b and Step c, wherein a difference is indicative the efficacy of the candidate treatment process in alleviating the neurological dysfunction.

A variation of the method involves over-expression of either wild-type or mutated aPKC in a transgenic animal, alone or in combination with one or more other transgenes expressing mutations or polymorphisms in genes associated with neurodegeneration, e.g. superoxide dismutase, tau, β-amyloid, α-synuclein, and apolipoprotein E.

A yet further embodiment of the present invention is directed to the genetic screening of DNA for mutations or polymorphisms in the DNA sequence of the aPKC genes, e.g. PKCζI/II and PKCι/λ, and regions regulating the expression of these genes including promoter regions, enhancer regions and negative regulatory regions. A method for such screening includes:
a. isolating DNA from a sample of a subject,
b. sequencing an aPKC gene or its regulating region of the DNA from Step a and,
c. comparing the DNA sequence from Step b to a reference DNA sequence, wherein the reference DNA is a known normal DNA sequence of the same region as sequenced DNA in Step b but without any mutation, whereby a difference between the DNA sequence from Step b and the reference sequence is indicative of genetic susceptibility to a neurological or psychiatric disorder.

A particular embodiment of the present invention is directed to the use of a known aPKC interacting protein for all of the above methods.

The present invention is also directed toward the diagnosis and treatment of other abnormal protein aggregates including α-synuclein seen in PD, multisystem atrophy (MSA) and dementia with Lewy bodies (DLB) and β-amyloid in AD and normal aging.

According to the present invention, abnormal aggregation of aPKC protein, such as PKCι/λ (one of the two members of aPKC) protein, can cause neurodegenerative disorders. It is a discovery of the present invention that PKCι/λ protein distribute in a variety of tauopathies and α-synucleinopathies. Specifically, using immunocytochemistry, the present invention demonstrates that an anti-PKCι/λ antibody can label tau-positive structures in Alzheimer's disease (AD), progressive supranuclear palsy (PSP), corticobasal degeneration (CBD) and Pick's disease (PiD); α-synuclein-positive Lewy bodies in idiopathic Parkinson's disease and dementia with Lewy bodies, and glial inclusions in multi-system atrophy, αB-crystalline-containing ballooned neurons in CBD and PiD; and actin-rich Hirano bodies in AD, PiD and elderly individuals. See Example 12.

Still another embodiment of the present invention provides methods for diagnosing various forms of cancer, such as neuroblastoma, oligodendroglioma, meningioma, lymphoma (myeloma), leukemia (including acute myelocytic leukemia (AML)), melanoma, squamous cell carcinoma, hepatocellular carcinoma, parathyroid tumors, pheochromocytoma, paraganglioma, intravascular lymphomatosis, breast cancer, liver cancer, lung cancer, prostate cancer, bladder cancer, ovarian cancer, endometrial cancer, head and neck cancer and gastrointestinal cancers including colorectal cancer and pancreatic cancer. According to the present invention, a method for diagnosing and/or staging a tumor is provided. The diagnostic method of the invention includes the steps of:
a. contacting a tumor sample, e. g. a human biopsy sample, from a subject, with an aPKC specific probe, preferably a PKCζ specific probe,
b. detecting the binding of the probe to the tumor sample to quantify the level, amount or activity of said aPKC in said tumor sample,
c. contacting a control sample with the aPKC specific probe,
d. detecting the binding of the probe to the control sample to quantify the level, amount or activity of the aPKC in the control sample, and
e. comparing the level, amount or activity of the aPKC in Step b with the level, amount or activity of the aPKC in Step d, wherein the difference of the level, amount or activity of the aPKC is indicative of the type and the staging of the tumor.

Another embodiment of the invention provides methods for drug screening for the purpose of treating and/or preventing cancer, e. g. neuroblastoma. According to the present invention, a method for screening molecular compounds, e. g. peptides and small molecules, is provided.

Still another embodiment of the invention provides methods for treating cancer with gene therapy.

According to the present invention, the therapeutic compositions provided herein, such as expression vectors or antibodies, can be administered to the subject being treated by standard routes, including, but not limited to, the oral, ophthalmic, nasal, topical, transdermal, parenteral (e.g., intravenous, intraperitoneal, intradermal, subcutaneous or intramuscular), intracranial, intracerebral, intraspinal, intravaginal, intrauterine, or rectal route. Depending on the condition being treated, one route may be preferred over others, which can be determined by those skilled in the art. For example, the topical or dermal route can be chosen when the target area includes tissues or organs readily accessible by topical application, such as neurological conditions of the eye or the facial tissue. For certain conditions, direct injection or surgical implantation in the proximity of the damaged tissues or cells is preferred in order to avoid the problems presented by the blood-brain barrier. Successful delivery to the central nervous system (CNS) by direct injection or implantation has been documented (Otto et al., J Neurosci Res, 22: 83-91, 1989; Goodman et al., Goodman & Gilman's the Pharmacological Basis of Therapeutics, 2001; Williams et al., Proc Natl Acad Sci USA, 83: 9231-35, 1986).

According to the present invention, the therapeutic ingredients are preferably administered to the subject in need thereof as early as possible, e.g., after the neuronal injury or neuronal death caused by NFT, or any other nervous system disorder or cancer occurs, in order to achieve the best therapeutic efficacy. The amount administered varies among patients and by route administered but should be sufficient enough to achieve a concentration to treat or prevent the disease or disorder or is sufficient to maintain said aPKC activity at a normal level. By "normal level" is meant that the level a biomolecule or compound functions or occurs in a natural way; lacks observable or scientifically detectable abnormalities or deficiencies. For example, normal level aPKC in a human body or an organ or tissue thereof is from about 0.005% to about 0.05% of total protein in the human body or an organ or tissue thereof, preferably, the organ is a human brain. In a particular embodiment of the present invention, ZIP or chelerythrine can be administered between about 100 nM and about 10 μM of in a desired tissue.

The present invention is further illustrated by the following non-limiting example. This example is included to demonstrate preferred embodiments of the invention. It should be appreciated by those of skill in the art that the techniques disclosed in the example represents techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings is to be interpreted as illustrative and not in a limiting sense. All references cited herein are hereby expressly incorporated-herein by reference.

EXAMPLE 1

Production of PKC Isozyme Antisera

Peptides used as immunogens were synthesized by Quality Controlled Biochemicals (Hopkinton, MA) and corresponded to the amino-terminal (ζN1, TDPKMDRSGGRVRLKC, SEQ ID NO: 1), catalytic-domain (ζ-C2, TLPPFQPQITDDYGLC, SEQ ID NO: 2) or carboxyl-tenninal (ζ-C1, EYINPLLLSAEESV, SEQ ID NO: 3) of PKCζ. In addition, a terminal cysteine residue was added to each of the sequences for coupling purposes. The peptides were coupled to maleimide-activated bovine serum albumin (BSA, Pierce, Rockford, Ill.), according to the manufacturer's instructions. Peptide conjugates were mixed with Titermax (CytRx Corp., Norcross, GA) and injected intramuscularly into female New Zealand rabbits, one to three weeks of age. After three boosts at four-week intervals, the antisera were affinity-purified on Sulpholink gel columns (Pierce, Rockford, Ill.), to which the immunizing peptide had been conjugated according to the manufacturer's instructions. The antiserum to ι/λ is a mouse monoclonal antibody prepared against the ι/λ catalytic domain (Transduction Laboratories, Lexington, Ky.).

EXAMPLE 2

Western Blot of AD Brain

Fresh frozen tissue from autopsy brain tissue derived from 4 neuropathologically confirmed cases of AD and 3 controls from individuals without neurological disease were homogenized in buffer containing protease inhibitors (50 mM HEPES, pH 7.5, 5 mM EDTA, 5 mM EGTA, 5 mM 2-mercaptoethanol, 0.1 mM phenylmethylsulfonyl fluoride, aprotinin (17 kallikrein units/ml), 5 mM benzamidine, 0.1 mM leupeptin) and phosphatase inhibitors (50 mM NaF, 40 mM β-glycerol phosphate, 10 mM pyrophosphate). Protein concentration was measured by Pierce assay. Sample buffer was added and samples boiled for 10 min. 15 μg of total protein was subjected to SDS-PAGE, transferred to nitrocellulose, and probed with specific anti-PKCζ and anti-PKCι/λ antibodies, and visualized by enhanced chemiluminescence (Amersham Biosciences, Freiburg, Germany).

EXAMPLE 3

Pathological Stains

Eight micron sections were cut from paraffin embedded tissue. All tissue was deparaffinized and rehydrated prior to use. For hematoxylin and eosin staining, sections were incubated in Gills hematoxylin for 5 minutes, rinsed in water, two changes, then dipped in bluing solution ten times and rinsed again. Next, sections were incubated in eosin Y for 4 minutes, dehydrated and coverslipped. For Sevier-Munger silver staining, slides were incubated in 60° C. silver nitrate solution (20%) for 15 min. Slides were rinsed and placed in a clean dry staining jar. Slides were then developed in ammoniacal silver solution for 5 to 30 minutes. Sections were then rinsed 3 changes of water and incubated in 5% sodium thiosulfate for 2 minutes. Last, slides were washed with water, dehydrated, and cover-slipped.

EXAMPLE 4

Antigen Retrieval

For antigen retrieval, deparaffinized and rehydrated slides were submerged in 10 mM citrate buffer (pH 6.0) and microwaved for 5 minutes. Slides were then transferred to a second container with heated distilled water and allowed to cool. Slides were then rinsed in PBS for 5 minutes. Some slides were treated with formic acid for 3 minutes prior to citrate treatment.

EXAMPLE 5

Immunohistochemical Staining

Slides were treated with 3% hydrogen peroxide for 10 minutes, rinsed in PBS for 5 minutes, and blocked in 4% normal horse serum for 20 minutes. Tissue was then incubated in primary antibody in a humidity chamber overnight on a rotator plate. The following day, slides were rinsed in two changes of PBS for 10 minutes each and incubated in biotinylated secondary (1:200) for 30 min. Slides were then rinsed again in two changes of PBS for 5 minutes each then incubated in R.T.U. ABC reagent (Vector Laboratories) for 30 minutes, and rinsed again in two changes of PBS for 5 minutes each. Tissue was then developed in DAB solution, rinsed in tap water and counterstained with hematoxylin, dehydrated and coverslipped.

EXAMPLE 6

PKMζ Protein is Present in Human Brain

Figure 3:
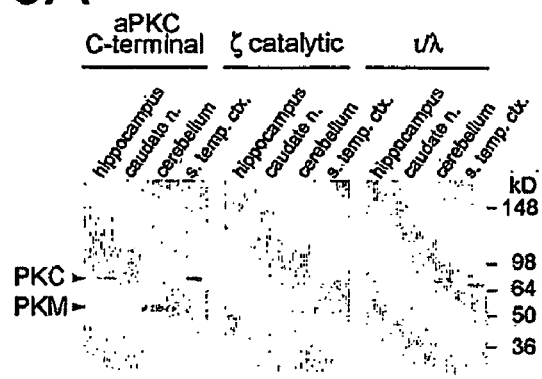
FIG. 3A illustrates a Western blot showing reactivity of aPKC antibodies in hippocampus, caudate nucleus, cerebellum, and superior temporal cortex. PKMζ was seen as a 55 kD band in all regions tested. PKCι/λ was seen as a 72 kD band in all regions tested. Full-length PKCζ was only seen in the cerebellum.
FIG. 3B illustrates the stability of aPKC in post-mortem rat brain tissue. The total level of aPKC was measured using quantitative Western blot with specific antisera to the catalytic domain of PKCζ and PKCι/λ.
Figure 3:
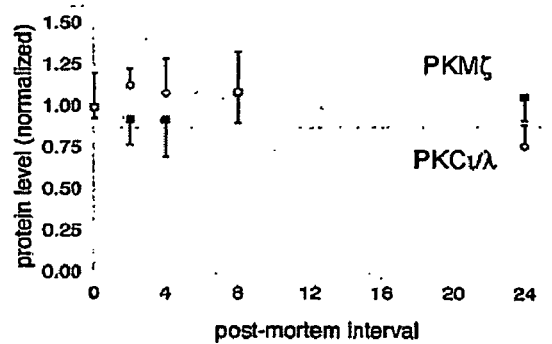

Western blot on homogenates of human brain samples were conducted to confirm antisera specificity and document PKMζ protein in humans (FIG. 3). Fresh frozen tissue was obtained from the Rush Alzheimer's Disease Center (Chicago, Ill.) (Table 1). The average PMI for the AD (4.75 h) and control (4.00 h) cases was the same. The average age for the AD (69.5 yr) cases was less than controls (86.7 yr). The diagnosis was confirmed pathologically for all patents.

TABLE 1

Summary of patient data (Western blot)

| Case | PMI (hours) | Age | Sex | Reagan Index | Braak Stage |
|---|---|---|---|---|---|
| 1 | 3 | 85 | F | Low likelihood of AD | I/II |
| 2 | 4 | 87 | M | Low likelihood of AD | I/II |
| 3 | 5 | 88 | F | Low likelihood of AD | I/II |
| 4 | 4.5 | 78 | M | High likelihood of AD | V/VI |
| 5 | 5.5 | 62 | F | High likelihood of AD | V/VI |
| 6 | 4.5 | 64 | F | High likelihood of AD | V/VI |
| 7 | 4.5 | 74 | M | High likelihood of AD | V/VI |

The PKCι antibody showed one band at ~79 kD in all regions tested. A faint, minor band at ~50 kD was seen suggesting the presence of a small amount of PKMl. The C-terminal antibody, ζ-C1, which detects both atypical forms, detected three bands at ~55, ~79 and ~160 kD. These bands represent aPKM, aPKC and an unidentified band respectively. The aPKC band was strongest in the cerebellum and weak in all other regions. The ζ specific antibody, ζ-C2, which does not cross-react with ι but reacts with both PKCζ and PKMζ detected major bands at ~55 kD and ~79 kD, and a minor band at ~60 kD. The ~79 kD band is PKCζ and was only present in the cerebellum. The 55 kD and 60 kD) bands were seen in all regions tested. The N-terminal antibody, ζ-N1, which reacts only with ζ forms with a regulatory domain showed one strong unidentified band at ~45 kD. There were no PKM or PKC forms seen with this antibody.

EXAMPLE 7

Figure 4:
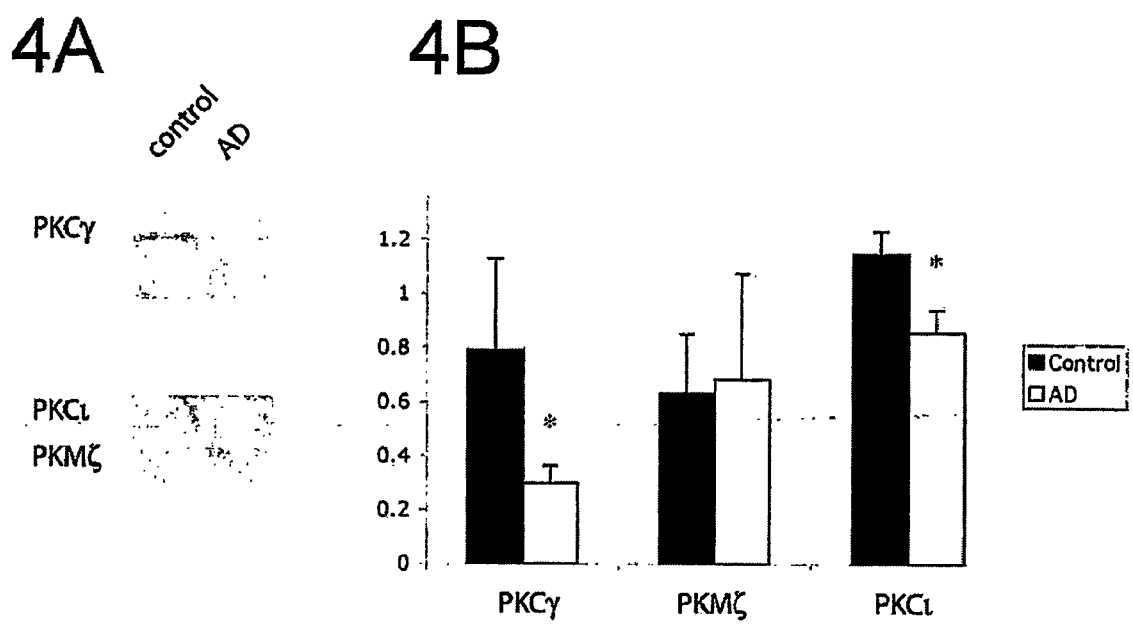
FIG. 4 illustrates that PKCγ and PKCι/λ but not PKMζ decreases in the superior temporal cortex in AD.

PKCγ and PKCι/λ But not PKM ζ Decrease in the Superior Temporal Cortex in AD To determine whether there are changes in the levels of aPKC, densitometric analysis of Western blots was done on total protein homogenates prepared from the superior temporal cortex derived from AD (n=4) and controls (n=3). PKCγ was included for comparison. PKCγ was significantly lower ($p=0.031$) in the AD samples ($0.30\pm0.07$) than controls ($0.79\pm0.34$) representing a 63% decrease. There was a smaller, but statistically significant decrease in PKCι ($p=0.006$) in AD ($0.86\pm0.08$) versus controls ($1.15\pm0.08$) representing a 25% decrease. In contrast, PKMζ was not significantly different in AD ($0.69\pm0.39$) versus controls ($0.63\pm0.22$). See, FIG. 4.

EXAMPLE 8

PKCι/λ But not PKMζ nor PKCγ Increase in the Caudate Nucleus in AD

Figure 5:
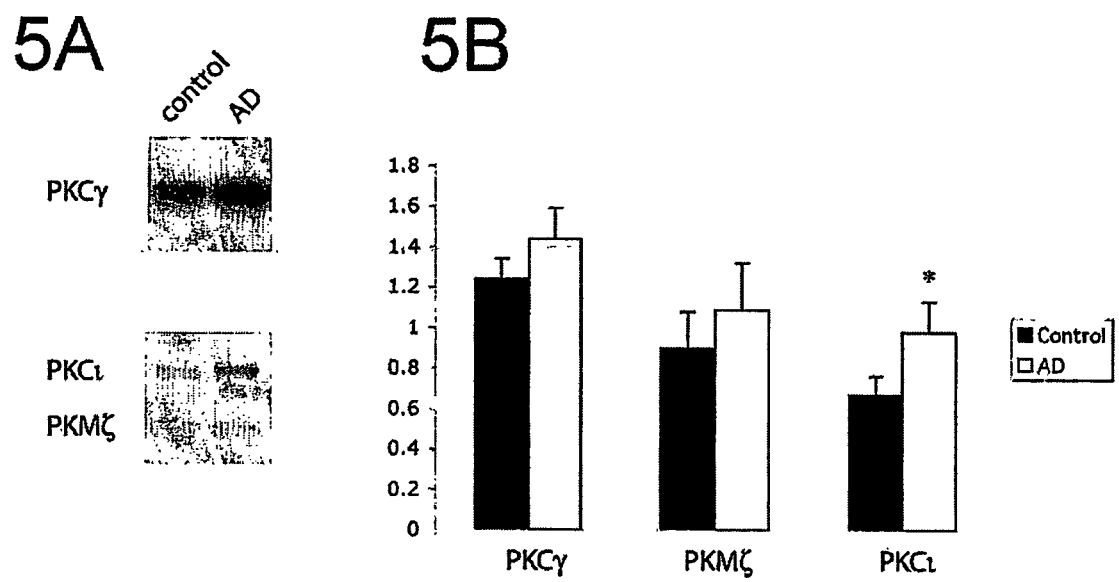
FIG. 5 illustrates that PKCι/λ but not PKMζ or PKCγ increase in the caudate nucleus in AD.

For comparison, Western blots were conducted on the caudate nucleus. PKCγ was not significantly changed in the AD samples ($1.44\pm0.15$) as compared to controls ($1.24\pm0.10$). There was a smaller, but statistically significant decrease in PKCι($p=0.006$) in AD ($0.86\pm0.08$) versus controls ($1.15\pm0.08$) representing a 25% decrease. In contrast, PKMζ was not significantly different in AD ($0.69\pm0.39$) versus controls ($0.63\pm0.22$). See FIG. 5.

EXAMPLE 9

Localization of aPKC in Human Brain

To localize aPKC in human brain, immunohistochemistry was done on paraffin-embedded sections from control cases (n=2).

TABLE 2

Summary of patient data (immunohistochemistry)

| Case | PMI | Age | Sex | Dx |
|---|---|---|---|---|
| 1 | 4.5 | 82 | F | AD |
| 2 | 6.5 | 86 | F | AD |
| 3 | 4.0 | 72 | F | AD |
| 4 | Na | 60 | F | AD |
| 5 | Na | 83 | F | AD |
| 6 | Na | 98 | M | Braak Stage II |
| 7 | 12 | 47 | F | control |

Figure 6:
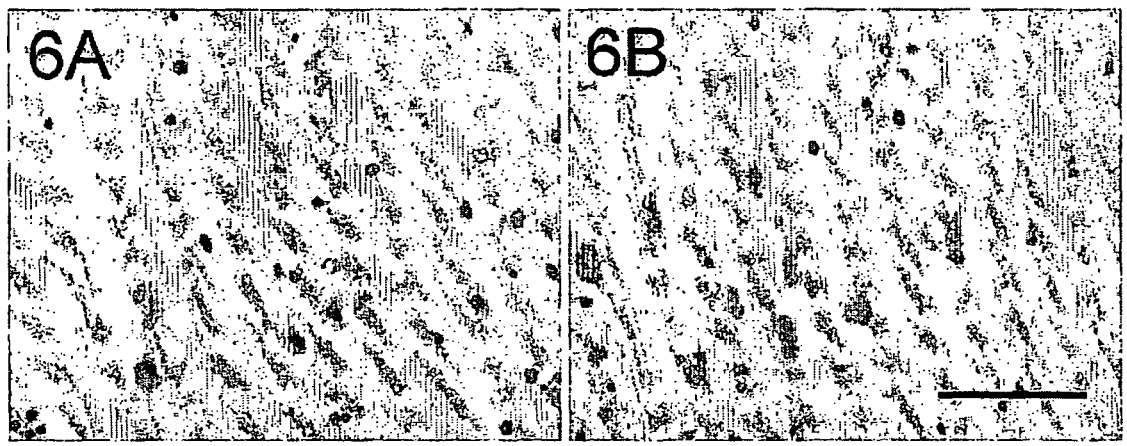
FIG. 6 illustrates localization of aPKC in human cerebral parahippocampal cortex. ζ-C1 (FIG. 6B). No primary antibody control (FIG. 6A). aPKC staining can be seen in perikarya and proximal dendrites. No neuronal nuclear staining was observed. Scale bar=100 μm.

Staining with ζ-C1 was evident in the perikarya of pyramidal cells, extending into proximal dendrites (FIG. 6B). There was no neuronal nuclear staining.

Figure 7:
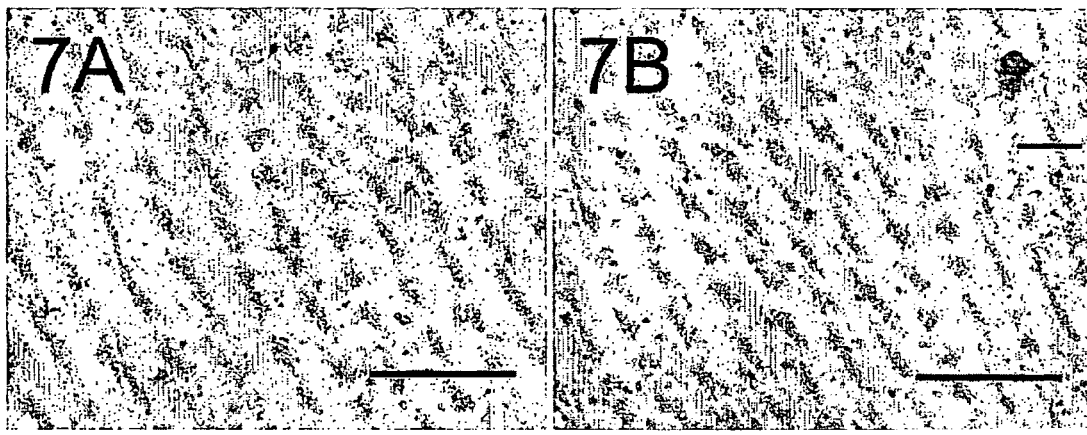
FIG. 7 illustrates localization of aPKC in human astrocytes. Astrocytes stained strongly with antiPKCι/λ in the cerebral cortex FIG. 7A). ζ-C1 reacted with astrocytes in CA-4 of the hippocampus (FIG. 7B). Scale bar=200 μm. Inset shows high power of an astrocyte. Scale bar=25 μm.

Staining was also observed in glia. The cytoplasm and nuclei of astrocytes in hippocampal area CA-4 stained strongly with ζ-C1 indicating the presence of aPKC (FIG. 7B). PKCι/λ immunoreactivity in astrocytes was also observed in cortex (FIG. 7A). ζ-C2 did not stain astrocytes.

Figure 8:
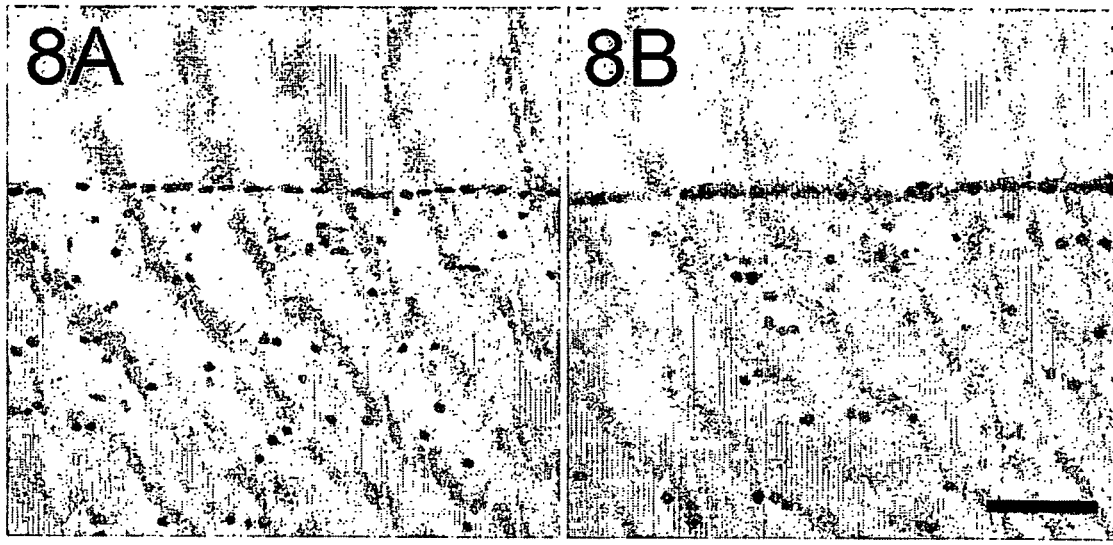
FIG. 8 illustrates localization of aPKC in ependymal glia ζ-C1 reacted with ependymal glia (FIG. 8B). No primary antibody control (FIG. 8A). bar=100 μm.

Ependymal cells also stained with ζ-C1 (FIG. 8). Similar results were seen with ζ-C2 and ι/λ, indicating the presence of both ζ and ι/λ forms in this cell type.

EXAMPLE 10

PKM ζ Colocalizes with Neurofibrillary Tangles and Hirano Bodies

Figure 9:
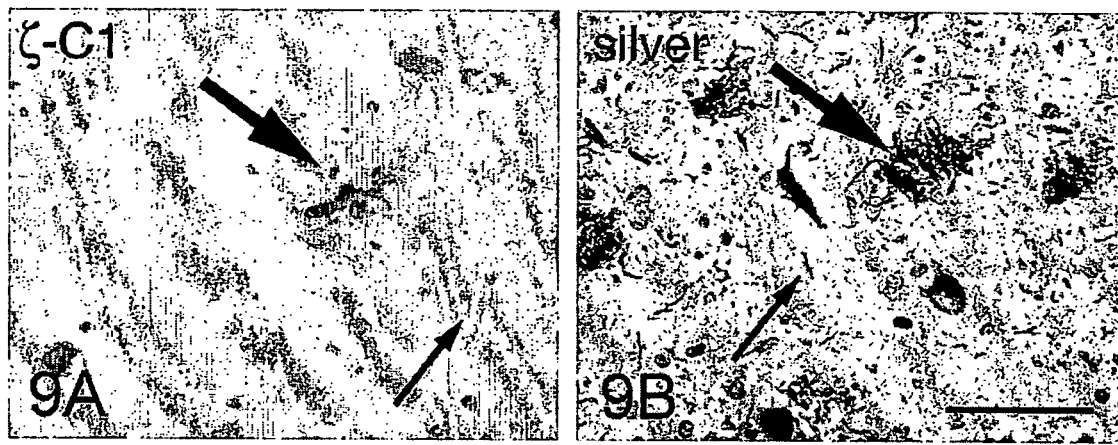
FIG. 9 illustrates that aPKC colocalizes with neuropil threads and dystrophic neurites.
Figure 10:
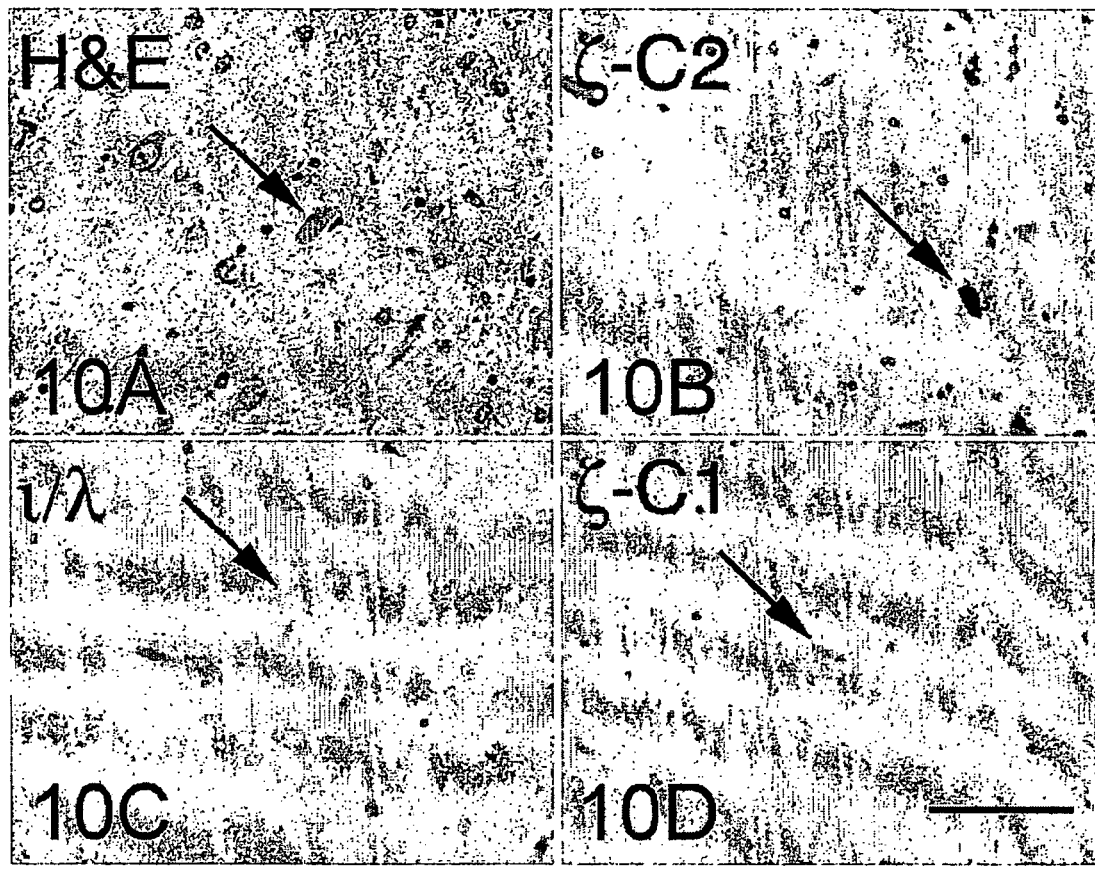
FIG. 10 illustrates that aPKC colocalizes with Hirano bodies (HB) in area CA-1 of the hippocampus. Arrows indicate HB can be seen as a brightly eosinophilic rod-like structure when stained with hematoxylin and eosin (H&E, FIG. 10A). HB can be seen with all of the aPKC antibodies, ζ-C1 (FIG. 10D), ζ-C2 (FIG. 10B) and 1/λ (FIG. 10C). bar=100 μm.

To examine changes in the distribution of aPKC in AD, sections of hippocampus from patients (n=4) with neuropathologically confirmed AD were stained with aPKC antibodies. Despite high staining in the neuropil, there was minimal ι/λ immunoreactivity in NFTs (FIG. 9, top right). In contrast, both ζ-C1 and ζ-C2 strongly reacted with NFTs (FIG. 9, middle right and left). Silver stain confirms the presence of SPs and NFTs in this region. Neuropil threads, dystrophic neurites and SPs failed to label. Since neuropil threads and dystrophic neurites both contain PHFs, sections were pre-treated with citrate and formic acid to unmask the epitopes. Immunoreactivity in distrophic neurites and neuropil threads was seen after unmasking when stained with ζ-C1 (FIG. 10). Silver stain from a non-adjacent section in the same region confirmed the presence of SPs.

Figure 11:
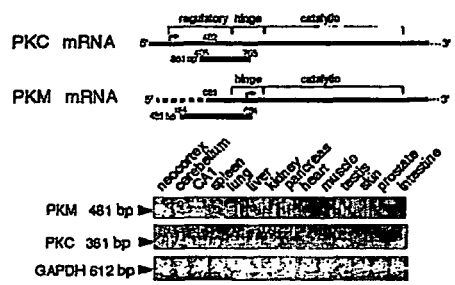
FIG. 11 illustrates PKMζ distribution correlates with unique brain-specific ζ RNA.
Figure 11:
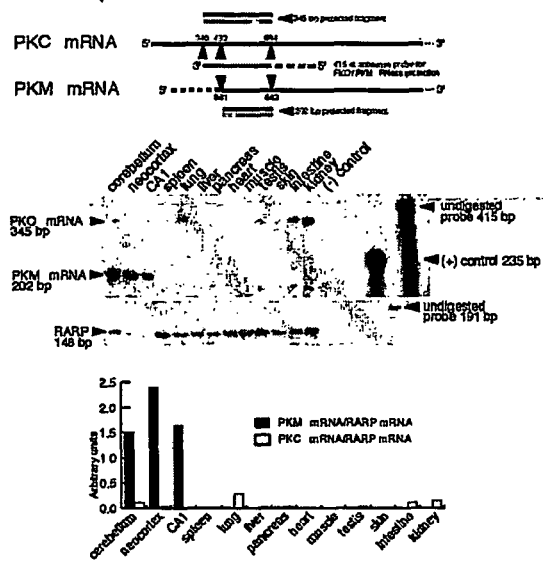
Figure 11:
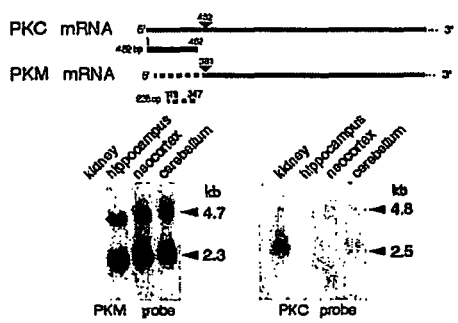

Strong staining was seen in HB with ζ-C1, ζ-C2 and ι/λ. On H&E, the presence of HB was confirmed. See FIG. 11.

EXAMPLE 11

Figure 12:
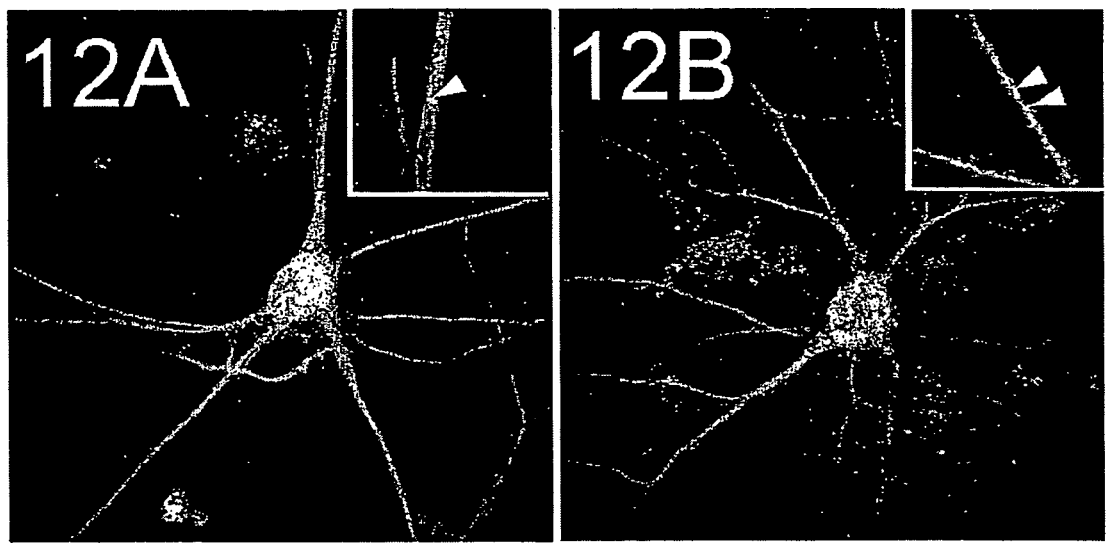
FIG. 12 illustrates that treatment of dissociated primary hippocampal neuronal cultures with high potassium results in increased levels of PKMζ (green) relative to MAP2 (red).
Figure 13:
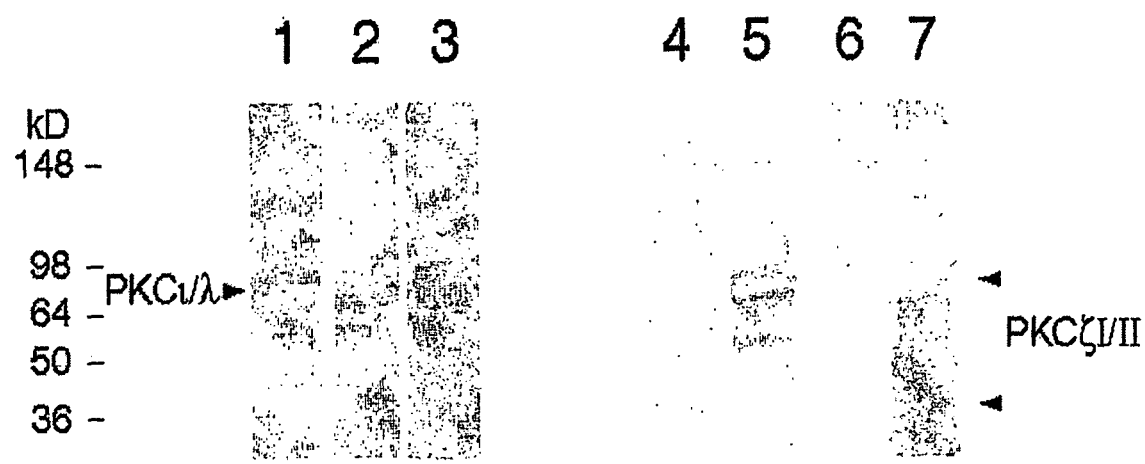
FIG. 13 depicts a Western blot showing the lack of expression of PKCζI/II in neuroblastoma cells (IMR-32 cell line). Lane 1 shows that a rat brain lysate when probed with an anti-PKCi/l antiserum displays a band at about 72 kD. Lysates of IMR-32 cells (lane 2) and pheochromocytoma cells (lane 3), when probed with specific anti-PKCι/λ antisera also show PKCi/l. In contrast, when IMR32 and PC12 cells are probed with a specific anti-PKCζI/II antiserum, IMR32 cells have no bands (lane 6), but PC12 cells show multiple bands (lane 7). When IMR-32 cells were transfected with PKCζII a doublet of two bands was detected for PKCζII at around 80 kDa (lane 5). In contrast, lysates of IMR-32 cells transfected with EGFP alone did not contain a band when probed with anti-PKCζII (lane 4).

The Distribution of PKMζ Correlates with that of a Unique Brain RNA Encoding an Independent ζ Catalytic Domain One explanation for the abundance of PKMζ in forebrain despite very low levels of PKCζ is that PKMζ is not a proteolytic product of PKCζ. The ζ gene produces two sets of RNAs: fill-length PKCζ mRNA and an RNA referred to as ζ' (FIG. 12A). The 3' end of ζ' RNA consists of sequence for a partial ζ regulatory domain and its complete hinge and catalytic domain, which are identical to that in PKCζ mRNA (FIG. 12A). The 5' end of ζ' RNA, however, is unique sequence that lacks an AUG to initiate translation of the ζ regulatory domain. The first AUG for an open reading frame (ORF) of the ζ sequence begins in its hinge (FIG. 12A). Therefore, the ζ' RNA can express PKMζ. To determine whether the distributions of the ζ RNAs correlate with the different ζ proteins, the expression of PKCζ mRNA and ζ' was analyzed by RT-PCR, RNase protection, and Northern blot analysis (FIGS. 12A-12C).

For reverse-transcription polymerase chain reaction (RT-PCR), total RNA isolated from rat tissue was used to synthesize cDNA with the SuperScript Preamplification System for First Strand cDNA Synthesis Kit (Gibco Invitrogen, Grand Island, N.Y.). 200 ng of cDNA was used in 100 μl final volume PCR reactions. Amplified was for 34 cycles with 94° C. for 30 sec, 60° C. for 1 minutes, and 72° C. for 1 minutes as cycle parameters, with a final step of 72° C. for 10 minutes. For amplification of PKCζ and PKMζ cDNAs, specific forward primers were F 5'-CCATGCCCAGCAGGACCACC-3' (SEQ ID NO: 12) and F 5'-CCTTCTATTAGATGCCTGCTCTCC-3' (SEQ ID NO: 13), respectively, and R 5'-TGAAGGAAG-GTCTACACCATCGTTC-3' (SEQ ID NO: 14), was the reverse primer for both. As a control we used GAPDH primers, F 5'-ACATGGTCTACATGTTCC-3' (SEQ ID NO: 15) and R 5'-CAGATCCACAACGGAATAC-3' (SEQ ID NO: 16).

Using specific forward primers that distinguish between the two ζ RNAs, RT-PCR analysis showed abundant expression of ζ' in brain, but not in non-neural tissues (FIG. 12A), in accordance with the distribution of PKMζ. Only with a higher number of PCR cycles could a small amount of ζ' RNA be detected in kidney (data not shown). In contrast, PKCζ mRNA was expressed in kidney, lung, testis, and cerebellum, but not in neocortex or hippocampus (FIG. 12A). This distribution correlates with the expression of PKCζ.

These findings by RNase protection were quantified using an antisense probe that protects a 345 nucleotide fragment of PKCζ mRNA and a 202 nucleotide fragment of ζ' RNA (FIG. 12B). Confirming the RT-PCR, the RNase protection product of ζ' RNA was found only in brain, whereas the protection product of the PKCζ mRNA was observed in kidney, lung, testis, and cerebellum, but not in neocortex or hippocampus (FIG. 12B). The relative levels of PKCζ mRNA and ζ' RNA were examined by comparing them to mRNA for the housekeeping rat acidic ribosomal protein (RARP, FIG. 12B, center and bottom). The expression of ζ' RNA in brain was higher than that of PKCζ mRNA in any of the tissues examined.

For Northern blot, total RNA from rat tissue (30 ug) was electrophoresed and transferred to nitrocellulose, rinsed, and UV cross-linked. Digestion of rat cDNAs with EcoRI-SphI and KpnI-EcoRI gave a 457 bp and 227 bp specific fragment for PKCζ and PKMζ respectively. The fragments were radiolabeled with $^{32}P$ using a Stratagene random octamer protocol (Stratagene Cloning Systems, La Jolla, Calf.). Hybridization conditions were performed according to instructions for Stratagene QuickHyb Hybridization. Blots were developed overnight by film exposure at –70° C. or by PhosphorImager (Molecular Dynamics Storm 860 gel and blot imaging system, Amersham Pharmacia Biotech, Piscataway, N.J.). The sizes of the ζ' RNA and PKCζ mRNAs in different brain regions and kidney were then determined by Northern blot, using probes specific to their unique 5' ends (FIG. 12C). The ζ' RNA was expressed as a 2.3 kb and 4.7 kb species in brain, but not kidney (FIG. 12C). PKCζ mRNA was expressed as a 2.5 kb and minor 4.8 kb species in kidney and cerebellum, but not in neocortex or hippocampus (FIG. 12C). These sizes were similar to those previously reported.

EXAMPLE 12

Figure 14:
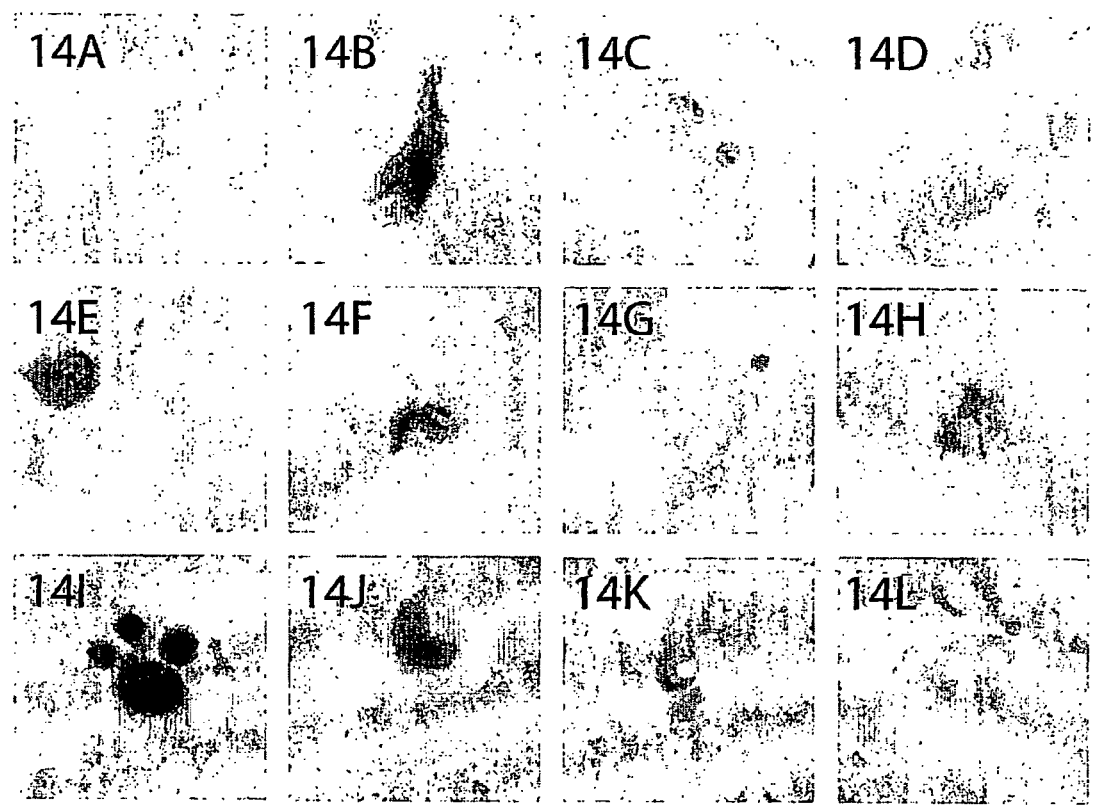
FIG. 14 depicts association of PKCι/λ with tauopathies and α-synucleinopathies. The PKCl/λ antibody weakly labeled cytoplasm of unremarkable hippocampal neurons and neuropil in a control case (FIG. 14a), while strongly labeling NFTs (FIG. 14b) and Hirano bodies (FIG. 14c) in an AD case. The antibody also labeled Pick bodies (FIG. 14d) and Pick cells in PiD; globose tangles (FIG. 14e) and tufted glial cells (FIG. 14f) in PSP; and ballooned neurons (FIG. 14g) and astrocytes (FIG. 14h) in CBD. In α-synucleinopathies, the antibody strongly labeled classic Lewy bodies in pigmented substantia nigra neurons (FIG. 14i) and Lewy bodies in amygdala (FIG. 14j) and cortex in PD and DLB. In MSA, glial inclusions were also immunoreactive (FIG. 14k). Omission of the primary antibody yielded no staining of any inclusions such as these nigral Lewy bodies (arrow) (FIG. 14l).

In all brains, whether those of neurologically normal individuals or those of patients with neurodegenerative diseases, the PKCι/λ antibody showed widespread weak, fine granular labeling of neuronal cell bodies and neuropil in cortex, subcortical gray matter, brainstem and cerebellum (FIG. 14a). The antibody consistently labeled ependymal cells and choroid plexus epithelial cells, but glial cells were immunonegative (data not shown).

In AD, the PKCι/λ antibody strongly labeled a subset of NFTs in hippocampal pyramidal cells and neocortical neurons (FIG. 14b) as well as most Hirano bodies in CA1 of the hippocampus (FIG. 14c). PKCι/λ-positive NFTs generally exhibited classic flame-shaped configurations. Interestingly, while 'early' perinuclear tangles were also labeled, the more advanced 'ghost' or 'extracellular' tangles failed to label. Neuropil threads, amyloid plaques and granulovacuolar bodies in hippocampal neurons were generally immunonegative.

The PKCι/λ antibody uniformly labeled Pick bodies and occasional Pick cells in neurons of hippocampal dentate gyrus and neocortex of PiD (FIG. 14d). In cases of PSP, the antibody labeled globose tangles and tufted astrocytes in the subthalamic, mesencephalic, inferior olivary and cerebellar dentate nuclei (FIGS. 14e-14f). In CBD, ballooned neurons, tau-immunoreactive astrocytic inclusions in cerebral cortex, as well as neuronal and glial inclusions in the basal ganglia were immunopositive (FIGS. 14g-14h).

In the aα-synucleinopathies, the PKCι/λ antibody strongly labeled all classic Lewy bodies found in the substantia nigra as well as the majority of Lewy bodies in cerebral cortex and amygdala in PD and DLB (FIGS. 14i-14j). Lewy neurites in amygdala, hippocampal CA2/3 or midbrain were labeled only rarely. The PKCι/λ antibody also labeled some glial α-synuclein-positive inclusions in MSA (FIG. 14k). Omission of the primary antibody resulted in no immunolabeling of any of these structures (FIG. 14l).

EXAMPLE 13

Single nucleotide polymorphisms were identified in the PKCζ and PKCι/λ genes (SEQ ID NOs: 6 and 7 respectively). The sequences obtained using the genome browser (UCSC, CA) and examined for SNPs from clone overlaps and SNPs from random reads. SNPs identified in the PKCζ and PKCι/λ genes are indicated in the sequence in bold letters. For reference, exons are indicated in capital letters.

What is claimed is:

1. A purified antibody ζ-C2 raised against the sequence set forth in SEQ ID NO:2, which specifically binds to the atypical isoform protein kinase M zeta (PKMζ).

* * * * *

UNITED STATES PATENT AND TRADEMARK OFFICE
CERTIFICATE OF CORRECTION

| | | |
|---|---|---|
| PATENT NO. | : 7,790,854 B2 | Page 1 of 1 |
| APPLICATION NO. | : 10/533595 | |
| DATED | : September 7, 2010 | |
| INVENTOR(S) | : Todd Charlton Sacktor et al. | |

It is certified that error appears in the above-identified patent and that said Letters Patent is hereby corrected as shown below:

Column 1, lines 5-9 should read:

This invention was made with government support under grant number AG000959 awarded by National Institute on Aging and grant number MH057068 awarded by National Institute of Health. The government has certain rights in the invention.

Signed and Sealed this

Eleventh Day of September, 2012

David J. Kappos
*Director of the United States Patent and Trademark Office*